(12) United States Patent
Machuy et al.

(10) Patent No.: US 8,933,046 B2
(45) Date of Patent: Jan. 13, 2015

(54) INFLUENZA TARGETS

(75) Inventors: Nikolaus Machuy, Hamburg (DE); Alexander Karlas, Berlin (DE); Thomas F. Meyer, Berlin (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 0 days.

(21) Appl. No.: 13/518,914

(22) PCT Filed: Dec. 22, 2010

(86) PCT No.: PCT/EP2010/070548
§ 371 (c)(1),
(2), (4) Date: Aug. 24, 2012

(87) PCT Pub. No.: WO2011/076873
PCT Pub. Date: Jun. 30, 2011

(65) Prior Publication Data
US 2013/0004502 A1    Jan. 3, 2013

(30) Foreign Application Priority Data
Dec. 23, 2009   (EP) .................................... 09015997

(51) Int. Cl.
C12N 15/113    (2010.01)
A61K 45/06     (2006.01)
A61K 31/7105   (2006.01)
A61K 31/711    (2006.01)
A61K 31/713    (2006.01)
A61K 31/7088   (2006.01)

(52) U.S. Cl.
CPC ........ *C12N 15/1131* (2013.01); *C12N 2320/12* (2013.01); *A61K 45/06* (2013.01); *C12N 2310/14* (2013.01); *A61K 31/7105* (2013.01); *C12N 2760/16111* (2013.01); *C12N 2320/11* (2013.01); *G01N 2333/11* (2013.01); *A61K 31/711* (2013.01); *G01N 2500/10* (2013.01); *A61K 31/713* (2013.01); *A61K 31/7088* (2013.01)
USPC ....................................................... 514/44 A

(58) Field of Classification Search
None
See application file for complete search history.

(56) References Cited

U.S. PATENT DOCUMENTS

2007/0172489 A1    7/2007   Ludwig et al.
2009/0042823 A1    2/2009   Templin

FOREIGN PATENT DOCUMENTS

WO    2008043561 A2    4/2008

OTHER PUBLICATIONS

Hao, L. et al.: "*Drosophila* RNAi screen identifies host genes important for influenza virus replication", Nature, vol. 454, Aug. 20, 2008, pp. 890-893.
Palamara A T et al: "Inhibition of Influenza A Virus Replication by Resveratrol", Journal of Infectious Diseases, University of Chicago Press, Chicago, IL, vol. 191, No. 10, Jan. 1, 2005, pp. 1719-1729.
Ludwig, L.Planz, Opleschka, S.Wolff, T.: "Influenza-virus-induced signaling cascades: targets for antiviral therapy?", Trends Mol. Med., vol. 9, Mar. 20, 2003, pp. 46-52.
Karlas A et al: "Genome-wide RNAi screen identifies human host factors crucial for influenza virus replication", Nature, Nature Publishing Group, London, GB, vol. 463, Feb. 11, 2010, pp. 818-822.

*Primary Examiner* — Tracy Vivlemore
(74) *Attorney, Agent, or Firm* — Rothwell, Figg, Ernst & Manbeck, P.C.

(57) ABSTRACT

The present invention relates to a pharmaceutical composition comprising an inhibitor of influenza virus replication. Yet another aspect is a screening method for identification of new targets for the prevention, alleviation or/and treatment of influenza.

1 Claim, 28 Drawing Sheets

INFLUENZA TARGETS

CROSS REFERENCE TO RELATED APPLICATION

Figure 1A:
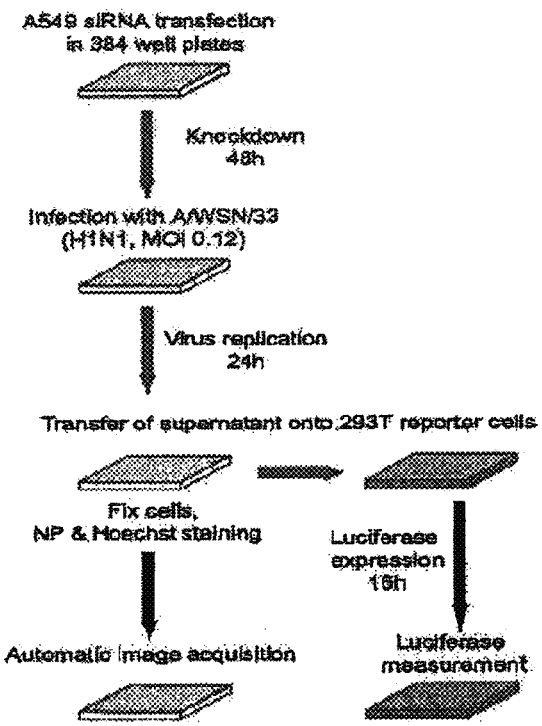

This application is a 35 U.S.C. 371 National Phase Entry Application from PCT/EP2010/070548, filed Dec. 22, 2010, which claims the benefit of European Patent Application No. 09015997.1 filed on Dec. 23, 2009, the disclosures of which are incorporated herein in their entirety by reference.

REFERENCE TO A SEQUENCE LISTING

The present application includes a Sequence Listing filed in electronic format. The Sequence Listing is entitled "2923-1157_ST25.txt" created on Sep. 7, 2012, and is 174,000 bytes in size. The information in the electronic format of the Sequence Listing is part of the present application and is incorporated herein by reference in its entirety.

The present invention relates to a pharmaceutical composition comprising an inhibitor of influenza virus replication. Yet another aspect is a screening method for identification of new targets for the prevention, alleviation or/and treatment of influenza.

In view of the threatening influenza pandemic, there is an acute need to develop and make available lastingly effective drugs. In Germany alone the annual occurrence of influenza causes between 5,000 and 20,000 deaths a year (source: Robert-Koch Institute). The recurring big influenza pandemics are especially feared. The first big pandemic, the so-called "Spanish Flu", cost about 40 million lives in the years 1918-1919 including a high percentage of healthy, middle-aged people. A similar pandemic could be caused by the H5N1 influenza virus, which at the moment replicates mainly in birds, if acquired mutations enable the virus to be transmitted from person to person. The probability of a human pandemic has recently grown more acute with the spreading of bird flu (H5N1) worldwide and the infection of domestic animals. It is only a question of time until a highly pathogenic human influenza-recombinant emerges. More recently, a novel influenza virus variant has emerged, i.e. the influenza A (H1N1) 'swine flu' strain, posing an unpredictable pandemic threat. The methods available at the moment for prophylaxis or therapy of an influenza infection, such as vaccination with viral surface proteins or the use of antiviral drugs (neuraminidase inhibitors or ion channel blockers), have various disadvantages. Already at this early stage resistance is appearing against one of our most effective preparations (Tamiflu), which may make it unsuitable to contain a pandemic. A central problem in the use of vaccines and drugs against influenza is the variability of the pathogen. Up to now the development of effective vaccines has required accurate prediction of the pathogen variant. Drugs directed against viral components can rapidly lose their effectiveness because of mutations of the pathogen.

An area of research which has received little attention up to now is the identification of critical target structures in the host cell. Viruses are dependent on certain cellular proteins to be able to replicate within the host. The knowledge of such cellular factors that are essential for viral replication but dispensable (at least temporarily) for humans could lead to the development of novel drugs. Rough estimates predict about 500 genes in the human genome which are essential for viral multiplication. Of these, 10% at least are probably dispensable temporarily or even permanently for the human organism. Inhibition of these genes and their products, which in contrast to the viral targets are constant in their structure, would enable the development of a new generation of antiviral drugs in the shortest time. Inhibition of such gene products could overcome the development of viral escape mutants that are not longer sensitive to antiviral drugs.

It is the object of the present invention to provide screenings methods for compounds suitable for the prevention, alleviation or/and treatment of an influenza virus infection.

In the context of the present invention, it was surprisingly found that modulation (activation or inhibition) of particular genes leads to reduction of influenza virus replication. Tables 1, 2, 3 and 4 describe targets for the prevention, alleviation or/and treatment of an influenza virus infection.

Examples of genes which upon downregulation increase the influenza virus replication are described in Tables 1, 2, 3 and 4. Thus, by increasing expression or/and activity of these genes or/and gene products, the influenza virus replication can be reduced.

Examples of genes which upon downregulation decrease the influenza virus replication are also described in Tables 1, 2, 3 and 4. Thus, by decreasing expression or/and activity of these genes or/and gene products, the influenza virus replication can be reduced.

Subject of the present invention is thus a screening method covering different aspects related to influenza virus infection, in particular influenza virus replication. A first aspect of the present invention is a screening method for identification of a compound suitable for the prevention, alleviation or/and treatment of an influenza virus infection, comprising the steps
  (a) providing a cell or/and a non-human organism capable of being infected with an influenza virus and capable of expressing a gene, wherein the gene or/and gene product thereof is capable of modulating an influenza virus replication,
  (b) contacting the cell or/and the organism of (a) with an influenza virus and with a compound known to be capable of modulating the expression or/and activity of the gene of (a) or/and the gene product thereof,
  (c) determining the amount of influenza virus produced by the cell or/and the organism, and
  (d) selecting a compound which reduces the amount of the influenza virus produced by the cell or/and the organism.

The gene of (a) may be selected from genes listed in Table 1, Table 2, Table 3 or Table 4. Preferably, the gene of (a) is selected from Table 4.

The method of the present invention may comprise a cellular screening assay. A cellular screening assay includes the determination of the activity or/and expression of a gene of (a) or/and the gene product thereof. The screening assay may be performed in vivo or/and in vitro.

Another aspect of the present invention is a screening method for identification of a compound suitable for prevention, alleviation or/and treatment of an influenza virus infection, comprising the steps
  (i) providing a cell or/and a non-human organism capable of expressing a gene, wherein the gene or/and gene product thereof is capable of modulating an influenza virus replication,
  (ii) contacting a compound with the cell or/and the organism of (i),
  (iii) determining the amount or/and the activity of gene product of the gene of (i), and
  (iv) selecting a compound which modulates the amount or/and the activity of the gene product of (i).

The gene of (i) may be selected from Table 1, Table 2, Table 3 and Table 4. Preferably, the gene of (i) is selected from Table 4.

The compound of (iv) may reduce the amount of the influenza virus produced by the cell or/and the organism.

"Modulation" in the context of the present invention may be "activation" or "inhibition". Modulation of the expression of a gene may be downregulation or upregulation, in particular of transcription or/and translation. It can easily be determined by a skilled person if a gene is upregulated or downregulated. In the context of the present invention, upregulation (activation) of gene expression may be an upregulation by a factor of at least 2, preferably at least 4. Downregulation (inhibition) in the context of the present invention may be a reduction of gene expression by a factor of at least 2, preferably at least 4. Most preferred is essentially complete inhibition of gene expression, e.g. by RNA interference.

Modulation of the activity of the gene may be decrease or increase of the activity. In the context of the present invention, "activity" of the gene or/and gene product includes transcription, translation, posttranslational modification, modulation of the activity of the gene or/and gene product. The activity may be modulated by ligand binding, which ligand may be an activator or inhibitor. "Inhibition of the activity" may be a decrease of activity of a gene or gene product by a factor of at least 2, preferably at least 4. "Inhibition of the activity" includes essentially complete inhibition of activity. "Activation of the activity" may be an increase of activity of a gene or gene product by a factor of at least 2, preferably at least 4.

The activity may also be modulated by an miRNA molecule, an shRNA molecule, an siRNA molecule, an antisense nucleic acid, a decoy nucleic acid or/and any other nucleic acid, as described herein. Modulation may also be performed by a small molecule, an antibody, an aptamer, or/and a spiegelmer (mirror image aptamer).

An activator of a gene identified by the method of the present invention may be suitable of reducing the amount of the influenza virus produced by a cell or/and an organism. In Tables 1, 2, 3 and 4, genes are described which upon inhibition (e.g. by siRNA) increase virus replication. Therefore, upon activation of these genes, virus replication may be reduced. In the tables, such genes are characterized by positive z-scores or/and by negative values of normalized percent inhibition (NPI).

An inhibitor of a gene identified by the method of the present invention is suitable of reducing the amount of the influenza virus produced by a cell or/and an organism. In Tables 1, 2, 3 and 4, genes are described which upon inhibition (e.g. by siRNA) decrease virus replication. In the tables, such genes are characterized by negative z-scores or/and by positive values of normalized percent inhibition (NPI).

Modulation may be performed by a single nucleic acid species or by a combination of nucleic acids comprising 2, 3 4, 5, 6 or even more different nucleic acid species, which may be selected from sequences of Tables 1, 2, 3, and 4 and fragments thereof. Preferred combinations are described in Table 4. It is also preferred that the combination modulates one gene, for instance selected from Tables 1, 2, 3, and 4. A combination of two nucleic acid species is preferred.

Modulation may be a knock-down performed by RNA interference. The nucleic acid or the combination of nucleic acid species may be an siRNA, which may comprise a sequence selected from the sequences of Tables 1, 2, 3, and 4 and fragments thereof. It is preferred that the combination knocks down one gene, for instance selected from Tables 1, 2, 3, and 4. A combination of two siRNA species is preferred.

In the context of the present invention, a "target" includes a nucleotide sequence in a gene or/and a genome, a nucleic acid, or/and a polypeptide which is involved in regulation of influenza virus replication in a host cell. The target may be directly or indirectly involved in regulation of influenza virus replication. In particular, a target is suitable for reduction of influenza virus replication, either by activation of the target or by inhibition of the target.

Examples of targets are genes and partial sequence of genes, such as regulatory sequences. The term "target" also includes a gene product such as RNA, in particular mRNA, tRNA, rRNA, miRNA, piRNA. A target may also include a polypeptide or/and a protein encoded by the target gene. Preferred gene products of a target gene are selected from mRNA, miRNA, polypeptide(s) and protein(s) encoded by the target gene. The most preferred gene product is a polypeptide or protein encoded by the target gene. A target protein or a target polypeptide may be posttranslationally modified or not.

"Gene product" of a gene as used herein includes RNA (in particular mRNA, tRNA, rRNA, miRNA and piRNA), a polypeptide or/and a protein encoded by said gene.

The cell employed in step (a) may be any cell capable of being infected with an influenza virus. Cell lines suitable for the production of an influenza virus are known. Preferably the cell is a mammalian cell or an avian cell. Also preferred is a human cell. Also preferred is an epithelial cell, such as a lung epithelial cell. The cell may be a cell line. A suitable lung epithelial cell line is A594. Another suitable cell is the human embryonic kidney cell line 293T. In one embodiment of the present invention, the method of the present invention employs a cell as described herein.

The non-human organism employed in step (a) may be any organism capable of being infected with an influenza virus.

The influenza virus employed in the method of the present invention may be an influenza A virus. The influenza A virus may be selected from influenza A viruses isolated so far from avian and mammalian organisms. In particular, the influenza A virus may be selected from H1N1, H1N2, H1N3, H1N4, H1N5, H1N6, H1N7, H1N9, H2N1, H2N2, H2N3, H2N4, H2N5, H2N7, H2N8, H2N9, H3N1, H3N2, H3N3, H3N4, H3N5, H3N6, H3N8, H4N1, H4N2, H4N3, H4N4, H4N5, H4N6, H4N8, H4N9, H5N1, H5N2, H5N3, H5N6, H5N7, H5N8, H5N9, H6N1, H6N2, H6N3, H6N4, H6N5, H6N6, H6N7, H6N8, H6N9, H7N1, H7N2, H7N3, H7N4, H7N5, H7N7, H7N8, H7N9, H9N1, H9N2, H9N3, H9N5, H9N6, H9N7, H9N8, H10N1, H10N3, H10N4, H10N6, H10N7, H10N8, H10N9, H11N2, H11N3, H11N6, H11N9, H12N1, H12N4, H12N5, H12N9, H13N2, H13N6, H13N8, H13N9, H14N5, H15N2, H15N8, H15N9 and H16N3. More particularly, the influenza A virus is selected from H1N1, H3N2, H7N7, H5N1. Even more particularly, the influenza A virus is strain Puerto Rico/8/34, the avian influenza virus isolate H5N1, the avian influenza strain A/FPV/Bratislava/79 (H7N7), strain A/WSN/33 (H1N1), strain A/Panama/99 (H3N2), or a swine flu strain H1N1, such as A/HH/04/2009.

The influenza virus may be an influenza B virus. In particular, the influenza B virus may be selected from representatives of the Victoria line and representatives of the Yamagata line.

The at least modulator of influenza virus replication employed in the method of the present invention of the present invention may be selected from the group consisting of nucleic acids, nucleic acid analogues such as ribozymes, peptides, polypeptides, antibodies, aptamers, spiegelmers, small molecules and decoy nucleic acids.

The modulator of influenza virus replication may be a compound having a molecular weight smaller than 1000 Dalton or smaller than 500 Dalton. In the context of the present invention, "small molecule" refers to a compound having a molecular weight smaller than 1000 Dalton or smaller than 500 Dalton.

The nucleic acid employed in the present invention may be an antisense nucleic acid or a DNA encoding the antisense nucleic acid.

The nucleic acid or/and nucleic acid fragment employed in the present invention may have a length of at least 15, preferably at least 17, more preferably at least 19, most preferably at least 21 nucleotides. The nucleic acid or/and the nucleic acid fragment may have a length of at the maximum 29, preferably at the maximum 27, more preferably at the maximum 25, especially more preferably at the maximum 23, most preferably at the maximum 22 nucleotides.

The nucleic acid employed in the present invention may be a microRNA (miRNA), a precursor, a fragment, or a derivative thereof. The miRNA may have the length of the nucleic acid as described herein. The miRNA may in particular have a length of about 22 nucleotides, more preferably 22 nucleotides.

A further aspect of the present invention is a pharmaceutical composition comprising at least one inhibitor of influenza virus replication optionally together with a pharmaceutically acceptable carrier, adjuvant, diluent or/and additive, for the prevention, alleviation or/and treatment of an influenza virus infection.

In the pharmaceutical composition of the present invention, the at least one inhibitor may be selected from the group consisting of nucleic acids, nucleic acid analogues such as ribozymes, peptides, polypeptides, and antibodies, and compounds having a molecular weight below 1000 Dalton.

The influenza virus infection may be an influenza A virus infection or an influenza B virus infection, as described herein.

The at least one inhibitor in the pharmaceutical composition of the present invention may be capable of modulating gene expression or/and gene product activity. Modulation of the expression or/and gene product activity may be activation, as described herein. Modulation of the expression or/and gene product activity may be inhibition, as described herein.

The inhibitor may be a modulator as described herein.

The pharmaceutical composition may comprise a nucleic acid being RNA or DNA. Preferably, the nucleic acid in the pharmaceutical composition is selected from
(a) RNA, analogues and derivatives thereof,
(b) DNA, analogues and derivatives thereof, and
(c) combinations of (a) and (b).

In the pharmaceutical composition of the present invention, the at least one inhibitor may comprise
(a) a nucleic acid comprising a nucleotide sequence selected from sequences of Table 1, Table 2, Table 3 and Table 4,
(b) a fragment of the sequence of (a) having a length of at least 70%, at least 80%, at least 90%, at least 95%, at least 98%, or at least 99% of the sequence of (a),
(c) a nucleic acid comprising a sequence which is at least 70%, at least 80%, at least 90%, at least 95%, at least 98%, or at least 99% identical to the sequence of (a) or/and (b), or/and
(d) a sequence complementary to the sequence of (a), (b) or/and (c).

In the pharmaceutical composition, the nucleic acid of (a) preferably comprises a nucleotide sequence selected from the sequences of Table 4 and fragments thereof.

Suitable inhibitors of influenza virus replication in the pharmaceutical composition of the present invention are RNA molecules capable of RNA interference. The nucleic acid in the pharmaceutical composition of the present invention may comprise
(i) an RNA molecule capable of RNA interference, such as siRNA or/and shRNA,
(ii) a miRNA,
(iii) a precursor of the RNA molecule (i) or/and (ii),
(iv) a fragment of the RNA molecule (i), (ii) or/and (iii),
(v) a derivative of the RNA molecule of (i), (ii) (iii) or/and (iv), or/and
(vi) a DNA molecule encoding the RNA molecule of (i), (ii) (iii) or/and (iv).

A preferred nucleic acid is
(i) a miRNA,
(ii) a precursor of the RNA molecule (i), or/and
(iii) a DNA molecule encoding the RNA molecule (i) or/and the precursor (ii).

Yet another preferred nucleic acid is
(i) an RNA molecule capable of RNA interference, such as siRNA or/and shRNA,
(ii) a precursor of the RNA molecule (i), or/and
(iii) a DNA molecule encoding the RNA molecule (i) or/and the precursor (ii).

RNA molecules capable of RNA interference are described in WO 02/44321 the disclosure of which is included herein by reference. MicroRNAs are described in Bartel D (Cell 136: 215-233, 2009), the disclosure of which is included herein by reference.

The RNA molecule of the present invention may be a double-stranded RNA molecule, preferably a double-stranded siRNA molecule with or without a single-stranded overhang alone at one end or at both ends. The siRNA molecule may comprise at least one nucleotide analogue or/and deoxyribonucleotide.

The RNA molecule of the present invention may be an shRNA molecule. The shRNA molecule may comprise at least one nucleotide analogue or/and deoxyribonucleotide.

In the pharmaceutical composition of the present invention the nucleic acid may be an antisense nucleic acid or a DNA encoding the antisense nucleic acid.

In the pharmaceutical composition of the present invention, the nucleic acid may have a length of at least 15, preferably at least 17, more preferably at least 19, most preferably at least 21 nucleotides. In the pharmaceutical composition of the present invention the nucleic acid may have a length of at the maximum 29, preferably at the maximum 27, more preferably at the maximum 25, especially more preferably at the maximum 23, most preferably at the maximum 21 nucleotides.

The pharmaceutical composition of the present invention may comprise an antibody. Preferably the antibody is directed against a polypeptide comprising
(a) an amino acid sequence encoded by a nucleic acid or/and gene selected from sequences of Table 1, Table 2, Table 3, and Table 4 and complementary sequences thereof,
(b) a fragment of the sequence of (a) having a length of at least 70%, at least 80%, at least 90%, at least 95%, at least 98%, or at least 99% of the sequence of (a), or/and
(c) an amino acid sequence comprising a sequence which is at least 70%, at least 80%, at least 90%, at least 95%, at least 98%, or at least 99% identical to the sequence of (a) or/and (b).

Preferably, the pharmaceutical composition comprises a polypeptide of (a) comprising an amino acid sequence encoded by a nucleic acid or/and gene selected from Table 4.

The antibody of the present invention may be a monoclonal or polyclonal antibody, a chimeric antibody, a chimeric single chain antibody, a Fab fragment or a fragment produced by a Fab expression library.

Techniques of preparing antibodies of the present invention are known by a skilled person. Monoclonal antibodies may be prepared by the human B-cell hybridoma technique or by the EBV-hybridoma technique (Köhler et al., 1975, Nature 256:495-497, Kozbor et al., 1985, J. Immunol. Methods 81, 31-42, Cote et al., PNAS, 80:2026-2030, Cole et al., 1984, Mol. Cell. Biol. 62:109-120). Chimeric antibodies (mouse/human) may be prepared by carrying out the methods of Morrison et al. (1984, PNAS, 81:6851-6855), Neuberger et al. (1984, 312:604-608) and Takeda et al. (1985, Nature 314:452-454). Single chain antibodies may be prepared by techniques known by a person skilled in the art.

Recombinant immunoglobulin libraries (Orlandi et al, 1989, PNAS 86:3833-3837, Winter et al., 1991, Nature 349:293-299) may be screened to obtain an antibody of the present invention. A random combinatory immunoglobulin library (Burton, 1991, PNAS, 88:11120-11123) may be used to generate an antibody with a related specifity having a different idiotypic composition.

Another strategy for antibody production is the in vivo stimulation of the lymphocyte population.

Furthermore, antibody fragments (containing F(ab')$_2$ fragments) of the present invention can be prepared by protease digestion of an antibody, e.g. by pepsin. Reducing the disulfide bonding of such F(ab')$_2$ fragments results in the Fab fragments. In another approach, the Fab fragment may be directly obtained from an Fab expression library (Huse et al., 1989, Science 254:1275-1281).

Polyclonal antibodies of the present invention may be prepared employing an amino acid sequence encoded by a nucleic acid or/and gene selected from Table 1, Table 2, Table 3 and Table 4 or immunogenic fragments thereof as antigen by standard immunization protocols of a host, e.g. a horse, a goat, a rabbit, a human, etc., which standard immunization protocols are known by a person skilled in the art.

The antibody may be an antibody specific for a gene product of a target gene, in particular an antibody specific for a polypeptide or protein encoded by a target gene.

Aptamers and spiegelmers share binding properties with antibodies. Aptamers and spiegelmers are designed for specifically binding a target molecule.

The nucleic acid or the present invention may be selected from (a) aptamers, (b) DNA molecules encoding an aptamer, and (c) spiegelmers.

The skilled person knows aptamers. In the present invention, an "aptamer" may be a nucleic acid that can bind to a target molecule. Aptamers can be identified in combinational nucleic acid libraries (e.g. comprising >$10^{15}$ different nucleic acid sequences) by binding to the immobilized target molecule and subsequent identification of the nucleic acid sequence. This selection procedure may be repeated one or more times in order to improve the specificity. The person skilled in the art knows suitable methods for producing an aptamer specifically binding a predetermined molecule. The aptamer may have a length of a nucleic acid as described herein. The aptamer may have a length of up to 300, up to 200, up to 100, or up to 50 nucleotides. The aptamer may have a length of at least 10, at least 15, or at least 20 nucleotides. The aptamer may be encoded by a DNA molecule. The aptamer may comprise at least one nucleotide analogue or/and at least one nucleotide derivatives, as described herein.

The skilled person knows spiegelmers. In the present invention, a "spiegelmer" may be a nucleic acid that can bind to a target molecule. The person skilled in the art knows suitable methods for production of a spiegelmer specifically binding a predetermined molecule. The spiegelmer comprises nucleotides capable of forming bindings which are nuclease resistant. Preferably the spiegelmer comprises L nucleotides. More preferably, the spiegelmer is an L-oligonucleotide. The spiegelmer may have a length of a nucleic acid as described herein. The spiegelmer may have a length of up to 300, up to 200, up to 100, or up to 50 nucleotides. The spiegelmer may have a length of at least 10, at least 15, or at least 20 nucleotides. The spiegelmer may comprise at least one nucleotide analogue or/and at least one nucleotide derivatives, as described herein.

The skilled person knows decoy nucleic acids. In the present invention, a "decoy" or "decoy nucleic acid" may be a nucleic acid capable of specifically binding a nucleic acid binding protein, such as a DNA binding protein. The decoy nucleic acid may be a DNA molecule, preferably a double stranded DNA molecule. The decoy nucleic acid comprises a sequence termed "recognition sequence" which can be recognized by a nucleic acid binding protein. The recognition sequence preferably has a length of at least 3, at least 5, or at least 10 nucleotides. The recognition sequence preferably has a length of up to 15, up to 20, or up to 25 nucleotides. Examples of nucleic acid binding proteins are transcription factors, which preferably bind double stranded DNA molecules. Transfection of a cell, an embryonated egg, or/and a non-human animal, as described herein, with a decoy nucleic acid may result in reduction of the activity of the nucleic acid binding protein to which the decoy nucleic acid binds. The decoy nucleic acid as described herein may have a length of nucleic acid molecules as described herein. The decoy nucleic acid molecule may have a length of up to 300, up to 200, up to 100, up to 50, up to 40, or up to 30 nucleotides. The decoy nucleic may have a length of at least 3, at least 5, at least 10, at least 15, or at least 20 nucleotides. The decoy nucleic acid may be encoded by a DNA molecule. The decoy nucleic acid may comprise at least one nucleotide analogue or/and at least one nucleotide derivatives, as described herein.

The pharmaceutical composition as described herein is preferably for use in human or veterinary medicine.

The pharmaceutical composition of any of the preceding claims further comprises an agent suitable of transportation of the at least inhibitor of influenza virus infection into a cell, in particular into a lung epithelial cell.

The carrier in the pharmaceutical composition may comprise a delivery system. The person skilled in the art knows delivery systems suitable for the pharmaceutical composition of the present invention. The pharmaceutical composition may be delivered in the form of a naked nucleic acid, in combination with viral vectors, non viral vectors including liposomes, nanoparticles or/and polymers. The pharmaceutical composition or/and the nucleic acid may be delivered by electroporation.

Naked nucleic acids include RNA, modified RNA, DNA, modified DNA, RNA-DNA-hybrids, aptamer fusions, plasmid DNA, minicircles, transposons.

Viral vectors include poxviruses, adenoviruses, adeno-associated viruses, vesicular stomatitis viruses, alphaviruses, measles viruses, polioviruses, hepatitis B viruses, retroviruses, and lentiviruses.

Liposomes include stable nucleic acid-lipid particles (SNALP), cationic liposomes, cationic cardiolipin analogue-based liposomes, neutral liposomes, liposome-polycation-DNA, cationic immunoliposomes, immunoliposomes, liposomes containing lipophilic derivatives of cholesterol, lauric acid and lithocholic acid. Examples of compounds suitable for liposome formation are 1,2-dilauroyl-sn-glycero-3-phosphoethanolamine (DLPE); 1,2-dioleoyl-sn-glycero-3-phospho-L-serine (DOPS); cholesterol (CHOL); 1,2-dioleoyl-sn-glycero-3-phosphocholine (DOPC).

Nanoparticles include $CaCO_3$ nanoparticles, chitosan-coated nanoparticle, folated lipid nanoparticle, nanosized nucleic acid carriers.

Polymers include polyethylenimines (PEI), polyester amines (PEA), polyethyleneglycol(PEG)-oligoconjugates, PEG liposomes, polymeric nanospheres.

The pharmaceutical composition may be delivered in combination with atelocollagen, carbon nanotubes, cyclodextrin-containing polycations, fusion proteins (e.g. protamine-antibody conjugates).

An RNA or/and a DNA molecule as described herein may comprise at least one nucleotide analogue. As used herein, "nucleotide analogue" may refer to building blocks suitable for a modification in the backbone, at least one ribose, at least one base, the 3' end or/and the 5' end in the nucleic acid. Backbone modifications include phosphorothioate linkage (PTs); peptide nucleic acids (PNAs); morpholino nucleic acids; phosphoroamidate-linked DNAs (PAs), which contain backbone nitrogen. Ribose modifications include Locked nucleic acids (LNA) e.g. with methylene bridge joining the 2' oxygen of ribose with the 4' carbon; 2'-deoxy-2'-fluorouridine; 2'-fluoro(2'-F); 2'-O-alkyl-RNAs (2-O-RNAs), e.g. 2'-O-methyl (2'-O-Me), 2'-O-methoxyethyl (2'-O-MOE). A modified base may be 2'-fluoropyrimidine. 5' modifications include 5'-TAMRA-hexyl linker, 5'-Phosphate, 5'-Amino, 5'-Amino-C6 linker, 5'-Biotin, 5'-Fluorescein, 5'-Tetrachloro-fluorescein, 5'-Pyrene, 5'-Thiol, 5'-Amino, (12 Carbon) linker, 5'-Dabcyl, 5'-Cholesterol, 5'-DY547 (Cy3™ alternate). 3' end modifications include 3'-inverted deoxythymidine, 3'-puromycin, 3'-dideoxy-cytidine, 3'-cholesterol, 3'-amino modifier (6 atom), 3'-DY547 (Cy3™ alternate).

In particular, nucleotide analogues as described herein are suitable building blocks in siRNA, antisense RNA, and aptamers.

As used herein, "nucleic acid analogue" refers to nucleic acids comprising at least one nucleotide analogue as described herein. Further, a nucleic acid molecule as described herein may comprise at least one deoxyribonucleotide and at least one ribonucleotide.

An RNA molecule of the present invention may comprise at least one deoxyribonucleotide or/and at least one nucleotide analogue. A DNA molecule of the present invention may comprise at least one ribonucleotide or/and at least one nucleotide analogue.

Derivatives as described herein refers to chemically modified compounds. Derivatives of nucleic acid molecules as described herein refers to nucleic acid molecules which are chemically modified. A modification may be introduced into the nucleic acid molecule, or/and into at least one nucleic acid building block employed in the production of the nucleic acid.

In the present invention the term "fragment" refers to fragments of nucleic acids, polypeptides and proteins. "Fragment" also refers to partial sequences of nucleic acids, polypeptides and proteins.

Fragments of polypeptides or/and peptides as employed in the present invention, in particular fragments of an amino acid sequence encoded by a nucleic acid or/and gene selected from Table 1, Table 2, Table 3 and Table 4 may have a length of at least 5 amino acid residues, at least 10, or at least 20 amino acid residues. The length of said fragments may be 200 amino acid residues at the maximum, 100 amino acid residues at the maximum, 60 amino acid residues at the maximum, or 40 amino acid residues at the maximum.

A fragment of an amino acid sequence as described herein may have a length of at least 70%, at least 80%, at least 90%, at least 95%, at least 98%, at least 99% of the sequence.

A fragment of a nucleotide sequence as described herein may have a length of at least 70%, at least 80%, at least 90%, at least 95%, at least 98%, at least 99% of the sequence.

A fragment of a nucleic acid molecule given in Tables 1, 2, 3, and 4 may have a length of up to 1000, up to 2000, or up to 3000 nucleotides. A nucleic acid fragment may have a length of an siRNA molecule, an miRNA molecule, an aptamer, a spiegelmer, or/and a decoy as described herein. A nucleic acid fragment may also have a length of up to 300, up to 200, up to 100, or up to 50 nucleotides. A nucleic acid fragment may also have a length of at least 3, at least 5, at least 10, at least 15, or at least 20 nucleotides.

In the present invention, specific embodiments refer to any individual gene, nucleic acid sequence or/and gene product described in the present application. In a specific embodiment, an individual gene is selected from the genes described in Table 1, Table 2, Table 3, and Table 4. In another specific embodiment, an individual gene product is selected from the gene products produced by the genes described in Table 1, Table 2, Table 3, and Table 4. In yet another specific embodiment, an individual nucleic acid sequence is selected from the nucleic acid molecules described in Table 1, 2, 3 and 4. Further specific embodiment refer to any combination of genes, gene products and nucleic acid molecules described in the Tables 1, 2, 3, and 4.

In the present invention, a reference to Table 4 is a reference to a target, gene or/and nucleotide sequence selected from ACTN1, ATP6AP2, ATP6V1B2, BNIP3L, BRUNOL6, CUEDC2, CYC1, FNTB, GCLC, GNRH2, GRIN2C, GRP, HARBI1, HSPD1, ICAM2, KCNJ12, KPNB1, LAMC2, LOC440733, MKL1, MRPS12, MYEF2, NDUFV3, NECAP2, ODZ4, PIK3R6, PPARA, RAB4A, SCAF1, SCARB1, SERPINA6, SERPINB2, SERPINE2, SEZ6L2, TBL3, TRERF1, TRIM60, and TUBB4.

In the present invention, a reference to Table 4 may also be a reference to a target gene or/and nucleotide sequence selected from ACTN1, BNIP3L, BRUNOL6, CUEDC2, CYC1, GCLC, GNRH2, GRIN2C, GRP, HARBI1, HSPD1, ICAM2, KCNJ12, LAMC2, LOC440733, MKL1, MRPS12, MYEF2, NDUFV3, NECAP2, ODZ4, PIK3R6, PPARA, RAB4A, SCAF1, SCARB1, SERPINA6, SERPINB2, SERPINE2, SEZ6L2, TBL3, TRERF1, TRIM60, and TUBB4.

Yet another aspect of the present invention is the use of an inhibitor of influenza virus replication capable of inhibiting or activating the expression of a gene selected from Table 1, Table 2, Table 3 and Table 4, or/and of inhibiting or activating a gene product thereof, for the manufacture of a medicament or/and vaccine for the prevention, alleviation or/and treatment of an influenza virus infection. Preferably, the gene is selected from Table 4. Preferably, those genes which upon inhibition by e.g. siRNA, as disclosed herein, result in decrease of virus production are activated, wherein those genes which upon inhibition by e.g. siRNA, as disclosed herein, result in increase of virus production are inhibited.

In the context of the present invention, "manufacture of a medicament or/and vaccine" includes the production of influenza virus, wherein the amount of influenza virus is increased by activating or inhibiting a gene selected from Tables 1, 2, 3 and 4, preferably Table 4. Preferably, those genes which upon inhibition by e.g. siRNA, as disclosed herein, result in decrease of virus production are activated, wherein those genes which upon inhibition by e.g. siRNA, as disclosed herein, result in increase of virus production are inhibited in the production of the medicament or/and vaccine.

Yet another aspect of the present invention is method for production of an influenza virus, wherein the amount of influenza virus is increased by activating or inhibiting a gene selected from Tables 1, 2, 3 and 4, preferably Table 4. Preferably, those genes which upon inhibition by e.g. siRNA, as disclosed herein, result in decrease of virus production are activated, wherein those genes which upon inhibition by e.g. siRNA, as disclosed herein, result in increase of virus production are inhibited in the production of the influenza virus. In the method for production of an influenza virus, at least one gene selected from Tables 1, 2, 3 and 4, preferably Table 4, may be overexpressed if activation leads to an increased virus production.

Suitable methods for the production of influenza viruses, for instance in embryonated eggs or/and cell culture, are known in the state of the art.

Yet another aspect of the present invention is a method of prevention, alleviation or/and treatment of an influenza virus infection, comprising administering to a subject in need thereof a therapeutically effective amount of an inhibitor of influenza virus replication, as described herein. In the method of prevention, alleviation or/and treatment of an influenza virus infection, delivery systems and delivery methods as described herein may be used.

Yet another aspect of the present invention is the use of a nucleic acid comprising a gene sequence or/and a nucleotide sequence selected from Table 1, Table 2, Table 3, and Table 4 and fragments thereof in a method for screening for compounds or/and targets suitable for the prevention, alleviation or/and treatment of an influenza virus infection. Preferably a combination of at least two nucleic acids is used. It is also preferred that the nucleic acid or the combination is selected from Table 4. The combination may inhibit expression or/and activity of a gene, preferably selected from Tables 1, 2, 3 and 4, more preferably selected from Table 4.

The invention is further illustrated by the following figures, tables and examples.

FIGURE AND TABLE LEGENDS

Figure 1B:
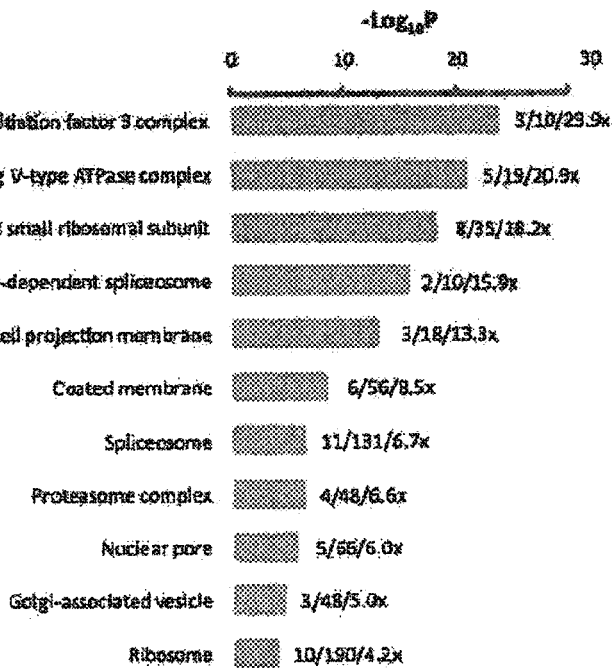
Figure 1C:
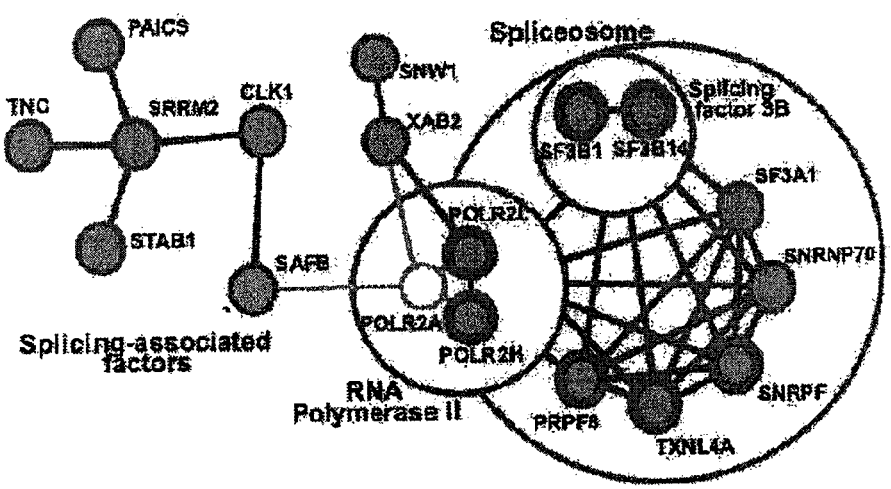

FIGS. 1A-C|Genome-wide RNAi screen reveals host factors required for the influenza infectious cycle. FIG. 1A, Outline of the screening procedures. FIG. 1B, Negative Log (p-values) of enriched terms according to the GO of the cellular compartments. Numbers of identified factors per ontology, numbers of genes associated with the GO term, and the enrichment factors are indicated. FIG. 1C, Interaction amongst hits associated with RNA splicing, as assessed using the STRING interaction database. Green circles, primary hit; white circle, non-hit. Members of ribosomal and spliceosomal multi-protein complexes are enclosed in larger circles. Thick grey border indicates hits identified in Reactome analysis (see FIG. 10A-C).

Figure 2A:
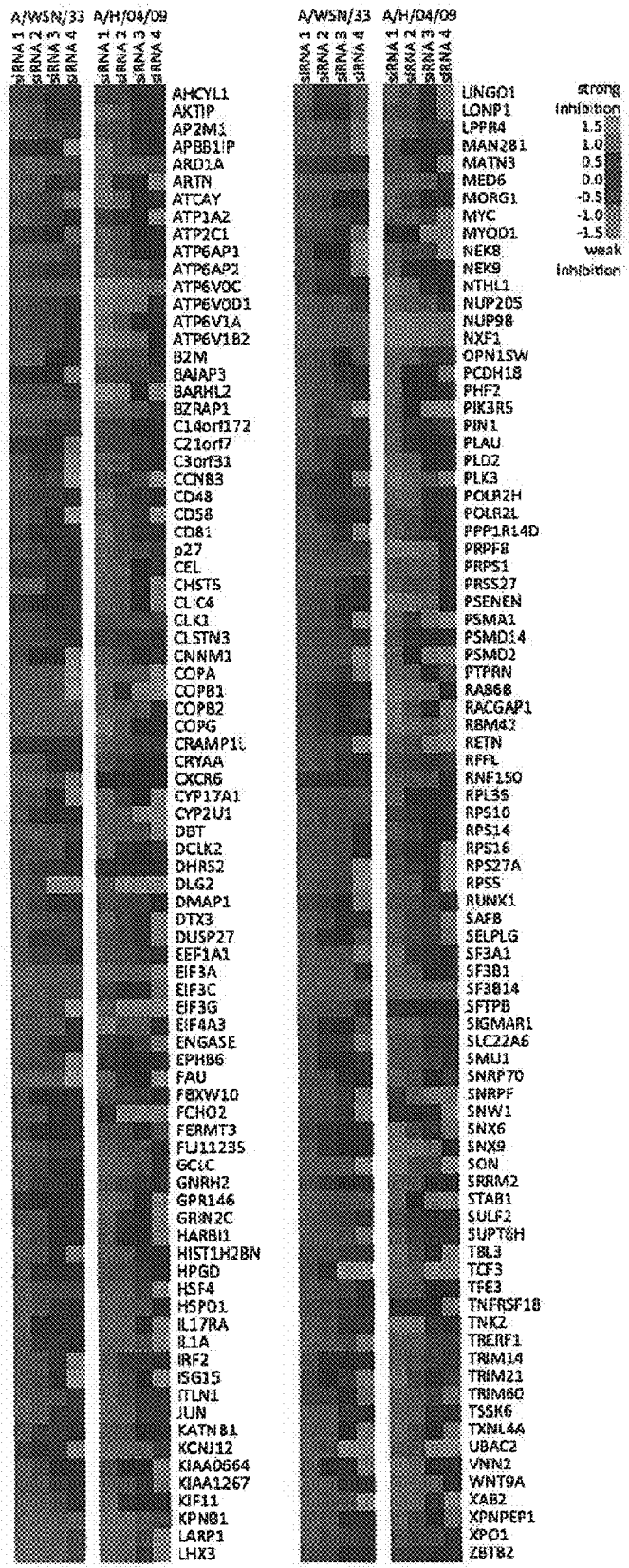
Figure 2B:
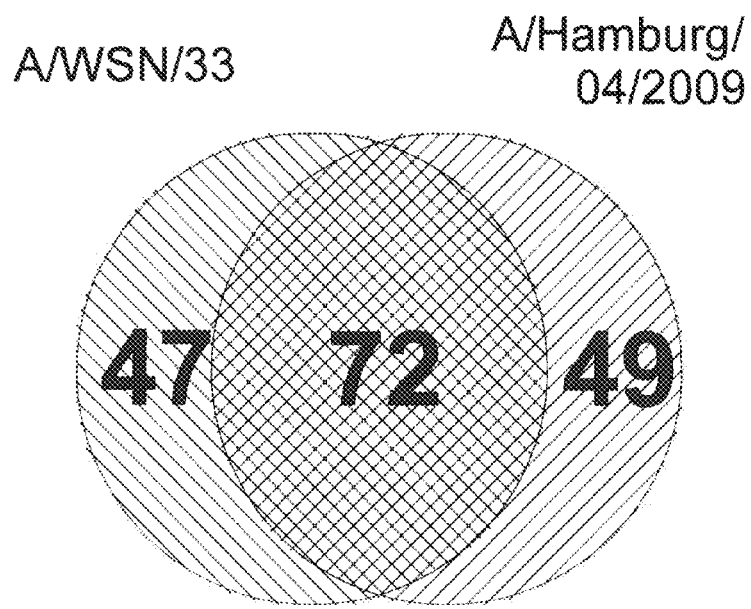
Figure 2C:
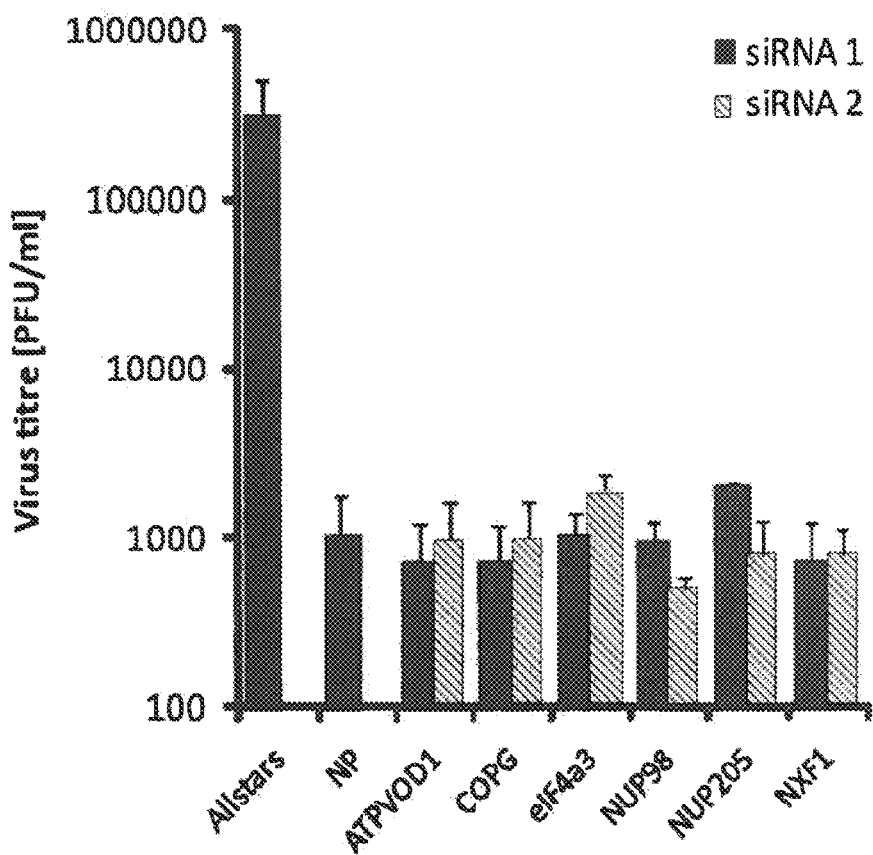

FIGS. 2A-C|Host cell factors affect replication of a broad range of influenza virus variants. FIG. 2A, Four siRNAs per gene were individually transfected in A549 cells followed by infection with influenza A/WSN/33 or A/Hamburg/04/2009 viruses (both at MOI 0.001) in four independent experiments. Infectious viral particles (IVP) were quantified at 48 h p.i. using the replication assay and analysed by calculating the normalised percent of inhibition. FIG. 2B, Venn diagram of hits validated in FIG. 2A. FIG. 2C, FsiRNAs (as indicated) were transfected in A549 cells and then infected (48 h later) with the avian H5N1 strain (A/Vietnam/1203/2004, MOI 0.1). Plaque forming units (PFU) were quantified at 20 h p.i. using the replication assay. Data show mean+standard error of the mean (S.E.M) of duplicate samples.

Figure 3A:
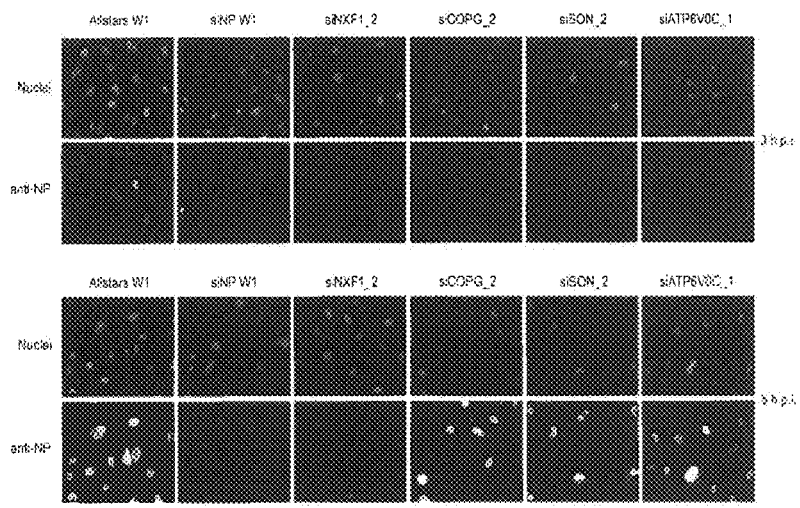
Figure 3B:
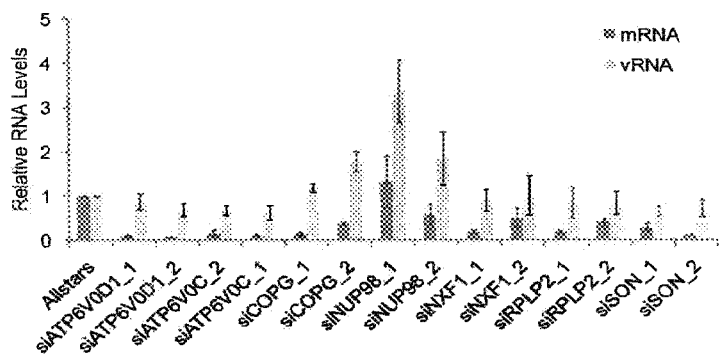
Figure 3C:
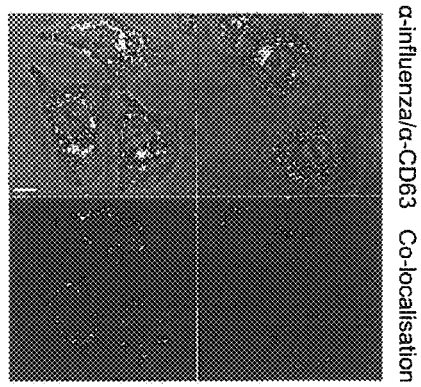

FIGS. 3 A-C|Dissection of infection processes affected by host cell factors. FIG. 3A, Transfected A549 cells were infected with influenza A/WSN/33 virus (MOI 5) for 3 h (upper panel) and 5 h (lower panel). Samples were stained for nuclei (blue) and NP (green). FIG. 3B, At 48 h p.t., A549 cells were infected with influenza A/WSN/33 virus (MOI 1). At 2 h p.i., vRNA and viral mRNA were quantified by qRT-PCR. RNA levels were normalized to the non-targeting (Allstars) siRNA control. FIG. 3C, Transfected A549 cells were infected with influenza A/WSN/33 virus (MOI 10) for 45 min. Samples were stained for influenza virus (green) and CD63 (red). Images are representative of three independent experiments in FIG. 3A and FIG. 3C.

Figure 4A:
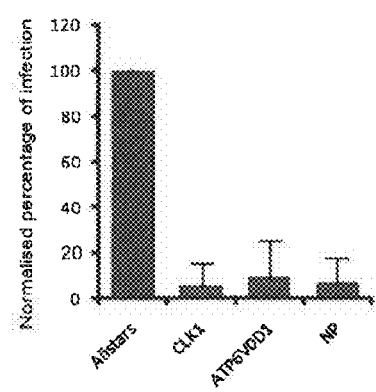
Figure 4B:
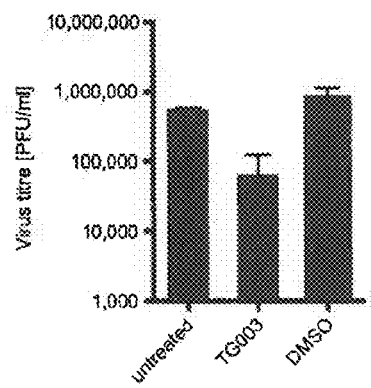
Figure 4C:
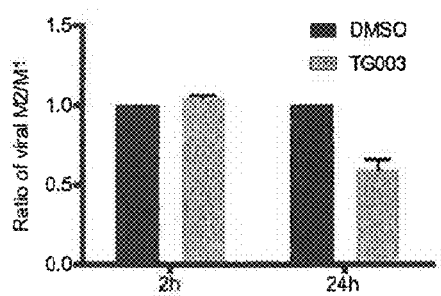
Figure 4D:
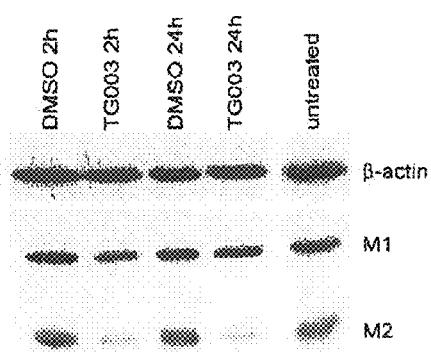
Figure 4E:
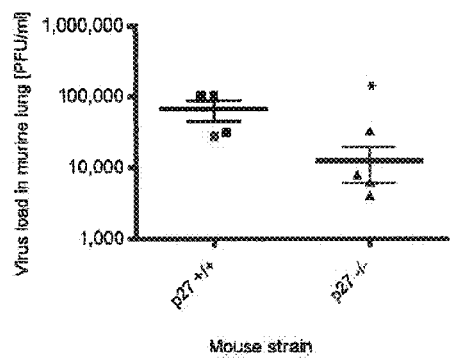

FIGS. 4A-E|In-depth analysis of the impact of p27 and CLK1 on influenza A virus infection. FIG. 4A, Quantification of virus replication in primary NHBE cells after siRNA-mediated target knockdown using the replication assay. Cells were infected with influenza A/WSN/33 virus (MOI 0.1) 48 h p.t. FIG. 4B, A549 cells were pretreated with TG003 (50 µM) or DMSO for 24 h and subsequently infected with influenza A/WSN/33 virus (MOI 0.01). IVPs were quantified at 40 h p.i. FIG. 4C, FIG. 4D, Ratio of spliced M2 to unspliced M1 after inhibition of CLK1 by TG003 at the RNA (c) or protein level (d). A549 cells were pretreated for 2 h or 24 h with TG003 (50 µM) or DMSO, then infected with influenza A/WSN/33 virus (MOI 4) for 5 h. FIG. E, C57BL/6 wild-type or homozygous p27$^{-/-}$ mice (n=4) were intranasally infected with influenza A/Puerto Rico/8/34 virus (10×LD50) and at 48 h p.i. IVPs within the lungs were quantified. Student's t-test was used to determine p value, *p=0.041. Data in FIGS. 4A,4B are mean+standard deviation (SD) of three independent experiments. Blots in FIGS. 4C, 4D are representative of three independent experiments.

Figure 5A:
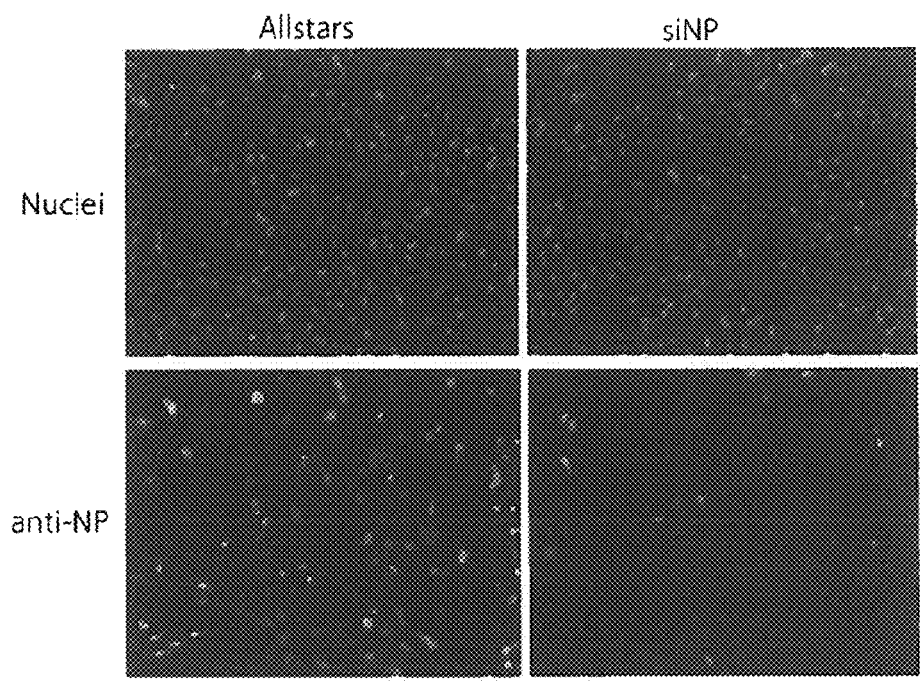
Figure 5B:
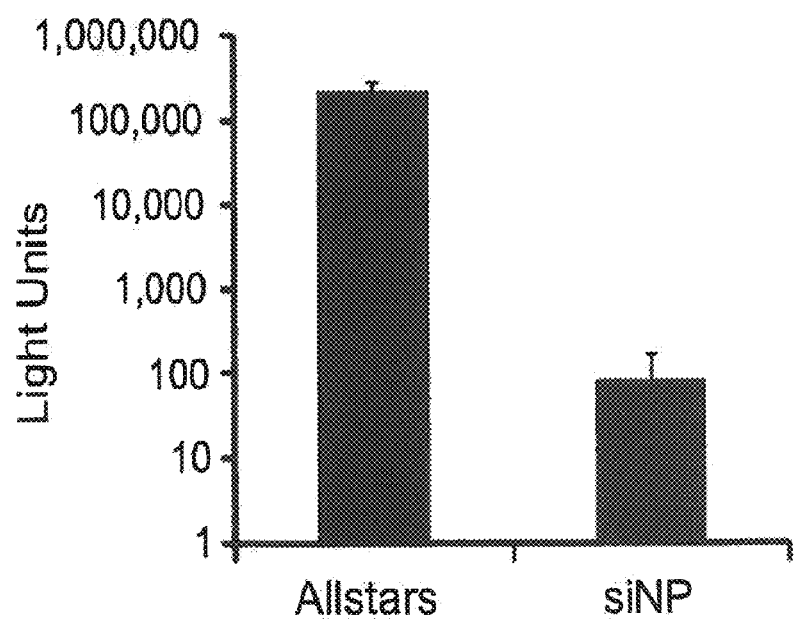

FIGS. 5A-B|FIG. 5A Screening Controls. Depicted are representative images of the non-targeting (Allstars) and inhibitory (siNP) control samples, stained with an anti-NP antibody and analysed by automatic microscopy. FIG. B, Graph depicts light units exerted by the corresponding supernatants transferred onto 293T reporter cells.

Figure 6:
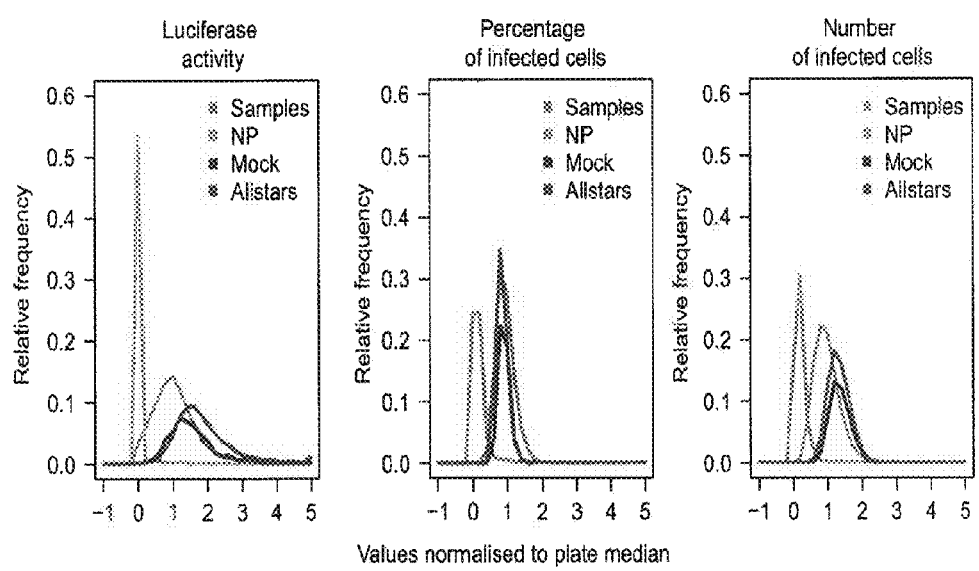

FIG. 6|Relative frequency distribution of screening data. Shown are data gained from the luciferase reporter assay (left panel), percentage of infected cells (middle panel), and the number of infected cells (right panel) across all screening samples and controls. All data are normalised to the plate median.

Figure 7:
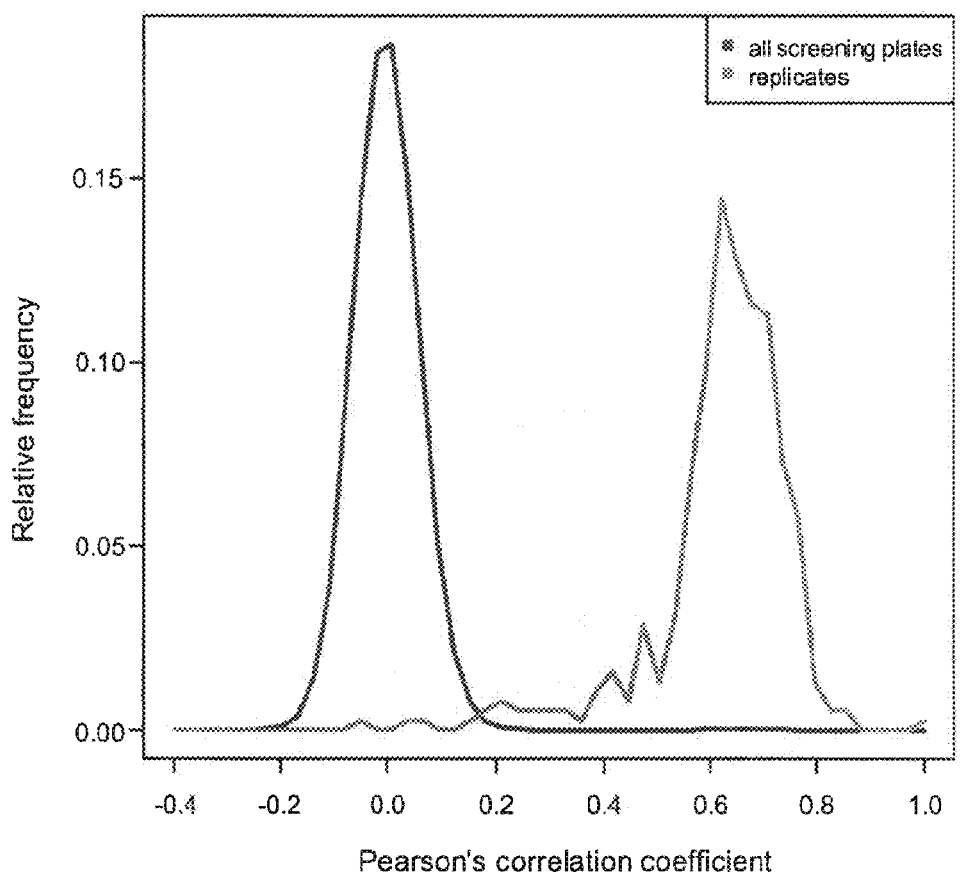

FIG. 7|Histogram of Pearson's correlation coefficients calculated for all siRNA screening plates. Distribution of pairwise correlations for the normalised values of number of infected cells derived from all siRNA screening plates. Blue lines indicates all plates, red line indicates sets of replicates. Only values originating from sample wells were used for calculating the correlation coefficients. Control well values were excluded from this analysis.

Figure 8:
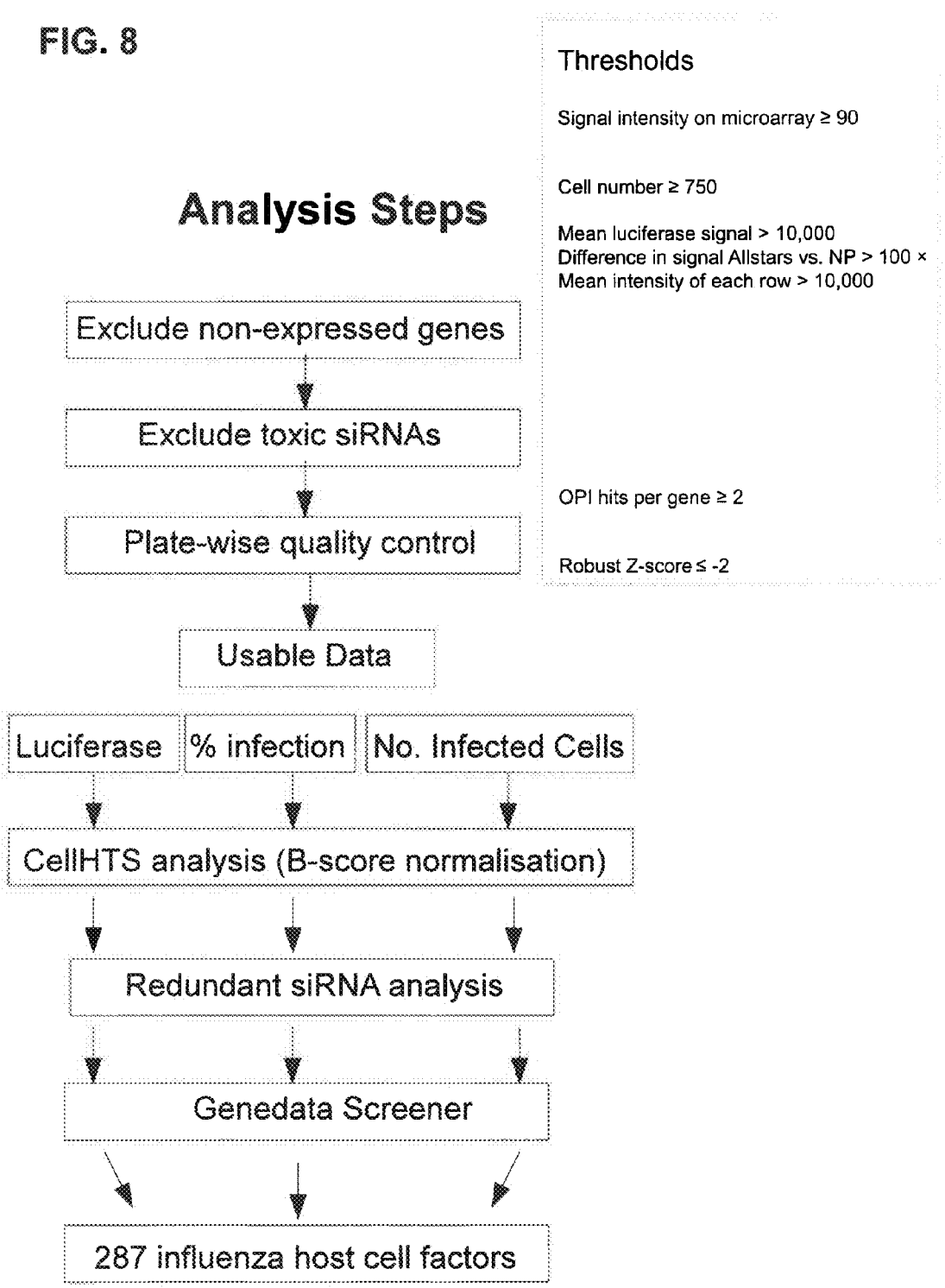

FIG. 8|Workflow of RNAi screen data analysis. Data analysis procedures (left panel) and associated applied thresholds (right panel) are shown. Raw screening data from all three read-out parameters was subjected to an analysis pipeline incorporating statistical thresholds at each stage. The data analysis workflow was done separately for all three read-outs and the final hit lists of each one were combined to provide a definitive primary hit list of 287 factors.

Figure 9:
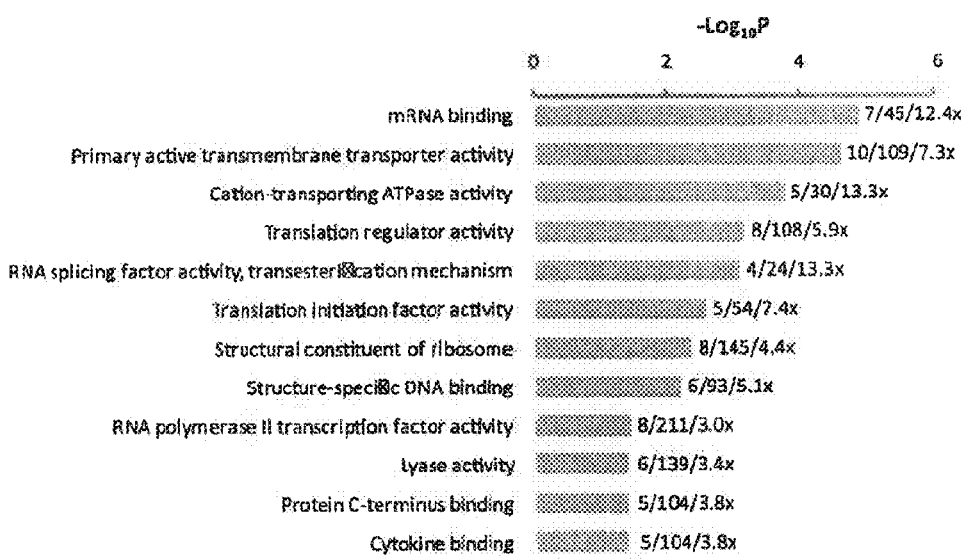
Figure 9:
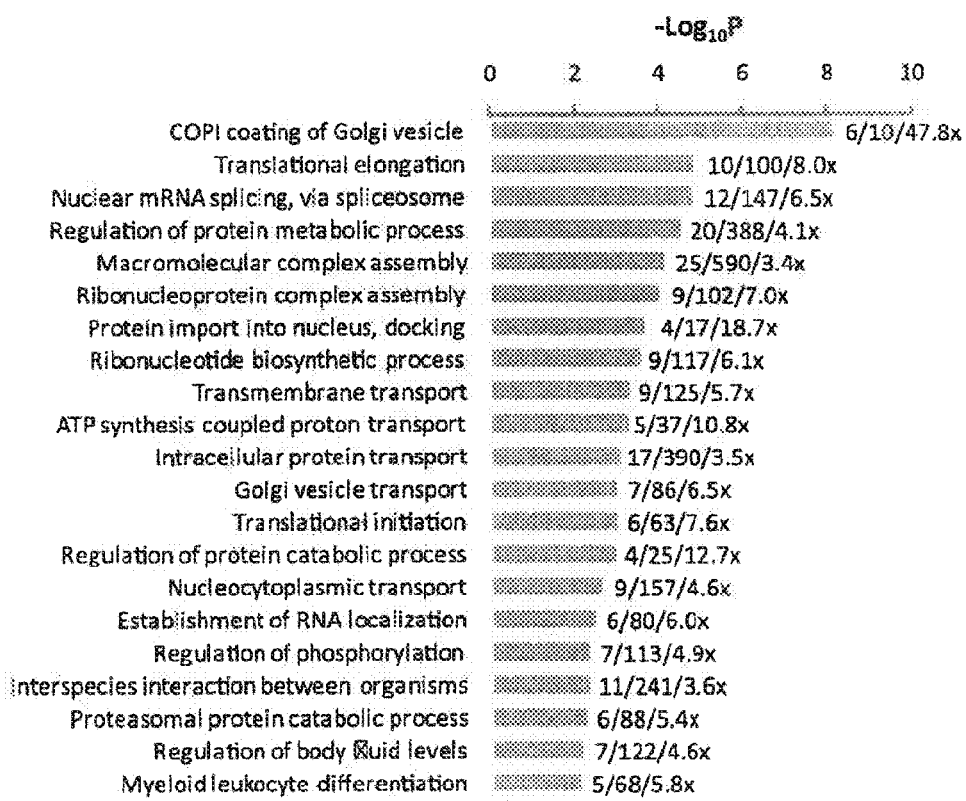

FIG. 9|Gene enrichment analysis. Negative Log 10(p-values) of enriched terms according to the gene ontology of the molecular function, biological process, and cellular compartments. Values at bars indicate the number of identified factors per ontology, the number of genes associated with the term and the enrichment factor.

Figure 10A:
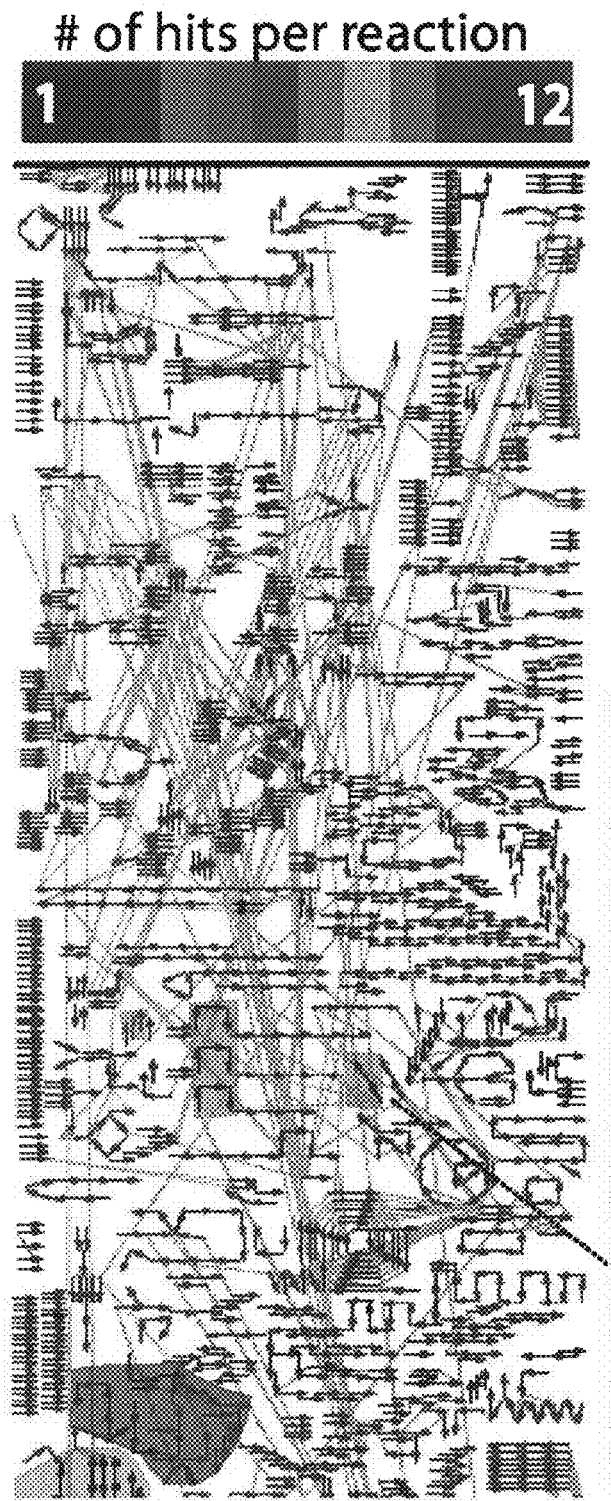
Figure 10B:
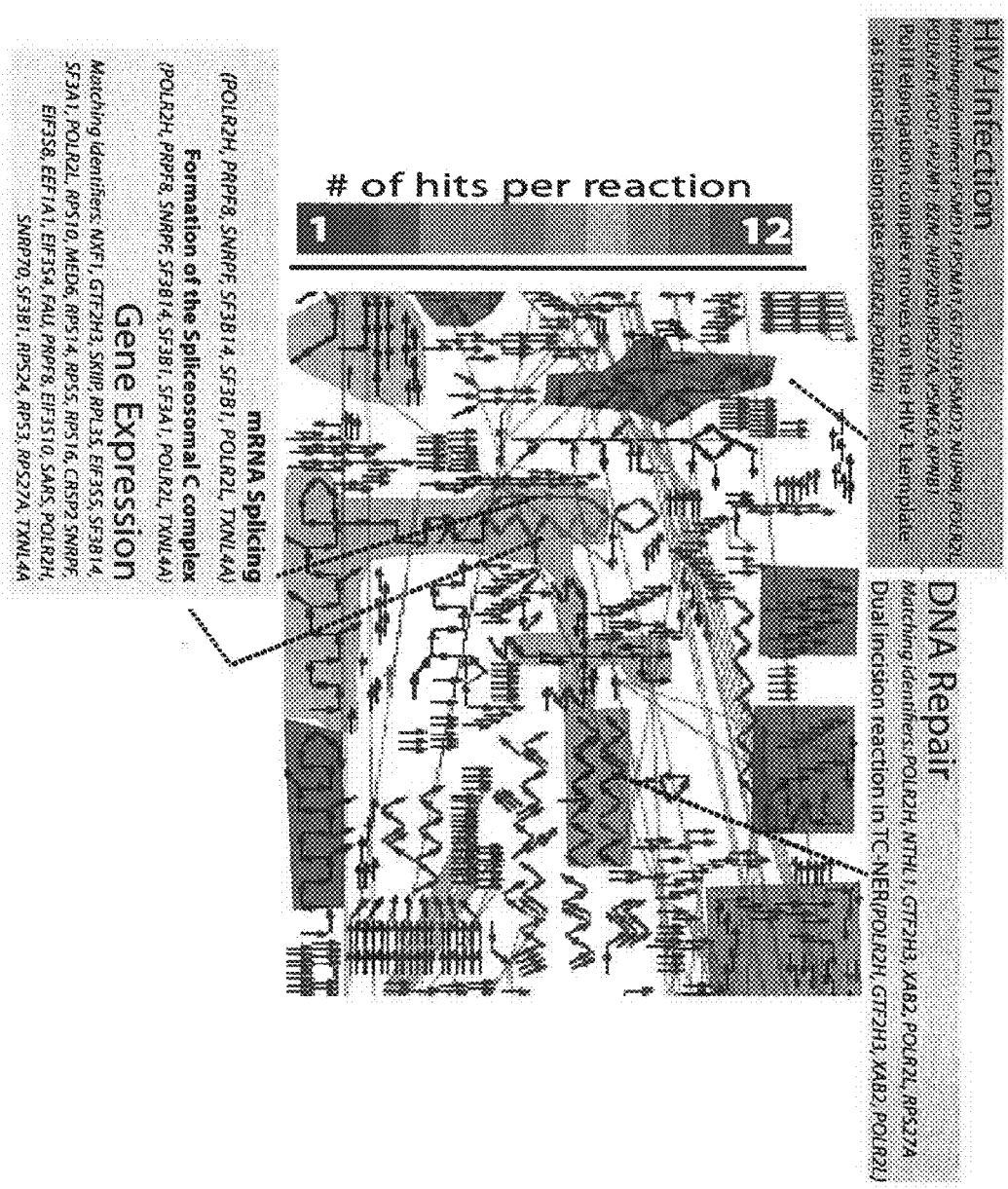
Figure 10C:
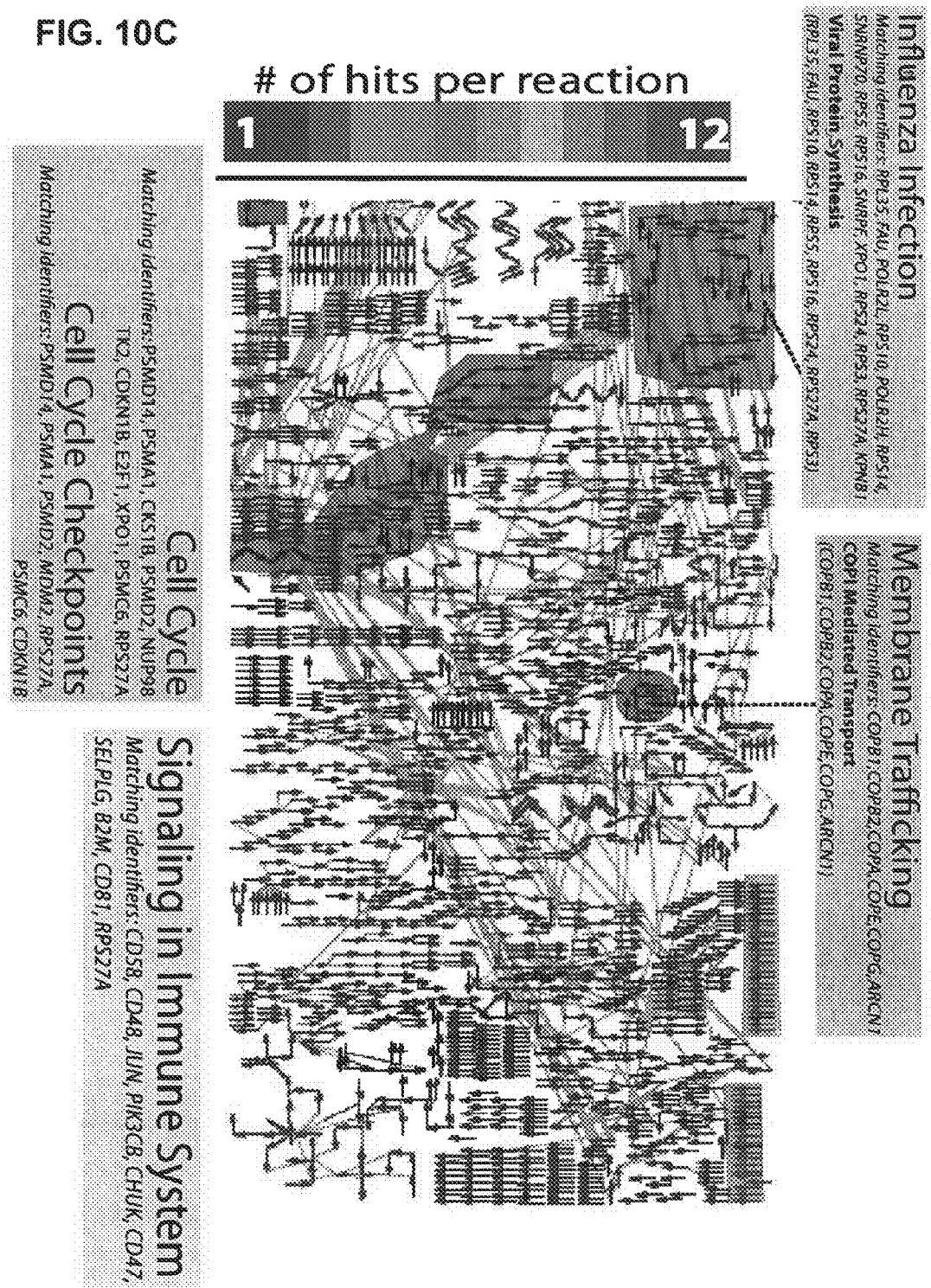

FIGS. 10A-C|Reactome analysis. The 287 'high-confidence' hits identified in the primary screen, were analyzed using the online web-resource Reactome (reactome.org), a database of biological pathways in human cells. Each pathway is referred to as an event. The hits were uploaded as gene-identifiers using the 'sky-painter' tool, calculating a one-tailed Fisher's exact test for the probability of observing at least N genes from an event. 104 identifiers could be matched to 399 out of 4374 events. Several categories showed a significant overrepresentation such as Gene Expression (p=3.4e-07, 29/384), Transcription (p=1.1e-03, 14/198), Membrane Trafficking (2.5e-03, 6/50) or Influenza-(1.9e-04, 15/187) and HIV-infection (2.5e-01, 14/406). Single events are coloured according to the number of matching identifiers from blue (1 matching identifier) to red (12 matching identifiers). Prominent categories showing overrepresentation of hits were coloured and important events were marked using an arrow. Several events were further analysed using the STRING database. (FIG. 11).

Figure 11:
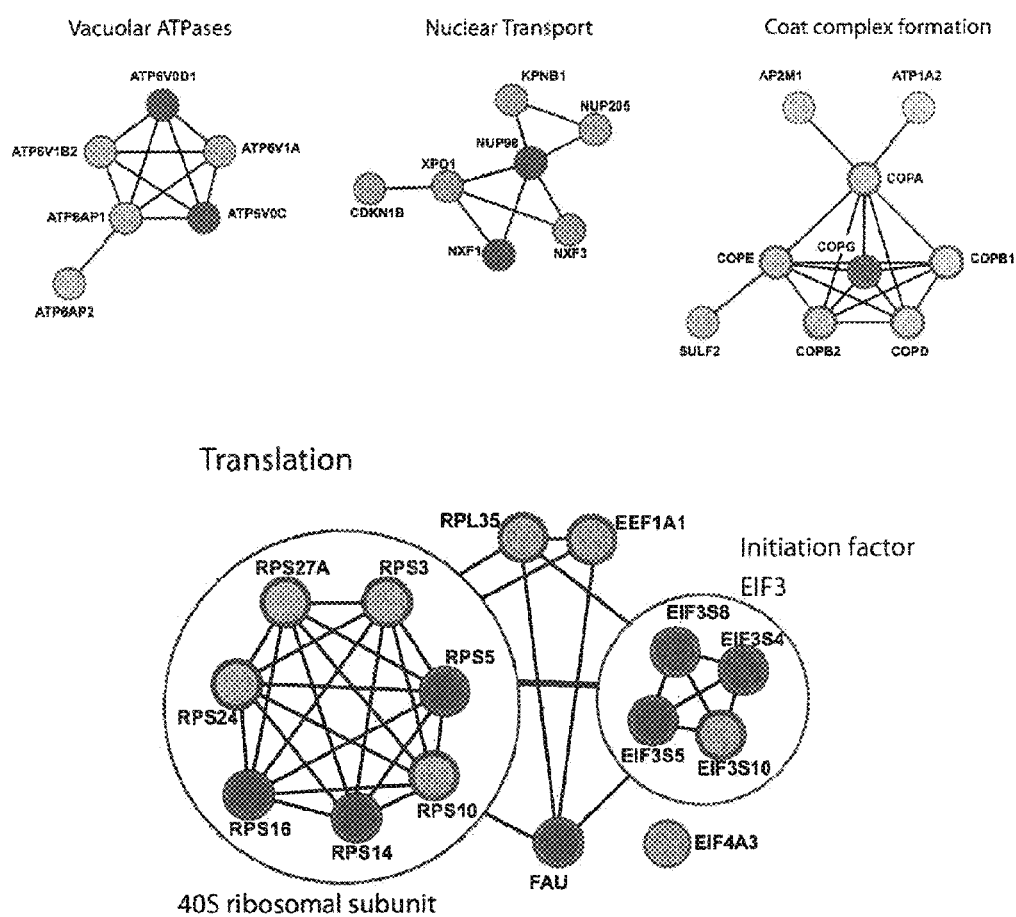

FIG. 11|Interaction networks of the identified hits. Interactions amongst hits associated with vacuolar ATPases, nuclear transport, coat complex formation and translation, as assessed using the STRING interaction database (http://string.embl.de). Green circles, primary hit; dark green circles, primary hit also identified by a Drosophila-based influenza screen (13). All hits included in one large circle: members of one multi-protein complex, e.g. 40S ribosomal subunit. Hits with a thick grey border are also included in the Reactome pathway analysis (FIG. 10).

Figure 12:
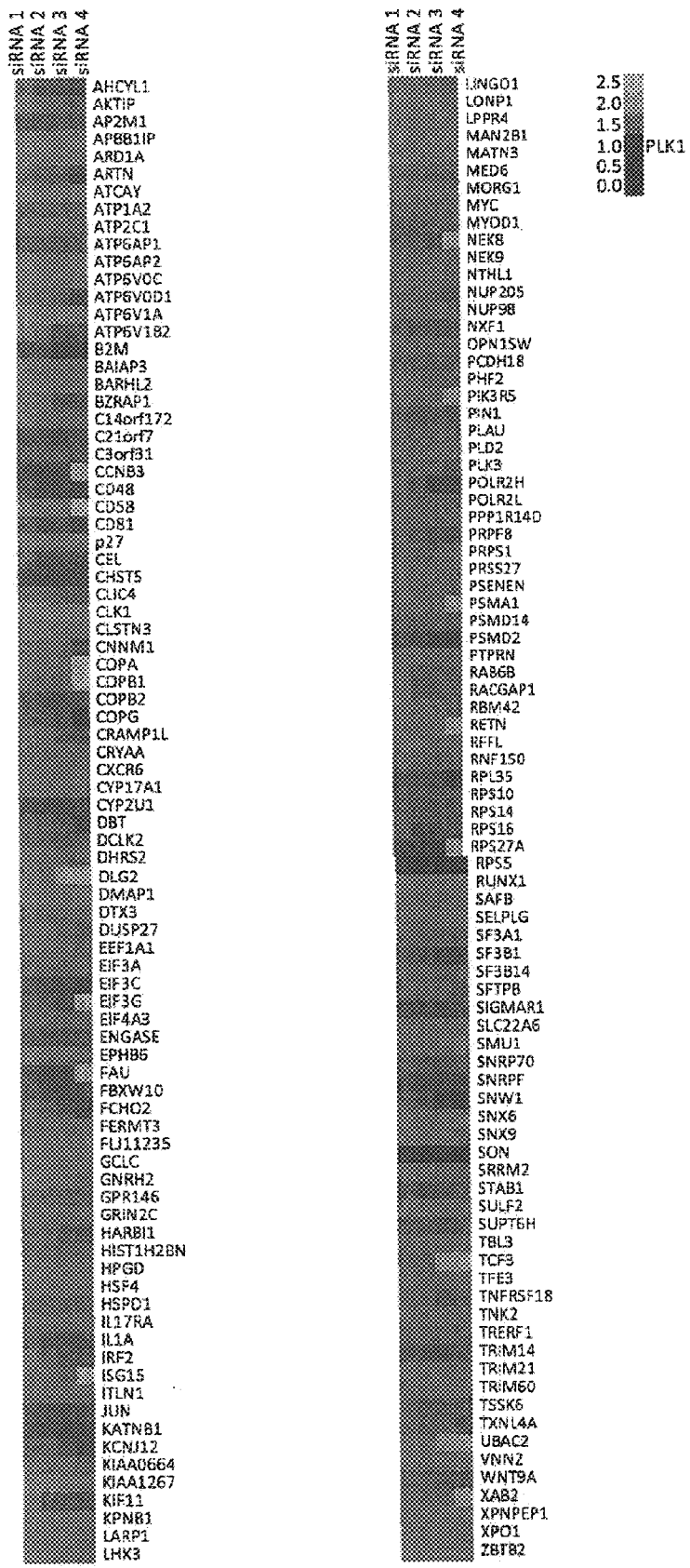

FIG. 12|Host cell viability determination by WST-1 assay. A549 cells were transfected with indicated siRNAs followed by adding the WST-1 reagent 48 h later to analyse eventually toxic effects due to siRNA transfections. Background subtracted mean values from two replicates are illustrated as a heat map. An siRNA targeting PLK1 was used as positive control. Missing siRNAs (less than four per gene) are indicated by grey boxes.

Figure 13A:
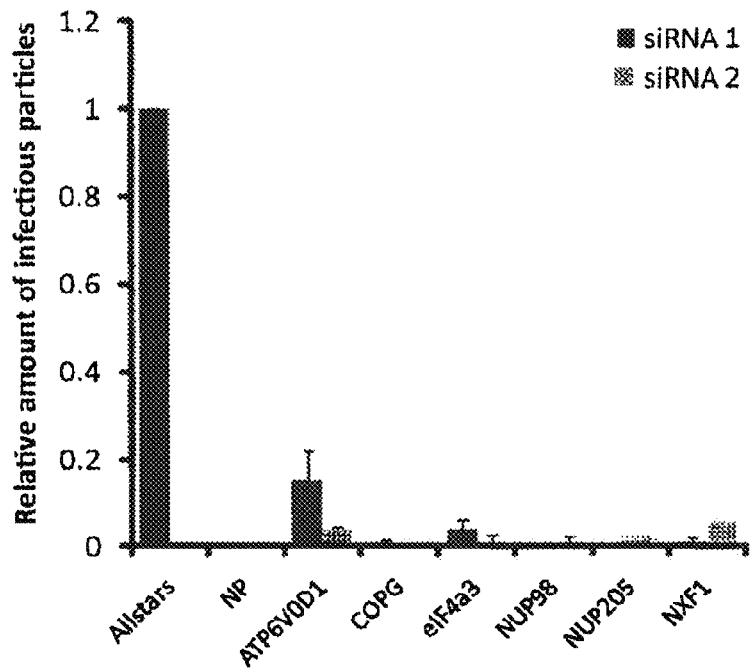
Figure 13B:
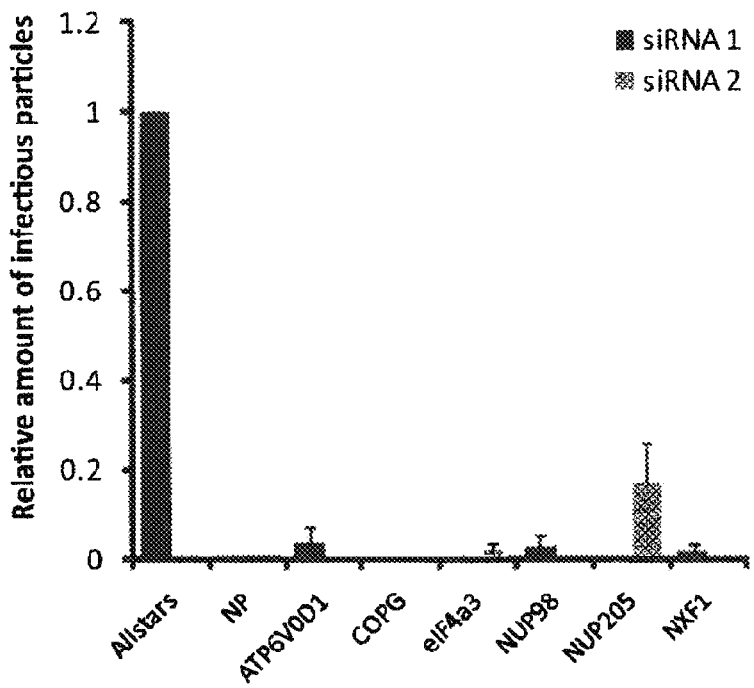
Figure 14A:
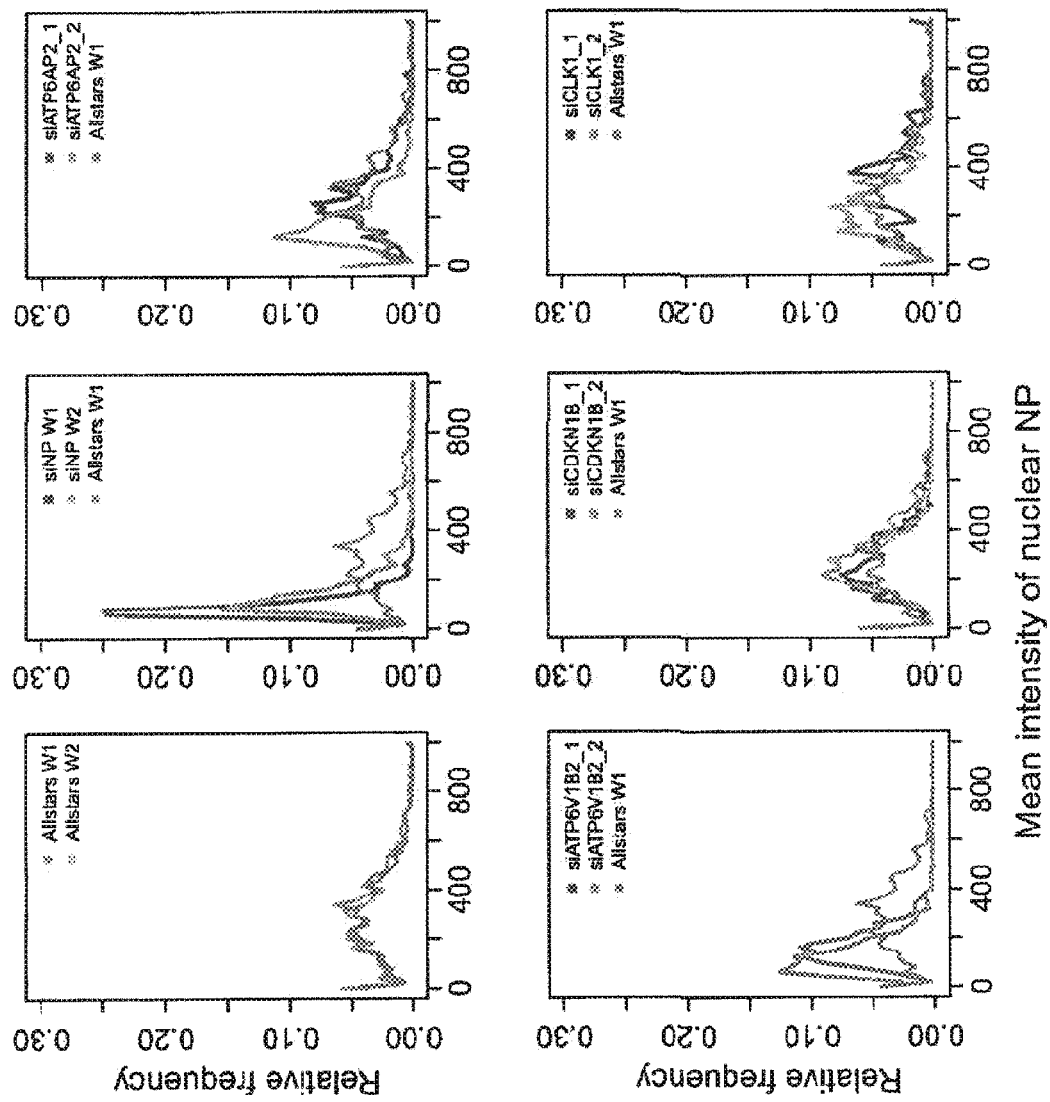
Figure 14B:
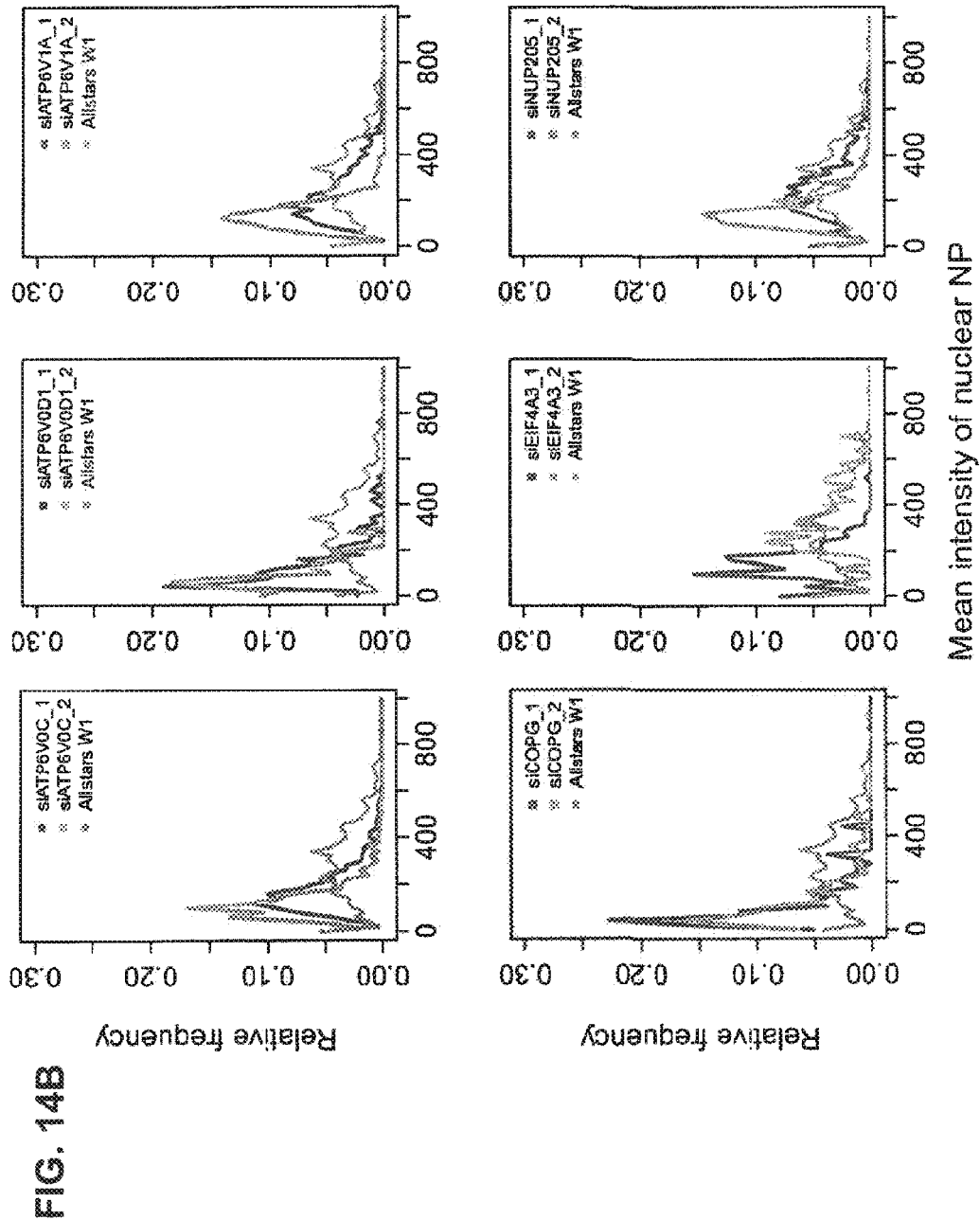
Figure 14C:
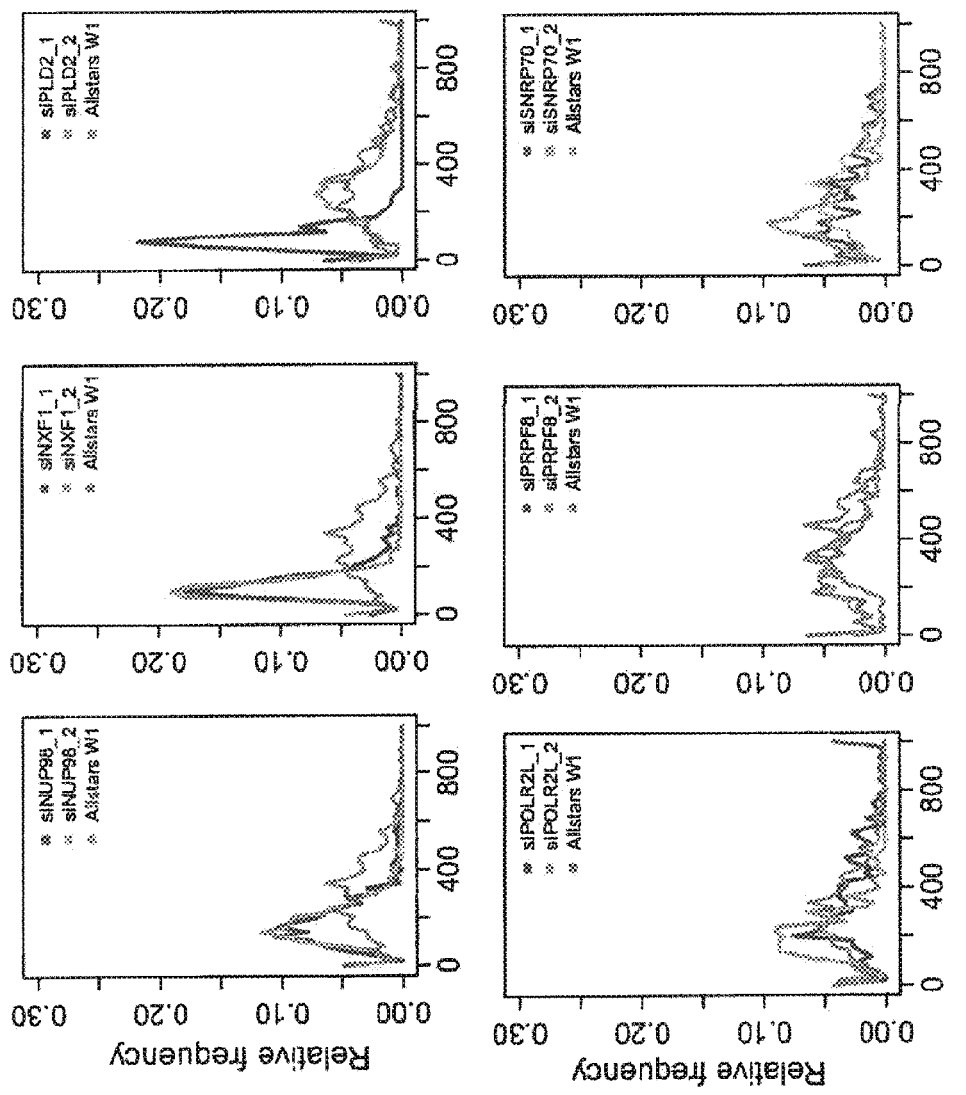
Figure 14D:
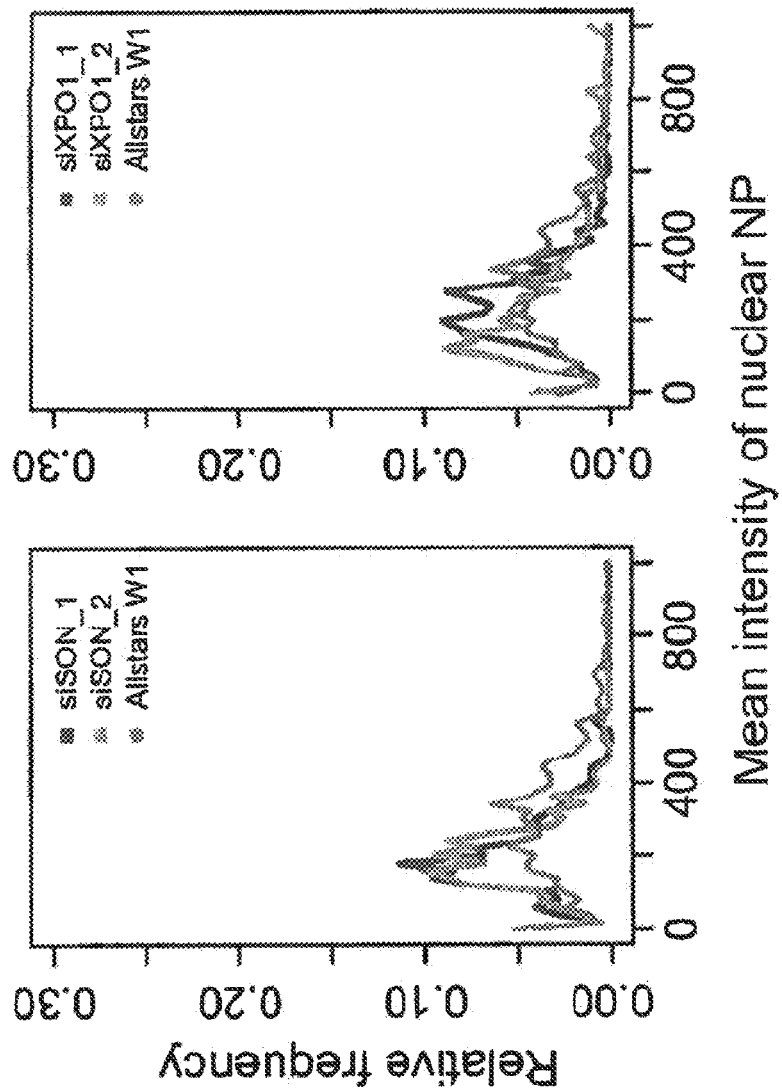

FIGS. 13A-B|Host cell factors affect replication of a H1N1 influenza virus variants. A subset of siRNAs was again transfected in A549 cells that were infected (48 h later) with the A/WSN/33 (FIG. 13A) or A/Hamburg/04/2009 (FIG. 13B) virus strains. IVPs in the virus containing supernatants were determined using the replication assay. Infection rate is expressed as a percentage of the non-targeting (Allstars) transfected control. Data show mean+S.E.M of duplicate samples. Cells transfected with the non-targeting control (Allstars) exhibited ca. $1.8 \times 10^6$ IVP/ml in the supernatant of A/WSN/33 infected and $6.6 \times 10^3$ IVP/ml upon A/Hamburg/04/2009 (A/H/04/09) virus infection. The inhibitory NP siRNA reduced the amount of infectious particles to $2.6 \times 10^4$ IVP/ml (A/WSN/33) and $4.5 \times 10^2$ IVP/ml (A/Hamburg/04/2009), respectively.

FIGS. 14A-D|Relative frequency distributions of NP expression. Relative frequency distributions of mean values of nuclear NP 3 h p.i. Shown are values gained from two separate wells of the Allstars (Allstars W1 and W2) and NP (siNP W1 and W2) control as well as two independent siRNAs for the indicated target genes. Results are representative profiles of three independent experiments.

Figure 15A:
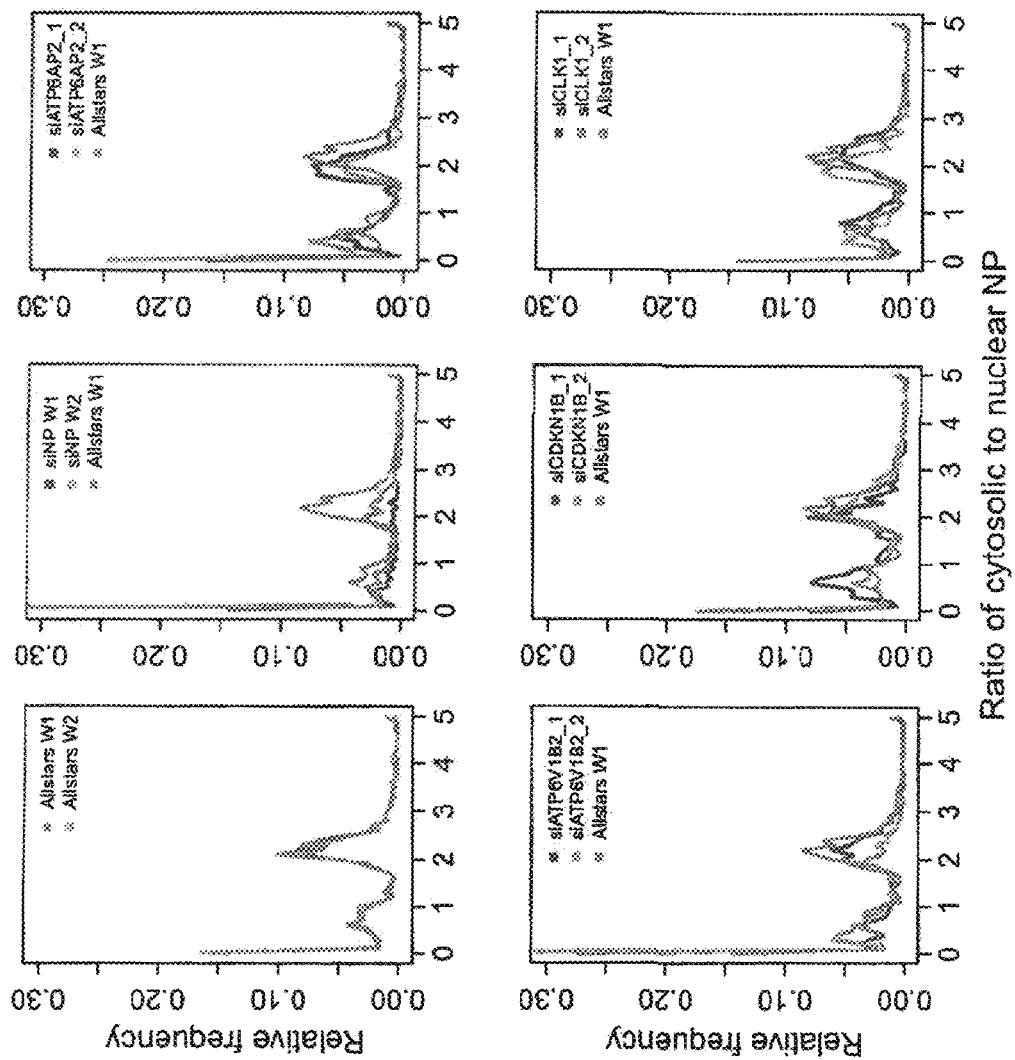
Figure 15B:
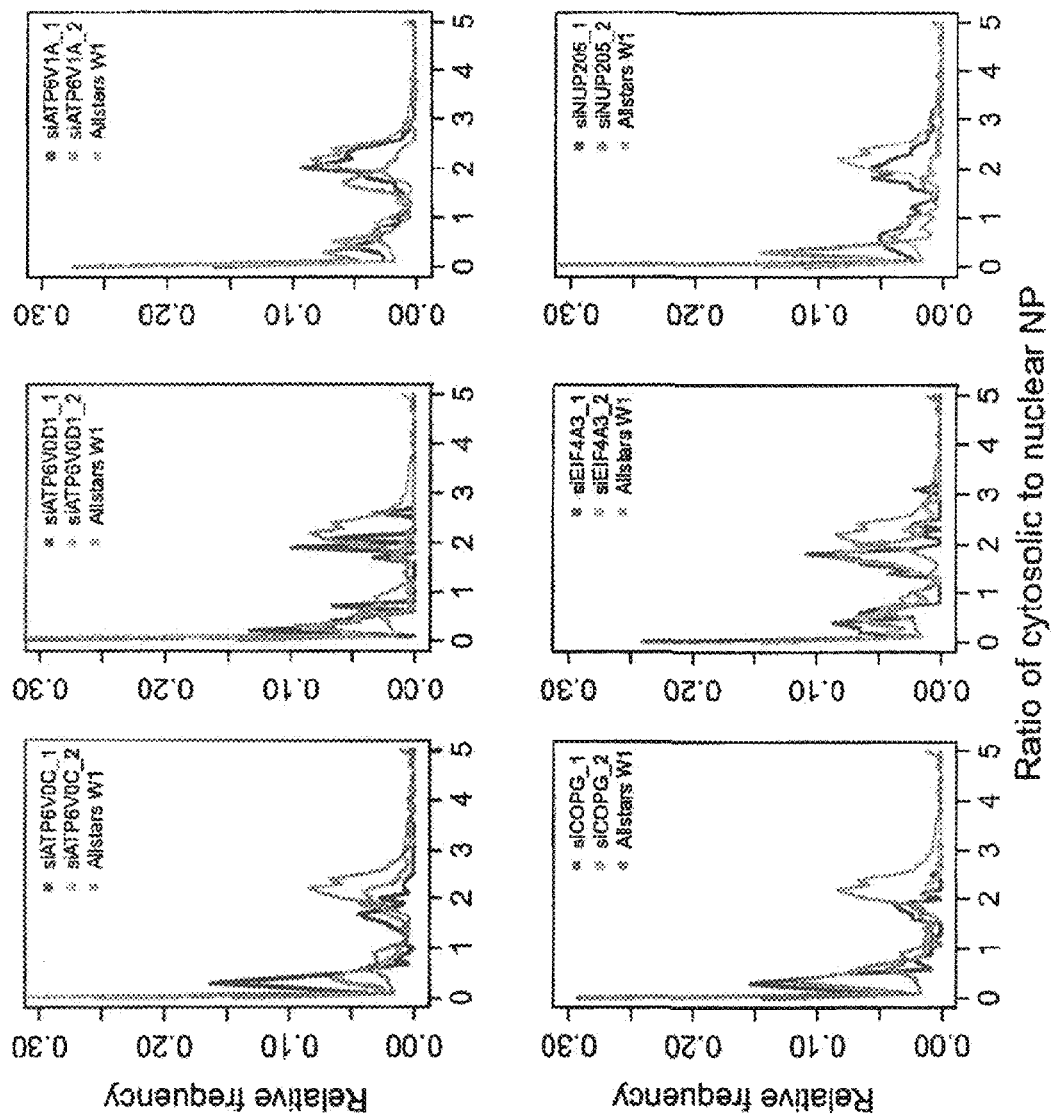
Figure 15C:
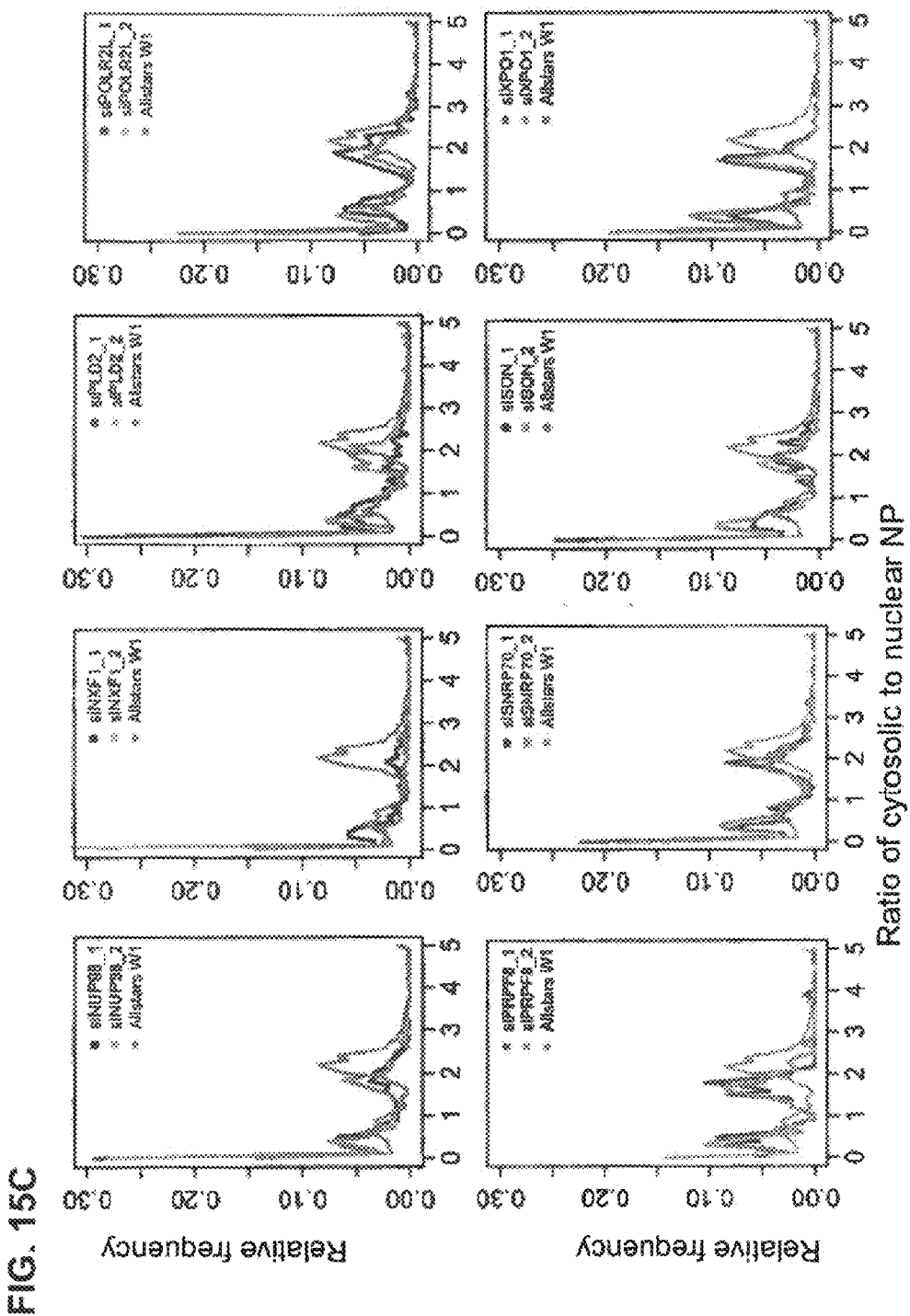

FIGS. 15A-C|Relative frequency distributions of nuclear export of NP. Relative frequency distributions of the ratios of cytosolic to nuclear NP 5 h p.i. Shown are values gained from two separate wells of the Allstars (Allstars W1 and W2) and NP (siNP W1 and W2) control as well as two independent siRNAs for the indicated target genes. Results are representative profiles of three independent experiments.

Figure 16A:
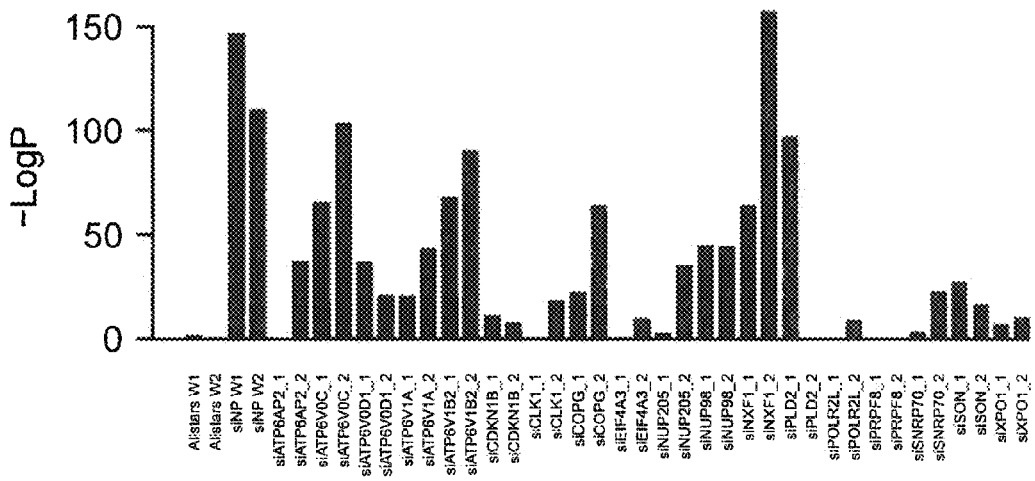
Figure 16B:
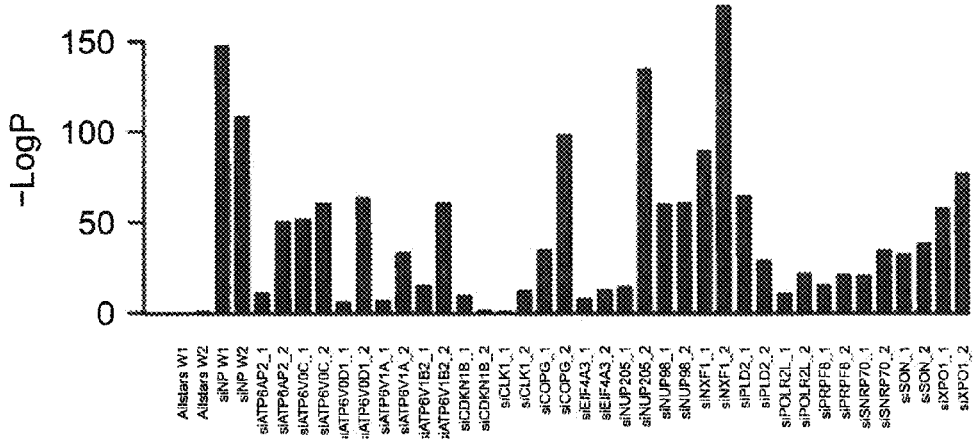

FIGS. 16A-B|P-values of differences between relative frequency distributions. Negative Log 10(p-values) of the samples shown in FIGS. 14A-D and 15A-C as assessed by the one-sided Kolmogorov-Smirnov test.

Figure 17:
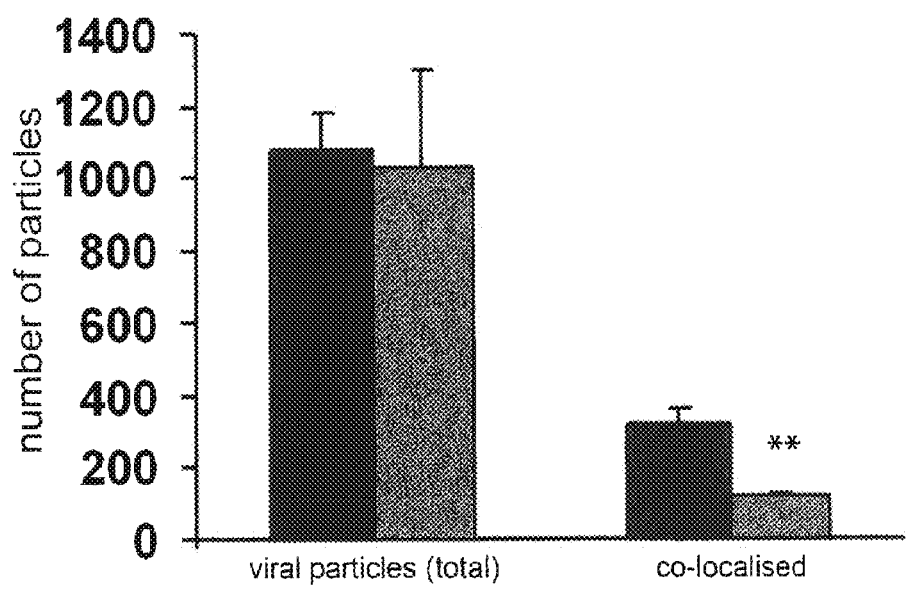

FIG. 17|Quantification of co-localised virus particles. SON knockdown and control cells were infected with influenza A virus (A/WSN/33) for 45 min at 37° C. after incubation on ice. Cells were fixed and stained for influenza A virus and CD63 as described. Confocal pictures were taken and co-localisation was determined as described in Methods. Total numbers of viral particles and co-localised particles were quantified using ImageJ "Analyse particle" function. In total 34 cells were quantified for each condition. Diagram shows mean numbers of particles for two independent experiments. Control, black bars; Son knockdown, hatched bars; **<0.005; standard error of the mean (S.E.) is depicted.

Figure 18:
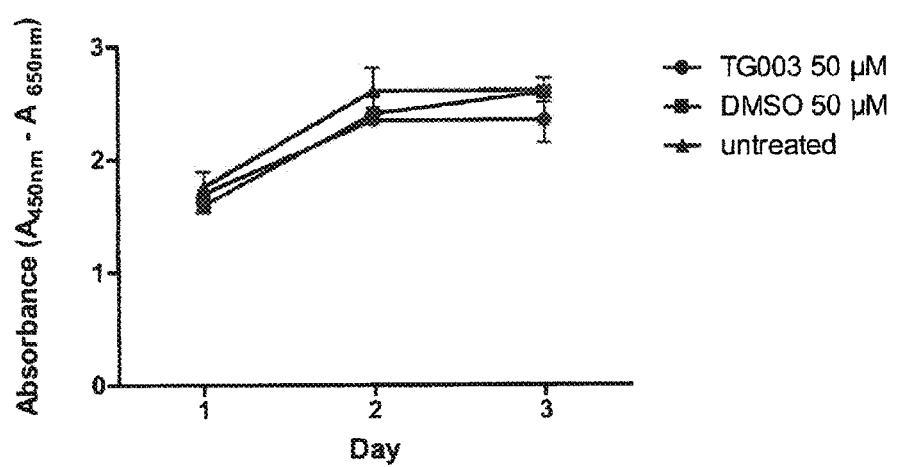

FIG. 18|Influence of the chemical CLK1 inhibitor TG003 on cell viability. A549 cells were incubated with TG003 (50 µM, dissolved in DMSO), with DMSO or left untreated. Cell viability was evaluated at the indicated time points using the WST-1 assay, according to the manufacturer's instructions. Shown are the mean values from three replicates. Error bars indicate the standard deviation.

Figure 19:
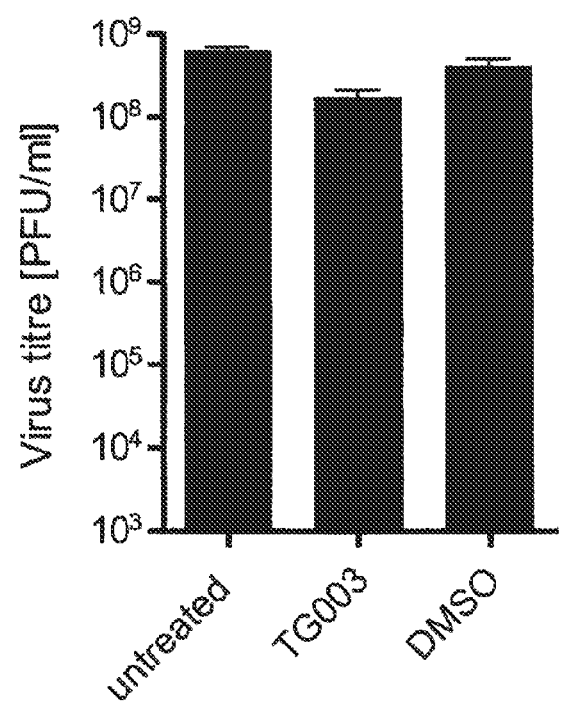

FIG. 19|Influence of the chemical CLK1 inhibitor TG003 on VSV replication. A549 cells were pretreated with TG003 (50 µM, dissolved in DMSO) or DMSO (as a control), for 24 h and subsequently infected with VSV (MOI 0.01). After infection, the inhibitor or DMSO was added again at identical concentrations. The supernatants of treated or untreated cells were harvested at 24 h p.i. and infectious virus particles quantified by detecting plaques on MDCK cells.

Table 1|Primary screening data and hit. Primary hit list and screening data. Shown are the Z-scores obtained from the CellHTS and the Genedata Screener® software analysis, and the RSA analysis for the classification of a particular siRNA as a hit. The mean cell number as an indicator for cell viability is shown. siRNAs leading to a mean cell number below 750 were defined as toxic. Gene expression fold changes upon infection, plus corresponding p-values and expression intensities as assessed by microarray analysis are also given.

Table 2|Hit validation data. Shown are the siRNA IDs as provided by the supplier, the WST assay data, and the normalised percent inhibition data together with the number of validated siRNAs per gene for both tested viruses.

Tables 3 and 4|Targets identified in the siRNA screen of the Example. Disclosed are oligonucleotide sequences (SEQ ID NO: 25-1173) employed in the siRNA screen of example 1. Up to four oligonucleotide sequences ("siRNA1 Target", "siRNA2 Target", "siRNA3 Target", "siRNA4 Target",) specific for a target gene were employed.

EXAMPLE

Human Host Cell Factors Crucial for Influenza Virus Replication Identified by Genome-Wide RNAi Screen Summary Influenza A virus, being responsible for seasonal epidemics and reoccurring pandemics, represents a global threat to public health (1). High mutation rates facilitate the generation of viral escape mutants rendering vaccines and drugs directed against virus-encoded targets potentially ineffective (2). In contrast, targeting host cell determinants temporarily dispensable for the host but crucial for virus replication could prevent viral escape.

In this example, the discovery of 287 human host cell genes influencing influenza A virus replication in a genome-wide RNAi screen is described. Using an independent assay we confirmed 168 hits (59%) inhibiting either the endemic H1N1 (119 hits) or the current pandemic swine-origin (121 hits) influenza A virus strains, with an overlap of 60%. Importantly, a subset of these common hits was also essential for replication of a highly pathogenic avian H5N1 strain. In-depth analyses of several factors provided insights into their infection stage relevance. Notably, SON DNA binding protein (SON) (3) was found to be important for normal trafficking of influenza virions to late endosomes early in infection. We also show that a small molecule inhibitor of CDC-like kinase 1 (CLK1) (4) reduces influenza virus replication by more than two orders of magnitude, an effect connected with impaired splicing of the viral M2 mRNA. Furthermore, influenza virus-infected p27$^{-/-}$ (cyclin-dependent kinase inhibitor 1B; Cdkn1b) mice accumulated significantly lower viral titers in the lung providing in vivo evidence for the importance of this gene. Thus, our results highlight the potency of genome-wide RNAi screening for the dissection of virus-host interactions and the identification of drug targets for a broad range of influenza viruses.

Introduction

During the course of infection, the influenza virus encounters numerous bottle necks, constituted by host cell functions essential or inhibitory for viral propagation (5). Comprehensive knowledge of such critical host cell determinants could provide valuable insight into the molecular mechanisms of viral replication and facilitate the development of a novel generation of drugs that target host cell factors and are thus less prone to select for resistant viral mutants. To identify host cell factors involved in the viral infection cycle in human cells, we conducted a genome-wide RNAi screen using a two-step approach (FIG. 1a): First, A549 human lung epithelial cells, transfected with siRNAs 48 h prior to infection with influenza A H1N1 virus (A/WSN/33), were stained with a virus-specific antibody at 24 h post infection (p.i.) to monitor cell infection rates. Second, virus supernatants from these transfected A549 cells were transferred onto 293T human embryonic kidney reporter cells, containing an inducible influenza virus-specific luciferase construct (FIaA) (6). Assay reliability was confirmed with an siRNA directed against influenza virus nucleoprotein (NP) mRNA (7). Knockdown of NP effectively blocked viral replication, as assessed by immunofluorescence staining and the luciferase reporter assay (FIG. 5). Statistical analyses further confirmed the robustness of our assay controls (NP and the non-targeting Allstars siRNA) and reproducibility of results (FIGS. 6 and 7). Using this bipartite assay, we screened a genome-wide siRNA library consisting of ca. 62,000 siRNAs targeting ca. 17,000 annotated genes and ca. 6,000 predicted genes.

For identification of primary hits, three parameters were included: luciferase expression, the percentage of infected cells, as determined by immunofluorescence microscopy, and the total number of infected cells. After excluding non-expressed genes and toxic siRNAs, primary screening data from all three parameters were separately subjected to an analyses pipeline with statistical checkpoints at each step, finally leading to hit selection based on Z-scores below −2 (FIG. 8 and Methods). Results from each of the three parameters were combined, and from a total of 22,843 human genes (annotated and predicted) 287 were designated primary hits (Table 1).

Among these high-confidence candidates we found several genes known to play a pivotal role in influenza virus replication, e.g. the nuclear export factors NXF1 (8) and XPO1 (9), as well as the vacuolar ATPase ATP6V0D1 (10,11). Gene ontology (GO) term enrichment analysis revealed our dataset was markedly enriched in gene categories associated with the proton-transporting two-sector ATPase complex, the spliceosome, the small ribosomal subunit, the eukaryotic translation initiation factor 3 (EIF3), the COPI coated vesicle transport and the nuclear pore complex (FIG. 1b and FIG. 9), which comprise functional categories already associated with viral replication. Further bioinformatic analysis using Reactome (12) corroborated the GO results (FIG. 10). In-depth analysis of selected enriched functional categories using the STRING database revealed numerous interactions between factors associated with the same GO term (FIG. 11). Interestingly, we found multiple factors connected with pre-mRNA splicing (FIG. 1c), which escaped detection in a previous RNAi screen using *Drosophila* cells (13). However, the small ribosomal subunit and EIF3 were enriched in the *Drosophila*-based influenza screen (13) but not in other viral RNAi screens (14, 15, 16, 17), indicating these factors could be influenza-specific (18).

Next, we independently ascertained the significance of all 287 primary hits for replication of the influenza A/WSN/33 (H1N1) and the current pandemic swine-origin influenza A/Hamburg/04/2009 (H1N1) viruses. The number of viruses released from siRNA transfected A549 cells was determined by titrating supernatants on Madin-Darby canine kidney (MDCK) cells. For each primary hit four different siRNAs were used individually to knockdown gene function. We found that 119 (A/WSN/33) and 121 (A/Hamburg/04/2009) of the 287 primary hits decreased virus number by more than fivefold in comparison to control samples, with a least two siRNAs (FIG. 2a), without impairing cell viability (FIG. 12). In total, 168 primary hits were validated, comprising an overall validation rate of ~59%. Remarkably, of the factors inhibiting viral replication, 72 were common to both influenza virus strains, indicative of their broad inhibitory potential (FIG. 2b and Table 2).

Validation was extended to the highly pathogenic avian-origin influenza A virus of the H5N1 subtype (A/Vietnam/1203/2004) using a subset of the common siRNAs. The knockdown efficiencies shown in the following Table (percentages of knockdown±standard deviation as obtained in three independent experiments):

| siRNA | Knockdown [%] | SD [%] |
|---|---|---|
| ATP6V0D1_1 | 95% | 2% |
| ATP6V0D1_2 | 98% | 1% |
| COPG_1 | 89% | 8% |
| COPG_2 | 63% | 25% |
| EIF4A3_1 | 96% | 2% |
| EIF4A3_2 | 95% | 3% |
| NUP205_1 | 85% | 12% |
| NUP205_2 | 83% | 7% |
| NUP98_1 | 86% | 10% |
| NUP98_2 | 83% | 6% |
| NXF1_1 | 53% | 39% |
| NXF1_2 | 79% | 17% |
| SON_1 | 77% | 19% |
| SON_2 | 81% | 16% |

Strikingly, H5N1 virus replication decreased by more than two orders of magnitude using these siRNAs (FIG. 2c). Likewise, knockdown of identical targets inhibited replication of influenza A/WSN/33 (H1N1) virus and the pandemic A/Hamburg/04/2009 (H1N1) strain (FIG. 13). The observation that a subset of common factors blocked replication of both swine and avian-origin virus variants corroborates that these proteins constitute crucial sub-type independent host-cell checkpoints.

The life-stage relevance of 18 targets, representing a variety of functional categories and affecting both H1N1 influenza viruses, was assessed by immunofluorescence staining for NP as a marker of viral ribonucleoprotein (vRNP) localisation (19). Typically, vRNP is confined to the nucleus early in infection, but enters the cytoplasm for packaging into progeny virions late in infection (19). Here, upon knockdown of all targets, NP gave a mainly nuclear signal at 3 h p.i. (FIG. 3*a*, upper panel), shifting towards cytoplasmic staining 2 h later (FIG. 3*a*, lower panel). In addition to the expected blockage of NP synthesis upon inhibition of NXF1 (8,20), knockdown of several identified hits such as COPG, SON, and ATP6V0C appeared to reduce NP expression levels (FIG. 3*a*, upper panel) and to delay export of NP from the nucleus (FIG. 3*a*, lower panel). Relative frequency distribution analysis of NP expression and cytosolic to nuclear NP ratios within single cells corroborated our microscopic observations (FIGS. 14-16). In total, knock down of 11 genes significantly reduced NP expression and interfered with nuclear export of NP.

To analyse the impact of targets, shown to affect NP synthesis and localisation, on the synthesis of viral RNA, we infected siRNA-transfected cells with influenza virus and determined the levels of viral genomic RNA (vRNA) and viral mRNA at 2 h p.i. by qRT-PCR (7). Most of the analysed targets had no effect on virus cell entry, as indicated by robust vRNA detection (FIG. 3*b*). However, for many targets, including identified ATPases and SON, a protein known to repress Hepatitis B virion production (3), plus several factors involved in RNA biogenesis, e.g. NXF1, viral mRNA, synthesis was substantially reduced (FIG. 3*b*). This demonstrates virus propagation is affected at a stage between virus entry and mRNA synthesis. Knockdown of SON also reduced vRNA levels (FIG. 3*b*), indicating it functions in an infection step preceding viral mRNA synthesis. Accordingly, considerably less virus particles co-localised with CD63-labelled late endosomes upon SON knockdown (FIG. 3*c*; FIG. 17), suggesting this factor is important for trafficking of influenza virions early in the infection cycle. Intriguingly, knockdown of the nucleoporin 98 kDa (NUP98) increased vRNA level (FIG. 3*b*), most likely due to accelerated de novo vRNA synthesis, but at the same time dramatically decreased viral progeny (FIG. 2*a*; FIG. 13). Consistent with its reported antiviral (8) and proviral functions (13), these seemingly contradictory results suggest NUP98 exerts an inhibitory effect early in the life cycle but is mandatory for completion of viral replication. Taken together, these data reveal that the 11 targets (identified as reducing NP expression levels) interfere with early events in virus replication. In contrast, knockdown of the remaining 7 factors analysed in this set of experiments, such as CLK1 or p27 (CDKN1B), probably exert their function during later infection stages.

To more closely mimic in vivo conditions, we tested the effect of target knockdown on influenza virus replication in primary normal human bronchial epithelial cells (NHBE). Most notably, knockdown of CLK1 and ATP6V0D1 strongly reduced viral growth in these cells (FIG. 4*a*). We independently assessed the function of CLK1 by treating A549 cells with TG003, a chemical inhibitor of CLK1 (4). Influenza virus propagation was inhibited by more than 93% (FIG. 4*b*) without exerting detectable toxic effects (FIG. 18). CLK1 regulates alternative splicing in mammalian cells by phosphorylating the splicing factor SF2/ASF (21, 22), therefore we hypothesized that inhibition of CLK1 would affect splicing of viral RNAs. In accordance, TG003 reduced levels of spliced M2 viral RNA, whereas unspliced M1 and NS1/NS2 were unaffected (FIG. 4*c*, data not shown). Immunoblot analysis corroborated our qRT-PCR results, revealing drastically reduced M2 protein levels following treatment with TG003, whereas M1 protein levels remained relatively constant (FIG. 4*d*). Since the SF2/ASF complex is important for splicing and the shuttling of spliced viral mRNAs to the cytoplasm (23), it is conceivable that reduction of M2 protein expression was at least partially caused by nuclear retention of its mRNA transcript. Our finding that CLK1 is involved in processing viral M2 mRNA is consistent with the essential role of the SF2/ASF splicing factor in viral M2 ion channel protein production (24). Interestingly, replication of vesicular stomatitis virus (VSV), which, unlike influenza, does not depend on splicing of its own viral RNA, was only slightly reduced in the presence of TG003 (FIG. 19).

During the primary screen and the hit validation, knockdown of the cell cycle regulator p27 led to a strong inhibition of influenza virus replication. To confirm the impact of p27 on viral replication under in vivo conditions, $p27^{-/-}$ mice were intranasally infected with influenza A/Puerto Rico/8/34 (H1N1) virus. At 2 d p.i., virus load within the lungs of $p27^{-/-}$ mice was significantly reduced (FIG. 4*e*). The observation that a lack of p27 reduces influenza virus replication in vivo but does not affect mouse viability, indicates certain cellular proteins involved in influenza virus replication are dispensable for the host organism.

Thus, this first genome-wide RNAi screen in human cells for factors affecting influenza virus replication has provided new and comprehensive information on host cell determinants of replication, and uncovered potential targets for novel antiviral strategies. We provide in vitro and in vivo evidence for the role of CLK1 and the tumor suppressor p27, using a small molecule inhibitor and a homozygous knockout model, respectively. The majority of the hits analysed in-depth appear to function during early infection processes such as viral protein synthesis and nuclear export of viral RNA. Importantly, most of the validated hits are essential for a broad spectrum of influenza viruses, including the pandemic swine-origin H1N1 influenza virus and even a highly pathogenic avian H5N1 strain. This holds promise for the therapeutic potential of these targets against novel emerging influenza viruses with minimised likelihood of developing drug resistant variants. In conclusion, transient interference with distinct host cell functions during infection is likely to extend our current armament, consisting of vaccines and virus-targeted drugs, in the battle against the recurring threat of seasonal and pandemic influenza virus infections.

In the present screen, a range of cellular functions were identified which were associated with influenza virus propagation. Amongst the significantly enriched functional categories are the small ribosomal subunit and the translation initiation factor EIF3, splicing associated genes, vesicular (coat complex formation) and nuclear transport, as well as vacuolar ATPases. In contrast, in other viral RNAi-based screens, including an influenza virus screen in *Drosophila* cells, mostly single metabolic functions were enriched in the hit lists (13, 14, 15, 17). This general observation strengthens the impact of performing RNAi screens in homologous host cell models.

The small ribosomal subunits and the translation initiation factor EIF3 components comprised a major cellular function enriched in a recent *Drosophila*-based influenza virus screen (13) but not in other viral RNAi screens (14-17). Yet, only single components of the large ribosomal subunit were included in either the previous or our current influenza screens. Toxicity, as determined by our WST assay (c.f. FIG. 11) and viable cell counts (c.f. Table 1), did not have a major impact on the knockdown cells. Kittler et al. found knockdown of many of these genes impacted the cell cycle (arrest) and division, but toxicity was a confounding factor in a minimal number of cases. A *Drosophila* C virus screen identified small as well as large ribosomal subunit genes as enriched and this finding was linked to IRES-mediated translation initiation (18). Translation of influenza mRNAs is initiated in a Cap-dependent and 5'-UTR-mediated manner (Garfinkel et al., Kash et al.) and the initiation factor EIF4E within the EIF4F complex is substituted by the viral polymerase (Burgui et al.). On the other hand, EIF4GI, another member of the EIF4F complex, is targeted by NS1, enhancing preferential translation of late viral mRNAs in particular (Aragon et al.). The eukaryotic 5'-UTR targeting factor GRSF-1, which also enhances translation of influenza mRNAs, was not identified as a hit in our screen (Kash et al.). Besides these known factors, other host cell proteins may play an important role in initiating translation of viral mRNAs (Burgui et al.). The identification of defined translation machinery components in two influenza virus RNAi screens but not other viral screens, suggests these factors could be influenza virus A specific. We speculate that the small ribosomal subunit as well as EIF3 complete the pre-initiation complex that initiates virus-specific, selective translation and probably contribute to the inhibition of host cell gene translation.

Since pre-mRNA splicing is a major cellular function known to be important for gene expression in a variety of viral systems (reviewed by e.g. Engelhardt et al.), we expected this function to be identified in our screen. Yet, the *Drosophila* influenza virus screen does not show the same enrichment of splicing factors. This could be due to the experimental limitations of the *Drosophila* host cell system for influenza A virus infection and replication, therefore other processes might be important in this experimental system. This might also apply to other cellular processes we identified. König et al. (17) found many splicing factors in their HIV early stage replication screen. HIV mRNA splicing is a very complex and highly regulated process that ensures co-ordinated expression of the different viral proteins as well as production of unspliced genomic RNA (reviewed by e.g. Stoltzfus et al). Brass et al. (16) detected several splicing associated factors amongst the HIV-dependency factors (HDFs) included in their screen. Because the individual flavivirus proteins are derived by co- and post-translational cleavage from a polyprotein translated from an unspliced RNA (e.g. Beasley et al), splicing factors are virtually missing in the Dengue and West Nile virus hit lists (14, 15). Furthermore, vacuolar ATPases are enriched in our screen as well as the West Nile virus screen (14). Both viruses rely upon acidification of the phagosome to enter the cytoplasm (reviewed by e.g. Bouvier et al.). Single vacuolar ATPase subunits were also included in the *Drosophila*-based influenza virus screen (13).

The nuclear transport factors are required for export of the viral RNA into the cytoplasm to be translated and incorporated into new virus particles. The cyclin-dependent kinase inhibitor 1B (p27, also CDKN1B) involved in cell cycle regulation and other cellular processes (Borriello et al.), is associated with this network. Phosphorylation at certain amino acid residues regulates cellular localisation and thereby function and stability (Ishida et al., Connor et al.). p27 is exported into the cytoplasm by XPO1/RanGTP. p27 is a tumour suppressor in the nucleus, whereas is acts as an oncogene with pro-metastatic capability in the cytoplasm. This functional versatility (reviewed by e.g. Borriello et al.) makes is difficult to trace the step involved in influenza virus replication. To connect it to the cell-cycle arrest associated with knockdown of many ribosomal subunits (see above) is one promising route for future investigation.

Two different COP vesicles operate in the early secretory pathway (reviewed by Lee et al.). COPII vesicles mediate exit from the endoplasmatic reticulum (ER) and transport to the ER-Golgi-intermediate compartment (ERGIC), whereas COPI vesicles are involved in retrograde transport from the Golgi apparatus to the ER or between different Golgi cisternae and in anterograde transport. The influenza glycoproteins HA and NA are synthesised at the ER, transported to the Golgi apparatus and then trafficked to the plasma membrane (Bouvier et al.). Therefore, factors involved in early secretory pathway of the host cell are likely candidates affecting influenza propagation. In the present work, we have shown that knockdown of COPA, COPB1, COPB2, COPD, COPE or COPG reduced number of infectious viruses, demonstrating that these factors are important for the production of infectious influenza A viruses. Specifically, knockdown of COPG dramatically reduced levels of NP at 3 h p.i. (FIG. 3a and FIGS. 14-16), hinting at a role in early infection processes. These observations are in agreement with a previous RNAi screen that identified COPG as essential for influenza A virus replication in insect cells (13). The underlying mechanism of COPI function in influenza A virus replication is still unknown. Knockdown of COPI constituents could directly affect transport of viral glycoproteins to the plasma membrane. This hypothesis is supported by recent work demonstrating that anterograde transport of proteins in COPB1 knockdown cells is blocked or at least reduced (Styers et al., Rennolds et al.). Interestingly, only components of the COPI machinery have been identified in the present screen. The involvement of COPII vesicles in normal trafficking of membrane proteins from the ER to the plasma membrane could hint to other functions of COPI during influenza A virus infection including maintenance of the steady-state distribution of Golgi proteins or ER quality control mechanisms (Tu et al., Zerangue et al.). In this scenario, knockdown of COPI proteins would result in incorrect folding or incorrect glycosylation of viral proteins including HA and NA, which either reduce transport of these proteins to the plasma membrane or interfere with the normal function of these proteins. Detailed analysis is on the way to clarify the role of COPI proteins during influenza virus infection.

In summary, these findings highlight the significance of our screen. Many molecular functions of the host cell known, or expected, to play important roles in influenza virus replication were recovered in our analysis. As an extension to previous RNAi-based viral screens (13, 14, 16, 17), which report single functional categories, our findings reveal a range of different molecular networks.

Methods

Summary: siRNA Screening

All siRNAs (4 l/well, 200 nM) were arrayed in 384-well plates. To each well, 8 µl of RPMI medium (Invitrogen, Karlsruhe, Germany) containing 0.35 µl HiperFect (Qiagen) was added and plates were shaken for 1 min. After 10 min incubation at room temperature (RT), a cell suspension (28 µl) of 500 cells was added to give a final siRNA concentration of 20 nM. Cells were incubated at 37° C. and 5% $CO_2$ for 48 h before infection at MOI 0.12. At 24 hours post infection (p.i.), supernatants were transferred onto freshly seeded 293T reporter cells, incubated for 16 h at 37° C. and 5% $CO_2$ and then luciferase activities were measured. The A549 cells were fixed, stained for nuclei and NP, and analysed using the Acumen $^e$X3 Cytometer (TTP Labtech, Royston, U.K.). All multiwell pipetting steps were performed using a Biomek® FX$^P$ Laboratory Automation Workstation (Beckman Coulter, Krefeld, Germany). An siRNA library (Qiagen Hu_Genome 1.0 and Human Druggable Genome siRNA Set V2.0; Qiagen, Hilden, Germany) containing four siRNAs per gene for the druggable genome (25) and two siRNAs per gene for non-druggable and predicted genes was screened three times independently. The following siRNAs with the indicated target sequence were included in all screening plates as controls: siNP (5'-AAGGAUCUUAUUUCUUCGGAG-3'), (SEQ ID NO: 1) siPLKl (5-CACCATATGAATTGTACAGAA-3') (SEQ ID NO: 2) and Allstars (Qiagen, Hilden, Germany).

Cells and Viruses

The A549 human lung epithelial cell line (CCL-185, ATCC-LGC, Wesel, Germany) was grown in DMEM media (Invitrogen, Karlsruhe, Germany) supplemented with 4 mM L-glutamine, 4 mM sodium pyruvate, 100 U/ml penicillin/streptomycin and 10% fetal calf serum (FCS, Biochrome, Berlin, Germany) (DMEM complete medium), at 37° C. and 5% $CO_2$. The human embryonic kidney cell line 293T (CRL-11268, ATCC-LGC) and the Madin Darby Canine Kidney cells (MDCK, CCL-34, ATCC-LGC) were grown in DMEM supplemented with 4 mM L-glutamine, 100 U/ml penicillin/streptomycin and 10% FCS. Primary normal human bronchial epithelial cells (NHBE, CC-2541, Lonza, Cologne, Germany) were grown in Clonetics® BEGM® BulletKit® (CC-3170, Lonza) supplemented with the following growth supplements: BPE, Hydrocortisone, hEGF, Epinephrine, Transferrin, Insulin, Retinoic Acid, Triiodothyronine, GA-1000. Supplements added at 0.5 ml/500 ml medium, except BPE (2 ml/500 ml). Cells were regularly checked for mycoplasma contamination by PCR. The influenza virus strains A/WSN/33 (H1N1) and A/Puerto Rico/8/34 (H1N1) were grown in the allantoic cavities of 11-day-old embryonated chicken eggs. Production of recombinant highly pathogenic influenza A/Vietnam/1203/2004 virus (H5N1) by reverse genetics was done essentially as described previously (26). The pandemic H1N1 A/Hamburg/04/2009 strain was provided by S. Becker (Philipps University, Marburg, Germany) and was propagated in MDCK cells in DMEM supplemented with 1 µg trypsin/ml in the absence of FCS. Virus stocks were titrated by standard plaque assay on MDCK cells using an agar overlay medium (27).

siRNA Screening

All siRNAs (4 µl/well, 200 nM) were arrayed in 384-well plates. To each well, 8 µl of RPMI medium (Invitrogen, Karlsruhe, Germany) containing 0.35 µl HiperFect (Qiagen) was added and plates were shaken for 1 min. After 10 min incubation at room temperature (RT), a cell suspension (28 µl) containing 500 cells was added to give a final siRNA concentration of 20 nM. Cells were incubated at 37° C. and 5% $CO_2$ for 48 h before infection at an MOI of 0.12 (see below). At 24 hours post infection (p.i.), supernatants were transferred onto freshly seeded 293T reporter cells, incubated for 16 h at 37° C. and 5% $CO_2$ and then luciferase activities were measured (see below). The A549 cells were fixed, stained for nuclei and NP, and analysed using the Acumen $^e$X3 Cytometer (TTP Labtech, Royston, UK). The number of automatically counted nuclei was further used to estimate cytotoxic effects of specific siRNAs. The siRNA was classified as being toxic, if 750 or fewer nuclei were determined within one well of a 384-well plate. All multiwell pipetting steps were performed using a Biomek® FX$^P$ Laboratory Automation Workstation (Beckman Coulter, Krefeld, Germany). An siRNA library (Qiagen Hu_Genome 1.0 and Human Druggable Genome siRNA Set V2.0; Qiagen, Hilden, Germany) containing four siRNAs per gene for the druggable genome (25) and two siRNAs per gene for non-druggable and predicted genes, was screened three times independently. The following siRNAs with the indicated target sequence were included in all screening plates as controls: siNP (5'-AAG-GAUCUUAUUUCUUCGGAG-3'), siPLK1 (5'-CAC-CATATGAATTGTACAGAA-3') and Allstars (Qiagen, Hilden, Germany).

Luciferase Reporter Assay

To quantify infectious viruses in the supernatants of siRNA transfected A549 cells during the primary RNAi screen, we used a luciferase-based reporter system. 293T cells were transfected in batches with a FluA luc plasmid (6), one day later seeded into 384-well plates at concentrations of $1\times10^4$/well, and subsequently infected with 12.5 µl of virus containing supernatant. At 16 h p.i., Bright-Glo™ firefly luciferase substrate (Promega, Madison, Wis., USA) was added and luciferase activities in cell lysates were measured using the Envision multilabel plate reader (PerkinElmer, Rodgau, Germany). Transfection of 239T cells with the influenza virus-specific luciferase construct (FlaA) induces expression of firefly luciferase transcripts flanked by the untranslated region of the influenza A/WSN/33 virus nucleoprotein (NP) segment. Luciferase expression is therefore only detectable in the presence of the viral polymerase, thus allowing quantification of infectious viruses.

siRNA Transfection for Validation Experiments in 96- and 12-Well Plates

All siRNAs were purchased from Qiagen. For siRNA transfection of A549 cells in 96-well plates, 20 µl of a 100 nM siRNA dilution in DMEM w/o supplements was mixed with 1 µl HiperFect+9 µl DMEM medium and incubated for 10 min at RT. Complex formation was stopped by addition of 25 µl DMEM complete medium. Next, 3000 A549 cells in 50 µl DMEM complete medium were seeded into each well and incubated at 37° C. and 5% $CO_2$ for the indicated time periods. For siRNA transfection of NHBE cells in 96-well plates, BEGM medium (with/without supplements) was used and 15,000 cells/well were seeded. For Western blot experiments, siRNA transfection was carried out in 12-well plates. For each well, 1 µl of a 20 µM siRNA solution was diluted in 99 µl RPMI (Invitrogen) supplemented with 25 mM HEPES (Invitrogen). The mix was incubated at RT for 5 min before addition of 5 µl HiperFect (Qiagen) and further 15 min incubation at RT. Each complex was added to 50,000 A549 cells in 900 µl DMEM complete medium, mixed carefully, and then transferred to 12-well plates. After 6 h incubation at 37° C. and 5% $CO_2$, the medium was exchanged for fresh DMEM complete medium and the cells were incubated for an additional 48 h using the same growth conditions.

Indirect Immunofluorescence Labeling

Cells were fixed with 3.7% formaldehyde and permeabilised with 0.3% Triton X-100, 10% FCS in PBS. Samples were sequentially incubated with a primary antibody against the viral nucleoprotein (NP, clone AA5H, AbD Serotec, UK) diluted 1:10000 in PBS with 10% FCS, 0.1% Tween 20 for 1 h at RT, followed by an incubation with the secondary Cy3 conjugated antibody directed against mouse IgG (1:100 in PBS with 10% FCS, 0.1% Tween 20 and 0.1% Hoechst dye used to stain cellular DNA). Numbers of infected versus non-infected cells were determined using automated microscopy (Olympus, Soft Imaging Solutions, München, Germany) or, for the primary siRNA screen, the Acumen eX3 microplate cytometer (TTP LabTech, Melbourn, UK).

Automated Microscopy and Image Analysis

The numbers of influenza infected and host cells were determined using an automated microscope (Olympus Soft Imaging Solutions). Images were taken with DAPI and Cy3 filter sets (AHF-Analysetechnik, Tübingen, Germany). Scan^R Analysis Software (Olympus Soft Imaging Solutions) was used to automatically identify and quantify influenza nuclear protein (NP) and cell nuclei. For determination of NP localisation, mean and total intensities of NP were analysed. NP located within the same area as the Hoechst staining was defined as nuclear NP. NP located within a 5-pixel-wide ring around the nuclei was defined as cytosolic NP. The distance between the inner edge of the ring and the nuclei was set at 1 pixel. For each experiments identical camera setting were used.

Host Cell Viability Determination by WST-1 Assay

Determination of host cell viability upon siRNA transfection was performed using cell proliferation assay WST-1 (Roche, Mannheim, Germany). WST-1 reagent was added to the cells 48 h after siRNA transfection and incubated at 37° C. for 1.5 h. Absorbance was measured at 460 nm and at the reference wavelength 590 nm. Non-targeting siRNA Allstars and siPLK1 were used as a positive and negative control, respectively.

Virus Infection

Cells were washed with PBS and then infected with influenza at the indicated MOIs in infection buffer (PBS supplemented with 0.2% bovine serum albumin) for 60 min at RT. Cells were washed again (in infection buffer) and incubated for the indicated time periods at 37° C. in DMEM supplemented with 0.2% bovine serum albumin, 4 mM L-glutamine and antibiotics (A549) or BEGM with supplements (NHBE), unless otherwise stated. All infection experiments with A/WSN/33, A/Puerto Rico/8/34 and with A/Hamburg/04/2009 H1N1 viruses were performed under biosafety level (BSL) 2 conditions, whereas BSL 3 conditions were used for experiments with A/Vietnam/1203/2004 (HN51).

Replication Assay

To quantify infectious virus particles in infected cell culture supernatants, 5,000 or 12,000 MDCK cells were seeded in 384- or 96-well plates, respectively. One day later the cells were washed twice, infected with a dilution series of cell culture supernatants and incubated at RT for 1 h. Infection buffer (as above) was added (40 μl or 100 μl/well) and plates were incubated at 37° C., 5% $CO_2$ for 6 h, followed by fixation with 3.7% formaldehyde, antibody staining and automatic image processing, as described in 'Indirect immunofluorescence labeling'.

Gene Enrichment and Network Analysis

For gene enrichment analysis, we modified the R-script available from the Gaggle web site (http://gaggle.systemsbiology.net/svn/gaggle/PIPE2.0/trunk/PIPEletResource Dir/GOTableEnrichment/GOEnrichmentScript.R). This script applies the R-package GOstats developed by Falcon, S, and Gentleman, R. (28) and is available at the Bioconductor web site (http://www.bioconductor.org). Briefly, we defined a gene universe consisting of 22843 genes contained and annotated in the genome-wide library and processed the hit list against this universe with respect to molecular function (MF), cellular component (CC) and biological process (BP). Each Gene Ontology term is associated with X number of genes, providing a relative frequency A. In the hit list, the same term is connected to Y genes giving a relative frequency B. B divided by A is the enrichment factor.

The 287 'high-confidence' hits were also uploaded as gene-identifiers using the Sky-Painter tool of the Reactome website (www.reactome.org). Significant events calculated by the application's Fisher's exact test were identified and coloured accordingly. Network analysis was carried out using the STRING database (http://string.embl.de/).

Confocal Microscopy

Fusion between influenza viruses and cellular endosomes was detected using confocal microscopy. A549 cells were plated onto cover slips in 12-well plates at a density of $5 \times 10^4$ cells/well and directly transfected in suspension with indicated siRNAs, followed by infection with influenza A/WSN/33 virus (MOI 10) 48 h post transfection. During the infection process, cells were kept on ice for 45 min, washed twice with cold infection buffer (see above) and subsequently incubated with pre-warmed infection media (DMEM supplemented with 0.2% bovine serum albumin, 4 mM L-glutamine and antibiotics). After 15, 45 and 90 min cells were fixed with 4% paraformaldehyde and permeabilised for 20 min with 0.2% BSA in PBS and 0.2% Triton X-100. Cells were then incubated for 1 h with antibodies targeting CD63 (Millipore) at a dilution of 1:70 and a polyclonal serum against influenza (1:1000), followed by incubation with a fluorescently labelled secondary antibody (dilution 1:100). Samples were mounted in MOWIOL. Images were taken with a Leica TCS-SP confocal microscope and processed using Adobe Photoshop 11.0.

Immunoblotting

For immunoblotting, cells were washed with PBS and lysed in 1×SDS sample buffer containing 75 mM Tris HCl (pH 6.8), 25% glycerol, 0.6% SDS, 7.5% β-mercaptoethanol and 0.001% bromphenol blue. Protein lysates (20 μl) were loaded and separated on a 10% SDS-polyacrylamide gel. Separated proteins were transferred to a PVDF membrane and detected using mouse monoclonal antibodies against viral matrix protein (M1, AbD Serotec, UK), viral ion channel protein (M2, Santa Cruz) or β-actin (Sigma, Germany) at 1:100, 1:1000 or 1:2500 dilution, respectively, followed by incubation with a secondary sheep anti-mouse IgG Horseradish peroxidase (1:10000). Staining was performed with ECL Western Blotting Detection Reagent (Amersham, Piscataway, N.J., USA). β-actin was used as a loading control. Band intensities were determined using the Aida image analyzer (V.4.03) (2D/Densitometry) and normalised to β-actin.

Quantitative RT-PCR

For the detection of viral RNA (vRNA) or viral mRNA, quantitative RT-PCR (qRT-PCR) was performed as previously described (7). Briefly, A549 cells infected with influenza A/WSN/33 virus (MOI 1) were lysed with RLT lysis buffer (Qiagen, Hilden, Germany). For reverse transcription of viral mRNA, an oligo(dT)18 primer was used: the negative stranded vRNA of the gene segment PA was converted to cDNA using a PA-specific oligonucleotide (5'-GCTTCT-TATCGTTCAGGCTCTTAGG-3') (SEQ ID NO: 3). Resulting cDNAs were quantified by qRT-PCR with oligonucleotides specific for PA (5'-GCTTCTTATCGTTCAGGCTCTTAGG-3'(SEQ ID NO: 3) and 5'-CCGAGAAGCATTAAGCAAAACCCAG-3') (SEQ ID NO: 4). GAPDH was amplified using the oligonucleotides, GAPDH for: 5'-GGTATCGTGGAAGGACTCAT-GAC-3' (SEQ ID NO: 5); GAPDH_rev: 5'-ATGCCAGT-GAGCTTCCCGTTCAG-3'(SEQ ID NO: 6). Levels of GAPDH were used for normalisation. All experiments were done in triplicate. To quantify the levels of spliced and unspliced mRNAs, infection of A549 cells with influenza A/WSN/33 virus was performed at an MOI of 4 for 5 h. RNA was then isolated using the RNeasy Mini Kit (Qiagen) and treated with DNase (Ambion) according to manufacturer's instructions. Reverse transcription of viral mRNA was performed using oligo(dT) primer and the synthesised cDNA was subjected to real-time PCR using primers specific for M1 (5'-GACCAATCCTGTCACCTC-3'(SEQ ID NO: 7) and 5'-GATCTCCGTTCCCATTAAGAG-3') (SEQ ID NO: 8)

and M2 (5-GAGGTCGAAACGCCTAT-3'(SEQ ID NO: 9) and 5'-CTCCAGCTCTATGTTGACAAA-3') (SEQ ID NO: 10), as described previously (29). Levels of M1 and M2 mRNA were normalised to GAPDH.

Validation of RNAi by Quantitative PCR siRNA validation was performed as previously described (30). Briefly, one day before transfection 3,000 cells per well were seeded onto a 96-well plate. Transfection was performed with a final siRNA concentration of 56 nM with 0.25 µl HiPerFect(Qiagen). Knockdown measurements were performed independently three times. After 48 h, RNA was isolated using the RNeasy 96 BioRobot 8000 system (Qiagen). The relative amount of target mRNA was determined by quantitative PCR using the Quantitect SYBR Green RT-PCR kit following the manufacturer's instructions (Qiagen) and the following primers:

```
GAPDH forward
5'-GGTATCGTGGAAGGACTCATGAC-3', (SEQ ID NO: 5)

GAPDH reverse
5'-ATGCCAGTGAGCTTCCCGTTCAG-3', (SEQ ID NO: 6)

ATP6V0D1 forward
5'-TGTCGCAACATCGTGTGGAT-3', (SEQ ID NO: 11)

ATP6V0D1 reverse
5'-GAGTGCAATTGAGAGCCTTGG-3', (SEQ ID NO: 12)

COPG forward
5'-TCCGCTATGCTGCTGTTCGTA-3', (SEQ ID NO: 13)

COPG reverse
5'-GCGGTTTGAATCTGTGACCAG-3', (SEQ ID NO: 14)

EIF4A3 forward
5'-TGATCTTGGCTCCCACAAGAG-3', (SEQ ID NO: 15)

EIF4A3 reverse
5'-ATTGGTGCCTCCAATGCAG-3', (SEQ ID NO: 16)

NUP98 forward
5'-TTCCGGAATCCGATGTCAGA-3', (SEQ ID NO: 17)

NUP98 reverse
5'-TGTAAAGCCTTTGGCCGGACT-3', (SEQ ID NO: 18)

NUP205 forward
5'-ACCTTCGGAAGGATCTTCCAA-3'; (SEQ ID NO: 19)

NUP205 reverse
5'-GGAGTCCCAGAATCACCACAA-3'; (SEQ ID NO: 20)

NXF1 forward
5'-TGAGCAAACGATACGATGGC-3', (SEQ ID NO: 21)

NXF1 reverse
5'-TCTGCGATTCAGGACAACGTC-3', (SEQ ID NO: 22)

SON forward
5'-CAAGCCTTAGAGCTGGCATTG-3', (SEQ ID NO: 23)

SON reverse
5'-GCTTGCGTGATTTGTGTTCAG-3', (SEQ ID NO: 24)
```

The relative expression levels of target mRNA were normalized against control transfected cells. GAPDH was used as an internal standard.

Chemical Inhibitors

The chemical inhibitor TG003 (Sigma-Aldrich, Munich, Germany) directed against the kinase CLK1 was dissolved in DMSO to a concentration of 10 mM.

Animal Experiments

Animals were housed and bred under pathogen free conditions, biosafety level 2 according to German Animal Protection Law (Tierschutzgesetz TierSchG). Animal testing was approved by the local authorities (Landesamt für Gesundheit and Soziales Berlin LAGeSo: Reference number G0217/08). C57BL/6/J and $p27^{-/-}$ mice (B6.129S4-Cdkn1b$^{tm1Mlf}$/J) were provided by Charles River (Sulzfeld, Germany) or bred in house, respectively. Mice aged between 7 and 15 weeks were intranasally infected with influenza A/Puerto Rico/8/34 virus ($10\times LD_{50}$; in 50 µl PBS). Two days later, lungs of infected animals were isolated and homogenised, followed by centrifugation at 800×g for 8 min at 4° C. The amount of infectious viruses in the supernatant was quantified using the replication assay (see above). Proteins for use in immunoblotting experiments were obtained by adding TRIZOL Reagent (GIBCO BRL) to the remaining cell pellet, according to the manufacturer's instructions.

Data Analysis

For identification of primary hits, three parameters were included: luciferase expression, the percentage of infected cells as determined by immunofluorescence microscopy, and the total number of infected cells. The latter parameter was informative because the number of viruses per well correlated with the number of infected cells, with minor influence of cells present. To maximize the robustness of the hit selection and to minimize false positives due to off-target effects, raw screening data from all three parameters were subjected separately to an analysis pipeline incorporating statistical checkpoints at each step (FIG. 8). First, we excluded non-expressed genes by determining constitutive or inducible expression via microarray profiling of non-infected and infected A549 samples (5814 genes were not expressed). Second, we excluded toxic siRNAs which reduced total cell numbers (<750 cells/well) upon transfection were also excluded (1520 siRNAs) using the microscopic assay applied throughout the primary screen. Third, non-toxic siRNAs targeting expressed genes were further analysed. For statistical analysis of luciferase assay data obtained from the genome-wide screen, the following plate-wise quality control criteria were used: (i) the average signal from the non-targeting control wells (Allstars) was greater than 10,000 counts, and (ii) the difference in signal strength between the non-targeting control (Allstars) and (iii) the inhibitory control (NP) was at least two orders of magnitude. Using Genedata's Screener® software (www-.genedata.com), we excluded wells with phenotypes attributable to positional effects. The revised raw data were subjected to statistical analysis using cellHTS (31), an R-implemented software package for the analysis of cell-based high-throughput RNAi screen data. Raw data were normalised using the B-score method to further exclude positional effects (32). Next, a z-score transformation was applied to center and scale the plate-wise data. The z-scores were calculated using the following equation:

$$z = \frac{X - \mu}{\sigma}.$$

where X is a raw score to be standardized, σ is the standard deviation of the population, and µ is the mean of the population. The medians of the centered and scaled values of at least three independent replicates were used for redundant siRNA activity (RSA) analysis (33), which applies a rank-based hypergeometric distribution test to identify hits. Only genes for which two corresponding siRNAs were scored as hits were analysed further. Next, Genedata's Screener® package was used to select all genes with a robust z-score of less than −2.

For the analysis of the hit validation data, for each siRNA the normalised percent inhibition of infectious virus particles was calculated. Briefly, the difference of each sample value subtracted from the median of the non-targeting control (Allstars) values of the particular plate was divided by the difference of the medians of the non-targeting control and the inhibitory control (siNP). An 80% normalised inhibition threshold was applied. Genes were scored as validated hits if at least two siRNAs, which did not impair cell viability, fulfilled this criteria.

The ratios of cytosolic to nuclear NP at 5 h p.i. and levels of total NP at 3 h p.i. in samples tested were non-normally distributed. Therefore, to assess the significance of differences between distributions of the target knockdown samples and non-targeting control reference samples (Allstars), we applied the minimal distance estimation Kolmogorov-Smirnov test using the statistical software environment R (http://www.r-project.org/). The samples sizes are individually defined as the number of main objects per well detected by the automated image analysis package Scan^R.

Significant differences in the amount of infectious viruses gained from the lungs of p27$^{-/-}$ and control mice were tested using a one-tailed t-test assuming different standard deviations for the samples and the controls (Welch-test).

REFERENCES

1. Horimoto, T. & Kawaoka, Y. Influenza: lessons from past pandemics, warnings from current incidents. Nat. Rev. Microbiol. 3 591-600 (2005).
2. Neumann, G., Noda, T. & Kawaoka, Y. Emergence and pandemic potential of swine-origin H1N1 influenza virus. Nature. 459, 931-939 (2009).
3. Sun, C. T. et al. Transcription repression of human hepatitis B virus genes by negative regulatory element-binding protein/SON. J. Biol. Chem. 276, 24059-24067 (2001).
4. Muraki, M. et al. Manipulation of alternative splicing by a newly developed inhibitor of Clks. J. Biol. Chem. 279, 24246-24254 (2004).
5. Ludwig, L., Planz, O, Pleschka, S. & Wolff, T. Influenza-virus-induced signaling cascades: targets for antiviral therapy? Trends Mol. Med. 9, 46-52 (2003).
6. Lutz, A., Dyall, J., Olivo, P. D. & Pekosz, A. Virus-inducible reporter genes as a tool for detecting and quantifying influenza A virus replication. J. Virol. Methods 126, 13-20 (2005).
7. Ge, Q. et al. RNA interference of influenza virus production by directly targeting mRNA for degradation and indirectly inhibiting all viral RNA transcription. Proc. Natl. Acad. Sci. U.S.A 100, 2718-2723 (2003).
8. Satterly, N. et al. Influenza virus targets the mRNA export machinery and the nuclear pore complex. Proc. Natl. Acad. Sci. U.S. A 104, 1853-1858 (2007).
9. Elton, E. et al. Interaction of the influenza virus nucleoprotein with the cellular CRM1-mediated nuclear export pathway. J. Virol. 75, 408-419 (2001).
10. Guinea, R. & Carrasco, L. Requirement for vacuolar proton-ATPase activity during entry of influenza virus into cells. J. Virol. 69, 2306-2312 (1995).
11. Perez, L. & Carrasco, L. Involvement of the vacuolar H(+)-ATPase in animal virus entry. J. Gen. Virol. 75, 2595-2606 (1994).
12. Joshi-Tope, G. et al. Reactome: a knowledgebase of biological pathways. Nucleic Acids Res. 33, D428-D432 (2005).
13. Hao, L. et al. *Drosophila* RNAi screen identifies host genes important for influenza virus replication. Nature 454, 890-893 (2008).
14. Krishnan, M. N. et al. RNA interference screen for human genes associated with West Nile virus infection. Nature 455, 242-245 (2008).
15. Sessions, O. M. et al. Discovery of insect and human dengue virus host factors. 458, 1047-1050 (2009).
16. Brass, A. L. et al. Identification of host proteins required for HIV infection through a functional genomic screen. Science 319, 921-926 (2008).
17. Konig, R. et al. Global analysis of host-pathogen interactions that regulate early-stage HIV-1 replication. Cell 135, 49-60 (2008).
18. Cherny, S. et al. Genome-wide RNAi screen reveals a specific sensitivity of IRES-containing RNA viruses to host translation inhibition. Genes Dev 19, 445-452 (2005).
19. Josset, L., Frobert, E. & Rosa-Calatrava, M. Influenza A replication and host nuclear compartments: many changes and many questions. J. Clin. Virol. 43, 381-390 (2008).
20. Cullen, B. R. Nuclear mRNA export: insights from virology. Trends Biochem. Sci. 28, 419-424 (2003).
21. Bullock, A. N. et al. Kinase domain insertions define distinct roles of CLK kinases in SR protein phosphorylation. Structure 17, 352-362 (2009).
22. Hagiwara, M. Alternative splicing: a new drug target of the post-genome era. Biochim. Biophys. Acta 1754, 324-331 (2005).
23. Huang, Y. Yario, T. A. & Steitz, J. A. A molecular link between SR protein dephosphorylation and mRNA export. Proc. Natl. Acad. Sci. U.S.A. 101, 9666-9670 (2004).
24. Shih, S. R. & Krug, R. M. Novel exploitation of a nuclear function by influenza virus: the cellular SF2/ASF splicing factor controls the amount of the essential viral M2 ion channel protein in infected cells. EMBO J. 15, 5415-5427 (1996).
25. Hopkins, A. L. & Groom, C. R. The druggable genome. Nat. Rev. Drug Discov. 1, 727-730 (2002).
26. Kittler, R. et al. Genome-scale RNAi profiling of cell division in human tissue culture cells. Nat Cell Biol 9, 1401-1412 (2007).
27. Garfinkel, M. S. & Katze, M. G. Translational control by influenza virus. Selective translation is mediated by sequences within the viral mRNA 5'-untranslated region. J Biol Chem 268, 22223-22226 (1993).
28. Kash, J. C. et al. Selective translation of eukaryotic mRNAs: functional molecular analysis of GRSF-1, a positive regulator of influenza virus protein synthesis. J Virol 76, 10417-10426 (2002).
29. Burgui, I., Yanguez, E., Sonenberg, N., & Nieto, A. Influenza virus mRNA translation revisited: is the eIF4E cap-binding factor required for viral mRNA translation? J Virol 81, 12427-12438 (2007).
30. Aragon, T. et al. Eukaryotic translation initiation factor 4GI is a cellular target for NS1 protein, a translational activator of influenza virus. Mol Cell Biol 20, 6259-6268 (2000).
31. Engelhardt, O. G. & Fodor, E. Functional association between viral and cellular transcription during influenza virus infection. Rev Med Virol 16, 329-345 (2006).
32. Stoltzfus, M. C. Chapter 1 Regulation of HIV-1 Alternative RNA Splicing and Its Role in Virus Replication in Advances in Virus Research (ed. Karl Maramorosch, A. J. S.) 1-40 (Academic Press, 2009).
33. Beasley, D. W. C. Recent advances in the molecular biology of west nile virus. Curr Mol Med 5, 835-850 (2005).

34. Bouvier, N. M. & Palese, P. The biology of influenza viruses. Vaccine 26 Suppl 4, 49-53 (2008).
35. Borriello, A., Cucciolla, V., Oliva, A., Zappia, V., & Della Ragione, F. p27Kip1 metabolism: a fascinating labyrinth. Cell Cycle 6, 1053-1061 (2007).
36. Ishida, N. et al. Phosphorylation of p27Kip1 on serine 10 is required for its binding to CRM1 and nuclear export. J Biol Chem 277, 14355-14358 (2002).
37. Connor, M. K. et al. CRM1/Ran-mediated nuclear export of p27(Kip1) involves a nuclear export signal and links p27 export and proteolysis. Mol Biol Cell 14, 201-213 (2003).
38. Lee, M. C., Miller, E. A., Goldberg, J., Orci, L., & Schekman, R. Bi-directional protein transport between the ER and Golgi. Annu. Rev. Cell Dev. Biol. 20, 87-123 (2004).
39. Styers, M. L., O'Connor, A. K., Grabski, R., Cormet-Boyaka, E., & Sztul, E. Depletion of beta-COP reveals a role for COP-I in compartmentalization of secretory compartments and in biosynthetic transport of caveolin-1. Am. J. Physiol Cell Physiol 294, C1485-C1498 (2008).
40. Rennolds, J. et al. Cystic fibrosis transmembrane conductance regulator trafficking is mediated by the COPI coat in epithelial cells. J. Biol. Chem. 283, 833-839 (2008).
41. Tu, L., Tai, W. C., Chen, L., & Banfield, D. K. Signal-mediated dynamic retention of glycosyltransferases in the Golgi. Science 321, 404-407 (2008).
42. Zerangue, N. et al. Analysis of endoplasmic reticulum trafficking signals by combinatorial screening in mammalian cells. Proc. Natl. Acad. Sci. U.S. A 98, 2431-2436 (2001).

TABLE 3

| GeneSymbol | LocusID | Gene Description | siRN1 ID | siRNA2 ID | siRNA3 ID |
|---|---|---|---|---|---|
| AAMP | 14 | angio-associated, migratory cell protein | Hs_AAMP_1 | Hs_AAMP_3 | Hs_AAMP_4 |
| ACTN1 | 87 | ACTININ, ALPHA 1 | Hs_ACTN1_13 | Hs_ACTN1_8 | Hs_ACTN1_7 |
| AHCYL1 | 18768 | S-ADENOSYLHOMOCYSTEINE HYDROLASE-LIKE 1 | Hs_AHCYL1_4 | Hs_AHCYL1_2 | Hs_AHCYL1_3 |
| AIG1 | 51390 | ANDROGEN-INDUCED 1 | Hs_AIG1_5 | Hs_AIG1_6 | Hs_AIG1_4 |
| AKR1C4 | 1199 | ALDO-KETO REDUCTASE FAMILY 1, MEMBER C4 (CHLORDECONE REDUCTASE; 3-ALPHA HYDROXYSTEROID DEHYDROGENASE, TYPE I; DIHYDRODIOL DEHYDROGENASE 4) | Hs_AKR1C4_3 | Hs_AKR1C4_2 | Hs_AKR1C4_1 |
| AKTIP | 64400 | AKT interacting protein | | | |
| ALDH7A1 | 581 | ALDEHYDE DEHYDROGENASE 7 FAMILY, MEMBER A1 | Hs_ALDH7A1_1 | Hs_ALDH7A1_4 | Hs_ALDH7A1_2 |
| ALX4 | 69529 | ARISTALESS-LIKE HOMEOBOX 4 | Hs_ALX4_3 | Hs_ALX4_2 | Hs_ALX4_1 |
| AP2M1 | 1173 | adaptor-related protein complex 2, mu 1 subunit | Hs_AP2M1_7 | Hs_AP2M1_3 | Hs_AP2M1_5 |
| APBB1IP | 54518 | AMYLOID BETA (A4) PRECURSOR PROTEIN-BINDING, FAMILY B, MEMBER 1 INTERACTING PROTEIN | Hs_APBB1IP_3 | Hs_APBB1IP_8 | Hs_APBB1IP_7 |
| ARD1A | 8260 | ARD1 homolog A, N-acetyltransferase (S. cerevisiae) | Hs_ARD1_1 | Hs_ARD1_3 | Hs_ARD1_5 |
| ARTN | 9948 | ARTEMIN | Hs_ARTN_8 | Hs_ARTN_7 | Hs_ARTN_9 |
| ASAH3L | 348485 | N-acylsphingosine amidohydrolase 3-like | Hs_ASAH3L_1 | Hs_ASAH3L_2 | Hs_ASAH3L_3 |
| ATCAY | 85300 | ATAXIA, CEREBELLAR, CAYMAN TYPE (CAYTAXIN) | Hs_ATCAY_2 | Hs_ATCAY_3 | Hs_ATCAY_4 |
| ATP1A2 | 477 | ATPase, Na+/K+ transporting, alpha 2 (+) polypeptide | Hs_ATP1A2_2 | Hs_ATP1A2_3 | Hs_ATP1A2_4 |
| ATP6AP1 | 537 | ATPase, H+ transporting, lysosomal accessory protein 1 | Hs_ATP6AP1_5 | Hs_ATP6AP1_6 | Hs_ATP6AP1_7 |
| ATP6AP2 | 10159 | ATPASE, H+ TRANSPORTING, LYSOSOMAL ACCESSORY PROTEIN 2 | Hs_ATP6AP2_7 | Hs_ATP6AP2_8 | Hs_ATP6AP2_6 |
| ATP6V9C | 527 | ATPASE, H+ TRANSPORTING, LYSOSOMAL 16KDA, V8 SUBUNIT C | Hs_ATP6V9C_7 | Hs_ATP6V9C_8 | Hs_ATP6V9C_6 |
| ATP6V9D1 | 9114 | ATPase, H+ transporting, lysosomal 38 kDa, V8 subunit d1 | Hs_ATP6V9D1_2 | Hs_ATP6V9D1_1 | Hs_ATP6V9D1_3 |
| ATP6V1A | 523 | ATPASE, H+ TRANSPORTING, LYSOSOMAL 78 KDA, V1 SUBUNIT A | Hs_ATP6V1A_1 | Hs_ATP6V1A_3 | Hs_ATP6V1A_2 |
| ATP6V1B2 | 526 | ATPASE, H+ TRANSPORTING, LYSOSOMAL 56/58 KDA, V1 SUBUNIT B2 | Hs_ATP6V1B2_2 | Hs_ATP6V1B2_4 | Hs_ATP6V1B2_5 |
| AZIN1 | 51582 | ANTIZYME INHIBITOR 1 | Hs_DAZIN_4 | Hs_DAZIN_2 | Hs_DAZIN_1 |
| B2M | 567 | beta-2-microglobulin | Hs_B2M_3 | Hs_B2M_4 | Hs_B2M_5 |
| B3GNT1 | 11041 | UDP-GLCNAC:BETAGAL BETA-1,3-N-ACETYLGLUCOSAMINYLTRANSFERASE 6 | Hs_B3GNT1_5 | Hs_B3GNT1_7 | Hs_B3GNT1_8 |
| BAIAP3 | 8938 | BAI1-associated protein 3 | Hs_BAIAP3_1 | Hs_BAIAP3_2 | Hs_BAIAP3_5 |
| BARHL2 | 343472 | BARH-LIKE 2 (DROSOPHILA) | Hs_BARHL2_7 | Hs_BARHL2_7 | Hs_BARHL2_6 |
| BNIP3L | 665 | BCL2/ADENOVIRUS E1B 19 KDA INTERACTING PROTEIN 3-LIKE | Hs_BNIP3L_7 | Hs_BNIP3L_12 | Hs_BNIP3L_10 |
| BRUNOL6 | 60677 | BRUNO-LIKE 6, RNA BINDING PROTEIN (DROSOPHILA) | Hs_BRUNOL6_8 | Hs_BRUNOL6_7 | Hs_BRUNOL6_5 |
| BZRAP1 | 9256 | benzodiazapine receptor (peripheral) associated protein 1 | Hs_BZRAP1_1 | Hs_BZRAP1_2 | Hs_BZRAP1_4 |
| C14orf172 | 115708 | CHROMOSOME 14 OPEN READING FRAME 172 | Hs_C14orf172_1 | Hs_C14orf172_4 | Hs_C14orf172_3 |
| C19orf47 | 126526 | HYPOTHETICAL PROTEIN FLJ36888 | Hs_FLJ36888_5 | Hs_FLJ36888_4 | Hs_C19orf47_1 |
| C21orf7 | 56911 | chromosome 21 open reading fram 7 | Hs_C21orf7_1 | Hs_C21orf7_2 | Hs_C21orf7_3 |
| C3orf31 | 132001 | chromosome 3 open reading fram 31 | Hs_C3orf31_1 | Hs_C3orf31_2 | Hs_C3orf31_3 |
| C4orf29 | 80167 | HYPOTHETICAL PROTEIN FLJ21106 | Hs_C4orf29_1 | Hs_C4orf29_2 | Hs_C4orf29_1 |
| CARD9 | 64170 | caspase recruitment domain family, member 9 | Hs_CARD9_1 | Hs_CARD9_2 | Hs_CARD9_3 |
| CASPBAP2 | 9994 | CASP8 ASSOCIATED PROTEIN 2 | Hs_CASPBAP2_5 | Hs_CASPBAP2_3 | Hs_CASPBAP2_6 |
| CCNB3 | 85417 | cyclin B3 | Hs_CCNB3_7 | Hs_CCNB3_6 | Hs_CCNB3_8 |
| CD48 | 962 | CD48 molecule | Hs_CD48_1 | Hs_CD48_2 | Hs_CD48_3 |
| CD58 | 965 | CD58 molecule | Hs_CD58_2 | Hs_CD58_5 | Hs_CD58_6 |
| CD6 | 923 | CD6 ANTIGEN | Hs_CD6_1 | Hs_CD6_2 | Hs_CD6_3 |
| CD63 | 967 | CD63 molecule | Hs_CD63_10 | Hs_CD63_7 | Hs_CD63_8 |
| CD81 | 975 | CD81 molecule | Hs_CD81_11 | Hs_CD81_10 | Hs_CD81_8 |
| CDC23 | 8697 | CDC23 (CELL DIVISION CYCLE 23, YEAST, HOMOLOG) | Hs_CDC23_5 | Hs_CDC23_4 | Hs_CDC23_7 |
| CDK4 | 1019 | CYCLIN-DEPENDENT KINASE 4 | Hs_CDK4_9 | Hs_CDK4_6 | Hs_CDK4_4 |
| CDKN1B | 1027 | CYCLIN-DEPENDENT KINASE INHIBITOR 1B (P27, KIP1) | Hs_CDKN1B_6 | Hs_CDKN1B_3 | Hs_CDKN1B_8 |
| CEL | 1056 | carboxyl ester lipase (bile salt-stimulated lipase) | Hs_CEL_1 | Hs_CEL_3 | Hs_CEL_5 |

TABLE 3-continued

| | | | | | |
|---|---|---|---|---|---|
| CHST5 | 23563 | carbohydrate (N-acetylglucosamine 5-0) sulfotransferase 5 | Hs_CHST5_2 | Hs_CHST5_5 | Hs_CHST5_7 |
| CLIC4 | 25932 | chloride intracellular channel 4 | Hs_CLIC4_5 | Hs_CLIC4_2 | Hs_CLIC4_3 |
| CLK1 | 1195 | CDC-LIKE KINASE 1 | Hs_CKLK1_1 | Hs_CKLK1_11 | Hs_CKL1_2 |
| CNNM1 | 26507 | cyclin M1 | Hs_CNNM1_3 | Hs_CNNM1_5 | Hs_CNNM1_6 |
| COPA | 1314 | coatomer protein complex, subunit alpha | Hs_COPA_5 | Hs_COPA_6 | Hs_COPA_7 |
| COPB1 | 1315 | coatomer protein complex, subunit beta 1 | Hs_COPB_5 | Hs_COPB1_4 | Hs_COPAB1_5 |
| COPB2 | 9276 | coatomer protein complex, subunit beta 2 (beta prime) | Hs_COPB2_6 | Hs_COPB2_7 | Hs_COPB2_1 |
| COPG | 22820 | coatomer protein complex, subunit gamma | Hs_COPG_1 | Hs_COPG_5 | Hs_COPG_6 |
| CRAMP1L | 57585 | Crm, cramped-like (Drosophila) | Hs_CRAMP1L_1 | Hs_CRAMP1L_2 | Hs_CRAMP1L_7 |
| CRYAA | 1409 | crystallin, alpha A | Hs_CRYAA_1 | Hs_CRYAA_2 | Hs_CRYAA_3 |
| CTA-216E10.6 | 79640 | HYPOTHETICAL PROTEIN FLJ23584 | Hs_CTA-216E10.6_1 | Hs_CTA-216E10.6_3 | Hs_CTA-216E10.6_2 |
| CUEDC2 | 79004 | CUE DOMAIN CONTAINING 2 | Hs_CUEDC2_5 | Hs_CUEDC2_6 | Hs_CUEDC2_4 |
| CXCR6 | 10663 | chemokine (C-X-C motif) receptor 6 | Hs_CXCR6_1 | Hs_CXCR6_2 | Hs_CXCR6_3 |
| CYC1 | 1537 | CYTOCHROME C-1 | Hs_CRC1_1 | Hs_CYC1_2 | Hs_CYC1_3 |
| CYP17A1 | 1586 | cytochrome P450, family 17, subfamily A, polypeptide 1 | Hs_CYP17A1_1 | Hs_CYP17A1_2 | Hs_CYP17A1_3 |
| CYP2U1 | 113612 | cytochrome P450, family 2, subfamily U, polypeptide 1 | Hs_CYP2U1_1 | Hs_CYP2U1_2 | Hs_CYP2U1_3 |
| DBT | 1629 | dihydrolipoamide branched chain transacylase E2 | Hs_DBT_2 | Hs_DBT_4 | Hs_DBT_5 |
| DCLK2 | 166614 | doublecortin-like kinase 2 | Hs_DCAMKL2_2 | Hs_DCAMKL2_3 | Hs_DCAMKL2_5 |
| DGKH | 169851 | diacylglycerol kinase, eta | Hs_DGKH_1 | Hs_DGKH_4 | Hs_DGKH_1 |
| DGUDK | 1716 | DEOXYGUANOSINE KINASE | Hs_DGUDK_7 | Hs_DGUDK_6 | Hs_DGUDK_1 |
| DHRS2 | 10202 | dehydrogenase/reductase (SDR family) member 2 | Hs_DHRS2_6 | Hs_DHRS2_9 | Hs_DHRS2_3 |
| DLG2 | 1740 | discs, large homolog 2 (Drosophila) | Hs_DLG2_2 | Hs_DLG2_5 | NA |
| DMAP1 | 55929 | DNA METHYLTRANSFERASE 1 ASSOCIATED PROTEIN 1 | Hs_DMAP1_6 | Hs_DMAP1_5 | Hs_DMAP1_4 |
| DMRT1 | 1761 | DOUBLESEX AND MAB-3 RELATED TRANSCRIPTION FACTOR 1 | Hs_DMRT1_3 | Hs_DMRT1_7 | Hs_DMRT1_8 |
| DTX3 | 196403 | deltex homolog 3 (Drosophila) | Hs_DTX3_4 | Hs_DTX3_5 | Hs_DTX3_6 |
| DUSP27 | 92235 | dual specificity phosphatase 27 (putative) | Hs_DUSP27_1 | Hs_DUSP27_2 | Hs_DUSP27_3 |
| E2F1 | 1869 | E2F TRANSCRIPTION FACTOR 1 | Hs_E2F1_3 | Hs_E2F1_4 | Hs_E2F1_7 |
| EEF1A1 | 1915 | eukaryotic translation elongation factor 1 alpha 1 | Hs_EEF1A1_10 | Hs_EEF1A1_11 | Hs_EEF1A1_12 |
| EIF3A | 8661 | eukaryotic translation initiation factor 3, subunit A | Hs_EIF3S10_6 | Hs_EIF3S10_2 | Hs_EIF3S10_7 |
| EIF3C | 8683 | eukaryotic translation initiation factor 3, subunit C | Hs_EIF3S8_5 | Hs_EIF3S8_6 | Hs_EIF3S8_1 |
| EIF3G | 8666 | eukaryotic translation initiation factor 3, subunit G | Hs_EIF3S4_1 | Hs_EIF3S4_10 | Hs_EIF3S4_2 |
| EIF4A3 | 9775 | eukaryotic translation initiation factor 4a, isoform 3 | Hs_DDX48_3 | Hs_DDX48_4 | Hs_DDX48_5 |
| ENGASE | 64772 | endo-beta-N-acetylglucosaminidase | Hs_FLJ21865_5 | Hs_FLJ21865_5 | Hs_FLJ21865_6 |
| EPB49 | 2039 | erythrocyte membrane protein band 4.9 (dematin) | Hs_EPB49_1 | Hs_EPB49_2 | Hs_EPB49_3 |
| EPHB6 | 2051 | EPH RECEPTOR B6 | Hs_EPHB6_3 | Hs_EPHB6_4 | Hs_EPHB6_6 |
| ERN2 | 10595 | ENDOPLASMIC RETICULUM TO NUCLEUS SIGNALLING 2 | Hs_ERN2_10 | Hs_ERN2_2 | Hs_ERN2_3 |
| FAU | 2197 | Finkel-Biskis-Reilly murine sarcoma virus (FBR-MuSV) ubiquitously expressed | Hs_FAU_2 | Hs_FAU_4 | Hs_FAU_5 |
| FBXW10 | 10517 | F-box and WD repeat domain containing 10 | Hs_FBXW10_11 | Hs_FBXW10_3 | Hs_FBXW10_6 |
| FCH02 | 115548 | FCH DOMAIN ONLY 2 | Hs_FCH02_3 | Hs_FCH02_8 | Hs_FCH02_7 |
| FCRL6 | 343413 | Fc receptor-like 6 | Hs_LOC343413_3 | Hs_LOC343413_4 | Hs_FCRL6_1 |
| FERMT3 | 83796 | fermitin family homolog 3 (Drosophila) | Hs_URP2_4 | Hs_URP2_5 | Hs_URP2_6 |
| FGF3 | 2248 | FIBROBLAST GROWTH FACTOR 3 (MURINE MAMMARY TUMOR VIRUS INTEGRATION SITE (V-INT-2) ONCOGENE HOMOLOG) | Hs_FGF3_3 | Hs_FGF3_4 | Hs_FGF3_6 |
| FLJ11235 | 54588 | hypothetical FLJ11235 | Hs_FLJ11235_1 | Hs_FLJ11235_2 | Hs_FLJ11235_3 |
| FLJ20489 | 55652 | HYPOTHETICAL PROTEIN FLJ20489 | Hs_FLJ20489_3 | Hs_FLJ20489_4 | Hs_FLJ20489_5 |
| FLJ34077 | 484033 | weakly similar to zinc finger protein 195 | Hs_FLJ34077_1 | Hs_FLJ34077_2 | Hs_FLJ34077_3 |
| FNTB | 2342 | FARNESYLTRANSFERASE, CAAX BOX, BETA | Hs_FNTB_7 | Hs_FNTB_1 | Hs_FNTB_10 |
| G6PC | 2538 | GLUCOSE-6-PHOSPHATASE, CATALYTIC (GLYCOBEN STORAGE DISEASE TYPE I, VON GIERKE DISEASE) | Hs_G6PC_3 | Hs_G6PC_7 | Hs_G6PC_6 |
| GCLC | 2729 | GLUTAMATE-CYSTEINE LIGASE, CATALYTIC SUBUNIT | Hs_GCLC_4 | Hs_GCLC_7 | Hs_GCLC_10 |
| GNMT | 27232 | glycine N-methyltransferase | Hs_GNMT_2 | Hs_GNMT_3 | Hs_GNMT_4 |
| GNRH2 | 2797 | GONADOTROPIN-RELEASING HORMONE 2 | Hs_GNRH2_8 | Hs_GNRH2_7 | Hs_GNRH2_6 |

TABLE 3-continued

| | | | | |
|---|---|---|---|---|
| GPR146 | 155330 | G protein-coupled receptor 146 | Hs_GPR146_1 | Hs_GPR146_3 | Hs_GPR146_4 |
| GRID2 | 2895 | GLUTAMATE RECEPTOR, IONOTROPIC, DELTA 2 | Hs_GRID2_3 | Hs_GRID2_3 | Hs_GRID2_4 |
| GRIN2C | 2905 | glutamate receptor, ionotropic, N-methyl D-aspartate 2C | Hs_GRIN2C_1 | Hs_GRIN2C_2 | Hs_GRIN2C_3 |
| GRP | 2922 | GASTRIN-RELEASING PEPTIDE | Hs_GRP_6 | Hs_GRP_9 | Hs_GRP_8 |
| GSK3A | 2931 | GLYCOGEN SYNTHASE KINASE 3 ALPHA | Hs_GSK3A_6 | Hs_GSK3A_12 | Hs_GSK3A_11 |
| HARBI1 | 9776 | KIAA8652 | Hs_KIAA9652_7 | Hs_KIAA9652_3 | Hs_KIAA9652_4 |
| HIBCH | 86275 | 3-hydroxyisobutyryl-Coenzyme A hydrolase | Hs_HIBCH_1 | Hs_HIBCH_2 | Hs_HIBCH_3 |
| HIST1H2BN | 8341 | histone cluster 1, H2bn | Hs_HIST1H2BN_10 | Hs_HIST1H2BN_2 | Hs_HIST1H2BN_4 |
| HPGD | 3248 | hydroxyprostaglandin dehydrogenase 15-(NAD) | Hs_HPGD_1 | Hs_HPGD_2 | Hs_HPGD_3 |
| HSF4 | 3299 | heat shock transcription factor 4 | Hs_HSF4_1 | Hs_HSF4_2 | Hs_HSF4_3 |
| HSPD1 | 3329 | heat shock 60 kDa protein 1 (chaperonin) | Hs_HSPD1_5 | Hs_HSPD1_7 | Hs_HSPD1_8 |
| ICAM2 | 3384 | INTERCELLULAR ADHESION MOLECULE 2 | Hs_ICAM2_4 | Hs_ICAM2_5 | Hs_ICAM2_7 |
| ICEBERG | 69082 | ICEBERG caspase-1 inhibitor | Hs_ICEBERG_1 | Hs_ICEBERG_2 | Hs_ICEBERG_4 |
| IL17RA | 23765 | interleukin 17 receptor A | Hs_IL17R_1 | Hs_IL17R_2 | Hs_IL17RA_1 |
| IL1A | 3552 | interleukin 1, alpha | Hs_IL1A_2 | Hs_IL1A_2 | Hs_IL1A_3 |
| IQCF2 | 389123 | IQ motif containing F2 | Hs_IQCF2_1 | Hs_IQCF2_2 | Hs_IQCF2_3 |
| IRF2 | 3660 | INTERFERON REGULATORY FACTOR 2 | Hs_IRF2_2 | Hs_IRF2_3 | Hs_IRF2_1 |
| ISG15 | 9636 | ISG15 ubiquitin-like modifier | Hs_G1P2_1 | Hs_ISG15_1 | Hs_ISG15_3 |
| ITLN1 | 55600 | intelectin 1 (galactofuranose binding) | Hs_ITLN1_1 | Hs_ITLN1_3 | Hs_ITLN1_4 |
| JARID1D | 8284 | jumonji, AT rich interactive domain 1D | Hs_SMCY_1 | Hs_SMCY_2 | Hs_SMCY_3 |
| JUN | 3728 | jun oncogene | Hs_JUN_5 | Hs_JUN_1 | Hs_JUN_2 |
| KATNB1 | 10300 | katanin p80 (WD repeat containing) subunit B 1 | Hs_KATNB1_1 | Hs_KATNB1_2 | Hs_KATNB1_3 |
| KCNAB3 | 9196 | POTASSIUM VOLTAGE-GATED CHANNEL, SHAKER-RELATED SUBFAMILY, BETA MEMBER 3 | Hs_KCNAB3_4 | Hs_KCNAB3_1 | Hs_KCNAB3_3 |
| KCNJ12 | 3768 | potassium inwardly-rectifying channel, subfamily J, member 12 | Hs_KCNJ12_2 | Hs_KCNJ12_4 | Hs_KCNJ12_5 |
| KIAA0664 | 23277 | KIAA0664 | Hs_KIAA0664_2 | Hs_KIAA0664_3 | Hs_KIAA0664_4 |
| KIAA0947 | 23379 | KIAA0947 PROTEIN | Hs_KIAA0947_2 | Hs_KIAA0947_5 | Hs_KIAA0947_4 |
| KIAA1128 | 54462 | KIAA1128 | Hs_KIAA1128_4 | Hs_KIAA1128_3 | Hs_KIAA1128_5 |
| KIAA1267 | 284958 | DKFZP727C091 PROTEIN | Hs_LOC284058_3 | Hs_KIAA1267_2 | Hs_LOC284058_4 |
| KIF11 | 3832 | kinesin family member 11 | Hs_KIF11_6 | Hs_KIF11_7 | Hs_KIF11_8 |
| KIF23 | 9493 | KINESIN FAMILY MEMBER 23 | Hs_KIF23-11 | Hs_KIF23_5 | Hs_KIF23_2 |
| KIF3A | 11127 | kinesin family member 3A | Hs_KIF3A_10 | Hs_KIF3A_4 | Hs_KIF3A_5 |
| KPNB1 | 3837 | KARYOPHERIN (IMPORTIN) BETA 1 | Hs_KPNB1_2 | Hs_KPNB1_3 | Hs_KPNB1_6 |
| LAMC2 | 3918 | LAMININ, GAMMA 2 | Hs_LAMC2_1 | Hs_LAMC2_4 | Hs_LAMC2_2 |
| LARP1 | 23367 | La ribonucleoprotein domain family, member 1 | Hs_LARP_4 | Hs_LARP1_1 | Hs_LARP1_2 |
| LHX3 | 8022 | LIM homeobox 3 | Hs_LHX3_2 | Hs_LHX3_3 | Hs_LHX3_4 |
| LINGO1 | 84894 | leucine rich repeat and Ig domain containing 1 | Hs_LRRN6A_1 | Hs_LRRN6A_4 | Hs_LRRN6A_5 |
| LOC162993 | 162993 | hypothetical protein LOC162993 | Hs_LOC162993_1 | Hs_LOC162993_2 | Hs_LOC162993_3 |
| LOC399940 | 399940 | similar to Tripartite motif protein 49 (RING finger protein 18) (Testis-specific ring-finger protein) | Hs_LOC399940_5 | Hs_LOC399940_6 | Hs_LOC399940_7 |
| LOC401431 | 401431 | hypothetical gene LOC401431 | Hs_LOC401431_1 | Hs_LOC401431_2 | Hs_LOC401431_3 |
| LOC440733 | 440733 | similar to 40S ribosomal protein S15 (RIG protein) | Hs_LOC440733_11 | Hs_LOC440733_12 | Hs_LOC440733_13 |
| LPPR4 | 9899 | plasticity related gene 1 | Hs_LPPR4_6 | Hs_LPPR4_7 | Hs_LPPR4_8 |
| MAN2B1 | 4125 | MANNOSIDASE, ALPHA, CLASS 2B, MEMBER 1 | Hs_MAN2B1_4 | Hs_MAN2B1_6 | Hs_MAN2B1_7 |
| MAP2K3 | 5606 | mitogen-activated protein kinase kinase 3 | Hs_MAP2K3_5 | Hs_MAP2K3_6 | Hs_MAP2K3_7 |
| MATN3 | 4148 | matrilin 3 | Hs_MATN3_1 | Hs_MATN3_2 | Hs_MATN3_3 |
| MED6 | 10001 | mediator complex subunit 6 | Hs_MED6_1 | Hs_MED6_2 | Hs_MED6_6 |
| MKL1 | 57591 | MEGAKARYOBLASTIC LEUKEMIA (TRANSLOCATION) 1 | Hs_MKL1_1 | Hs_MKL1_8 | Hs_MKL1_6 |
| MRPS12 | 6183 | MITOCHONDRIAL RIBOSOMAL PROTEIN S12 | Hs_MRPS12_7 | Hs_MRPS12_1 | Hs_MRPS12_3 |
| MYC | 4609 | v-myc myelocytomatosis viral oncogene homolog (avian) | Hs_MYC_5 | Hs_MYC_6 | Hs_LOC731404_4 |
| MYEF2 | 50804 | MYELIN EXPRESSION FACTOR 2 | Hs_MYEF2_4 | Hs_MYEF2_5 | Hs_MYEF2_8 |
| MYOD1 | 4654 | myogenic differentiation 1 | Hs_MYOD1_1 | Hs_MYOD1_3 | Hs_MYOD1_4 |
| NAE1 | 8883 | AMYLOID BETA PRECURSOR PROTEIN BINDING PROTEIN 1 | Hs_APPBP1_5 | Hs_APPBP1_7 | Hs_APPBP1_8 |

TABLE 3-continued

| | | | | | |
|---|---|---|---|---|---|
| NDUFV3 | 4731 | NADH DEHYDROGENASE (UBIQUINONE) FLAVOPROTEIN 3, 10 KDA | Hs_NDUFV3_3 | Hs_NDUFV3_4 | Hs_NDUFV3_5 |
| NECAP2 | 55707 | NECAP ENDOCYTOSIS ASSOCIATED 2 | Hs_FLJ10420_3 | Hs_NECAP2_1 | Hs_NECAP2_3 |
| NEK8 | 284086 | NIMA (never in mitosis gene a) - related kinase 8 | Hs_NEK8_5 | Hs_NEK8_6 | Hs_NEK8_10 |
| NEK9 | 91754 | NIMA (never in mitosis gene a) - related kinase 9 | Hs_NEK9_7 | Hs_NEK9_10 | Hs_NEK9_11 |
| NSF | 4905 | N-ETHYLMALEIMIDE-SENSITIVE FACTOR | Hs_NSF_12 | Hs_NSF_11 | Hs_NSF_10 |
| NTHL1 | 4913 | nth endonuclease III-like 1 (E. coli) | Hs_NTHL1_3 | Hs_NTHL1_4 | Hs_NTHL1_5 |
| NUP205 | 23165 | nucleoporin 205 kDa | Hs_NUP205_3 | Hs_NUP205_4 | Hs_NUP205_8 |
| NUP98 | 4928 | nucleoporin 98 kDa | Hs_NUP98_3 | Hs_NUP98_5 | Hs_NUP98_7 |
| NXF1 | 10482 | nuclear RNA export factor 1 | Hs_NXF1_1 | Hs_NXF1_2 | Hs_NXF1_3 |
| ODZ4 | 26011 | odz, odd Oz/ten-m homolog 4 (Drosophila) | Hs_ODS4_2 | Hs_ODS4_3 | Hs_ODS4_4 |
| OPN1SW | 611 | opsin 1 (cone pigments), short-wave-sensitive | Hs_OPN1SW_1 | Hs_OPN1SW_2 | Hs_OPN1SW_3 |
| P76 | 196463 | mannose-6-phosphate protein p76 | Hs_LOC196463_1 | Hs_LOC196463_2 | Hs_LOC196463_3 |
| PCDH18 | 54510 | protocadherin 18 | Hs_PCDH18_1 | Hs_PCDH18_2 | Hs_PCDH18_3 |
| PHF2 | 5253 | PHD FINGER PROTEIN 2 | Hs_PHF2_3 | Hs_PHF2_4 | Hs_PHF2_5 |
| PIK3R5 | 23533 | phosphoinositide-3-kinase, regulatory subunit 5 | Hs_PIK3R5_2 | Hs_PIK3R5_3 | Hs_PIK3R5_4 |
| PIK3R6 | 146850 | CHROMOSOME 17 OPEN READING FRAME 38 | Hs_C17orf38_3 | Hs_C17orf38_4 | Hs_C17orf38_5 |
| PIN1 | 5300 | peptidylprolyl cis/trans isomerase, NIMA-interacting 1 | Hs_PIN1_5 | Hs_PIN1_6 | Hs_PIN1_3 |
| PKHD1 | 5314 | polycystic kidney and hepatic disease 1 (autosomal recessive) | Hs_PKHD1_1 | Hs_PKHD1_3 | Hs_PKHD1_5 |
| PKN1 | 5585 | PROTEIN KINASE N1 | Hs_PKN1_6 | Hs_PKN1_3 | Hs_PKN1_7 |
| PLAU | 5328 | PLASMINOGEN ACTIVATOR, UROKINASE | Hs_PLAU_2 | Hs_PLAU_10 | Hs_PLAU_11 |
| PLD2 | 5338 | phopholipase D2 | Hs_PLD2_2 | Hs_PLD2_3 | Hs_PLD2_5 |
| PLK3 | 1263 | polo-like kinase 3 (Drosophila) | Hs_PLK3_5 | Hs_PLK3_6 | Hs_PLK3_7 |
| POLK | 51426 | POLYMERASE (DNA DIRECTED) KAPPA | Hs_POLK_4 | Hs_POLK_3 | Hs_POLK_2 |
| POLR2H | 5437 | POLYMERASE (RNA) II (DNA DIRECTED) POLYPEPTIDE H | Hs_POLR2H_2 | Hs_POLR2H_3 | Hs_POLR2H_4 |
| POLR2L | 5441 | polymerase (RNA) II (DNA directed) polypeptide L, 7.6 kDa | Hs_POLR2L_1 | Hs_POLR2L_2 | Hs_POLR2L_3 |
| PPARA | 5465 | PEROXISOME PROLIFERATIVE ACTIVATED RECEPTOR, ALPHA | Hs_PPARA_8 | Hs_PPARA_7 | Hs_PPARA_6 |
| PPP1R14D | 54866 | protein phosphatase 1, regulatory (inhibitor) subunit 14D | Hs_PP1R14D_1 | Hs_PP1R14D_2 | Hs_PP1R14D_5 |
| PRDX5 | 25824 | PEROXIREDOXIN 5 | Hs_PRDX5_1 | Hs_PRDX5_3 | Hs_PRDX5_4 |
| PRPF8 | 10594 | PRP8 pre-mRNA processing factor 8 homolog (S. cerevisiae) | Hs_PRPS1_1 | Hs_PRPS1_3 | Hs_PRPS1_4 |
| PRSS27 | 83886 | protease, serine 27 | Hs_MPN_1 | Hs_MPN_2 | Hs_PRSS27_1 |
| PRX | 57716 | PERIAXIN | Hs_PRX_3 | Hs_PRX_6 | Hs_PRX_7 |
| PSENEN | 55851 | PRESENILIN ENHANCER 2 HOMOLOG (C. ELEGANS) | Hs_PEN2_1 | Hs_PEN2_6 | Hs_PSENEN_1 |
| PSMA1 | 5682 | proteasome (prosome, macropain) subunit, alpha type, 1 | Hs_PSMA1_1 | Hs_PSMA1_12 | Hs_PSMA1_3 |
| PSMD2 | 5788 | proteasome (prosome, macropain) 26S subunit, non-ATPase, 2 | Hs_PSMD2_5 | Hs_PSMD2_6 | Hs_PSMD2_2 |
| PTPLA | 9200 | PROTEIN TYROSINE PHOSPHATASE-LIKE (PROLINE INSTEAD OF CATALYTIC ARGININE), MEMBER A | Hs_PTPLA_8 | Hs_PTPLA_3 | Hs_PTPLA_1 |
| PTPRN | 5798 | protein tyrosine phosphatase, receptor type, N | Hs_PTPRN_3 | Hs_PTPRN_4 | Hs_PTPRN_5 |
| RAB4A | 5867 | RAB4A, MEMBER RAS ONCOGENE FAMILY | Hs_RAB4A_5 | Hs_RAB4A_11 | Hs_RAB4A_10 |
| RAB6B | 51560 | RAB6B, member RAS oncogene family | Hs_RAB6B_2 | Hs_RAB6B_3 | Hs_RAB6B_4 |
| RACGAP1 | 29127 | RAC GTPASE ACTIVATING PROTEIN 1 | Hs_RACGAP1_1 | Hs_RACGAP1_5 | Hs_RACGAP1_3 |
| RAX | 30062 | retina and anterior neural fold homeobox | Hs_RAX_2 | Hs_RAX_3 | Hs_RAX_5 |
| RBM42 | 79171 | RNA binding motif protein 42 | Hs_MGC10433_1 | Hs_MGC10433_2 | Hs_MGC10433_4 |
| RETN | 56729 | RESISTIN | Hs_RETN_3 | Hs_RETN_2 | Hs_RETN_5 |
| RFFL | 117584 | RING FINGER AND FYVE-LIKE DOMAIN CONTAINING 1 | Hs_RFFL_4 | Hs_RFFL_1 | Hs_RFFL_3 |
| RNF150 | 57484 | ring finger protein 150 | Hs_RNF150_3 | Hs_RNF150_5 | Hs_RNF150_6 |
| RPL35 | 11224 | ribosomal protein L35 | Hs_RPL35_5 | Hs_RPL35_6 | Hs_RPL35_3 |
| RPLP2 | 6181 | ribosomal protein, large, P2 | Hs_RPLP2_1 | Hs_RPLP2_2 | Hs_RPLP2_3 |
| RPS10 | 6204 | ribosomal protein S10 | Hs_RPS10_2 | Hs_RPS10_5 | Hs_RPS10_7 |
| RPS14 | 6208 | ribosomal protein S14 | Hs_RPS14_4 | Hs_RPS14_6 | Hs_RPS14_8 |
| RPS16 | 6217 | RIBOSOMAL protein S16 | Hs_RPS16_5 | Hs_RPS16_8 | Hs_RPS16_7 |
| RPS27A | 6233 | ribosomal protein S27a | Hs_RPS27A_2 | Hs_RPS27A_3 | Hs_RPS27A_7 |
| RPS5 | 6193 | ribosomal protein S5 | Hs_RPS5_2 | Hs_RPS5_5 | Hs_RPS5_6 |
| RPS6KA6 | 27330 | ribosomal protein S6 kinase, 90 kDa, polypeptide 6 | Hs_RPS6KA6_10 | Hs_RPS6KA6_3 | Hs_RPS6KA6_6 |

TABLE 3-continued

| | | | | | |
|---|---|---|---|---|---|
| RUNX1 | 861 | RUNT-RELATED TRANSCRIPTION FACTOR 1 (ACUTE MYELOID LEUKEMIA 1; AML1) | Hs_RUNX1_5 | Hs_RUNX1_4 | Hs_RUNX1_6 |
| SAFB | 6294 | scaffold attachment factor B | Hs_SAFB_1 | Hs_SAFB_3 | Hs_SAFB_4 |
| SCAF1 | 58506 | SERINE ARGININE-RICH PRE-MRNA SPLICING FACTOR SR-A1 | Hs_SR-A1_2 | Hs_SR-A1_3 | Hs_SR-A1_4 |
| SCAMP4 | 113178 | SECRETORY CARRIER MEMBRANE PROTEIN 4 | Hs_SCAMP4_7 | Hs_SCAMP4_3 | Hs_SCAMP4_4 |
| SCARB1 | 949 | scavenger receptor class B, member 1 | Hs_SCARB1_6 | Hs_SCARB1_7 | Hs_SCARB1_8 |
| SDC1 | 6382 | SYNDECAN 1 | Hs_SDC1_1 | Hs_SDC1_1 | Hs_SDC1_6 |
| SELPLG | 6404 | selectin P ligand | Hs_SELPLG_2 | Hs_SELPLG_3 | Hs_SELPLG_4 |
| SERPINA6 | 866 | SERPIN PEPTIDASE INHIBITOR, CLADE A (ALPHA-1 ANTIPROTEINASE, ANTITRYPSIN), MEMBER 6 | Hs_SERPINA6_4 | Hs_SERPINA6_3 | Hs_SERPINA6_1 |
| SERPINB2 | 5055 | serpin peptidase inhibitor, clade B (ovalbumin), member 2 | Hs_SERPINB2_2 | Hs_SERPINB2_5 | Hs_SERPINB2_6 |
| SERPINE2 | 5270 | SERPIN PEPTIDASE INHIBITOR, CLADE E (NEXIN, PLASMINOGEN ACTIVATOR | Hs_SERPINE2_6 | Hs_SERPINE2_1 | Hs_SERPINE2_7 |
| SEZ6L2 | 26470 | seizure related 6 homolog (mouse)-like 2 | Hs_SEZ6L2_7 | Hs_SEZ6L2_7 | Hs_SEZ6L2_8 |
| SF3A1 | 10291 | splicing factor 3a, subunit 1, 120 kDa | Hs_SF3A1_1 | Hs_SF3A1_2 | Hs_SF3A1_3 |
| SF3B1 | 23451 | splicing factor 3b, subunit 1, 155 kDa | Hs_SF3B1_4 | Hs_SF3B1_5 | Hs_SF3B1_6 |
| SF3B14 | 51639 | splicing factor 3B, 14 kDa subunit | Hs_SF3B14_5 | Hs_SF3B14_5 | Hs_SF3B14_6 |
| SFTPB | 6439 | surfactant protein B | Hs_SFTPB_15 | Hs_SFTPB_16 | Hs_SFTPB_17 |
| SIGMAR1 | 10280 | sigma non-opiod intracellular receptor 1 | Hs_OPRS1_1 | Hs_OPRS1_3 | Hs_OPRS1_4 |
| SLC12A4 | 6560 | SOLUTE CARRIER FAMILY 12 (POTASSIUM/CHLORIDE TRANSPORTERS), MEMBER 4 | Hs_SLC12A4_4 | Hs_SLC12A4_5 | Hs_SLC12A4_6 |
| SLC22A6 | 9356 | solute carrier family 22 (organic anion transporter), member 6 | Hs_SLC22A6_3 | Hs_SLC22A6_6 | Hs_SLC22A6_7 |
| SLC25A19 | 60385 | solute carrier family 25 (mitochondrial thiamine pyrophosphate carrier), member 19 | Hs_SLC25A19_1 | Hs_SLC25A19_3 | Hs_SLC25A19_5 |
| SLC4A8 | 9498 | solute carrier family 4, sodium bicarbonate cotransporter, member 8 | Hs_SLC4A8_1 | Hs_SLC4A8_2 | Hs_SLC4A8_3 |
| SLC7A1 | 6541 | solute carrier family 7 (cationic amino acid transporter, y+ system), member1 | Hs_SLC7A1_1 | Hs_SLC7A1_2 | Hs_SLC7A1_3 |
| SMU1 | 55234 | SMU-1 SUPPRESSOR OF MEC-8 AND UNC-52 HOMOLOG (C. ELEGANS) | Hs_SMU1_7 | Hs_LOC728623_1 | Hs_LOC728623_2 |
| SNRP70 | 6625 | small nuclear ribonucleoprotein 70 kDa polypeptide (RNP antigen) | Hs_SNRP70_2 | Hs_SNRP70_3 | Hs_SNRP70_4 |
| SNRPF | 6636 | small nuclear ribonucleoprotein polypeptide F | Hs_SNRPF_5 | Hs_SNRPF_7 | Hs_SNRPF_8 |
| SNX6 | 58533 | SORTING NEXIN 6 | Hs_SNX6_10 | Hs_SNX6_11 | Hs_SNX6_4 |
| SNX9 | 51429 | sorting nexin 9 | Hs_SNX9_1 | Hs_SNX9_2 | Hs_SNX9_3 |
| SON | 6651 | SON DNA binding protein | Hs_SON_2 | Hs_SON_4 | Hs_SON_5 |
| SRRM2 | 23524 | SERINE/ARGININE REPETITIVE MATRIX 2 | Hs_SRRM2_4 | Hs_SRRM2_7 | Hs_SRRM2_5 |
| STAB1 | 23166 | stabilin 1 | Hs_STAB1_2 | Hs_STAB1_2 | Hs_STAB1_3 |
| SULF2 | 55959 | sulfatase 2 | Hs_SULF2_10 | Hs_SULF2_5 | Hs_SULF2_6 |
| SUPT6H | 6830 | suppressor of Ty 6 homolog (S. cerevisiae) | Hs_SUPT6H_5 | Hs_SUPT6H_6 | Hs_SUPT6H_7 |
| TBL3 | 10607 | TRANSDUCIN (BETA)-LIKE 3 | Hs_TBL3_4 | Hs_TBL3_3 | Hs_TBL3_5 |
| TCF3 | 6929 | transcription factor 3 (E2A immunoglobulin enhancer binding factors E12/E47) | Hs_TCF3_1 | Hs_TCF3_5 | NA |
| TFE3 | 7030 | transcription factor binding to IGHM enhancer 3 | Hs_TFE3_1 | Hs_TFE3_2 | Hs_TFE3_3 |
| TMEN50B | 757 | transmembrane protein 50B | Hs_C21orf4_3 | Hs_C21orf4_5 | Hs_C21orf4_7 |
| TNFRSF18 | 8784 | tumor necrosis factor receptor superfamily, member 18 | Hs_TNFRSF18_2 | Hs_TNFRSF18_4 | Hs_TNFRSF18_5 |
| TNK2 | 10188 | tyrosine kinase, non-receptor, 2 | Hs_TNK2_4 | Hs_TNK2_5 | Hs_TNK2_6 |
| TRERF1 | 55809 | transcriptional regulating factor 1 | Hs_TRERF1_3 | Hs_TRERF1_6 | Hs_TRERF1_7 |
| TRIM14 | 9830 | tripartite motif-containing 14 | Hs_TRIM14_1 | Hs_TRIM14_5 | Hs_TRIM14_6 |
| TRIM21 | 6737 | tripartite motif-containing 21 | Hs_TRIM21_11 | Hs_TRIM21_6 | Hs_TRIM21_7 |
| TRIM60 | 166655 | tripartite motif-containing 60 | Hs_TRIM60_3 | Hs_TRIM60_6 | Hs_TRIM60_7 |
| TSSK6 | 83983 | testis-specific serine kinase 6 | Hs_SSTK_2 | Hs_SSTK_3 | Hs_SSTK_4 |
| TUBB4 | 10382 | TUBULIN, BETA 4 | Hs_TUBB4_2 | Hs_TUBB4_3 | Hs_TUBB4_6 |
| TXNL4A | 10907 | thioredoxin-like 4A | Hs_TXNL4A_3 | Hs_TXNL4A_3 | Hs_TXNL4A_5 |
| UBAC2 | 337867 | UBA domain containing 2 | Hs_PHGDHL1_5 | Hs_PHGDHL1_6 | NA |
| UBE2N | 7334 | UBIQUITIN-CONJUGATING ENZYME E2N (UBC13 HOMOLOG, YEAST) | Hs_UBE2N_5 | Hs_UBE2N_6 | Hs_UBE2N_7 |
| VNNZ | 8875 | VANIN 2 | Hs_VNN2_1 | Hs_VNN2_4 | Hs_VNN2_2 |
| WNT3A | 89780 | WINGLESS-TYPE MMTV INTEGRATION SITE FAMILY, MEMBER 3A | Hs_WNT3A_4 | Hs_WNT3A_2 | Hs_WNT3A_1 |
| WNT9A | 7483 | wingless-type MMTV integration site family, member 9A | Hs_WNT9A_1 | Hs_WNT9A_2 | Hs_WNT9A_3 |

TABLE 3-continued

| Gene Symbol | Locus ID | siRNA4ID | siRNA1 Target | siRNA2 Target | siRNA3 Target | Hs_XAB2_5<br>Hs_XPNPEP1_1<br>Hs_XPO1_1<br>Hs_XRCC6_2<br>siRNA3 Target | Hs_XAB2_6<br>Hs_XPNPEP1_2<br>Hs_XPO1_2<br>Hs_XRCC6_3<br>siRNA4 Target | Hs_XAB2_4<br>Hs_XPNPEP1_3<br>Hs_XPO1_5<br>Hs_XRCC6_4<br>siRNA1 WST | SEQ ID NOS: |
|---|---|---|---|---|---|---|---|---|---|
| XAB2 | 56949 | XPA binding protein 2 | | | | | | | |
| XPNPEP1 | 7511 | X-prolyl aminopeptidase (aminopeptidase P) 1, soluble | | | | | | | |
| XPO1 | 7514 | exportin 1 (CRM1 homolog, yeast) | | | | | | | |
| XRCC6 | 2547 | X-ray repair complementing defective repair in Chinese hamster cells 6 (Ku autoantigen, 70 kDa) | | | | | | | |
| AAMP | 14 | Hs_AAMP_5 | GAGGAAGAAGAATACTAGTTAAA | CTGGATGTGGAAAGTCCGAA | CTGGACTTTGCCCTCAGCAA | CCGCATGGAGTCCGAATCGGA | 1.71 | 25-28 |
| ACTN1 | 87 | Hs_ACTN1_4 | AACACCATGCATGCCATGCAA | CCGACCCGAGCTGATTGACTA | AAGGATGAACTCATCACAAAT | AACGATTACATGCAGCCAGAA | 1.74 | 29-32 |
| AHCYL1 | 10768 | Hs_AHCYL1_1 | CCCACTTGGATTTATAGTATA | AAACAGTTGTATCGTATGCAA | CTGATAGAACTCATAATGCA | CAGGGTGTAAAGCTAAATGA | 1.36 | 33-36 |
| AIG1 | 51390 | Hs_AIG1_3 | CACGACGGTTCTGCCCTTTAT | AAAGCCTAAATTGGAATGAGA | ATGCAAATGCTGACTAATAAA | GAGAAATATGTTAAAGTCAAA | 1.85 | 37-40 |
| AKR1C4 | 1109 | Hs_AKR1C4_5 | ATGGACCATCCTGATTATCCA | GAGGGTGTTGCACGACATCTA | CAGGTGAGCAGCCATACCAA | CAGGTGAGACGCCTACCAA | 1.63 | 41-44 |
| AKTIP | 64400 | Hs_FTS_4 | AAGGTGAAGAAGAACATTAA | CTGCACTGTTCTACTGATTG | TCAGCACTACTTAATAGTTTA | TTGCATTCATTTAAACTAATA | 1.62 | 45-48 |
| ALDH7A1 | 501 | Hs_ALDH7A1_3 | AAGGTCTACTTGTACTATCAA | AAGGATGATTGGAGAGACCTAT | TCCGATTCTCTATGTCTTTAA | CGGGAGAAGATCAAGTACTA | 1.77 | 49-52 |
| ALX4 | 60529 | Hs_ALX4_5 | CAGCAGCTACCTGAGTGTCAA | CCGGACCACCTTCACCAGCTA | CAGGTTCCCTGCTACGCTAAA | CCCGTCCTGGCTCGGCAACAA | 1.62 | 53-56 |
| AP2M1 | 1173 | Hs_AP2M1_6 | TGCCATCGTGTGGAAAGTCAA | ACGTGTGACTTCGTCCAGTTA | TGGAGGCTTATTCATCTATA | TTGGAGGCTTATTCATCTATA | 1.61 | 57-60 |
| APBB1IP | 54518 | Hs_APBB1IP_6 | CAGAATATTCTGTCCAAATGTA | CACTGGATTCAGCCAATATGA | AACCAATTAAACCAGTAGAGT | CCAAGCTGAATTAACTACA | 1.82 | 61-64 |
| ARD1A | 8260 | Hs_ARD1A_1 | AACTTTCAGATCAGTGAAGTG | CACAGAGACAGAGTGTCAA | CCGGGCCGCCTGCACTCTA | ATCAGTGAAGTGGAGCCCAAA | 1.81 | 65-68 |
| ARTN | 9048 | Hs_ARTN_1 | ACCCTGCGGATCCAGCCTAA | CCGGAAAGGTGCCTAGAAGAA | CAGGCCCTGTAGGGACCAGCAT | CTGCAAAGCACCTAACACATA | 1.57 | 69-72 |
| ASAH3L | 340485 | Hs_ASAH3L_4 | CAACAAAGAAATATCAGTCAA | TTGGGTCAGATGCTTGATGAA | CACGATCAGCAATGTCTTATT | CAGAAGGTATCTACCAAAGAT | 1.67 | 73-76 |
| ATCAY | 85300 | Hs_ATCAY_4 | CTGCCCTTTGTTGCCAGTAA | TCCCAACACGCTAAATTTCAA | ACGAGTTCCCTCTAATCCTA | ATGATCCGGCCTTACATGAAA | 1.82 | 77-80 |
| ATP1A2 | 477 | Hs_ATP1A2_5 | CCGATTAATTGGAGATTACTA | AACAATCAGATTAGACACTAT | ACCCATAGCAATGGAGATTGA | CAAGGAGATCCGCTCGACAA | 1.65 | 81-84 |
| ATP6AP1 | 537 | Hs_ATP6AP1_8 | CTGGTGATGTTGTCTAACAA | TCCGAAGATGTCCCATACACA | CAGCAATGGCTCCGTCGCCTA | AAACTTCTCTGTGGCGTACAA | 1.62 | 85-88 |
| ATP6AP2 | 10159 | Hs_ATP6AP2_4 | GGGAACAGAGTTTAGTATATTA | ATGTGCTTATATAATCGCTTA | AACATGGATCGTCTGGATATGAT | TCCCTATAACCTTGCATATA | 1.84 | 89-92 |
| ATP6V0C | 527 | Hs_ATP6V0C_5 | GCGCGGAGCGTGTCCAATA | GCGGATGATTAGAATTGTCA | CACAAAGTAGACCCTCTCCGA | CCCCACCAGCCACAGAATATTA | 1.83 | 93-96 |
| ATP6V0D1 | 9114 | Hs_ATP6V0D1_4 | CACTTTCATGTTCCTCCCTAA | CGCGCCTTCATCATCACCAT | AAGGCTCTCAATTGCACTCTT | CAACTACATCCTATCTTCTA | 1.66 | 97-100 |
| ATP6V1A | 523 | Hs_ATP6V1A_4 | ATGGAGGTGATGGGTAAGGTA | GAGCTTGAATTTGATAGCAIAA | ACCCAAATTGTCATTATAIGAA | TAAGGTAGAGTCAATTATGAA | 1.9 | 101-104 |
| ATP6V1B2 | 526 | Hs_ATP6V1B2_6 | CGGATTTGCTTGTTCCAGTAA | ACCATTGTAACCCTGTAATTAA | GAGGGTAATCTTTGTCGGGTA | CAGGGTAATCTTTGTGGCACA | 1.55 | 105-108 |
| AZIN1 | 51582 | Hs_AZIN1_1 | AAGTGGGATCGAGACATGTAA | CAGGTTAAGCTGTTCCAGTIA | CCGGATTGTTGTTCCAGTA | ACGTTCGCAGTTAATATCATA | 1.7 | 109-112 |
| B2N | 567 | Hs_B2M_6 | CAGCACAATAAGATCCTATAT | CTGGGTTTCATCCATCCGACA | AACATCTTGGTCAGATTTGAA | AAGTAGTTAAGCGTGCATAA | 1.34 | 113-116 |
| B3GNT1 | 11041 | Hs_B3GNT1_6 | TGGGATCATGACGACGATGTA | GTCAACCTGCTGGACATTAA | CTGCCTGACTCCATCCAGAA | ACGGTCCGTGGACCAGGTCAA | 1.4 | 117-120 |
| BAIAP3 | 8938 | Hs_BAIAP3_6 | CAGCACACCAAACTCGACAA | CAGAGTGCAACCAGTAAGTGA | CAGGTGCAACAGTAAGTGA | CCCGCTCATGAAGTACCTGA | 1.71 | 121-124 |
| BARHL2 | 343472 | Hs_BARHL2_4 | TAGCATTGATGTCTAAATAA | TGCCTATTTCTATCACCCA | CAGAGTGGAGCTACCATGAA | TCCGACCACCAGTCAATCAA | 1.77 | 125-128 |
| BNIP3L | 665 | Hs_BNIP3L_1 | CCACCTGTAAAGTAGAATTCA | AAACGAGATCAGGTTAGCAA | AAACGAGATTAGAGTTGGAA | AAGAAAGTGCGACTGGGTA | 1.63 | 129-132 |
| BRUNOL6 | 60677 | Hs_BRUNOL6_9 | CACAGTTGAGTATGTAACTTGA | TACCTTCGTCTCTTAGTCTA | AAGCTGATCAATGGTGGTGAA | CTGAAGGCTCTGATCTGATA | 1.87 | 133-136 |
| BZRAP1 | 9256 | Hs_BZRAP1_5 | CAAGTGTGAGTGATGAGCAA | CAGCCGTCTGGTGTCCTCAA | CAGAGTAAATGCCTCCTAA | CTGGAAGACATGCCTGGATTA | 1.8 | 137-140 |
| C14orf172 | 115708 | Hs_C14orf172_2 | TCGAGCCTGTTGAAGACTGTTA | CCGTGTAGTTTTGTGGATAA | CAGGCCGCAGCGCCATGAA | CACCATGAGCTTGTGGCATA | 1.77 | 141-144 |
| C19orf47 | 126526 | Hs_FLJ36888_3 | CTGAGAATTGTTGTAAAGTAA | TGCCGTGATGTTTGTAGGAA | TGCCGTGATGTTTGTAGGAATA | CTCGTGCACTGTGTCCAACAA | 1.6 | 145-148 |
| C21orf7 | 56911 | Hs_C21orf7_4 | AGCCCTCGATAGAAAATCTGAA | ACCCTGTGCATGCATTCAA | TTCAAAATATGCTCAAATTTAA | AAGGAGCTCATTGCCAAGTTA | 1.63 | 149-152 |
| C3orf31 | 132001 | Hs_C3orf31_4 | CCGCGTTCTTCTCCATGATCAT | TGGGTGTGAGCAAGTTAGATA | CAGTCCATCCATGATTAAAGAA | CTGTGGGTGACCTTCCGCAA | 1.7 | 153-156 |
| C4orf29 | 00167 | Hs_FLJ21106_4 | CCGCGTTCTTCTCCATGATCAT | ATGGTCGAGTTTGTCTTAGA | GCCGTCATCCATGATTAGAATA | TACCACTTACTTAGTAAAGAA | 1.7 | 157-160 |
| CARD9 | 64170 | Hs_CARD9_5 | CAGCAGGATGTACTACTCAT | ATGTCGAGTTTGTCTTAGA | CTGGTCATCCGCAAACAGATA | ACGTAAGGAGTCCAAGATGTA | 1.72 | 161-164 |
| CASP8AP2 | 9994 | Hs_CASP8AP2_1 | GCGGTGAAGGAGGAATGAAA | CAGCTGATGTGCGAAGTCAA | CACATACGTAGATCAAGAA | AAGCTGATCACAGAGCTAAA | 1.73 | 165-168 |
| CCNB3 | 85417 | NA | CACCTCAGTGTCAAGAAACTA | CTGACTCCGTCATTTAATAAA | CGTCTGAGTCGGATCTTCGA | AAGCTGATCACAGAGCTAAA | 1.78 | 169-171 |
| CD48 | 962 | Hs_CD48_4 | CAGTCTGTGTATTACAAGTAT | AGCTGGGTGACATGTTAA | AGCTGGGTGATCTCTACCTA | NA | 1.5 | 172-175 |
| CD58 | 965 | NA | TAGCAGTAATTACAACATGTA | CACCCATTATGCCACATAA | CAGTGTACTACGCATCCAA | NA | 1.46 | 176-178 |
| CD6 | 923 | Hs_CD6_5 | CCGGCAGGATGTACTACTCAT | AAGCATTGAAGTCCACATGCAT | CAGTGTACTCTTAGCAATCCA | AAGAAAACGTTATACTTGTA | 1.88 | 179-182 |
| CD63 | 967 | Hs_CD63_9 | GCGGTGAAGGAGGAATGAAA | ATGGTCGAGTTTGTCTTAGA | ATGTTGAAGTCTGATCAGA | TAGAGTAAGGTGATGTCAGA | 1.65 | 183-186 |
| CD81 | 975 | Hs_CD81_9 | CACCTCAGTGTCAAGAACAA | CTGACTCCGTCATTTAATAAA | ATGTTGAAGTTGCTCTCTA | ACGTAAGGAATCAAGTA | 1.69 | 187-190 |
| CDC23 | 8697 | Hs_CDC23_8 | TACGAGAAACTCAATCAACTA | CTGCAATAGCAAGAAGCCTA | CGTCTGAGTCATGATCTTCGA | AAGGACGAATGAAACAGTTGAT | 1.55 | 191-194 |
| CDK4 | 1019 | Hs_CDK4_13 | TGCCTATGGACAGTGTACAA | TGCCTATGGACAGTGTACAA | AAGCCTCTCTTCTGTGTTGAG | AAGGATCGATGCCAGTTT | 1.79 | 195-198 |

TABLE 3-continued

| Gene | ID | Identifier | Seq1 | Seq2 | Seq3 | Value | Range |
|---|---|---|---|---|---|---|---|
| CDKN1B | 1027 | Hs_CDKN1B_7 | ACCGACGATTCTTCTACTCAA | CTGTAAGTAACTTCACATTAA | CAACAACACAATAACACTAAA | CCAATTATTGTTACACATTAA | 1.86 | 199-202 |
| CEL | 1056 | Hs_CEL_6 | AGCCCTGACGCTGGCCTATAA | CCCGTTATGCATCGGATCTAT | TGGGTTCGTGGAAGGCGTCAA | CATCGTGGTCACCTTCAACTA | 1.58 | 203-206 |
| CHST5 | 23583 | Hs_CHST5_8 | CAGGGAGTAAGTTACTGCTAA | CCACGCGTTGCCCTTCACTAA | CACGGGTAAAGTGATCGTCA | CAGCAAGCAGGACGTATGCAA | 1.47 | 207-210 |
| CIB3 | 117286 | Hs_CIB3_7 | CTGGAGCAGAGCGGTGACCAAA | TGGCAGCATGCCCGAGCTGAA | CCGGACCTCAAGGCTTACTA | CCAGGAGATTGCCCAGGTATT | 1.57 | 211-214 |
| CLIC4 | 25932 | Hs_CLIC4_4 | TAGCAGTAGCAATGATTAGTAA | CAGGGAAGTTAGTCACACGTAA | CACGAACATGCAGTTATTGAA | TGGGATATGTACTAACGAATA | 1.77 | 215-218 |
| CLK1 | 1195 | Hs_CLK1_6 | CACGAGTAGTAAGGAGCATTTA | CAGGACGATGAAGACACTCAAA | AACGTGATGAAACGCACCTTAA | GAGAAAGATTATCATAGTCGA | 1.89 | 219-222 |
| CNNM1 | 26507 | Hs_CNNM1_7 | CTGGGTTATCTGCATCTCAAA | CTCACTGAACTCATTGATCGA | TGGCGCGTGATGAACATTACA | CACGCTGGAGGATATCATAGA | 1.72 | 223-226 |
| COPA | 1314 | NA | CACACGGGTGAAGGCAACAA | AGAGATGTTAACCAAATTCGA | AGATTACCGAGGAGCATTA | NA | 1.73 | 227-229 |
| COPB1 | 1315 | NA | AACTCCAGATGGAGGACTTTT | CACGTTAATTAACGTGCCAAT | AAGATTAACGTGGCCAAT | NA | 1.69 | 230-232 |
| COPB2 | 9276 | Hs_COPB2_3 | ACGATTCTTCAAGGATATGCAA | CAGGTTATTTGGCATTCAA | CAGTACGATTTGGCATTCAA | AGGCGTGAATTGCATTGATTA | 1.56 | 233-236 |
| COPG | 22820 | Hs_COPG_7 | CCGAGCCACCTTCTACCTAA | CACCGACTCCACTATGTTGAA | AGGCCCGTGTATTTAATGAAA | TCCGTCGGATGTGCTACTTGA | 1.6 | 237-240 |
| CRAMP1L | 57585 | Hs_CRAMP1L_8 | CCCGACAAACCTGCCACCCAA | CTGCATAATGATCCCATTTCA | AGGCGGGAACCTGCGGATCAA | CTGGTGTGCATGATGAACGAA | 1.64 | 241-244 |
| CRYAA | 1400 | Hs_CRYAA_4 | GAGGGACACCTCACCGTGAA | CCCGGAGGACCTCACCGTGAA | CAGCCGCGGCAATCAATAAA | ACCGCACCTCACACTCCTTTA | 1.8 | 245-248 |
| CTA-216E10.6 | 19640 | Hs_FLJ23584_3 | CCCGACGGAGGACAGAGAGA | CCCGAGAAATGCCAACACGAA | TTCAGGAACTAGGGAATGAT | AAGGTGGATAAGAAAGCTA | 1.65 | 249-252 |
| CUEDC2 | 79004 | Hs_CUEDC2_3 | TCGTTTCATTGTAGTGGTTAA | TTGCTCCATAGTGTTAACCTA | TTGCTCCATAGTGTTAACCTA | ATGCTGGTAGAGGAAAGGAA | 1.72 | 253-256 |
| CXCR6 | 10663 | Hs_CXCR6_4 | CCATCATGGCGAATAAAATAA | CAGGTCATGTGCAAGAGCCTA | CTBCTATTCAGTCATAATCAA | CACCAGCATGTTCCAGTTATA | 1.83 | 257-260 |
| CYC1 | 1537 | Hs_CYC1_4 | CAGGCTGGAGGTAGCACCTAA | CAGCATGGACTTCGTTGGCCTA | TACCATGTCCAGATAGCCAA | GCGGGAAGGTCTCTACTTCAA | 1.8 | 261-264 |
| CYP17A1 | 1586 | Hs_CYP17A1_5 | CAAGGATATACCATTCCTAAA | CCGGAGATTTTCACCCTAAT | TGAGTTGAAATGTCATACAGAA | CAGACACGGCCATATGCATAA | 1.85 | 265-268 |
| CYP2U1 | 113612 | Hs_CYP2U1_5 | TAGCCATATACAGACAGTATA | TAGCACTCCACTATTGTTGAA | CAGCGGTTTTCTACCTAAT | CTGGAGCTGATTACACTAAT | 1.44 | 269-272 |
| DBT | 1629 | Hs_DBT_6 | CCGCACTATCTACACCATCGA | ATGACTGTTCCTATACTAGTA | CAGGGTTTGATTGTCCCTAAT | CTGGTTAAGCTCCGAGAAGAA | 1.7 | 273-276 |
| DCLK2 | 166614 | Hs_DCAMKL2_6 | CCGGATCTAGATTCCGTAGAT | CTGAGCTTGACCGTTGCATAA | ACCATTTCGTAAAGTCGATTA | CTCGGTGTACCGCGGGACAAA | 1.57 | 277-280 |
| DGKH | 160851 | Hs_DGKH_6 | CTGTAGCAACATGGCAGTTTA | CTCCTAGTGCTTAGTGCTAA | CTGGTGGAGTTCGATTATCAA | TGGGAGTTCGATTATCAACAA | 1.47 | 281-284 |
| DGUOK | 1716 | Hs_DGUOK_5 | CTCTCTGTAATTTGTGCTTTA | CAGCTGCATGGCCAACACGAA | ACCCTTCAGTTCACATGGCTT | CCGGATCACATTACATGGCTT | 1.77 | 285-288 |
| DHRS2 | 10202 | Hs_DHRS2_5 | TACGCTCGATTTGAGGCCAAA | TAGATTTGGCTGATCCAATTA | CTGGAAGAACTTCAAGGAACA | CAGGAAGGGCGTCCTGGCTAA | 1.65 | 289-292 |
| DLG2 | 1740 | NA | ACAGACTTAAGATACCAGTA | CAGAGCCATGTTCGACTACGA | NA | NA | 1.8 | 293-294 |
| DMAP1 | 55929 | Hs_DMAP1_3 | CTGCATGATTTAAGTGCTTTA | CCCATACACAGCAGCTTCTA | CAGGTTCAATAAGACTGTGCA | CAGGTTCAATAAGACTGTGCA | 1.83 | 295-298 |
| DMRT1 | 1761 | Hs_DMRT1_6 | TCAGATACAGTTCTCCCTTAA | CAACTACTACAGCAGCATTTA | CCAGTACAGGAGCATTCTTA | AAGAGAACAATGGCAGTAA | 1.59 | 299-302 |
| DTX3 | 196403 | Hs_DTX3_7 | AAGCTTTGGTGTTTCACTTAA | TGGGCGGATGCTGGTCTCTAA | AAGGGTATCACAGATGACTGA | TGGCGAGACTTCTGACATCTA | 1.67 | 303-306 |
| DUSP27 | 92235 | Hs_DUSP27_4 | CAGATGTTTGATTATGGTAAA | CAGAAAGTTCTATCCGATCTA | CTACCTGATGATCTTCCACAA | TACATCCAGAAAGGCCATGAA | 1.85 | 307-310 |
| E2F1 | 1869 | Hs_E2F1_5 | AAGTTGAATCTTTAAGATCAA | CAGATGTTTTGGGATACTCAT | CTCACTGAAATCTGACCACCAA | AACTCCTCCAGATCGTCATC | 1.88 | 311-314 |
| EEF1A1 | 1915 | Hs_EEF1A1_9 | CCCTGCACTCTTTAACATA | AAGTTGAATATTTAAACAAA | CAAGTCTGAATTGAAGTGTTA | AAGGAAATATCATTTAAAGCTA | 1.76 | 315-318 |
| EIF3A | 8661 | Hs_EIF3S10_8 | GAGGAATTCTAGATATATTTAA | GAGGATCTACTTGGACAGATTA | ATGCTAAACAGGTTGAACAA | CAGCGTCGCCTTCAACACTA | 1.69 | 319-322 |
| EIF3C | 8663 | Hs_EIF3C_2 | CCGCGACGCATGATCAGCAA | AACGAATGGAATGAAGAATTA | CTGAACCTAGAGGACTATCTTA | CCCGAGCAGTCTGCGATGAA | 1.62 | 323-326 |
| EIF3G | 8666 | NA | AAGAGGACCTGAACTGCCAGG | CTCCCCGCATCTACCTGGCTAA | CAAGGAGGTTCATCAACGGAAA | NA | 1.71 | 327-329 |
| EIF4A3 | 9775 | Hs_DDX48_6 | CAGGATCAAATGACATATCACA | CCCATAAACTCTATACTTCTA | CCGCATTCTTGCGTGAAACGTGA | ATGATTCGTCGCAGAAGCTA | 1.65 | 330-333 |
| ENGASE | 64772 | Hs_FLJ21865_7 | CAGGGAATTAATTAGGAGTAA | ATGGATAGAAATTAAGCCTA | CCGGCAGGTCACAGTTGCTT | CGGCCGGGAAGGAGCATCAA | 1.6 | 334-337 |
| EPB49 | 2039 | Hs_EPB49_4 | CCGCCCAGATTCCAAACATCTA | CAGGAAGATCTATCCCATGAA | GTGGATATAATGATATCTATA | CTGGCTGTTGTGGAGACAGAA | 1.79 | 338-341 |
| EPHB6 | 2051 | Hs_EPHB6_10 | CTGGAGCTTTGGGATACTCAT | CGCCAATTCTCTAGATACTACTA | CTCTGGATTACATCTACTTA | CGGAAGTGGATCCTGCTTAT | 1.86 | 342-345 |
| BRN2 | 10595 | Hs_BRN2_2 | CACCTGCACTCTTTAACATTA | AGGGATGATCATGCATCGAA | AGTGCTAAACAAACTCCTA | ACCAAATGTACGTCACAGAAAT | 1.61 | 346-349 |
| FAU | 2197 | NA | CCGCCGTTCAGTCTGCCAATAT | AACGAATGGAGTAAGAGATTA | AGTGAGAGGGTTGAGACTTCAA | NA | 1.6 | 350-352 |
| FBXW10 | 10517 | Hs_FBXW10_7 | CAGGATCAATGACATATCACA | AAGGCGAATTATACTCTCTTA | CAAGGAGGTTCATCCGAGGCAT | GAGAACGAAGAATGAGTACAA | 1.56 | 353-356 |
| FCHO2 | 115548 | Hs_FCHO2_4 | AAACATGTAATATATATTTA | ATGGATAGAAATTAAGCCTA | TAGTTGAATATATCAGGCCTAA | AAACCACTAATTGTTCCGTTA | 1.81 | 357-360 |
| FCRL6 | 343413 | Hs_FCRL6_2 | CTGTGGTGCATAGAAACTCAA | CAGGGAAATGGAAGAATACACCA | TGGCCACGCGTCACAGTTGCTT | CCCGTTTCCAGCGAAAGTTCA | 1.81 | 361-364 |
| FERMT3 | 83706 | Hs_URP2_7 | CTGGCACATTGTACAGGTA | CAGGTTGTACATAAACTCCTA | AGTTCTGCATTAAAACATCCCTA | CCGGATTCGATTCCTCCTCTA | 1.74 | 365-368 |
| FGF3 | 2248 | Hs_FGF4_5 | TTGTGTCATCACACATTAAA | TTGTGTCATCACACATTAAA | CGGGCGGTACCTGGCCATGAA | CAGCGCCGAGAGACTGTGGTA | 1.83 | 369-372 |
| FLJ11235 | 54508 | Hs_FLJ11235_4 | CAGGATCAGCATAACCGCCAA | CAGGTTAGCACAGTAGCCTAA | CCGTAGCACAGTAGAAAATGAA | CTCATAGTGATTTGCCACAAA | 1.8 | 373-376 |
| FLJ20489 | 55652 | Hs_FLJ20489_6 | CACACGTGATGATGCATGCAA | CAGCCTCTACATGCCACCGTA | ACCTAGGACGTTAGCCCTAA | CAGAGTGGATTCATCCTGTAT | 1.8 | 377-380 |
| FLJ34077 | 484033 | Hs_FLJ34077_4 | AGCCGTCATAGAACAGGCAA | AAGGGAAAACAAGAGACATAAAT | TTGGAACTGGGTGTTGAAATA | CAGAGTAGCTCACATCTGTAT | 1.73 | 381-384 |
| FNTB | 2342 | Hs_FNTB_3 | CACGTCCATAGAACAGGCAAA | ACCCATATATGCAGCAGTCAA | CCAAGTCGAGCTGTCTTCTA | TCCGCTCGCGTAGCGCTTTA | 1.67 | 385-388 |
| G6PC | 2538 | Hs_G6PC_5 | TGGGATTCCAGTCAACACAATTA | TAGCAGAGCAATCACCACCAA | CACCCTTGTCAGTAGTTGA | AGGGATTGAGGAGGACTACTA | 1.56 | 389-392 |
| GCLC | 2729 | Hs_GCLC_11 | AACACATTATTTACATGGAT | CATCGACGATAGATAA | CACATCCAGTCGATAGTGAA | ATCAGGCTCTTTGCCAATAA | 1.81 | 393-396 |
| GNMT | 27232 | Hs_GNMT_5 | AGGGAAGAACAATCTACTATAA | CCGCCATCCTCCAATAAAGT | AACATCAGTTGCTGATAGTGAA | CAGACGGAAGGGTAAACAATA | 1.78 | 397-400 |
| GNRH2 | 2797 | Hs_GNRH2_5 | CCCGCCATCCTCCAATAAAGT | CTGAAGGAGCCATCTCATCCA | TGGCTGGTAGCTGGAGGAAA | CAGACTGCCCATGGCCTCCCA | 1.83 | 401-404 |

TABLE 3-continued

| Gene | ID | Probe | Seq1 | Seq2 | Value | Range |
|---|---|---|---|---|---|---|
| GPR146 | 115330 | Hs_GPR146_5 | CAGGGTCTCTGAGAACATTTCA | CTGGTGTGTTAAATGGAGCTATT | CAGTATGAACCTGTCCTAAAT | 1.65 | 405-408 |
| GRID2 | 2895 | Hs_GRID2_5 | AACGATGTGGACGTACAGGAA | CACGATTACAAATGGGATCAA | CACCGGATCACAAATACGGAA | 1.87 | 409-412 |
| GRIN2C | 2905 | Hs_GRIN2C_5 | CTGGACGAGAATCAGCAGGGTA | CCCAGCTTTCACTATCGGCAA | GTCGATGTGCTTGCCGATCTA | 1.75 | 413-416 |
| GRP | 2922 | Hs_GRP_7 | ATCAGTTCTACGGATCATCAA | CCAGCTGAACCAGCACTTACCTA | CGGAGGGACCGTGCTGACCAA | 1.75 | 417-420 |
| GSK3A | 2931 | Hs_GSK3A_7 | AAGCTTTAACTGAGACTCCGA | AAGAAAGACGAGCTTTACCTA | CAAAGGTGTTCAAATCTCGAA | 1.78 | 421-424 |
| HARBI1 | 9776 | Hs_KIAA8652_5 | CTGGGCGTATGATTGACTTAA | CAGGAAGTCCTGGGTGCTAAA | AAGGCGGAGTTGACCGCTTAA | 1.51 | 425-428 |
| HIBCH | 26275 | Hs_HIBCH_4 | CACGGGAGTCATAACACTAAA | CAACTTAGGTATACAAATAA | TAGCCTTGAAATCTCCTTCAA | 1.36 | 429-432 |
| HIST1H2BN | 8341 | Hs_HIST1H2BN_9 | CTCCTTCGTCAATGACATCTT | CAAGGCCATGGGCATCATGAA | CCGCCTGGCGCATTACAACAA | 1.76 | 433-436 |
| HPGD | 3248 | Hs_HPGD_4 | CTGGCAGTGACTAATCAGTAA | CAAGAGCTTCTTAGAGTAGTA | CAAGACTATGAATACAACTCCA | 1.73 | 437-440 |
| HSF4 | 3299 | Hs_HSF4_4 | CCGACTATCCCTGCACATAAA | CAGACGTTTCGCCAAGGAA | AAGGGCGAGAATGGACCCTGA | 1.82 | 441-444 |
| HSPD1 | 3329 | Hs_HSPD1_1 | AAGGCTTCGAGAAGATTAGCA | CACCACCAGATGAGAAGTTTA | CGGGCTTATGCCAAAGATTGCA | 1.63 | 445-448 |
| ICAM2 | 3384 | Hs_ICAM2_3 | CGGGAAGCAGGAGGAGTCAATGAA | TCCCATGACACGGTCCTCCAA | AACATCTTTCACAAACACTCA | 1.81 | 449-452 |
| ICEBERG | 59082 | Hs_ICEBERG_5 | CAGTGGGTGCAGGCACAATAA | AGCCAGGAAGACACATGAACAAA | AACCTGATTAATTTCATCAAT | 1.51 | 453-456 |
| IL17RA | 23765 | Hs_IL17RA_2 | CAGCGGTCTGGTTATCGTCTA | CGGCACCTACGTAAGACATCTA | TCCGACTGGTTCGAATGTGA | 1.77 | 457-460 |
| IL1A | 3552 | Hs_IL1A_4 | AAGGCAAAGCACGAAATGTTA | CAGCGCTACTTAAGACAATTA | TCGAGTTGAATGAACATGAAA | 1.59 | 461-464 |
| IQCF2 | 389123 | Hs_IQCF2_4 | CAGGGCTAAATGAACCATCTAA | AAGCAATTGAATGGAAGACATT | TCGAGGGTGCTGGAGAAGAAA | 1.76 | 465-468 |
| IRF2 | 3660 | Hs_IRF2_4 | CACCTTATCTTAAAGCACTTA | CGGTTCTGACTTCAACTATAA | ACGGTGAACATCATAGTTGTA | 1.68 | 469-472 |
| ISG15 | 9636 | NA | CGGAAAATAAAGGCTGTTTGTA | AAGATGCTGGCGGCAACGAA | CTCATCTTTGCCAGTACAGGA | 1.69 | 473-475 |
| ITLN1 | 55600 | Hs_ITLN1_5 | CTGCGGGATTTGTTCAGTTCA | ACCCAGTAGCTAGAAATGTTAA | CCGTGTATCCCTGTGGTCTA | 1.79 | 476-479 |
| JARID1D | 8284 | Hs_SMCY_4 | CCCAGAGACGTTGGATCTCAA | CAGGGTAGAAACGTTGAGAAT | CTGACGATTGCTTAGCATTAA | 1.81 | 480-483 |
| JUN | 3725 | Hs_JUN_3 | AAGAACGTGACAGATGAGCAG | AAGAAGTGTCCGAGAACCTAAA | TTCGTTAACATTGAACCAAGAA | 1.46 | 484-487 |
| KATNB1 | 10300 | Hs_KATNB1_5 | CTGCTGTAATTTATAAGGCAA | CAGGAGAGGCTGCAATAA | CTGAACATCGTCAACCAGAAA | 1.46 | 488-491 |
| KCNAB3 | 9196 | Hs_KCNAB3_5 | AGGGAACATCCTCAAGAGCAA | CCGAGGGAGGTTTAAGCGCAA | AACCTGTTTGAACACGCGTAA | 1.62 | 492-495 |
| KCNJ12 | 3768 | Hs_KCNJ12_6 | TTGGGTGAGACTGTTTACAAA | TGCGAAGGATCTGGTAGAGAA | CAGCTCCTACCTGGCCAATGA | 1.64 | 496-499 |
| KIAA0664 | 23277 | Hs_KIAA0664_5 | CTCGCCAAGCACATCTTCAA | AAGGGCCATATTCAAGGTGCA | CAGCCCGACCTTCAAGAAGAA | 1.59 | 500-503 |
| KIAA0947 | 23379 | Hs_KIAA0947_3 | CTGGCAGTTATTGCTCTTAA | TCGGTTGCCTAATCAAGTA | CAGGTAGGATTTCTACACCTA | 1.82 | 504-507 |
| KIAA1128 | 54462 | Hs_KIAA1128_6 | ACCGTATATTTATGAAGCATA | GAGCATAATTATCTCAGGTAA | ATGGATTAGTTCTCAAATCTA | 1.83 | 508-511 |
| KIAA1267 | 284058 | Hs_KIAA1267_1 | CAGCCTAGATTTCCGAAATAA | TGCCGTAGAAAACTGCAATA | AAGAGCTCAACAATATCAAA | 1.7 | 512-515 |
| KIF11 | 3832 | Hs_KIF11_14 | ACGGAGGAGATAGAACGTTTA | GCCGATAAGGATAGAAGGATCAA | GAGACGCAGGTCAGAATGGAA | 1.37 | 516-519 |
| KIF23 | 9493 | Hs_KIF23_3 | CACGCACAACCAAGCGCAAA | AACGACATAACTTACGACAAA | AACTGGATCGTAAGAAGGCAG | 1.82 | 520-523 |
| KIF3A | 11127 | Hs_KIF3A_6 | CAAGAACGCTGGATATTGAA | GCCGATCCAATAAATCAGGAA | CCATAGCGTGTTCAACATTAA | 1.46 | 524-527 |
| KPNB1 | 3837 | Hs_KPNB1_4 | CAAGAACTCTTTTGACATCTAA | AAGGGCGGAGATGCGAAGACTA | CTGGTACAACCAGAGTAGAA | 1.73 | 528-531 |
| LAMC2 | 3918 | Hs_LAMC2_3 | CAGGGCATATGGATGAGTTCAA | CCCAATTGGTTTCTACAACGA | CGGGACGGTGCTGTGGTGCAA | 1.64 | 532-535 |
| LARP1 | 23367 | Hs_LARP1_3 | CACCTAATCCACAGAAAAGTAA | CAAGCGCCAGATTGAATACTA | TACTTTGAGTATCGAAGGTTA | 1.67 | 536-539 |
| LHX3 | 8022 | Hs_LHX3_5 | CACTCTTTCCAAGACTTCAA | CTGCCTGTGTAAGTCAA | CAGAGGAGGTCAGCAACCTAA | 1.64 | 540-543 |
| LRRN6A | 84894 | Hs_LRRN6A_6 | AAGGACTTCCCTGATGTGCTA | CCGCTGGCGGCTCAACTTCAA | CTCCATCAGATCCTTTGGGAA | 1.47 | 544-547 |
| LPPR4 | 9890 | Hs_LPPR4_9 | CAGGTATTCCACATACCTTAA | CAGCACTTGCTAAACATCTAA | CCCATTCGGTTCTACATTA | 1.53 | 548-551 |
| MAN2B1 | 4125 | Hs_MAN2B1_5 | CGCCAAGGAGCTGGTCGATTA | TGGACACTAAATTACACATCA | TCGGGCCTTAGTACCCATTTA | 1.86 | 552-555 |
| MAP2K3 | 5606 | Hs_MAP2K3_8 | TTGATCAAAGTTCCCTGATAT | CTCAGTGATTCAGAGTTGAT | TGCAGCCTGAAAGAACCAATA | 1.72 | 556-559 |
| MATN3 | 4148 | Hs_MATN3_5 | CAGGGAATTATTCACATGGCA | ATGGGACAAATAAGTTACATT | AAGCTCAGCTGAGTTCAGCAA | 1.56 | 560-563 |
| MED6 | 10001 | Hs_MED6_7 | AAGGGTATTGGTGGCACTTCA | AGACTTTGATTTCTGCATAA | AACAACTTTAGATATGCAAA | 1.64 | 564-567 |
| MKL1 | 57591 | Hs_MKL1_7 | TAGTGTCTTGGTTGAGTGTAA | AGCAAGATGCCATCCAACGAA | AAGGGCCTGAATGCAAGGTTA | 1.81 | 568-571 |
| MRPS12 | 6183 | Hs_MRPS12_8 | TTCCATCAGACCACTATTAA | CACGTTACCGCCAAGCCGAA | TCGGCCGGCCCTCAAAGCTA | 1.86 | 572-575 |
| MYC | 4609 | Hs_MYC_1 | GATCCCGGAGTTGGAAACATA | CTCGGTTGCAGCCGTATTCTA | ACCATTGGCAGAGAAACTTT | 1.69 | 576-579 |
| MYEF2 | 50894 | Hs_MYEF2_3 | CAGAATAATGAATGGCATAAA | CCGTAGGGCATTGCAGCGAA | TGACTGTTTCTACACTGTCA | 1.87 | 580-583 |
| MYOD1 | 4654 | Hs_MYOD1_5 | TACAGGGTATTGGTGGCACTTCA | CTGCACGTCAGCCAATCCAAA | CAGGTAAATACATCCTTAAA | 1.67 | 584-587 |
| NAE1 | 8883 | Hs_APPBP1_6 | ATGGACTAGGTTAGCCATTA | AAAGAATGATTATTGTGCAGTAA | AAGCCTGTTCCAGTGATCAA | 1.61 | 588-591 |
| NDUFV3 | 4731 | Hs_NDUFV3_6 | ACACTGATTTATCCACATATA | ATCCATATAATTAGAAGAATTT | ATCACGGTGATTGACATGTA | 1.69 | 592-595 |
| NECAP2 | 55707 | Hs_NECAP2_2 | AAGGAGCTCAGTAAACTAGAA | CAGGTACTTCGATCCGCAT | CCCGGTCATAATCGTTT | 1.87 | 596-599 |
| | | | | CAACATGCAAACATGAAGAA | ACCTGGCGTTTGACAACACTA | 1.69 | 600-603 |
| | | | | | TCTTTAATGTGTAATTGAA | 1.44 | 604-607 |
| | | | | | GTGGTAATCATGTTGCCAAA | 1.8 | 608-611 |
| | | | | | CTGCAGCTTGAGCTACAATCA | | 612-615 |

TABLE 3-continued

| | | | | | | |
|---|---|---|---|---|---|---|
| NEK8 | 284086 | NA | ACGGACAGTTGGGCACCAATA | CCAGAAGCTGGTGATCATCAA | TAGAGTTGAAGGCAGACCTA | NA | 1.66 | 616-618 |
| NEK9 | 91754 | Hs_NEK9_2 | CAGGTGTCATGTGGTGATGAT | TGCCTTCGGATCAGATTATA | CAGAGCTCGTCAAGGAGTAA | TACACTTGGGTGAACATGCAA | 1.81 | 619-622 |
| NSF | 4905 | Hs_NSF_9 | AGGCAGACTTTCTACATGCAA | GTGGGTCAATTCCTTAGTATA | ATCCAACTTCCCGTTCATCAA | TTGGCCCTTCTTAAGAGAAGAA | 1.64 | 623-626 |
| NTHL1 | 4913 | Hs_NTHL1_6 | GAGCAAGGTGGACCAAGAA | CAGGCTGAGGTGGACCAAGAA | ACCGTCTGTGAAGTGGCTTTA | GTGGACCAAGAAGGCAACCAA | 1.85 | 627-630 |
| NUP205 | 23165 | Hs_NUP205_9 | CAGCACTTCCTGGAATATAA | CAAGATGTGCATGAATAAGATA | GAGAGTCAACTGGCTCTAATA | AGGGTGCATTAGAGCTGCTAA | 1.72 | 631-634 |
| NUP98 | 4928 | Hs_NUP98_8 | CTGGAGTTAGCACTAACATAA | CAGTGTATTACTGCTATGAAA | AACCTATTGCAAACCTATT | CTCACTAAGGTTGGTTACTAT | 1.79 | 635-638 |
| NXF1 | 10482 | Hs_NXF1_4 | CAGAACAAGTAGAACAGCTAA | AACGCGTTAATTTCCCTCAAA | CCGAAGGATATCTATCATCAT | CGCGAACGATTTCACCAAGTTA | 1.66 | 639-642 |
| ODZ4 | 26011 | Hs_ODZ4_5 | CCGGCCGGCCTTTAACCTCAA | CGCCAGGGTGATATACAAGTA | TCGGTTTATCCGAAGAACAA | CTGCGGGTTCACAACCGAAAT | 1.81 | 643-646 |
| OPN1SW | 611 | Hs_OPN1SW_4 | CAAGAGTGCTTGCCATCTACAA | CGCATGTCATGGTCAACAA | GCGCTACATTGTCATCTGTAA | TTGGCCTGTTTGCAACAGCTA | 1.76 | 647-650 |
| P76 | 196463 | Hs_LOC196463_4 | CTGGATGAAACACGGTTGGTGAA | CTGGATGAAGGTAACAATGA | GTGATGAGGTGGACTACAA | CCGGAAGTTCGCGCCTGTCAA | 1.48 | 651-654 |
| PCDH18 | 54510 | Hs_PCDH18_4 | CTGATATAGTTTGACTGTAA | CAAGCAACTGCAGTTGTTCA | CTGCGCCAGTAGCAGTGTAA | CCGGAGAATATTTCTCACA | 1.6 | 655-658 |
| PHF2 | 5253 | Hs_PHF2_6 | TTGAACATTTATATATAATCTAA | CCGCTCTAGCTGGAAAACAAA | AGGACCGCTTATTCCACTTTA | CCGCATCGTCTCCAAACAACA | 1.72 | 659-662 |
| PIK3R5 | 23533 | NA | ATCGCAGATCAAAGTGGACAA | TAGGATCCTTTCTAGAAGGAA | CAGGATCTATAAACTCTTCAA | NA | 1.83 | 663-665 |
| PIL3R5 | 23533 | NA | ATCGCAGATCAATCTTAGTAT | CACCTTCAGGACGAACAATAT | CAGGGATGTTGGTCAGATTGA | NA | 1.83 | 663-665 |
| PIK3R6 | 146850 | Hs_C17orf38_6 | TCGCTGGACAAGGAGCATCAA | CAGTATTTATTGTTCCCACAA | CAGGGATGTGGTCAGATTGA | TCGCCGCACCCTGGAGCACTA | 1.7 | 666-669 |
| PIN1 | 5300 | Hs_PIN1_4 | GACCGCCAGATTCTCCCTTAA | CACGAGATAGCTGTACTTTCA | CTGATAGTATTGAAGTACTA | CGGCTACATCCAGAAGATCAA | 1.66 | 670-673 |
| PKHD1 | 5314 | Hs_PKHD1_7 | CACCGGACATATTGGAAGTGTA | CCGGAAGGAGCTGAAGCTGAA | CAGGGCGACATATCGGTGGA | CAAGATTACTGAGATACGGAA | 1.66 | 674-677 |
| PKN1 | 5585 | Hs_PKN1_8 | CTGCCTGCCCTGATGTGAA | CAGGGCTCTGATATTTCAA | TGCTCAAGGACTTAACTCAA | AAGGCTTAACTCCAACAACGCA | 1.64 | 678-681 |
| PLAU | 5328 | Hs_PLAU_4 | ATGCAGGAACTGGCAAATCT | AGCGCTGCTAACAGACACTAA | TGGGGCGGACCGTTCTGAACAA | CAGCAAGGTGCTCATCGCAGA | 1.76 | 682-685 |
| PLD2 | 5338 | Hs_PLD2_6 | CCGGGCCTTTCGAAGATTTCAT | CAGAAAGACTGTGCACTACAA | CTGCATCAAGCAGGTTCACTA | CCCGCAGAGCGCGTCGCCAA | 1.78 | 686-689 |
| PLK3 | 1263 | Hs_PLK3_8 | CAAGAGTCTAATCTTAGATGA | TAGGATGGGACTTAATGATAA | AAGGATAAACCATTGCTGTA | CAGGCGAGAAGATCCTAAAT | 1.6 | 690-693 |
| POLK | 51426 | Hs_POLK_5 | ATGATCTTTCAGAACCACTAA | CAGGTCATGGACGTTTCATCAA | AACATTCAAATTTACCTGTA | TGGAATTAGAACAAAGCCGAA | 1.85 | 694-697 |
| POLR2H | 5437 | Hs_POLR2H_5 | AAGGTCTTTCAGAACCACTAA | CCGGAAGGAACATCCAGTAA | GGGGAGGTTGCCACTGCAAA | TTGAGTATGTAATGTATGGAA | 1.39 | 698-701 |
| POLR2L | 544 | Hs_POLR2L_4 | TCGGCGAACGATTCGACTCAA | CAGTGGAGCATTGAACATCGA | CAAGAGAACATTTGCACTCCTA | CGGAACAAGTGGAGGCTTA | 1.68 | 702-705 |
| PPARA | 5465 | Hs_PPARA_5 | CGCCTGACAGTGAAGTATGA | CAGGAGCTCTTCAGGATCAA | AGGGACATTTGCACTACCTA | AAGCTTTGGCTTCCAGAATA | 1.71 | 706-709 |
| PPP1R14D | 54866 | Hs_PP1R14D_6 | CAGGCAGGAGGCGGAGTGAA | CCGGCAGGAGGCGGAGTGAA | ATGGTTGGTACAGGATGGCAA | CACCCGGACTTCCTCCAAGTA | 1.72 | 710-713 |
| PRDX5 | 25824 | Hs_PRDX5_5 | CTGAGTGTTAATGATGCCTTT | CTGAGTGTTAATGATGCCTTT | ATGGTTGGTACAGGATGGCAT | TGGGAAGGAGACGACTTATT | 1.87 | 714-717 |
| PRPF8 | 10594 | Hs_PRPF8_8 | ACGGGCATGTATCGATACAAA | ACGGGCATGTATCGATACAAA | CAACGTCGTCATCAACTATAA | CTCATCGTGGACCAACATA | 1.46 | 718-721 |
| PRPS1 | 5631 | Hs_PRPS1_5 | AACATGCTTCCGTCTATGTAA | CCCAAGGTCTATGCTATGTAA | CACCATCTGCTTGACTATGTA | CCGGGCGCCAATCTCAGCCAA | 1.7 | 722-725 |
| PRSS27 | 83886 | Hs_PRSS27_2 | CCACCAGACTCATTTGTAA | ACCAGTGCCCTTCACCAATTA | AATATAATAATAATGAATGA | CACCTCTGAGACGTCCCTGTA | 1.82 | 726-729 |
| PRX | 57716 | Hs_PRX_5 | CAGGGCTACTTCGAAGACTAA | CCGGTCTTCGAAGCACTTT | GGCGGAGGCTTCATTGAAATAT | CCCGGCGCCAAGGTGGCCAA | 1.87 | 730-733 |
| PSENEN | 55851 | Hs_PSEN_3 | CTCGCCCAAAGAAGACTACAA | CCGGCCCAAAGAAGACTACAA | CGCGCAAACGTCCATAACTGA | CAGAGCCAAATCAAAGGCTAT | 1.72 | 734-737 |
| PSMA1 | 5682 | NA | CTGCCTGTGTCTCGTCTGTA | CAGGGCAGGATTCATCAAATT | CACAGTTGGTCTGAAATCAA | NA | 1.72 | 738-740 |
| PSMD2 | 5708 | Hs_PSMD2_4 | TGGGTGTTCCGAAAGTTTA | CTCCGGAGGGCTGTACCTTA | CAGGGTTCCAGACGCATACAA | TAGCGAACACTTTGACTCCAA | 1.53 | 741-744 |
| PTPLA | 9200 | HS_PTPLA_2 | CACTGTTAATTGAATTGTA | AAGTGCATCTTTACTACTAA | TTGAGATAGTTCACTGTTTA | AAGTATTCAGAAGACACTTAA | 1.66 | 745-748 |
| PTPRN | 5798 | Hs_PTPRN_6 | CTGGTGAAGTTGAACATGGAA | CAGGAAGGTGAACAAGTGCTA | CACCAGTGACCTCCACCAGTAT | CCCTATGACCATGCCCGATA | 1.65 | 749-752 |
| RAB4A | 5867 | Hs_RAB4A_9 | AATGCAGGAACTGGCAAATCT | CACACTTGAAATACTAGAATCA | AAGATGACTCAAATCATCAA | CAGGTCCGTGACGAGAAGTTA | 1.73 | 753-756 |
| RAB6B | 51560 | Hs_RAB6B_6 | ATCCATGTTCTTAGAGCCTCA | ATGGCCAGATGGGTCGTCAA | AACAATTAACTGACGAAATTA | CAGGGATCACATCACTCTTAA | 1.59 | 757-760 |
| RACGAP1 | 29127 | Hs_RACGAP1_4 | CACCACAGACACCAGTATTA | CTGGTAGATAGAGAGCTAA | CAGGTGATGTAGAGATCAA | AGGATGAGTTCATGGAATTTAA | 1.56 | 761-764 |
| RAX | 30062 | Hs_RAX_6 | CAGGGTCTACCACCTTCAA | CCGGGGAGGCTGCCGGCAA | ACCGGGAAGGCAAACTGTCA | CACGACTTTCACCAAGTACCA | 1.76 | 765-768 |
| RBM42 | 79171 | Hs_MGC10433_5 | CCGCCCAATTATCGCGACAA | CCGGAGGTCGCGGCTCCCTA | CTCCAGTACCTGGAATCCAA | GAGCATGTGGAAGGACCGGAA | 1.63 | 769-772 |
| RETN | 56729 | NA | CAGGAGGTCGCGGCTCCCTA | ATCGGTTTCTTCAGTGCCTTA | TCCCTAATATTTAGGGCAATA | NA | 1.77 | 773-775 |
| RFFL | 117584 | Hs_RFFL_5 | AACCCGGACTTGCAGAATCAA | AGAGTCATCTTTACTACTAA | TGCAACTTTGTCAACTCAA | CTCCATGCATCTTCACCGAA | 1.75 | 776-779 |
| RNF150 | 57484 | Hs_RNF150_7 | CCGTGTTCTCAGTGAGCTGAA | TGCAGCAATGGCCAAGATCAA | ATGGCAATGTTCTCTCATCCAA | CGCCTTGTGAACATCACCTA | 1.76 | 780-783 |
| RPL35 | 11224 | Hs_RPL35_4 | AATGCAGGAACTGGCAAATCT | TGCAGCAATGGCCAAGATCAA | CAGGAAATTCTACAAGGCAA | CGAGGAGAACCTGAAGACCAA | 1.53 | 784-787 |
| RPLP2 | 6181 | Hs_RPLP2_4 | CAGGTATCAGTGAGCTGAA | ATCCATGTTCTAGAGCCTCA | CAGGGCCAAGGACATCAAGAA | CAGCGTGGGTATCGAGGCGGA | 1.38 | 788-791 |
| RPS10 | 6204 | Hs_RPS10_8 | ACCGGCATGCTCCTTCCTTT | CCATATCTTTGCATCCTTCAA | GACATTTCTACTTGGTACTTA | ACCAATGAGGGTATCCAGTAT | 1.69 | 792-795 |
| RPS14 | 6208 | Hs_RPS14_9 | CCATATCTTTGCATCCTTCAA | TCGGGCGGATTGAGGATGTCA | ATCACCGCCGTCACACATCAA | TGGGATGAAGGTAAGGCAGA | 1.57 | 796-799 |
| RPS16 | 6217 | Hs_RPS16_5 | ATGATTGAGCGCGACGCTA | ACGGGCAATGGTCTCATCAA | TCGGACGCAAGAAGACAGGGA | CCCGCGCTCGCTACCAGAAAT | 1.49 | 800-803 |
| RPS27A | 6233 | NA | CTGACTTACTGTTTCAACAAA | CTGACTTACTGTTTCAACAAA | TCGAGGTTGAACCCTCGGATA | NA | 1.46 | 804-806 |
| RPS5 | 6193 | Hs_RPS5_7 | CGCAACTCCTATGCCATTAA | TTGGATCAATCTGCACCAATA | TTCCCAGCTGCTCTACGCCAGTGA | CTCCATGCATCTCTACCTA | 1.33 | 807-810 |
| RPS6KA6 | 27330 | H_sRPS6KA6_9 | CAGGTCCACAATATTCATACT | CAGGTGTGGATAAATGGCTAA | GGAGTACAAGGCAGATCCAA | TTCATCTGATCTTAAACCTA | 1.82 | 811-814 |
| RUNX1 | 861 | Hs_RUNX1_2 | CTCCCTTTCATGTTAATCAA | CAGGTCGTTCTTATCGCAATAGA | CAGGATACAAGGCAGATCCAA | CCGCACCTTATCAATTGCAA | 1.82 | 815-818 |

| Gene | ID | Probe1 | Probe2 | Probe3 | Ratio | Range |
|---|---|---|---|---|---|---|
| SAFB | 6294 | Hs_SAFB_5 | ACGGACTGTAGTAATGGATAA | CTGCCATATTGTAGCTCAATTA | AGGGTGCGTGAACGCAGTGAA | 1.79 | 819-822 |
| SCAF1 | 58506 | Hs_R-A1_5 | CTGGGCTCCATTGGCGTCAAA | CTGGACGTATTTATGGCTCCA | CACGGCTACTGTGTTGGACAT | 1.64 | 823-826 |
| SCAMP4 | 113178 | Hs_SCAMP4_5 | ACCCGTGTTCATCATCCGA | CAGGATGCGTTGCTGTAGGA | CCGTCAAATCTGTGCCTTAT | 1.88 | 827-830 |
| SCARB1 | 949 | Hs_SCARB1_9 | CCGATCCATGAAGCTAATGTA | TAGGGAGGAGCTCGTCAACAA | CAGCGAGATCCTGAAGGGCGA | 1.41 | 831-834 |
| SDC1 | 6382 | Hs_SDC1_2 | CAGGGCCTCCTGGACAGGAAA | TCCGACTGCTTTGGACCTAAA | CAGGTGCTTGCAAGATATCA | 1.75 | 835-838 |
| SELPLG | 6404 | Hs_SELPLG_5 | CAGCAATTTGTCCGTCAACTA | ATGGAGATACAGACCACTCAA | CCGGAGACAGGCCACCGAATA | 1.88 | 839-842 |
| SERPINA6 | 866 | Hs_SERPINA6_5 | CAGCAGACAGATCAACAGCTA | CAACAGCTATGTCAAGAATAA | AGGGTTATGAAACCAGTGTAA | 1.75 | 843-846 |
| SERPINB2 | 5055 | Hs_SERPINB2_7 | CAGAAGGGTAGTTATCCTGAT | ACCTATGACAAACTCAACAA | TGCGAGCTTCCGGGAAGAATA | 1.73 | 847-850 |
| SERPINE2 | 5270 | Hs_SERPINE2_10 | CTGGGAGGTATTTGTAAGGAAA | AACCCGTGTTTGTTTAAGAAT | AACTCCTGTCTTGCTAGAACAA | 1.45 | 851-854 |
| SEZ6L2 | 26470 | Hs_SEZ6L2_9 | TCCATGCTTGGAGAAGGACAA | CAGGAGCCACTATCAGGCCTA | CTCATTCAGGAGCGCTATGAA | 1.4 | 855-858 |
| SF3A1 | 10291 | Hs_SF3A1_5 | CAGGATAAGACGGAAATTGAA | CGCAAGGATTATGAATCCCAA | TACGAGTTTGCTTGGTCAGAA | 1.63 | 859-862 |
| SF3B1 | 23451 | Hs_SF3B1_7 | ACGATGACTATTCATCATCTA | GACCGGGAAGAATGAATACAAA | AAATATGGACCTATTCGTCAA | 1.65 | 863-866 |
| SF3B14 | 51639 | Hs_SF3B14_7 | AACAATTCGACTTCCACCTGAA | AACAGCTTTGATGGAACTCA | CAGGATCTCCGAGCAGCAA | 1.8 | 867-870 |
| SFTPB | 6439 | Hs_SFTPB_4 | CACGATGAGGAAGTTCCTGGA | CCGAGCTTTCCATTCCAGAA | TCCATCTGCTGTTTCTATTA | 1.76 | 871-874 |
| SIGMAR1 | 10280 | Hs_OPRS1_5 | CCGGCTTGACTCCACCTA | AGGGATATCATGCTTATGTA | CAGCGTCTTCCATTCCAGAAA | 1.45 | 875-878 |
| SLC12A4 | 6560 | Hs_SLC12A4_7 | CAAGAACATGATGGAAATTGA | TCCCGTGTTTCCGTATGCAT | CGCCGGCATGATCTACAAATA | 1.44 | 879-882 |
| SLC22A6 | 9356 | Hs_SLC22A6_8 | CACCTTGATTGGCTATGTCTA | CACGGACCAGTCCATTGTCCGA | TGCCACTAGCTTTGCATACTA | 1.87 | 883-886 |
| SLC25A19 | 60386 | Hs_SLC25A19_6 | CTCCCGTGATCACTTCTGTAA | CTCGTATGAATCACTTCTGTAA | TCCGTGGACTCTTCAAGAA | 1.58 | 887-890 |
| SLC4A8 | 9498 | Hs_SLC4A8_5 | AGCCGTCATTATTAACAGGAA | GACGGTCATCTAAAGTTTAT | TGGGACCAGTACAAATTCTCAA | 1.81 | 891-894 |
| SLC7A1 | 6541 | Hs_SLC7A1_4 | GAGGGTTGGTTTATTATCAAA | ACGGATCTGGATATACACTAT | ATGATCGGCGATGATTATTA | 1.79 | 895-898 |
| SMU1 | 55234 | Hs_SMU1_6 | TTGCACGAAGCTCGCATTGAA | TAGGAGCCGTTAAGTATATAT | CAGCACCAATAGACTATTTA | 1.82 | 899-902 |
| SNRP70 | 6625 | Hs_SNRP70_5 | AAGATTGAGCGGCGACAGCAA | CTCGGAGAATGGGTATTTGA | TACGATGTTACGCAACCACTA | 1.59 | 903-906 |
| SNRPF | 6636 | Hs_SNRPF_9 | AAGGGCTATCTGTATCTGTA | TTGGCGGCCATTCTCGGAGTA | CTCCTCCAACTCGTCGTGAAA | 1.43 | 907-910 |
| SNX6 | 58533 | Hs_SNX6_3 | AAGGTCTAGGTCACTAGTGA | TAGACTAAACAAGTATTGTA | AAAGATTACTCACTGAACTA | 1.83 | 911-914 |
| SNX9 | 51429 | Hs_SNX9_4 | CAGCCGCTTTCCAGTGATGTA | ACAGATCTCAATGATGCAATA | ACCGCGGACTTAAAGCAATAA | 1.54 | 915-918 |
| SON | 6651 | Hs_SON_6 | ATGAATGTTGATTTATCTTAA | AAAGATAATTCATCCTATAATA | ATGGAATGCTTTCGTGGTCAAA | 1.31 | 919-922 |
| SRRM2 | 23524 | Hs_SRRM2_3 | GCCACCTAAACAGAAAATCTA | CCCGGCGTATCTCCGGAGCTA | TAGGTCTTTGCATACTA | 1.85 | 923-926 |
| STAB1 | 23166 | Hs_STAB1_4 | CACGAAATATCCTACAAGTA | CAGCCAACTGTAGCCAGGTA | CAGGATGTCTTCAAATCAGA | 1.48 | 927-930 |
| SULF2 | 55959 | Hs_SULF2_9 | AGGGATGTCCTCAACCAGCTA | ATGACAGATTCTGGAGGATAA | TAGGAACAATGGTCACTTGTA | 1.67 | 931-934 |
| SUPT6H | 6830 | Hs_SUPT6H_8 | TCAGTGTATGCTAGGCAACAA | CTGCCGCATCATGAAGATTGA | CACATCGACCACGAGATTGAA | 1.51 | 935-938 |
| TBL3 | 10607 | Hs_TBL3_6 | CCGTATCTGAAGCTTGAACACAA | CTGCTCACGTGGAACACCAA | CTGCAAGGAACTGCCGCCAA | 1.75 | 939-942 |
| TCF3 | 6929 | NA | CCCGATCACTCAAGCAATAA | CCAGGTTGTGTCGTGCCTCCAA | CTGGCATCGTGCGGCACTA | 1.71 | 943-944 |
| TFE3 | 7030 | Hs_TFE3_4 | TCGCAGGCGATTCAACATTAA | GAGCGGAACCTGAATCCCAA | NA | 1.82 | 945-948 |
| TMEM50B | 757 | Hs_THEM50B_2 | AATGGAGTAGATTGTACATTA | TCCGGATTGTGCTGACAATA | AAGGAGATTGATGATGTCATT | 1.77 | 949-952 |
| TNFRSF18 | 8784 | Hs_TNFRSF18_6 | CAGGAGGAGGAGAGAGACACA | AAGGGATAATACATGATCAAA | TGGGTCGGGATTCTCAGGTCA | 1.58 | 953-956 |
| TNK2 | 10188 | Hs_TNK2_8 | CAAGCTGCACATCCAGATGAA | CGGCAAGTGCGTCAGATCTGCAGGAA | TGGGTCGGGATTCTCAGGTCA | 1.74 | 957-960 |
| TRERF1 | 55809 | Hs_TRERF1_8 | CGCAACAAATTCGCCCATCA | AGAGTGGGTACTGTTCGGTAA | TACCTGCTTCTTCCAGAGAA | 1.81 | 961-964 |
| TRIM14 | 9830 | Hs_TRIM14_7 | CACCGAGAAGCTCAAGGCTAA | CACGTGCAGAAACTCAGCCAA | CTGGAAGCCTGTCAGGTTA | 1.52 | 965-968 |
| TRIM21 | 6737 | Hs_TRIM21_8 | CAGCCTTGAGGAATAATATA | CAGCAGCATACCTGAAATGAA | GGCCAAGAAATTCATTGATAA | 1.69 | 969-972 |
| TRIM60 | 166655 | Hs_TRIM60_8 | GAGCCTTGGAGAAGATTAATATA | TTGCGTCAGGTCTAGAACAA | AAGGATGTAGATGATACTT | 1.78 | 973-976 |
| TSSK6 | 83983 | Hs_TSSK6_1 | CCGGTTGGAACCTGCAATAAA | CAAGGTACCGTGGCCATCAA | AGCTCCGTAATTTGCCAGAA | 1.56 | 977-980 |
| TUBB4 | 10382 | Hs_TUBB4_5 | CTGCCTCACCCTCAATAATA | TGAGCCTAATTTATCTTTAA | GAAGGTGGCCACATCCAAGAA | 1.77 | 981-984 |
| TXNL4A | 10907 | Hs_IXNL4A_6 | AAGGTTCTCTGGTTATAAA | CAGCATCCGCGAGAAGGTTAA | CTCGAGGCTTCTGACCTTGA | 1.62 | 985-988 |
| UBAC2 | 337867 | NA | CCGGCAGCTGATGTTCTCTCA | TACATCTGGATTGTAGCCATA | CAAGGACTACTCCAACCAAGTA | 1.89 | 989-990 |
| UBE2N | 7334 | Hs_UBE2N_8 | AAGATAGTACTGAATGGAGTA | CTGGCCCTGAGCATGCATAAA | NA | 1.78 | 991-994 |
| VNN2 | 8875 | Hs_VNN2_9 | AACACACATCATGTCAGCCTA | CAGCAATTCAGCAATAACTTA | TCCCAATTTGACAATCGTATT | 1.83 | 995-998 |
| WNT3A | 89780 | Hs_WNT3A_3 | ACCCGCCATCCTCTGCTCCAA | CCGTGTTGGACTTCCACACTTCAA | CTGAAGTGCTACTTACCGAAA | 1.85 | 999-1002 |
| WNT9A | 7483 | Hs_WNT9A_4 | CCGGCTGAAGCTGGAGCGGAA | CAAGTATGGACGCGACACTCAA | CAGCAACTACGTGGAGATCAT | 1.4 | 1003-1006 |
| XAB2 | 56949 | NA | CAGTACAACACGCAGGTCAA | CCGGACCTTGTCTTCGAGGAA | CAGCAACAAGTTCGTCAAGGA | 1.65 | 1007-1009 |
| XPNPEP1 | 7511 | Hs_XPNPEP1_4 | AAGGAGAACCTCGTTGACAAA | CCCGACTCTTTTGGCCAGTGA | NA | 1.74 | 1010-1013 |
| XPO1 | 7514 | Hs_XPO1_6 | CCCATTGTAAGGACTTCAA | TACATGTTACTCCCTAATCAA | CCCGACTGGAACCAAAGGTCA | 1.64 | 1014-1017 |
| XRCC6 | 2547 | Hs_G22P1_3 | TTTGTACTATATACTGTTAAA | AAGCTCTATCGGGAAAACAAAT | ATGTTAGTCGAATGGCTAAA | 1.42 | 1018-1021 |

TABLE 3-continued

| GeneSymbol | LocusID | siRNA2 WST | siRNA3 WST | siRNA4 WST | siRNA1 NP1 WSN | siRNA2 NP1 WSN | siRNA3 NP1 WSN | siRNA4 NP1 WSN | Hits per gene WSN | siRNA1 NP1 HH | siRNA2 NP1 HH | siRNA3 NP1 HH | siRNA4 NP1 HH | Hits per gene HH |
|---|---|---|---|---|---|---|---|---|---|---|---|---|---|---|
| AAMP | 14 | 1.74 | 1.83 | 1.72 | 0.69 | 0.06 | −0.33 | 0.02 | 0 | 0.87 | 0.07 | 0.4 | 0.97 | 2 |
| ACTN1 | 87 | 1.64 | 1.68 | 1.9 | −1.68 | 0.63 | −0.42 | 0.13 | 0 | 1.03 | 0.97 | 0.26 | −0.4 | 2 |
| AHCYL1 | 10768 | 1.47 | 1.55 | 1.71 | 0.72 | 0.87 | −0.15 | 0.73 | 1 | 0.8 | 0.82 | 0.17 | 0.32 | 2 |
| AIG1 | 51390 | 1.87 | 1.87 | 1.78 | 0.97 | 0.74 | 0.83 | 0.81 | 3 | −1.56 | 0.4 | 0.83 | 0.93 | 2 |
| AKR1C4 | 1109 | 1.63 | 1.83 | 1.78 | 0.87 | 0.53 | 0.78 | 0.9 | 2 | 0.68 | 0.11 | 0.52 | 0.83 | 1 |
| ALDH7A1 | 64400 | 1.68 | 1.81 | 1.76 | 0.96 | 0.58 | 0.38 | 0.17 | 1 | 0.98 | 0.6 | 0.29 | 1.06 | 2 |
| ALX4 | 501 | 1.9 | 1.9 | 1.87 | 0.88 | 1.01 | 0.74 | 0.84 | 3 | 0.83 | 0.9 | −0.08 | 0.87 | 3 |
| AP2M1 | 60529 | 1.67 | 1.6 | 1.71 | 0.91 | 0.85 | 0.62 | 0.95 | 3 | 1.38 | 0.9 | 0.99 | −0.85 | 3 |
| APBB1IP | 1173 | 1.51 | 1.57 | 1.59 | 0.86 | 0.92 | 0.81 | 0.62 | 3 | 0.89 | 0.26 | 0.45 | 0.94 | 2 |
| ARD1A | 54518 | 1.86 | 1.91 | 1.9 | 0.49 | −0.5 | 0.47 | 0.28 | 0 | 0.98 | 0.62 | −0.21 | 0.9 | 2 |
| ARTN | 8260 | 1.83 | 1.72 | 1.88 | 1 | 0.99 | 0.87 | 0.86 | 4 | 1 | 1.05 | 0.92 | 1 | 4 |
| ASAH3L | 9048 | 1.38 | 1.63 | 1.68 | 0.8 | 0.96 | −0.15 | 0.97 | 2 | 0.59 | 1.11 | −0.45 | −2.59 | 1 |
| ATCAY | 340485 | 1.79 | 1.85 | 1.72 | 0.86 | 0.96 | −0.88 | 0.6 | 2 | 0.9 | 0.85 | 0.51 | 0.81 | 3 |
| ATP1A2 | 85300 | 1.81 | 1.9 | 1.83 | 0.91 | 0.84 | 0.42 | −1.46 | 2 | 0.08 | 1.13 | 0.44 | 1.04 | 2 |
| ATP6AP1 | 477 | 1.67 | 1.64 | 1.61 | −0.04 | 1 | 0.76 | 0.87 | 2 | 0.35 | 0.83 | 0.64 | −239.08 | 1 |
| ATP6AP2 | 537 | 1.63 | 1.89 | 1.7 | 1 | 0.78 | 0.98 | 0.92 | 3 | 1.02 | 0.53 | 0.31 | 0.95 | 3 |
| ATP6V0C | 10159 | 1.87 | 1.93 | 1.84 | 0.8 | 0.67 | 0.83 | 0.49 | 2 | 1.01 | 0.92 | 0.98 | 0.93 | 4 |
| ATP6V0D1 | 527 | 1.91 | 1.88 | 1.85 | 0.75 | 0.91 | 0.96 | 0.96 | 3 | 1.33 | 1.22 | 1.11 | 1.03 | 4 |
| ATP6V1A | 9114 | 1.46 | 1.84 | 1.78 | 0.84 | 0.75 | 0.89 | 0.46 | 2 | 0.6 | 1.14 | 1.23 | 1.1 | 3 |
| ATP6V1B2 | 523 | 1.93 | 1.91 | 1.86 | 0.89 | −0.71 | 0.83 | 0.93 | 2 | 1.11 | 0.8 | 0.3 | 0.98 | 3 |
| AZIN1 | 526 | 1.55 | 1.8 | 1.89 | 0.88 | 0.8 | 0.46 | 0.99 | 2 | 1.25 | 1.13 | −0.26 | 1.02 | 3 |
| B2N | 51582 | 1.82 | 1.86 | 1.69 | 0.53 | 0.94 | 0.92 | 0.47 | 2 | 0.31 | 1.32 | 0.8 | 0.7 | 1 |
| B3GNT1 | 567 | 1.35 | 1.57 | 1.59 | 1 | 0.05 | 0.09 | 0.99 | 2 | 0.85 | 0.88 | −0.38 | 1.02 | 3 |
| BAIAP3 | 11041 | 1.53 | 1.56 | 1.7 | 0.87 | 0.91 | −2.1 | 0.81 | 3 | 0.38 | −1.6 | −1.1 | 0.98 | 1 |
| BARHL2 | 8938 | 1.78 | 1.77 | 1.84 | 0.56 | 0.43 | −0.87 | −1.03 | 0 | 0.66 | 0.81 | 0.87 | 0.85 | 3 |
| BNIP3L | 343472 | 1.9 | 1.88 | 1.82 | −0.19 | 0.32 | 0.81 | 0.64 | 1 | 0.12 | −0.6 | 1.25 | 1.17 | 2 |
| BRUNOL6 | 665 | 1.65 | 1.8 | 1.87 | 0.87 | −0.67 | 0.72 | 0.92 | 2 | 0.72 | 0.95 | 0.66 | 0.98 | 3 |
| BZRAP1 | 60677 | 1.88 | 1.88 | 1.77 | 0.12 | −0.66 | 0.87 | 0.83 | 2 | −0.01 | −4.07 | 1.38 | 1.32 | 2 |
| C14orf172 | 9256 | 1.63 | 1.55 | 1.86 | 0.8 | 0.99 | 0.99 | 0.96 | 4 | 0.96 | 1 | 1.04 | −0.45 | 3 |
| C19orf47 | 115708 | 1.8 | 1.91 | 1.79 | 0.83 | 0.86 | 0.56 | 0.87 | 3 | 0.82 | 0.43 | 0.85 | −0.18 | 2 |
| C21orf7 | 126526 | 1.57 | 1.58 | 1.73 | −0.47 | 0.85 | 0.86 | 0.98 | 3 | 0.44 | 0.9 | −0.36 | 0.93 | 2 |
| C3orf31 | 56911 | 1.57 | 1.62 | 1.58 | 0.51 | 0.44 | −0.51 | 0.38 | 0 | 0.91 | 0.85 | −0.22 | 0.94 | 2 |
| C4orf29 | 132001 | 1.63 | 1.72 | 1.73 | 0.65 | 0.89 | −0.59 | −3.54 | 1 | 1.01 | 0.99 | 0.7 | 0.47 | 3 |
| CARD9 | 00167 | 1.53 | 1.68 | 1.64 | 0.67 | 0.78 | 0.09 | 0.98 | 3 | −1.47 | 1.04 | −1.21 | 1.01 | 2 |
| CASP8AP2 | 64170 | 1.81 | 1.87 | 1.61 | 0.71 | 0.49 | −1.44 | 0.49 | 1 | 0.86 | −2.13 | 1.23 | 0.44 | 1 |
| CCNB3 | 9994 | 1.88 | 1.9 | 1.83 | 0.8 | 0.96 | 0.53 | −0.73 | 1 | 0.55 | 0.84 | 0.81 | −0.75 | 1 |
| CD48 | 85417 | 1.52 | 1.49 | NA | −0.57 | −0.15 | −0.13 | 0.73 | 0 | 0.73 | 0.85 | −0.7 | NA | 2 |
| CD58 | 962 | 1.48 | 1.37 | 1.64 | 0.78 | 0.99 | 0.35 | 1 | 2 | 0.18 | 0.7 | 0.85 | 1.08 | 2 |
| CD6 | 965 | 1.88 | 1.84 | NA | 0.76 | 0.96 | −0.25 | 1 | 2 | 0.87 | 0.77 | 0.97 | NA | 2 |
| CD63 | 923 | 1.83 | 1.83 | 1.8 | 0.75 | 0.84 | 0.23 | 0.62 | 1 | 1.01 | 0.6 | 0.95 | 0.89 | 2 |
| CD81 | 967 | 1.79 | 1.86 | 1.81 | 0.66 | 0.72 | 0.74 | 0.86 | 3 | −0.11 | 0.1 | 1.21 | 0.85 | 2 |
| CDC23 | 975 | 1.36 | 1.53 | 1.64 | 0.99 | 0.58 | 0.7 | 1 | 3 | 0.85 | 0.66 | 0.38 | 1.00 | 3 |
| CDK4 | 8697 | 1.59 | 1.85 | 1.52 | 0.85 | 0.88 | 0.04 | 0.86 | 2 | 0.64 | 0.38 | −0.04 | 0.74 | 0 |
| CDKN1B | 1019 | 1.62 | 1.88 | 1.87 | 0.66 | 0.84 | 0.68 | 1 | 3 | 0.53 | −0.27 | 0.86 | 0.99 | 2 |
| CEL | 1027 | 1.89 | 1.88 | 1.84 | 0.99 | 0.72 | 0.23 | 0.62 | 1 | 0.17 | 0.7 | 0.91 | 1.08 | 2 |
| CHST5 | 1056 | 1.72 | 1.56 | 1.52 | 0.85 | 0.58 | 0.7 | 0.86 | 3 | 0.64 | 1.01 | 0.99 | −0.54 | 2 |
| CIB3 | 23583 | 1.45 | 1.48 | 1.44 | −0.41 | 0.88 | 0.04 | 1 | 1 | 0.5 | 1.02 | 0.94 | −1.5 | 2 |
| CLIC4 | 117286 | 1.52 | 1.61 | 1.84 | 0.68 | 0.68 | −0.28 | 0.81 | 0 | −1.57 | 0.82 | 1.1 | 0.21 | 2 |
| CLK1 | 25932 | 1.77 | 1.68 | 1.62 | −0.41 | 0.68 | −0.28 | −0.29 | 0 | −1.85 | 0.94 | 0.05 | 1 | 2 |
| | 1195 | 1.92 | 1.89 | 1.85 | 0.84 | 0.58 | 0.88 | 0.51 | 2 | 0.9 | 0.82 | 6.89 | 0.87 | 1 |

TABLE 3-continued

| | | | | | | | | | | |
|---|---|---|---|---|---|---|---|---|---|---|
| CNNM1 | 26507 | 1.76 | 1.71 | 1.39 | 0.88 | 0.17 | 0.28 | −1.88 | 1 | 0.86 | 1 | −8.59 | 0.43 | 2 |
| COPA | 1314 | 1.75 | 1.8 | NA | 1 | 1 | 1 | NA | 3 | 1.01 | 1.05 | 1.05 | NA | 3 |
| COPB1 | 1315 | 1.65 | 1.74 | NA | 0.97 | 1 | 0.99 | NA | 1 | 0.85 | 1 | −2.35 | NA | 1 |
| COPB2 | 9276 | 1.48 | 1.43 | 1.63 | 1 | 1 | 1 | 1 | 4 | 0.16 | 1.01 | 0.98 | 1 | 3 |
| COPG | 22820 | 1.3 | 1.66 | 1.67 | 0.91 | 0.07 | 0.22 | 1 | 3 | 0.9 | 0.94 | 0.22 | 1.16 | 3 |
| CRAMP1L | 57585 | 1.5 | 1.85 | 1.81 | 0.6 | 0.69 | 0.7 | 0.57 | 0 | 0.82 | 0.93 | 0.75 | 1 | 1 |
| CRYAA | 1400 | 1.7 | 1.76 | 1.74 | 0.95 | 0.92 | 0.59 | 0.49 | 2 | 0.73 | −0.26 | 0.48 | 0.9 | 1 |
| CTA-216F10.6 | | 1.51 | 1.71 | 1.5 | 0.51 | 0.99 | 0.19 | 1.01 | 2 | 0.25 | 1.04 | 0.28 | −0.35 | 2 |
| CUEDC2 | 79004 | 1.5 | 1.33 | NA | 0.78 | 1 | 0.82 | 0.89 | 3 | 1.16 | 0.48 | 1.00 | 0.29 | 0 |
| CXCR6 | 10663 | 1.79 | 1.8 | 1.83 | −1.15 | 1 | 1 | 0.9 | 2 | 0.42 | 0.47 | 0.15 | 0.21 | 1 |
| CYC1 | 1537 | 1.47 | 1.7 | 1.84 | −0.93 | 0.39 | 0.85 | 0.93 | 3 | 0.18 | 0.5 | 1.1 | 0.36 | 2 |
| CYP17A1 | 1586 | 1.89 | 1.84 | 1.82 | −1.63 | 0.92 | 0.18 | 0.88 | 2 | −1.89 | 1.84 | −0.27 | 0.82 | 2 |
| CYP2U1 | 113612 | 1.58 | 1.46 | 1.49 | −0.12 | 0.47 | 0.91 | 0.6 | 1 | −2.14 | 1 | 1 | −2.33 | 0 |
| DBT | 1629 | 1.36 | 1.63 | 1.67 | 0.77 | 1 | 1 | 0.93 | 3 | 1.02 | 0.92 | −2 | | 3 |
| DCLK2 | 166614 | 1.58 | 1.68 | 1.65 | 0.95 | 0.95 | −0.01 | 0.95 | 3 | 1.02 | −0.51 | 0.66 | −0.16 | 1 |
| DGKH | 160851 | 1.37 | 1.53 | 1.63 | −0.51 | −0.23 | 0.63 | 0.92 | 1 | −0.44 | 0.98 | −4.95 | 1.02 | 2 |
| DGUOK | 1716 | 1.67 | 1.7 | 1.76 | 0.56 | 0.72 | 0.86 | 0.98 | 2 | 0.04 | −1.78 | 0.7 | 0.37 | 0 |
| DHRS2 | 10202 | 1.78 | 1.77 | 1.64 | 0.8 | 0.11 | 0.93 | 0.68 | 2 | 0.33 | 0.18 | 0.43 | −0.23 | 2 |
| DLG2 | 1740 | 1.79 | NA | NA | 0.91 | 1 | NA | NA | 1 | −2.41 | 0.98 | NA | 1 | 3 |
| DMAP1 | 55929 | 1.87 | 1.91 | 1.82 | 1.61 | 0.48 | −0.69 | 0.68 | 3 | 0.82 | 0.11 | 0.02 | 0.9 | 1 |
| DMRT1 | 1761 | 1.93 | 1.92 | 1.71 | 0.91 | 0.94 | 0.94 | 0.6 | 1 | 0.98 | 0.73 | −1.2 | 0.73 | 2 |
| DTX3 | 196403 | 1.75 | 1.67 | 1.67 | 0.84 | 0.68 | 0.91 | 0.98 | 3 | 0.8 | −17.71 | 0.84 | 1.01 | 1 |
| DUSP27 | 92235 | 1.81 | 1.7 | 1.54 | 0.63 | −0.48 | −0.50 | 0.97 | 3 | 0.8 | 0.8 | −17.12 | 0.89 | 2 |
| E2F1 | 1869 | 1.76 | 1.9 | 1.74 | 0.87 | 0.75 | −0.81 | 0.79 | 2 | 0.29 | 0.03 | 1.01 | −4.6 | 1 |
| EEF1A1 | 1915 | 1.75 | 1.87 | 1.64 | 0.93 | 0.05 | 0.29 | 0.77 | 1 | 0.6 | 0.94 | 0.79 | 0.9 | 2 |
| EIF3A | 8661 | 1.72 | 1.75 | 1.69 | 1 | 0.98 | 0.98 | 0.93 | 4 | 1 | 1 | 1.05 | −6.63 | 3 |
| EIF3C | 8663 | 1.52 | 1.36 | 1.44 | 0.88 | 0.96 | 0.99 | 0.98 | 4 | 0.82 | −0.94 | 0.58 | 0.53 | 1 |
| EIF3G | 8666 | 1.47 | 1.63 | NA | −0.71 | 0.95 | 0.99 | NA | 2 | −0.14 | −1.61 | 0.99 | NA | 0 |
| EIF4A3 | 9775 | 1.77 | 1.71 | 1.77 | 0.98 | 0.63 | 0.91 | 0.61 | 2 | 0.98 | 0.23 | 1.19 | 0.98 | 3 |
| ENGASE | 64772 | 1.53 | 1.47 | 1.64 | 0.86 | 0.93 | −0.05 | 0.17 | 2 | −0.62 | −0.24 | 0.73 | −0.98 | 1 |
| EPB49 | 2039 | 1.72 | 1.86 | 1.79 | 0.9 | 0.63 | 0.10 | −0.84 | 1 | 0.98 | 0.94 | 0.77 | −0.98 | 2 |
| EPHB6 | 2051 | 1.77 | 1.94 | 1.85 | 0.97 | 0.98 | 0.39 | 0.89 | 1 | 0.32 | −0.66 | 0.59 | 0.28 | 0 |
| ERN2 | 10595 | 1.42 | 1.75 | 1.86 | −0.04 | 0.61 | 0.95 | 0.49 | 3 | 0.57 | 0.81 | 1.02 | −0.12 | 2 |
| FAU | 2197 | 1.45 | 1.49 | NA | 1 | 1 | 1 | NA | 3 | 0.28 | 1.02 | 0.64 | 0.95 | 0 |
| FBXW10 | 10517 | 1.45 | 1.48 | 1.66 | −1.32 | 0.17 | −2.43 | 0.88 | 1 | 0.83 | 0.94 | 0.9 | NA | 3 |
| FCHO2 | 115548 | 1.43 | 1.69 | 1.82 | 0.94 | 0.94 | 0.45 | 0.59 | 2 | −1.75 | −0.56 | −0.86 | 0.38 | 1 |
| FCRL6 | 343413 | 1.65 | 1.86 | 1.75 | 0.78 | 0.95 | 0.32 | 0.32 | 1 | 1.02 | 1.1 | 1.88 | −1.94 | 0 |
| FERMT3 | 83706 | 1.73 | 1.73 | 1.75 | 0.51 | −0.36 | 0.86 | −0.25 | 2 | −0.35 | −0.71 | 0.89 | 0.86 | 4 |
| FGF3 | 2248 | 1.57 | 1.79 | 1.81 | 0.22 | 0.98 | 0.96 | 0.88 | 1 | 0.87 | 0.64 | 0.99 | 0.86 | 2 |
| FLJ11235 | 54508 | 1.85 | 1.85 | 1.82 | 0.95 | 1 | 0.76 | 0.77 | 3 | 1 | 0.28 | 0.99 | 0.04 | 2 |
| FLJ20489 | 55652 | 1.65 | 1.74 | 1.86 | −1.1 | 0.76 | 0.75 | −1.8 | 1 | 0.82 | 0.8 | 0.93 | 0.95 | 3 |
| FLJ34077 | 484033 | 1.74 | 1.81 | 1.6 | 0.61 | 0.44 | 0.42 | 0.94 | 0 | 0.23 | −0.1 | 1.86 | 1.15 | 3 |
| FNTB | 2342 | 1.82 | 1.92 | 1.81 | 0.94 | 0.9 | 0.77 | 0.35 | 1 | 0.6 | −1.3 | 0.98 | 1.35 | 2 |
| G6PC | 2538 | 1.57 | 1.85 | 1.85 | 0.85 | 0.95 | 0.73 | 0.98 | 3 | 0.2 | 0.5 | 0.02 | 0.08 | 0 |
| GCLC | 2729 | 1.78 | 1.83 | 1.83 | 1 | 0.36 | 0.77 | 0.39 | 2 | 1.02 | 0.6 | 0.99 | 0.67 | 3 |
| GNMT | 27232 | 1.78 | 1.8 | 1.74 | 0.96 | 0.03 | 0.87 | 0.01 | 1 | 1.02 | −5.16 | 0.99 | 0.89 | 3 |
| GNRH2 | 2797 | 1.64 | 1.85 | 1.9 | 0.71 | 0.93 | 0.73 | 0.99 | 2 | 0.86 | 1 | 0.7 | 1.19 | 3 |
| GPR146 | 115330 | 1.55 | 1.61 | 1.7 | −0.06 | 0.57 | 0.09 | −0.25 | 1 | 1.02 | −3.24 | 0.96 | 0.94 | 2 |
| GRID2 | 2895 | 1.8 | 1.81 | 1.85 | 0.96 | 0.11 | 0.59 | −0.3 | 2 | 1.3 | 0.71 | 1.02 | −0.35 | 2 |
| GRIN2C | 2905 | 1.75 | 1.79 | 1.83 | 0.85 | 0.86 | 0.39 | 0.28 | 3 | 0.33 | −47.73 | 0.64 | 0.57 | 1 |
| GRP | 2922 | 1.61 | 1.79 | 1.75 | 0.82 | 0.57 | 0.86 | 0.83 | 1 | −0.33 | 0.73 | 0.89 | 0.92 | 0 |
| GSK3A | 2931 | 1.71 | 1.85 | 1.87 | 0.62 | 0.96 | 0.37 | 0.71 | 1 | 0.93 | 0.64 | 0.94 | 0.56 | 2 |
| HARBI1 | 9776 | 1.46 | 1.77 | 1.74 | 0.31 | 0.88 | 0.74 | 0.83 | 2 | 0.54 | 0.9 | −1.17 | 0.48 | 1 |

TABLE 3-continued

| | | | | | | | | | | |
|---|---|---|---|---|---|---|---|---|---|---|
| HIBCH | 26275 | 1.49 | 1.53 | 1.73 | 0.2 | 0.36 | −0.29 | 0.11 | 0 | 1.06 | 0.8 | −0.46 | 0.98 | 3 |
| HIST1H2BN | 8341 | 1.69 | 1.64 | 1.67 | 0.89 | 0.99 | −1.17 | −0.04 | 1 | 1 | 1 | 0.64 | −0.01 | 2 |
| HPGD | 3248 | 1.77 | 1.83 | 1.83 | 0.47 | 0.38 | 0.93 | 0.19 | 2 | 1.02 | 0.28 | 0.9 | 0.94 | 3 |
| HSF4 | 3299 | 1.86 | 1.72 | 1.81 | 0.99 | 0.91 | 0.84 | 0.86 | 4 | 0.81 | 10 | −8.36 | 1.01 | 3 |
| HSPD1 | 3329 | 1.53 | 1.71 | 1.67 | 0.93 | 0.97 | −0.21 | 0.59 | 2 | 1.02 | 0.3 | 0.98 | 0.95 | 3 |
| ICAM2 | 3384 | 1.89 | 1.9 | 1.85 | 0.98 | 0.94 | 0.46 | 0.21 | 2 | 0.95 | −1.1 | 0.82 | 1.11 | 3 |
| ICEBERG | 59082 | 1.48 | 1.44 | 1.74 | 0.55 | 0.53 | −0.7 | 0.39 | 0 | 1.02 | 0.94 | −0.54 | 0.94 | 2 |
| IL17RA | 23765 | 1.81 | 1.8 | 1.78 | 1 | 0.03 | −0.09 | −0.05 | 1 | 1.04 | 0.48 | 1.01 | −1.44 | 3 |
| IL1A | 3552 | 1.58 | 1.67 | 1.43 | 0.7 | 0.97 | 0.35 | −0.66 | 1 | 1.15 | 1 | 0.95 | −4.12 | 2 |
| IQCF2 | 389123 | 1.79 | 1.89 | 1.8 | 0.85 | −0.26 | 0.57 | −0.86 | 1 | 0.97 | −0.37 | 1.19 | 0.35 | 2 |
| IRF2 | 3660 | 1.6 | 1.59 | 1.8 | 0.12 | 0.95 | −0.66 | 0.95 | 2 | 1 | 0.66 | 0.41 | 0.81 | 1 |
| ISG15 | 9636 | 1.82 | 1.79 | NA | 0.85 | 0.49 | 0.97 | NA | 2 | 1 | 0.85 | 0.21 | NA | 2 |
| ITLN1 | 55600 | 1.74 | 1.77 | 1.72 | 0.91 | 0.99 | 0.89 | 0.59 | 3 | 0.59 | 0.86 | 1.02 | 0.71 | 2 |
| JARID1D | 8284 | 1.85 | 1.89 | 1.75 | 0.02 | −0.43 | 0.6 | 0.56 | 0 | 0.29 | 0.1 | 0.83 | 1.26 | 2 |
| JUN | 3725 | 1.47 | 1.57 | 1.52 | 0.81 | 1 | 0.57 | 0.97 | 1 | 0.75 | 0.99 | 1.01 | 0.65 | 2 |
| KATNB1 | 10300 | 1.38 | 1.38 | 1.55 | 0.73 | 0.96 | −0.26 | 0.7 | 2 | 0.9 | 0.97 | 0.35 | 0.31 | 2 |
| KCNAB3 | 9196 | 1.01 | 1.87 | 1.71 | 0.91 | 0.79 | 0.99 | 0.91 | 0 | 0.53 | 0.13 | −0.12 | 0.88 | 1 |
| KCNJ12 | 3768 | 1.85 | 1.34 | 1.49 | 0.76 | 0.55 | 0.72 | 0.77 | 1 | 0.97 | 1.01 | 1 | 0.94 | 3 |
| KIAA0664 | 23277 | 1.71 | 1.7 | 1.75 | −1.52 | −0.14 | 0.98 | 0.79 | 2 | −0.16 | −0.20 | 0.86 | 0.73 | 3 |
| KIAA0947 | 23379 | 1.83 | 1.9 | 1.67 | 0.97 | 0.99 | 0.49 | 0.1 | 0 | 0.82 | 1.01 | 1 | −10.73 | 1 |
| KIAA1128 | 54462 | 1.87 | 1.91 | 1.83 | 0.73 | 0.85 | 0.68 | 0.53 | 1 | 0.48 | 0.82 | −1 | 0.94 | 3 |
| KIAA1267 | 284058 | 1.98 | 1 | 1.74 | 0.46 | 0.41 | 0.89 | 0.4 | 0 | 0.88 | 0.94 | 0.1 | 1.32 | 2 |
| KIF11 | 3832 | 1.42 | 1.46 | 1.76 | 0.86 | 0.88 | 0.96 | −0.35 | 2 | −.21 | 0.32 | 0.62 | −0.06 | 1 |
| KIF23 | 9493 | 1.9 | 1.91 | 1.72 | 1 | 0.86 | −0.13 | 0.93 | 3 | 0.91 | 0.42 | 1 | 0.04 | 1 |
| KIF3A | 11127 | 1.43 | 1.54 | 1.46 | 0.98 | 0.82 | 0.34 | 1 | 2 | 0.44 | 1.02 | 0.52 | 0.7 | 2 |
| KPNB1 | 3837 | 1.71 | 1.84 | 1.68 | −.00 | 0.98 | 0.98 | 0.91 | 4 | 0.85 | 1.11 | 0.54 | 1.35 | 4 |
| LAMC2 | 3918 | 1.62 | 1.59 | 1.89 | 0.9 | 0.9 | 0.72 | 0.77 | 1 | 1 | 0.7 | 0.91 | 1.05 | 3 |
| LARP1 | 23367 | 1.54 | 1.7 | 1.66 | 0.76 | 0.98 | 0.98 | 0.79 | 1 | −2.57 | 1 | 0.99 | 0.85 | 2 |
| LHX3 | 8022 | 1.71 | 1.72 | 1.5 | 0.97 | 1 | 0.84 | 0.99 | 4 | 1 | 1 | 0.98 | 0.83 | 3 |
| LINGO1 | 84894 | 1.60 | 1.72 | 1.52 | 0.88 | 0.99 | −0.72 | 0.64 | 1 | 0.42 | −3.65 | 0.58 | 0.96 | 2 |
| LOC162993 | 162993 | 1.79 | 1.01 | 1.75 | 0.70 | 0.32 | −0.21 | −0.57 | 3 | 1.19 | 1 | 0.88 | −1.74 | 2 |
| LOC399940 | 399940 | 1.32 | 1.58 | 1.73 | 0.66 | −1.57 | 0.37 | 0.38 | 0 | 0.31 | 0.98 | −2.52 | 0.94 | 1 |
| LOC401431 | 401431 | 1.65 | 1.36 | 1.7 | −1.91 | 1 | −0.33 | 0.45 | 0 | −0.21 | 0.98 | −0.23 | 1.07 | 0 |
| LOC440733 | 440733 | 1.64 | 1.58 | 1.71 | −0.67 | 0.84 | −0.12 | 0.45 | 1 | 0.73 | 0.87 | 0.56 | 1.04 | 2 |
| LPPR4 | 9890 | 1.86 | 1.78 | 1.78 | 0.93 | 1 | −1.09 | 0.85 | 1 | 0.89 | 0.94 | 0.76 | 0.8 | 3 |
| MAN2B1 | 4125 | 1.81 | 1.02 | 1.81 | 0.94 | 1 | 0.88 | −1.08 | 3 | −0.23 | 0.5 | 0.71 | 0.92 | 2 |
| MAP2K3 | 5606 | 1.65 | 1 | 1.87 | 0.87 | 0.83 | 0.28 | 0.83 | 3 | 0.51 | 0.4 | 0.84 | −0.41 | 1 |
| MATN3 | 4148 | 1.75 | 1.82 | 1.75 | 0.38 | 0.78 | 0.62 | 0.64 | 3 | −2.05 | 0.87 | −1.89 | −0.65 | 0 |
| MED6 | 10001 | 1.54 | 1.53 | 1.71 | 1 | 0.98 | 1 | 0.96 | 4 | 0.62 | 0.92 | 0.87 | 0.31 | 2 |
| MKL1 | 57591 | 1.58 | 1.73 | 1.87 | 0.86 | 0.7 | 0.64 | 0.71 | 1 | 0.37 | 0.88 | 1 | 1 | 3 |
| MRPS12 | 6183 | 1.82 | 1.80 | 1.78 | 0.85 | 0.8 | 0.98 | 0.3 | 3 | 0.19 | 0.88 | 0.89 | 0.95 | 2 |
| MYC | 4609 | 1.72 | 1.76 | 1.63 | 0.96 | 0.66 | 1 | 0.83 | 3 | 0.85 | −0.13 | 0.23 | −0.66 | 0 |
| MYEF2 | 50894 | 1.86 | 1.9 | 1.85 | 0.9 | 0.87 | −0.05 | 0.59 | 3 | −3.19 | 0.99 | 1 | −2.51 | 3 |
| MYOD1 | 4654 | 1.67 | 1.69 | 1.7 | −0.89 | 0.86 | 0.87 | 0.67 | 2 | −0.12 | −0.05 | −5.79 | 0.75 | 0 |
| NAE1 | 8883 | 1.82 | 1.85 | 1.72 | 0.86 | 0.88 | 0.83 | 0.97 | 4 | −1.3 | 0.08 | −9.36 | −15.75 | 0 |
| NDUFV3 | 4731 | 1.51 | 1.5 | 1.68 | 0.48 | 0.9 | 0.37 | 0.88 | 2 | −1.67 | −155.63 | 0.8 | 0.44 | 1 |
| NECAP2 | 55707 | 1.88 | 1.01 | 1.85 | 0.96 | −0.91 | 0.89 | −0.27 | 1 | 1 | 1.02 | 0.56 | −0.49 | 1 |
| NEK8 | 284086 | 1.7 | 1.57 | NA | 0.93 | 0 | −0.02 | NA | 0 | 1 | 0.18 | 1.29 | 0.6 | 3 |
| NEK9 | 91754 | 1.77 | 1.04 | 1.79 | 0.66 | −1.3 | 0.83 | 0.94 | 2 | 0.51 | 0.64 | 0.88 | NA | 1 |
| NSF | 4905 | 1.94 | 1.9 | 1.74 | 0.48 | 0.55 | 0.48 | 0.83 | 1 | 0.82 | 0.46 | 0.99 | 0.46 | 2 |
| NTHL1 | 4913 | 1.84 | 1.83 | 1.71 | 0.48 | 0.86 | −0.11 | 0.67 | 1 | 1.2 | 0.28 | 0.9 | 0.53 | 2 |
| NUP205 | 23165 | 1.57 | 1.79 | 1.79 | 0.53 | 0.98 | −2.15 | 0.88 | 2 | 1.13 | 0.92 | 0.6 | 0.69 | 4 |
| NUP98 | 4928 | 1.83 | 1.87 | 1.8 | 0.98 | 0.93 | 0.01 | 0.99 | 4 | 1.28 | 1.11 | 1.14 | 1.24 | 4 |

TABLE 3-continued

| | | | | | | | | | | | | |
|---|---|---|---|---|---|---|---|---|---|---|---|---|
| NXF1 | 10482 | 1.57 | 1.55 | 1.64 | 0.92 | 0.94 | 1 | 0.38 | 4 | 1.21 | 1.81 | 1.17 | 1.25 | 4 |
| ODZ4 | 26011 | 1.85 | 1.89 | 1.84 | 0.38 | 0.74 | 0.73 | −.71 | 0 | 0.53 | 1.25 | 1.2 | 0.02 | 2 |
| OPN1SW | 611 | 1.84 | 1.79 | 1.87 | 0.86 | 0.95 | 0.18 | −1.38 | 2 | 0.96 | 1.81 | 0.74 | 0.7 | 2 |
| P76 | 196463 | 1.44 | 1.4 | 1.66 | 0.13 | 0.89 | −0.36 | 0.91 | 1 | 1.15 | 0.98 | 0.81 | 0.42 | 3 |
| PCDH18 | 54510 | 1.66 | 1.68 | 1.65 | 0.16 | 0.68 | 0.97 | 0.99 | 2 | −1.01 | 0.2 | 1.01 | 0.25 | 1 |
| PHF2 | 5253 | 1.82 | 1.89 | 1.68 | 0.07 | 0.97 | 0.75 | NA | 2 | −0.23 | 1.05 | 0.07 | −0.4 | 1 |
| PIK3R5 | 23533 | 1.84 | 1.88 | NA | 0.98 | −0.7 | 0.83 | 0.99 | 3 | 0.99 | −3.35 | 0.1 | NA | 1 |
| PIK3R6 | 146850 | 1.65 | 1.73 | 1.68 | −0.11 | 0.99 | 0.63 | 0.96 | 2 | −0.63 | 1.1 | 0.26 | 0.42 | 1 |
| PIN1 | 5300 | 1.65 | 1.72 | 1.51 | −0.95 | 0.9 | 1 | 0.61 | 2 | −.59 | 1 | 0.77 | 0.46 | 2 |
| PKHD1 | 5314 | 1.48 | 1.76 | 1.03 | −1.01 | 0.8 | −1.25 | −0.14 | 3 | 0.7 | 1.13 | 0.89 | −1.49 | 0 |
| PKN1 | 5585 | 1.53 | 1.69 | 1.32 | 0.9 | 0.97 | 0.59 | 1 | 0 | 0.7 | 0.5 | −1.9 | 0.78 | 1 |
| PLAU | 5328 | 1.78 | 1.84 | 1.69 | 0.98 | 0.92 | 0.51 | 0.83 | 3 | 0.87 | 0.33 | 1.24 | −0.3 | 2 |
| PLD2 | 5338 | 1.83 | 1.9 | 1.83 | 0.32 | 0.97 | 0.64 | 0.52 | 1 | 1.01 | 1.09 | −0.66 | −0.27 | 3 |
| PLK3 | 1263 | 1.82 | 1.76 | 1.81 | 0.79 | 0.01 | 0.45 | −0.67 | 0 | 1.2 | 1.07 | 0.97 | −1.89 | 2 |
| POLK | 51426 | 1.69 | 1.66 | 1.81 | 0.78 | 0.55 | 0.96 | 0.78 | 1 | 1.18 | 0.36 | 0.87 | 0.7 | 2 |
| POLR2H | 5437 | 1.43 | 1.79 | 1.65 | 0.95 | 0.82 | 0.65 | 0.94 | 3 | 1.02 | 1.05 | 0.56 | 0.61 | 2 |
| POLR2L | 544 | 1.59 | 1.78 | 1.72 | 0.65 | 0.94 | −0.15 | 0.58 | 1 | 0.8 | 0.92 | 0.51 | 0.46 | 2 |
| PPARA | 5465 | 1.85 | 1.9 | 1.84 | 0.54 | 0.38 | 0.68 | 0.75 | 0 | −6.98 | 0.57 | 0.81 | 0.91 | 1 |
| PPP1R14D | 54866 | 1.82 | 1.76 | 1.85 | 0.93 | 0.84 | 0.56 | 0.74 | 0 | 0.77 | 0.58 | 0.02 | 0.07 | 2 |
| PRDX5 | 25824 | 1.62 | 1.74 | 1.87 | −0.3 | 0.62 | 0.12 | 0.1 | 2 | 1.01 | 0.99 | 0.21 | 0.12 | 1 |
| PRPF8 | 10594 | 1.6 | 1.67 | 1.74 | 0.66 | 0.65 | 0.96 | 0.83 | 2 | 1.09 | 0.29 | 1.29 | 1.88 | 2 |
| PRPS1 | 5631 | 1.79 | 1.67 | 1.76 | 0.91 | 0.99 | 0.9 | 1 | 4 | 0.98 | 0.37 | 0.00 | 0.94 | 3 |
| PRSS27 | 83886 | 1.88 | 1.78 | 1.78 | 0.06 | 1 | 0.79 | 0.02 | 2 | 0.99 | 0.9 | 0.93 | 0.5 | 3 |
| PRX | 57716 | 1.85 | 1.88 | 1.86 | 1.01 | 0.07 | 0.85 | −1.64 | 2 | 1.21 | −0.35 | 0.97 | −1.56 | 2 |
| PSENEN | 55851 | 1.62 | 1.74 | 1.87 | 0.93 | 1 | 0.28 | 0.36 | 4 | 1.84 | 1.07 | 0.07 | 1.24 | 3 |
| PSMA1 | 5682 | 1.56 | 1.79 | NA | 0.94 | 0.71 | 0.97 | NA | 2 | 0.77 | 1.03 | −1.2 | NA | 1 |
| PSMD2 | 5708 | 1.34 | 1.47 | 1.27 | 0.98 | 0.94 | 0.99 | NA | 2 | −5.45 | −0.07 | 1.02 | 0.66 | 1 |
| PTPLA | 9200 | 1.52 | 1.82 | 1.75 | 0.92 | 0.82 | 0.41 | 0.87 | 3 | 0.02 | 1.01 | 0.5 | −0.75 | 2 |
| PTPRN | 5798 | 1.76 | 1.86 | 1.82 | 0.98 | 0.67 | 0.34 | −1.40 | 2 | 1.26 | 0.86 | −0.37 | 0.33 | 0 |
| RAB4A | 5867 | 1.89 | 1.84 | 1.78 | 0.81 | 0.85 | 0.72 | 0.66 | 3 | −1.67 | 0.44 | −0.3 | 1.13 | 3 |
| RAB6B | 51560 | 1.58 | 1.59 | 1.8 | 0.75 | 0.94 | 0.41 | −0.07 | 1 | 1.24 | 0.43 | 1.13 | −0.21 | 2 |
| RACGAP1 | 29127 | 1.64 | 1.54 | 1.88 | 0.33 | −0.25 | 0.69 | −0.48 | 0 | 1.24 | 0.5 | 0.97 | 0.51 | 2 |
| RAX | 30062 | 1.66 | 1.9 | 1.82 | 0.98 | 0.81 | 0.57 | 0.14 | 2 | 1.25 | 0.57 | 1.00 | 1.1 | 3 |
| RBM42 | 79171 | 1.78 | 1.89 | 1.83 | 0.73 | 0.4 | −0.23 | 0.05 | 0 | 1.11 | 0.99 | −0.75 | NA | 1 |
| RETN | 56729 | 1.83 | 1.8 | NA | 0.87 | 0.83 | 0.86 | NA | 0 | 0.9 | −1.57 | 0.99 | 1.1 | 3 |
| RFFL | 117584 | 1.68 | 1.92 | 1.88 | 0.91 | 0.97 | 0.42 | −0.18 | 2 | 0.69 | 0.87 | −0.8 | 0.77 | 1 |
| RNF150 | 57484 | 1.7 | 1.82 | 1.68 | 0.37 | 0.49 | −0.47 | 0.59 | 0 | 0.9 | 0.99 | −0.32 | 0.95 | 3 |
| RPL35 | 11224 | 1.61 | 1.48 | 1.31 | 0.98 | 0.96 | 0.98 | 0.96 | 4 | 1 | 0.1 | 0.5 | 0.55 | 1 |
| RPLP2 | 6181 | 1.31 | 1.33 | 1.49 | 0.86 | 0.97 | 0.87 | 0.99 | 3 | 1.26 | 1.00 | 1.2 | 1.04 | 4 |
| RPS10 | 6204 | 1.59 | 1.55 | 1.67 | 1 | 0.88 | 0.95 | 0.98 | 2 | 0.85 | −0.26 | 0.8 | −0.43 | 2 |
| RPS14 | 6208 | 1.85 | 1.73 | 1.55 | 1 | 1 | −0.06 | 1 | 4 | 0.97 | −0.29 | 0.49 | 0.02 | 1 |
| RPS16 | 6217 | 1.51 | 1.76 | 1.49 | 0.98 | 0.96 | 0.02 | 0.99 | 3 | 0.82 | 0.9 | 0.42 | 0.7 | 2 |
| RPS27A | 6233 | 1.39 | 1.42 | NA | 1 | 0.96 | 0.87 | NA | 0 | 0.74 | 0.98 | 0.47 | NA | 2 |
| RPS5 | 6193 | 1.31 | 1.3 | 1.2 | 0.85 | 1 | 0.93 | NA | 2 | 0.98 | 1 | 0.17 | NA | 1 |
| RPS6KA6 | 27330 | 1.75 | 1.9 | 1.69 | 0.17 | 0.92 | 0.96 | 0.1 | 3 | −1.26 | 0.95 | 0.4 | 0.69 | 3 |
| RUNX1 | 861 | 1.86 | 1.92 | 1.84 | 0.84 | −0.15 | 0.73 | 0.16 | 2 | 0.91 | 0.87 | 0.95 | −0.29 | 1 |
| SAFB | 6294 | 1.78 | 1.73 | 1.83 | 0.5 | 0.48 | 1 | 0.01 | 1 | 0.9 | 1 | 0.82 | 0.82 | 3 |
| SCAF1 | 58506 | 1.64 | 1.65 | 1.79 | 0.92 | 0.5 | 0.93 | −0.02 | 1 | −5.89 | 0.95 | −0.13 | −0.03 | 1 |
| SCAMP4 | 113178 | 1.82 | 1.87 | 1.37 | 0.68 | 0.96 | 0.97 | 0.66 | 4 | 1.01 | 1 | 0.5 | 1.04 | 2 |
| SCARB1 | 949 | 1.32 | 1.52 | 1.77 | 0.94 | 0.99 | 0.27 | 0.71 | 2 | 0.1 | 0.02 | 1.2 | −0.43 | 1 |
| SDC1 | 6382 | 1.64 | 1.62 | 1.63 | 1 | 0.72 | 0.88 | 0.91 | 1 | 0.17 | 0.57 | 0.8 | 0.02 | 2 |
| SELPLG | 6404 | 1.85 | 1.86 | 1.84 | 0.08 | 0.94 | −0.74 | 0.53 | 2 | 0.4 | −2.22 | 0.49 | 0.7 | 1 |
| SERPINA6 | 866 | 1.53 | 1.83 | 1.88 | 0.57 | 0.95 | 0.95 | 0.78 | 2 | −0.96 | −0.08 | 0.42 | 0.36 | 2 |
| | | | | | | | | | | 0.28 | 0.34 | 0.47 | 0.78 | 1 |
| | | | | | | | | | | | | 0.17 | −0.75 | 0 |

TABLE 3-continued

| | | | | | | | | | | |
|---|---|---|---|---|---|---|---|---|---|---|
| SERPINB2 | 5055 | 1.73 | 1.83 | 1.76 | 0.64 | -0.25 | 0.83 | -0.38 | 2 | 0.34 | 0 | 0.12 | 0.15 | 0 |
| SERPINE2 | 5270 | 1.45 | 1.54 | 1.83 | 0.75 | 0.89 | 0.41 | 0.85 | 2 | 1.2 | 0.8 | 0.3 | 0.4 | 1 |
| SEZ6L2 | 26470 | 1.3 | 1.75 | 1.57 | 0.83 | 0.95 | -0.43 | 0.93 | 2 | 0.6 | -0.16 | -1.49 | 1.00 | 2 |
| SF3A1 | 10291 | 1.8 | 1.88 | 1.69 | 0.94 | 0.91 | -0.65 | 0.84 | 3 | 1.10 | 0.24 | 0.65 | 0.8 | 2 |
| SF3B1 | 23451 | 1.6 | 1.46 | 1.41 | -0.03 | 0.99 | 1 | 1 | 3 | 0.13 | 1 | 0.98 | 0.46 | 2 |
| SF3B14 | 51639 | 1.72 | 1.72 | 1.03 | 1 | 1 | 1 | 1 | 4 | 1.04 | 0.96 | 1 | 1.06 | 4 |
| SFTPB | 6439 | 1.82 | 1.84 | 1.5 | 0.29 | 0.97 | 0.87 | 0.99 | 3 | 0.59 | 0.7 | 0.16 | 0.45 | 0 |
| SIGMAR1 | 10280 | 1.54 | 1.58 | 1.49 | 0.97 | -0.75 | 0.56 | 0.36 | 1 | 1 | 1 | 0.8 | 0.7 | 2 |
| SLC12A4 | 6560 | 1.69 | 1.66 | 1.8 | 0.44 | 0.68 | 0.82 | 0.98 | 2 | -0.8 | -0.16 | 0.35 | 0.74 | 0 |
| SLC22A6 | 9356 | 1.75 | 1.87 | 1.85 | -1.58 | 0.78 | -0.6 | 0.91 | 1 | 0.87 | 0.09 | 0.61 | 0.91 | 2 |
| SLC25A19 | 60386 | 1.48 | 1.72 | 1.63 | 0.95 | 0.44 | -0.83 | 0.89 | 2 | 0.48 | 0.29 | -0.57 | -3.18 | 0 |
| SLC4A8 | 9498 | 1.67 | 1.5 | 1.05 | 0.95 | -0.02 | 0.27 | -0.69 | 0 | -0.24 | 0.9 | 0.83 | 0.5 | 2 |
| SLC7A1 | 6541 | 1.73 | 1.84 | 1.83 | 0.71 | 0.74 | -0.79 | 0.18 | 0 | 0.57 | 0.95 | 0.96 | 0.8 | 2 |
| SMU1 | 55234 | 1.84 | 1.83 | 1.83 | 0.16 | 0.8 | -0.42 | -0.21 | 2 | -0.96 | 0.79 | -0.02 | 0.93 | 2 |
| SNRP70 | 6625 | 1.84 | 1.65 | 1.71 | 0.89 | 0.88 | -0.01 | 0.01 | 2 | 0.41 | 1.03 | -0.22 | 0.91 | 2 |
| SNRPF | 6636 | 1.6 | 1.49 | 1.59 | 0.23 | 0.78 | -0.83 | 0.91 | 3 | 0.48 | 0.89 | -0.57 | -3.18 | 0 |
| SNX6 | 58533 | 1.88 | 1.85 | 1.81 | 0.95 | -2.32 | 0.99 | 0.61 | 3 | -3.57 | 0.75 | -2.57 | -0.79 | 2 |
| SNX9 | 51429 | 1.83 | 1.89 | 1.83 | 0.81 | 0.91 | 0.8 | 0.82 | 3 | 0.33 | 1.18 | -0.93 | 0.91 | 2 |
| SON | 6651 | 1.31 | 1.32 | 1.21 | 0.89 | 0.36 | 0.3 | 0.55 | 1 | 1.27 | 1.13 | 0.24 | 1.2 | 3 |
| SRRM2 | 23524 | 1.62 | 1.76 | 1.89 | 0.94 | 0.94 | 0.89 | NA | 3 | 0.87 | 1.28 | 0.93 | NA | 3 |
| STAB1 | 23166 | 1.47 | 1.55 | 1.47 | 0.59 | 0.22 | 0.29 | 0.88 | 3 | -0.04 | 0.97 | 1.13 | 0.87 | 3 |
| SULF2 | 55959 | 1.79 | 1.87 | 1.85 | 0.98 | 1 | 0.95 | 0.92 | 4 | 1 | -1.21 | -2.27 | 0.36 | 1 |
| SUPT6H | 6830 | 1.50 | 1.62 | 1.64 | 0.01 | 0.67 | 0.93 | 0.95 | 2 | 0.87 | 0.67 | 0.7 | 0.51 | 1 |
| TBL3 | 10607 | 1.83 | 1.87 | 1.78 | -1.15 | 1 | 0.98 | 0.99 | 3 | 0.77 | 0.64 | 0.57 | 0.99 | 1 |
| TCF3 | 6929 | 1.72 | NA | NA | 0.95 | 0.89 | 0.73 | 0.8 | 2 | 1.17 | 0.48 | 0.86 | -11.7 | 2 |
| TFE3 | 7030 | 1.74 | 1.7 | 1.68 | 0.88 | 0.51 | NA | NA | 1 | 1.82 | 1 | NA | NA | 2 |
| TMEM50B | 757 | 1.77 | 1.84 | 1.79 | 0.93 | 0.83 | 0.98 | 0.49 | 3 | 0.05 | 0.96 | -0.21 | 0.38 | 2 |
| TNFRSF18 | 8784 | 1.58 | 1.74 | 1.75 | 0.01 | 0.63 | 0.28 | -0.44 | 0 | 0.25 | 0.91 | 1 | 0.95 | 3 |
| TNK2 | 10188 | 1.87 | 1.9 | 1.81 | 0.36 | 0.89 | 0.7 | 0.89 | 2 | 0.47 | -0.05 | 0.55 | 0.51 | 0 |
| TRERF1 | 55809 | 1.8 | 1.57 | 1.78 | 0.55 | 0.96 | 0.91 | 0.13 | 2 | 1.06 | 1.25 | 0.7 | 0.06 | 2 |
| TRIM14 | 9830 | 1.83 | 1.49 | 1.57 | 1 | -1.72 | 1 | 0.96 | 3 | 1 | 0.75 | 1.02 | 0.82 | 3 |
| TRIM21 | 6737 | 1.83 | 1.89 | 1.84 | -0.2 | 0.49 | 0.07 | 0.89 | 1 | 0.63 | 0.01 | 0.76 | 1 | 0 |
| TRIM60 | 166655 | 1.83 | 1.82 | 1.83 | -1.27 | 0 | 0.38 | 0.64 | 0 | 0.43 | 0.84 | -0.62 | 1.16 | 2 |
| TSSK6 | 83983 | 1.48 | 1.57 | 1.72 | -0.89 | 0.83 | 0.51 | 0.82 | 2 | 0.88 | 0.79 | 0.93 | -1.02 | 2 |
| TUBB4 | 10382 | 1.84 | 1.87 | 1.81 | -0.44 | 0.55 | -0.05 | 0.99 | 1 | 0.92 | 0.4 | 0.63 | 1.01 | 2 |
| TXNL4A | 10907 | 1.43 | 1.84 | 1.74 | 0.9 | 0.94 | 0.88 | 0.78 | 3 | 0.94 | -0.79 | 0.97 | 0.2 | 1 |
| UBAC2 | 337867 | NA | NA | NA | -0.72 | 0.95 | -0.28 | 0.97 | 2 | 0.14 | 1.04 | -1.89 | 0.87 | 2 |
| UBE2N | 7334 | 1.85 | 1.8 | 1.8 | 1 | 0.88 | NA | NA | 2 | 0.9 | 0.95 | NA | NA | 1 |
| VNN2 | 8875 | 1.86 | 1.91 | 1.82 | 0.88 | 0.25 | 0.47 | 0.88 | 2 | 0.52 | 0.49 | 0.7 | 1.05 | 2 |
| WNT3A | 89780 | 1.82 | 1.88 | 1.77 | 0.28 | 0.4 | 0.51 | 1 | 1 | 0.48 | 0.11 | 1.02 | 1.1 | 2 |
| WNT9A | 7483 | 1.91 | 1.87 | 1.45 | 0.36 | -0.16 | 0.64 | 0.81 | 2 | 0.53 | 0.4 | 0.91 | 1.1 | 3 |
| XAB2 | 56949 | 1.53 | 1.62 | NA | 1 | 0.55 | 0.01 | NA | 2 | 1.02 | -0.3 | 1 | 1 | 2 |
| XPNPEP1 | 7511 | 1.68 | 1.78 | 1.82 | 0.95 | 1 | 0.92 | NA | 3 | 0.67 | 1.86 | 1.05 | NA | 1 |
| XPO1 | 7514 | 1.84 | 1.82 | NA | -0.34 | 0.97 | 0.42 | 0.92 | 2 | 0.8 | 0.99 | -1.13 | 0.06 | 2 |
| XRCC6 | 2547 | 1.83 | 1.84 | 1.8 | 0.91 | 0.96 | -0.37 | 0.28 | 2 | 0.87 | 0.86 | 0.48 | 0.79 | 1 |
| | | 1.63 | 1.61 | 1.69 | 0.47 | -0.46 | 0 | -0.32 | 0 | -0.27 | 1.13 | 0.84 | -0.22 | 2 |

TABLE 4

| GeneSymbol | LocusID | Gene Description | siRNA1 ID | siRNA2 ID | siRNA3 ID | siRNA4 ID |
|---|---|---|---|---|---|---|
| ACTN1 | 87 | ACTININ, ALPHA 1 | Hs_ACTN1_13 | Hs_ACTN1_8 | Hs_ACTN1_7 | Hs_ACTN1_4 |
| ATP6AP2 | 10159 | ATPASE, H+ TRANSPORTING, LYSOSOMAL ACCESSORY PROTEIN 2 | Hs_ATP6AP2_7 | Hs_ATP6AP2_8 | Hs_ATP6AP2_6 | Hs_ATP6AP2_4 |
| ATP6V1B2 | 526 | ATPASE, H+ TRANSPORTING, LYSOSOMAL 56/58 KDA, V1 SUBUNIT B2 | Hs_ATP6V1B2_2 | Hs_ATP6V1B2_4 | Hs_ATP6V1B2_5 | Hs_ATP6V1B2_6 |
| BNIP3L | 665 | BCL2/ADENOVIRUS E1B 19 KDA INTERACTING PROTEIN 3-LIKE | Hs_BNIP3L_7 | Hs_BNIP3L_12 | Hs_BNIP3L_10 | Hs_BNIP3L_1 |
| BRUNOL6 | 60677 | BRUNO-LIKE 6, RNA BINDING PROTEIN (DROSOPHILA) | Hs_BRUNOL6_8 | Hs_BRUNOL6_7 | Hs_BRUNOL6_5 | Hs_BRUNOL6_9 |
| CUEDC2 | 79004 | CUE DOMAIN CONTAINING 2 | Hs_CUEDC2_5 | Hs_CUEDC2_6 | Hs_CUEDC2_4 | Hs_CUEDC2_3 |
| CYC1 | 1537 | CYTOCHROME C-1 | Hs_CYC1_1 | Hs_CYC1_2 | Hs_CYC1_3 | Hs_CYC1_4 |
| FNTB | 2342 | FARNESYLTRANSFERASE, CAAX BOX, BETA | Hs_FNTB_7 | FNTB_1 | FNTB_7 | FNTB_3 |
| GCLC | 2729 | GLUTAMATE-CYSTEINE LIGASE, CATALYTIC SUBUNIT | Hs_GCLC_4 | Hs_GCLC_7 | Hs_GCLC_10 | Hs_GCLC_11 |
| GNRH2 | 2797 | GONADOTROPIN-RELEASING HORMONE 2 | Hs_GNRH2_8 | Hs_GNRH2_7 | Hs_GNRH2_6 | Hs_GNRH2_5 |
| GRIN2C | 2905 | glutamate receptor, ionotropic, N-methyl D-aspartate 2C | Hs_GRIN2C_1 | Hs_GRIN2C_2 | Hs_GRIN2C_3 | Hs_GRIN2C_5 |
| GRP | 2922 | GASTRIN-RELEASING PEPTIDE | Hs_GRP_6 | Hs_GRP_9 | Hs_GRP_8 | Hs_GRP_7 |
| HARBI1 | 9776 | KIAA0652 | Hs_KIAA0652_7 | Hs_KIAA0652_5 | Hs_KIAA0652_4 | Hs_KIAA0652_5 |
| HSPD1 | 3329 | heat shock 60 kDa protein 1 (chaperonin) | Hs_HSPD1_5 | Hs_HSPD1_7 | Hs_HSPD1_8 | Hs_HSPD1_1 |
| ICAM2 | 3384 | INTERCELLULAR ADHESION MOLECULE 2 | Hs_ICAM2_4 | Hs_ICAM2_5 | Hs_ICAM2_7 | Hs_ICAM2_3 |
| KCNJ12 | 3768 | potassium inwardly-rectifying channel, | Hs_KCNJ12_2 | Hs_KCNJ12_4 | Hs_KCNJ12_5 | Hs_KCNJ12_6 |
| KPNB1 | 3837 | KARYOPHERIN (IMPORTIN) BETA 1 | Hs_KPNB1_2 | Hs_KPNB1_3 | Hs_KPNB1_6 | Hs_KPNB1_4 |
| LAMC2 | 3918 | LAMININ, GAMMA 2 | | Hs_LAMC2_1 | Hs_LAMC2_4 | Hs_LAMC2_3 |
| LOC440733 | 440733 | similar to 40S ribosomal protein S15 (RIG) | Hs_LOC440733_11 | Hs_LOC440733_12 | Hs_LOC440733_13 | Hs_LOC440733_14 |
| MKL1 | 57591 | MEGAKARYOBLASTIC LEUKEMIA (TRANSLOCATION) | Hs_MKL1_1 | Hs_MKL1_8 | Hs_MKL1_6 | Hs_MKL1_7 |
| MRPS12 | 6183 | MITOCHONDRIAL RIBOSOMAL PROTEIN S12 | Hs_MRPS12_7 | Hs_MRPS12_1 | Hs_MRPS12_3 | Hs_MRPS12_8 |
| MYEF2 | 50804 | MYELIN EXPRESSION FACTOR 2 | Hs_MYEF2_4 | Hs_MYEF2_5 | Hs_MYEF2_8 | Hs_MYEF2_3 |
| NDUFV3 | 4731 | NADH DEHYDROGENASE (UBIQUINONE) FLAVOPROTEIN 3, 10 KDA | Hs_NDUFV3_3 | Hs_NDUFV3_4 | Hs_NDUFV3_5 | Hs_NDUFV3_6 |
| NECAP2 | 55707 | NECAP ENDOCYTOSIS ASSOCIATED 2 | Hs_FLJ10420_3 | Hs_NECAP2_1 | Hs_NECAP2_3 | Hs_NECAP2_2 |
| ODZ4 | 26011 | odz, odd Oz/ten-m homolog 4 (Drosophila) | Hs_ODZ4_2 | Hs_ODZ4_3 | Hs_ODZ4_4 | Hs_ODZ4_5 |
| PIK3R6 | 146850 | CHROMOSOME 17 OPEN READING FRAM 38 | Hs_C17orf38_3 | Hs_C17orf38_4 | Hs_C17orf38_5 | Hs_C17orf38_6 |
| PPARA | 5465 | PEROXISOME PROLIFERATIVE ACTIVATED RECEPTOR, ALPHA | Hs_PPARA_8 | Hs_PPARA_7 | Hs_PPARA_6 | Hs_PPARA_5 |
| RAB4A | 5867 | RAB4A, MEMBER RAS ONCOGENE FAMILY | Hs_RAB4A_5 | Hs_RAB4A_11 | Hs_RAB4A_10 | Hs_RAB4A_9 |
| SCAF1 | 58506 | SERINE ARGININE-RICH PRE-MRNA SPLICING | Hs_SR-A1_4 | Hs_SR-A1_2 | Hs_SR-A1_5 | Hs_SR-A1_6 |
| SCARB1 | 949 | scavenger receptor class B, member 1 | Hs_SCARB1_6 | Hs_SCARB1_7 | Hs_SCARB1_8 | Hs_SCARB1_9 |
| SERPINA6 | 866 | SERPIN PEPTIDASE INHIBITOR, CLADE A (ALPHA-1 ANTIPROTEINASE, ANTITRYPSIN), MEMBER 6 | Hs_SERPINA6_4 | Hs_SERPINA6_3 | Hs_SERPINA6_1 | Hs_SERPINA6_5 |
| SERPINE2 | 5055 | serpin peptidase inhibitor, clade B (ovalbumin), member 2 | Hs_SERPINE2_2 | Hs_SERPINE2_5 | Hs_SERPINE2_6 | Hs_SERPINE2_9 |
| SERPINE2 | 5270 | SERPIN PEPTIDASE INHIBITOR, CLADE E (NEXIN, PLASMINOGEN ACTIVATOR INHIBITOR TYPE 1), MEMBER 2 | Hs_SERPINE2_6 | Hs_SERPINE2_1 | Hs_SERPINE2_7 | Hs_SERPINE2_10 |
| SEZ6L2 | 26470 | seizure related 6 homolog (mouse)-like 2 | Hs_SEZ6L2_10 | Hs_SEZ6L2_7 | Hs_SEZ6L2_8 | Hs_SEZ6L2_9 |
| TBL3 | 10607 | TRANSDUCIN (BETA)-LIKE 3 | Hs_TBL3_4 | Hs_TBL3_3 | Hs_TBL3_5 | Hs_TBL3_6 |
| TRERF1 | 55809 | transcriptional regulating factor 1 | Hs_TRERF1_3 | Hs_TRERF1_6 | Hs_TRERF1_7 | Hs_TRERF1_8 |
| TRIM60 | 166655 | tripartite motif-containing 60 | Hs_TRIM60_3 | Hs_TRIM60_6 | Hs_TRIM60_7 | Hs_TRIM60_8 |

TABLE 4-continued

| TUBB4 | | 10382 TUBULIN, BETA 4 | | Hs_TUBB4_3 | | Hs_TUBB4_2 | | Hs_TUBB4_6 | | Hs_TUBB4_5 | | |
|---|---|---|---|---|---|---|---|---|---|---|---|---|
| Gene Symbol | Locus ID | siRNA1Target | siRNA2Target | siRNA3Target | siRNA4Target | siRNA1 WST | siRNA2 WST | siRNA3 WST | siRNA4 WST | SEQ ID NOS.: |
| ACTN1 | 87 | AACACCATGCATGCATGCAA | CCGGCCCGAGCTGATTGACTA | AAGGATGATCCACTGCACAAAT | AACGATTACATGCAGCCAGAA | 1.74 | 1.64 | 1.68 | 1.9 | 1022-1025 |
| ATP6AP2 | 10159 | GGGAACGAGTTTAGTATATTA | ATGTGCTTATATAATCGCTTA | AACATGGATCCTGGATAATGAT | TCCCTATAACCTTGCATATAA | 1.84 | 1.87 | 1.93 | 1.84 | 1026-1029 |
| ATP6V1B2 | 526 | CAGGCTGGTTTGGTAAAGAAA | ACCATGTTACCCTGTAATTAA | GAGGATATGCTTGGTCGGGTA | CAGGGTAATCTTTGTGGCACA | 1.55 | 1.55 | 1.8 | 1.89 | 1030-1033 |
| BNIP3L | 665 | TAGCATTTGATGTCTAAATAA | AAACGAGATCAGGTTAGCAAA | CTGGGTGGAGCTACCATGAA | AAGAAAAGTGCGGACTGGGTA | 1.63 | 1.65 | 1.8 | 1.87 | 1034-1037 |
| BRUNO6 | 60677 | CCCACCTIGTAAAGTAGAATTCA | TACCTTCTGCTCTTAGTCTA | AAGCTGATCAATGGTGTAACCTA | CTGAAGGCTGTGATCTGATA | 1.87 | 1.88 | 1.88 | 1.77 | 1038-1041 |
| CUEDC2 | 79004 | CCCGACGGAGCAAGAAGAGAA | CGGCCCGAAATGCTCAAAGAA | AAGCTCCCATAGTGTAACCTA | ATGCTGGTAGAGGAAAGGAA | 1.72 | 1.5 | 1.33 | 1.77 | 1042-1045 |
| CYC1 | 1537 | CCCATCATGGGAATAAATTAA | CAGCATGGACTTCGTGGCCTA | TACCATGTCCAGATAGCCAA | GCGGGAAGGTCTCTACTTCAA | 1.8 | 1.47 | 1.7 | 1.5 | 1046-1049 |
| FNTB | 2342 | CACGTCCATAGAACAGGCAAA | ACCCACATATGCAGCAGTCAA | CTCCGTAGCCTCGCTGACCAA | TCCGCTCGCCGTAGCGCTTTA | 1.67 | 1.82 | 1.92 | 1.75 | 1050-1053 |
| GCLC | 2729 | CCGGATCATATTTACATGGAT | CATCGACTTGACGATAGATAA | CACCCTGCTTCAGTACCTTA | ATCAGGCTCTTTGCACAATAA | 1.78 | 1.78 | 1.83 | 1.75 | 1054-1057 |
| GNRH2 | 2797 | CCCGCATTCTCCAATAAAGT | CTGAAGGCCATCTCATCCA | TGGCTGGTACCCTGGCAGGAAA | CAGACTGCCCATGGCCTCCA | 1.83 | 1.64 | 1.85 | 1.81 | 1058-1061 |
| GRIN2C | 2905 | CTGGACGAGATCAGCAGGGTA | CCCAGCTTTCACTATCGGCAA | CACCCACATGGTCAAGTTCAA | GTCGATGTGCTTGCCGATCTA | 1.75 | 1.75 | 1.79 | 1.77 | 1062-1065 |
| GRP | 2922 | ATCAGTTCTACGGATCATCAA | CCAGCTGAACCAGCAATGATA | CAGAGGATAGCAGCAACTTCA | CGGAGGGACCGTGCTGACCAA | 1.75 | 1.61 | 1.79 | 1.74 | 1066-1069 |
| HARBI1 | 9776 | CTGGGCTGATGATTGACTTAA | CAGGAAGTCTGGGTGCTAAA | CAGGTATTGTTACTTGAATAA | AAGGCGGGAGTGACCCTTAA | 1.51 | 1.46 | 1.77 | 1.77 | 1070-1073 |
| HSPD1 | 3329 | AAGGCTTCGAGAAGATTAGCA | CACCACGATGAGAAGTTAA | CAGGGTTTGGTGACAATGTAA | CGGGCTTATGCCAAAGATGTA | 1.63 | 1.53 | 1.71 | 1.55 | 1074-1077 |
| ICAM2 | 3384 | CGGGAAGCAGGAGTCAATGAA | TCCCATGACACGGTCCTCCAA | CACGGTGGTCACTGGAACTCA | AACATCTTTCACAAACACTCA | 1.81 | 1.89 | 1.9 | 1.63 | 1078-1081 |
| KCNJ12 | 3768 | TTGGGTGAGACTCTTTACAA | TGCGAAGGATCTGGTAGAGAA | CAGCTCCTACCTGGCCAATGA | CTCGCACTTCCACAAGACCTA | 1.64 | 1.65 | 1.34 | 1.81 | 1082-1085 |
| KPNB1 | 3837 | CAAGAACTCTTTGACATCTAA | AAGGGCGGAGATCGAAGACTA | CAGGGTTGGTGCAGGGATTAA | CTGGTACAACCCAGAGTAGAA | 1.73 | 1.71 | 1.84 | 1.64 | 1086-1089 |
| LAMC2 | 3918 | CAGGCATATGGATGAGTTCAA | CCCAATTGGTTTTCACAAGGA | CCGGACGGTGCTGTGGTGCAA | TACTTTGAGTATCGAAGGTTA | 1.64 | 1.62 | 1.59 | 1.77 | 1090-1093 |
| LOC440733 | 440733 | ATCATGATTGTTAGCCATTTA | CAGCTGAAACTTTCTTGATCA | AAAGAGCATTATCTAAGTAAT | AACAACCTTTAGATAATGCAAA | 1.64 | 1.64 | 1.58 | 1.75 | 1094-1097 |
| MKL1 | 57591 | TAGTGTCTTGGTGTAGTGTAA | AGCAAGATTGCCATCACGAAA | AGGGCCTGGATGCCAAGGTTA | ATCACGTGTGATTGACATGTA | 1.67 | 1.58 | 1.73 | 1.67 | 1098-1101 |
| MRPS12 | 6183 | TTCCATCAGGACCACTATTAA | CACGTTTACCCGACAAGCCGAA | CACACTCAGAGCAGGCTAAA | ACCCTGGCGCTTGTGATGTAA | 1.61 | 1.82 | 1.88 | 1.61 | 1102-1105 |
| MYEF2 | 50804 | CAGAATAATGAATGGCATAAA | ATCGATATGGATCGAGGATTT | CTCGTAGGGCATTGCAGCGAA | TCCTTTAATGTTGTAATTGAA | 1.87 | 1.86 | 1.9 | 1.87 | 1106-1109 |
| NDUFV3 | 4731 | ACACTGATTATCAACATATA | ATCCATATAATTAGAGAATTT | CCCGCTGTGCATAATCGTTT | CTGAGCCGTTTGACAACACTA | 1.44 | 1.51 | 1.6 | 1.44 | 1110-1113 |
| NECAP2 | 55707 | AAGGAGCTCAGTAAACTAGAA | CAGGTACTTCGTGATCCGAT | CAACATGCAAACATGAAGAA | CTGCAGCTTGAGCTACAATCA | 1.8 | 1.88 | 1.81 | 1.8 | 1114-1117 |
| OD24 | 26011 | CCGGCCGCCTTTAACCTCAA | CCGAGGGTGGTATACAAGTA | TCGGTTTATCCGGAAGAACAA | CTGCGGGTTCACAACCGAAAT | 1.81 | 1.85 | 1.89 | 1.81 | 1118-1121 |
| PIK3R6 | 146850 | TCGGACGACAGACGATCTAA | CACCTTCAGGACGAACAATAT | CAGGGATGGTCAACAATCGA | TCGCCGCACCCTGGAGCACTA | 1.7 | 1.65 | 1.73 | 1.7 | 1122-1125 |
| PPARA | 5465 | TCGGCGAACGATTCGACTCAA | CACTGTGAGCATTGAACATGA | CAAGAGAATCTACGAGGCCTA | AAGCTTGGCTTACGGAATA | 1.71 | 1.85 | 1.9 | 1.71 | 1126-1129 |
| RAB4A | 5867 | AATGCAGGAACTGGCAAATCT | CACACTTGAAATACTAGAATCA | AAGATGACTCAAATCATACAA | CAGGTCCGTGACGAGAAGTTA | 1.73 | 1.89 | 1.84 | 1.73 | 1130-1133 |
| SCAF1 | 58506 | CTGGGCTCCATTGGCGTCAAA | CTGGACGTATTTATGCTCCA | CACGTGGGCGGCTTGACAA | CACGGCTACTGTGTTGGACAT | 1.64 | 1.64 | 1.65 | 1.64 | 1134-1137 |
| SCARB1 | 949 | CCGATCCATGAAGCTAATGTA | TAGGGAGAGGCTCGTCAACAA | CACGTGCCTTCCTTCCTGAGTA | CAGGAGATCCTGAAGGGCGA | 1.41 | 1.32 | 1.52 | 1.41 | 1138-1141 |
| SERPINA6 | 866 | CAGACAGACAGATCAACAGCTA | CAACATGTATGTCAAGAATAA | CACCAGCTTAGAAAATGACTAT | AGGGTTATGAACCCAGTGTAA | 1.75 | 1.63 | 1.83 | 1.75 | 1142-1145 |
| SERPINB2 | 5055 | CAGAAGGGTAGTTATCCTGAT | CAACCATGACAAACTCAACAA | CTGGAAAGTGAAATAACCTAT | TGCGAGCTTCCGGGAAGAATA | 1.73 | 1.73 | 1.83 | 1.73 | 1146-1149 |
| SERPINE2 | 5270 | CTGGGAGGTATTGGAGGGAAA | AACGCCGTGTTGTTTAAGAAT | CGGCGTAAATGGAGTTGGTAA | AACTCCTGTCTTGCTAGACAA | 1.45 | 1.45 | 1.54 | 1.45 | 1150-1153 |
| SEZ6L2 | 26470 | TCCATGCTTGGGAAGGGAAA | CAGGATCCACTATCAGGCCTA | CCGGTGTCTTCTGCACTTCCAA | CTGCTGATGAGGACACTGA | 1.4 | 1.3 | 1.75 | 1.4 | 1154-1157 |
| TBL3 | 10607 | CCGTATCTGGAGAATGAACAA | CTGCTCACGTGGACAGACCAA | CAGGATCGTCCATGCAAGAA | CTGGAAGCCTGTCAGGTTA | 1.75 | 1.83 | 1.87 | 1.75 | 1158-1161 |
| TRERF1 | 55809 | CCGCAACAAATTCGCCCATCA | TTGCGTCAGGTCCTAAGACAA | CAGGGTATCCATGCAAGAA | AGCTCCGTAATTTGACTGAAA | 1.57 | 1.8 | 1.52 | 1.57 | 1162-1165 |
| TRIM60 | 166655 | GAGCCCTTGAGGAATAATATA | TTGCGTCAGGTCCTAAGACAA | AAGGATCTAGATGATACCTTT | AGCTCCGTAATTTGACTGAAA | 1.81 | 1.83 | 1.83 | 1.81 | 1166-1169 |
| TUBB4 | 10382 | CTGCCTCACCCTCAATAAATA | TGAGCCCTGTAATTTATCTTTAA | CTCTGAAAACCGACACCTTAA | CTGAGGCTTCTGACCTTTGA | 1.77 | 1.84 | 1.87 | 1.77 | 1170-1173 |

| GeneSymbol | Locus ID | siRNA1 NPI WSN | siRNA2 NPI WSN | siRNA3 NPI WSN | siRNA4 NPI WSN | Hits per Gene WSN | siRNA1 NPI HH | siRNA2 NPI HH | siRNA3 NPI HH | siRNA4 NPI HH | siRNA4 NPI HH | Hits per gene HH |
|---|---|---|---|---|---|---|---|---|---|---|---|---|
| ACTN1 | 87 | -1.68 | 0.63 | -0.42 | 0.13 | 0 | 1.03 | 0.97 | 0.26 | -0.4 | | 2 |
| ATP6AP2 | 10159 | 0.8 | 0.67 | 0.83 | 0.49 | 2 | 1.01 | 0.74 | 0.98 | 0.93 | | 3 |
| ATP6V1B2 | 526 | 0.88 | 0.8 | 0.46 | 0.99 | 2 | 1.25 | 1.13 | -0.26 | 1.02 | | 3 |
| BNIP3L | 665 | 0.87 | -0.67 | 0.72 | 0.92 | 3 | 0.72 | 0.95 | 0.66 | 0.98 | | 2 |
| BRUNO6 | 60677 | 0.12 | -0.66 | 0.87 | 0.83 | 2 | -0.01 | -4.07 | 1.30 | 1.32 | | 2 |
| CUEDC2 | 79004 | 0.78 | 1 | 0.82 | 0.89 | 3 | 1.16 | 0.48 | 1.08 | -0.29 | | 2 |

TABLE 4-continued

| | | | | | | | | | |
|---|---|---|---|---|---|---|---|---|---|
| CYC1 | 1537 | 1.84 | -0.93 | 0.39 | 0.85 | 0.93 | 2 | 0.18 | 0.5 | 1.1 | 0.36 | 1 |
| FNTB | 2342 | 1.81 | 0.94 | 0.9 | 0.77 | 0.35 | 2 | 0.6 | -1.3 | 0.98 | 0.08 | 1 |
| GCLC | 2729 | 1.83 | 1 | 0.36 | 0.77 | 0.39 | 1 | 1.02 | 0.6 | 0.99 | 0.89 | 3 |
| GNRH2 | 2797 | 1.9 | 0.71 | 0.93 | 0.73 | 0.99 | 2 | 0.86 | 1 | 0.7 | 0.94 | 3 |
| GRIN2C | 2905 | 1.83 | 0.85 | 0.86 | 0.39 | 0.28 | 2 | 0.33 | -47.73 | 0.64 | 0.92 | 1 |
| GRP | 2922 | 1.75 | 0.82 | 0.57 | 0.86 | 0.83 | 2 | -0.33 | 0.73 | 0.09 | 0.56 | 0 |
| HARBI1 | 9776 | 1.74 | 0.31 | 0.88 | 0.74 | 0.83 | 3 | 0.54 | 0.9 | -1.17 | 0.48 | 1 |
| HSPD1 | 3329 | 1.67 | 0.93 | 0.97 | -0.21 | 0.57 | 2 | 1.02 | 0.3 | 0.98 | 0.95 | 3 |
| ICAM2 | 3384 | 1.85 | 0.98 | 0.94 | 0.46 | 0.21 | 2 | 0.95 | -1.1 | 0.82 | 1.11 | 3 |
| KCNJ12 | 3768 | 1.49 | -1.52 | 0.55 | 0.74 | -0.41 | 0 | 0.97 | 1.01 | 1 | 0.73 | 3 |
| KPNB1 | 3837 | 1.68 | 0.9 | 0.98 | 0.98 | 0.91 | 4 | 0.85 | 1.11 | 0.91 | 1.05 | 4 |
| LAMC2 | 3918 | 1.89 | 0.76 | 0.9 | 0.72 | 0.77 | 1 | 1 | 0.7 | 0.99 | 0.85 | 3 |
| LOC440733 | 440733 | 1.71 | -0.67 | 0.84 | -0.12 | 0.46 | 1 | 0.73 | 0.94 | 0.78 | 0.8 | 2 |
| MKL1 | 57591 | 1.87 | 0.86 | 0.7 | 0.64 | 0.71 | 1 | 0.37 | 0.68 | 0.89 | 0.96 | 2 |
| MRPS12 | 6183 | 1.78 | 0.085 | 0.8 | 0.98 | 0.3 | 3 | 0.19 | -0.13 | 0.23 | -0.66 | 0 |
| MYBF2 | 50804 | 1.85 | 0.9 | 0.87 | -0.05 | 0.59 | 2 | -3.19 | -0.05 | -5.79 | 0.75 | 0 |
| NDUFV3 | 4731 | 1.68 | 0.48 | 0.9 | 0.37 | 0.88 | 2 | -1.67 | 1.02 | 0.56 | -0.49 | 1 |
| NECAP2 | 55707 | 1.85 | 0.96 | -0.91 | 0.89 | -0.27 | 2 | 1.1 | 0.18 | 1.29 | 0.6 | 2 |
| ODZ4 | 26011 | 1.84 | 0.38 | 0.74 | 0.73 | 0.36 | 2 | 0.53 | 1.25 | 1.2 | 0.02 | 2 |
| PIK3R6 | 146850 | 1.68 | -0.11 | 0.99 | 0.63 | 0.96 | 0 | -0.63 | 1.1 | 0.26 | 0.42 | 1 |
| PPARA | 5465 | 1.84 | 0.54 | 0.38 | 0.68 | 0.75 | 2 | -6.98 | 0.57 | 0.81 | 0.91 | 2 |
| RAB4A | 5867 | 1.78 | 0.81 | 0.85 | 0.72 | 0.88 | 0 | -1.57 | 0.44 | -0.3 | 0.33 | 0 |
| SCAF1 | 58506 | 1.79 | 0.92 | 0.5 | 0.93 | -0.02 | 3 | 1.01 | 0.62 | -0.13 | -0.63 | 0 |
| SCARB1 | 949 | 1.77 | 0.94 | 0.99 | 0.27 | 0.71 | 2 | 0.17 | -2.22 | 0.82 | -0.2 | 1 |
| SERPINA6 | 866 | 1.88 | 0.67 | 0.95 | 0.95 | 0.78 | 2 | 0.28 | 0.36 | -2.4 | -0.75 | 0 |
| SERPINB2 | 5055 | 1.76 | 0.84 | -0.25 | 0.83 | -0.36 | 2 | 0.34 | 0 | 0.12 | 0.15 | 0 |
| SERPINE2 | 5270 | 1.83 | 0.75 | 0.89 | 0.41 | 0.85 | 2 | 1.2 | 0.8 | 0.3 | 0.4 | 1 |
| SEZ6L2 | 26470 | 1.58 | 0.03 | 0.95 | -0.43 | 0.93 | 2 | 0.6 | -0.16 | -1.49 | 1.08 | 1 |
| TBL3 | 10607 | 1.78 | 0.96 | 0.89 | 0.73 | 0.8 | 3 | 1.17 | 0.48 | 0.86 | -11.7 | 2 |
| TRERF1 | 55809 | 1.78 | 1 | -1.72 | 1 | 0.96 | 2 | 1 | 0.75 | 1.02 | 0.82 | 3 |
| TRIM60 | 166655 | 1.83 | -0.89 | 0.83 | 0.51 | 0.82 | 2 | 0.98 | 0.79 | 0.93 | -1.02 | 2 |
| TUBB4 | 10382 | 1.81 | 0.9 | 0.94 | 0.88 | 0.78 | 3 | 0.94 | -0.79 | 0.97 | 0.2 | 2 |

The invention claimed is:

1. A method of treating an influenza virus infection in a patient in need thereof, comprising administering to said patient an effective amount of a TNK2 inhibiting siRNA capable of inhibiting expression of at least one of SEQ ID NO: 957 and SEQ ID NO: 960 in said patient.

* * * * *

SEQUENCE LISTING

```
<160> NUMBER OF SEQ ID NOS: 1173

<210> SEQ ID NO 1
<211> LENGTH: 21
<212> TYPE: RNA
<213> ORGANISM: Artificial Sequence
<220> FEATURE:
<223> OTHER INFORMATION: siNP

<400> SEQUENCE: 1
aaggaucuua uucuucgga g                                              21

<210> SEQ ID NO 2
<211> LENGTH: 21
<212> TYPE: DNA
<213> ORGANISM: Artificial Sequence
<220> FEATURE:
<223> OTHER INFORMATION: siPLK1

<400> SEQUENCE: 2
caccatatga attgtacaga a                                             21

<210> SEQ ID NO 3
<211> LENGTH: 25
<212> TYPE: DNA
<213> ORGANISM: Artificial Sequence
<220> FEATURE:
<223> OTHER INFORMATION: QRT-PCR PA-specific oligonucleotide 1

<400> SEQUENCE: 3
gcttcttatc gttcaggctc ttagg                                         25

<210> SEQ ID NO 4
<211> LENGTH: 25
<212> TYPE: DNA
<213> ORGANISM: Artificial Sequence
<220> FEATURE:
<223> OTHER INFORMATION: QRT-PCR PA-specific oligonucleotide

<400> SEQUENCE: 4
ccgagaagca ttaagcaaaa cccag                                         25

<210> SEQ ID NO 5
<211> LENGTH: 23
<212> TYPE: DNA
<213> ORGANISM: Artificial Sequence
<220> FEATURE:
<223> OTHER INFORMATION: GAPDH forward oligonucleotide

<400> SEQUENCE: 5
ggtatcgtgg aaggactcat gac                                           23

<210> SEQ ID NO 6
<211> LENGTH: 23
<212> TYPE: DNA
<213> ORGANISM: Artificial Sequence
<220> FEATURE:
<223> OTHER INFORMATION: GAPDH_rev oligonucleotide

<400> SEQUENCE: 6
atgccagtga gcttcccgtt cag                                           23

<210> SEQ ID NO 7
<211> LENGTH: 18
<212> TYPE: DNA
<213> ORGANISM: Artificial Sequence
```

```
<220> FEATURE:
<223> OTHER INFORMATION: M1 Oligonucleotide 1

<400> SEQUENCE: 7
gaccaatcct gtcacctc                                                 18

<210> SEQ ID NO 8
<211> LENGTH: 21
<212> TYPE: DNA
<213> ORGANISM: Artificial Sequence
<220> FEATURE:
<223> OTHER INFORMATION: M1 Oligonucleotide 2

<400> SEQUENCE: 8
gatctccgtt cccattaaga g                                             21

<210> SEQ ID NO 9
<211> LENGTH: 17
<212> TYPE: DNA
<213> ORGANISM: Artificial Sequence
<220> FEATURE:
<223> OTHER INFORMATION: M2 Oligonucleotide 1

<400> SEQUENCE: 9
gaggtcgaaa cgcctat                                                  17

<210> SEQ ID NO 10
<211> LENGTH: 21
<212> TYPE: DNA
<213> ORGANISM: Artificial Sequence
<220> FEATURE:
<223> OTHER INFORMATION: M2  Oligonucleotide 2

<400> SEQUENCE: 10
ctccagctct atgttgacaa a                                             21

<210> SEQ ID NO 11
<211> LENGTH: 20
<212> TYPE: DNA
<213> ORGANISM: Artificial Sequence
<220> FEATURE:
<223> OTHER INFORMATION: ATP6V0D1 forward

<400> SEQUENCE: 11
tgtcgcaaca tcgtgtggat                                               20

<210> SEQ ID NO 12
<211> LENGTH: 21
<212> TYPE: DNA
<213> ORGANISM: Artificial Sequence
<220> FEATURE:
<223> OTHER INFORMATION: ATP6V0D1 reverse

<400> SEQUENCE: 12
gagtgcaatt gagagccttg g                                             21

<210> SEQ ID NO 13
<211> LENGTH: 21
<212> TYPE: DNA
<213> ORGANISM: Artificial Sequence
<220> FEATURE:
<223> OTHER INFORMATION: COPG forward

<400> SEQUENCE: 13
tccgctatgc tgctgttcgt a                                             21
```

```
<210> SEQ ID NO 14
<211> LENGTH: 21
<212> TYPE: DNA
<213> ORGANISM: Artificial Sequence
<220> FEATURE:
<223> OTHER INFORMATION: COPG reverse

<400> SEQUENCE: 14
gcggtttgaa tctgtgacca g                                            21

<210> SEQ ID NO 15
<211> LENGTH: 21
<212> TYPE: DNA
<213> ORGANISM: Artificial Sequence
<220> FEATURE:
<223> OTHER INFORMATION: EIF4A3 forward

<400> SEQUENCE: 15
tgatcttggc tcccacaaga g                                            21

<210> SEQ ID NO 16
<211> LENGTH: 19
<212> TYPE: DNA
<213> ORGANISM: Artificial Sequence
<220> FEATURE:
<223> OTHER INFORMATION: EIF4A3 reverse

<400> SEQUENCE: 16
attggtgcct ccaatgcag                                               19

<210> SEQ ID NO 17
<211> LENGTH: 20
<212> TYPE: DNA
<213> ORGANISM: Artificial Sequence
<220> FEATURE:
<223> OTHER INFORMATION: NUP98 forward

<400> SEQUENCE: 17
ttccggaatc cgatgtcaga                                              20

<210> SEQ ID NO 18
<211> LENGTH: 21
<212> TYPE: DNA
<213> ORGANISM: Artificial Sequence
<220> FEATURE:
<223> OTHER INFORMATION: NUP98 reverse

<400> SEQUENCE: 18
tgtaaagcct ttggccggac t                                            21

<210> SEQ ID NO 19
<211> LENGTH: 21
<212> TYPE: DNA
<213> ORGANISM: Artificial Sequence
<220> FEATURE:
<223> OTHER INFORMATION: NUP205 forward

<400> SEQUENCE: 19
accttcggaa ggatcttcca a                                            21

<210> SEQ ID NO 20
<211> LENGTH: 21
<212> TYPE: DNA
<213> ORGANISM: Artificial Sequence
<220> FEATURE:
<223> OTHER INFORMATION: NUP205 reverse
```

```
<400> SEQUENCE: 20
ggagtcccag aatcaccaca a                                              21

<210> SEQ ID NO 21
<211> LENGTH: 20
<212> TYPE: DNA
<213> ORGANISM: Artificial Sequence
<220> FEATURE:
<223> OTHER INFORMATION: NXF1 forward

<400> SEQUENCE: 21
tgagcaaacg atacgatggc                                                20

<210> SEQ ID NO 22
<211> LENGTH: 21
<212> TYPE: DNA
<213> ORGANISM: Artificial Sequence
<220> FEATURE:
<223> OTHER INFORMATION: NXF1 reverse

<400> SEQUENCE: 22
tctgcgattc aggacaacgt c                                              21

<210> SEQ ID NO 23
<211> LENGTH: 21
<212> TYPE: DNA
<213> ORGANISM: Artificial Sequence
<220> FEATURE:
<223> OTHER INFORMATION: SON forward

<400> SEQUENCE: 23
caagccttag agctggcatt g                                              21

<210> SEQ ID NO 24
<211> LENGTH: 21
<212> TYPE: DNA
<213> ORGANISM: Artificial Sequence
<220> FEATURE:
<223> OTHER INFORMATION: SON reverse

<400> SEQUENCE: 24
gcttgcgtga tttgtgttca g                                              21

<210> SEQ ID NO 25
<211> LENGTH: 21
<212> TYPE: DNA
<213> ORGANISM: Homo sapiens

<400> SEQUENCE: 25
gaggaagaga tactagttaa a                                              21

<210> SEQ ID NO 26
<211> LENGTH: 21
<212> TYPE: DNA
<213> ORGANISM: Homo sapiens

<400> SEQUENCE: 26
ctggatgtgg aaagtcccga a                                              21

<210> SEQ ID NO 27
<211> LENGTH: 21
<212> TYPE: DNA
<213> ORGANISM: Homo sapiens
```

```
<400> SEQUENCE: 27
ctggactttg ccctcagcaa a                                              21

<210> SEQ ID NO 28
<211> LENGTH: 21
<212> TYPE: DNA
<213> ORGANISM: Homo sapiens

<400> SEQUENCE: 28
ccgcatggag tccgaatcgg a                                              21

<210> SEQ ID NO 29
<211> LENGTH: 21
<212> TYPE: DNA
<213> ORGANISM: Homo sapiens

<400> SEQUENCE: 29
aacaccatgc atgccatgca a                                              21

<210> SEQ ID NO 30
<211> LENGTH: 21
<212> TYPE: DNA
<213> ORGANISM: Homo sapiens

<400> SEQUENCE: 30
ccggcccgag ctgattgact a                                              21

<210> SEQ ID NO 31
<211> LENGTH: 21
<212> TYPE: DNA
<213> ORGANISM: Homo sapiens

<400> SEQUENCE: 31
aaggatgatc cactcacaaa t                                              21

<210> SEQ ID NO 32
<211> LENGTH: 21
<212> TYPE: DNA
<213> ORGANISM: Homo sapiens

<400> SEQUENCE: 32
aacgattaca tgcagccaga a                                              21

<210> SEQ ID NO 33
<211> LENGTH: 21
<212> TYPE: DNA
<213> ORGANISM: Homo sapiens

<400> SEQUENCE: 33
cccacttgga tttatagtat a                                              21

<210> SEQ ID NO 34
<211> LENGTH: 21
<212> TYPE: DNA
<213> ORGANISM: Homo sapiens

<400> SEQUENCE: 34
aaacagttgt atcgtatgca a                                              21

<210> SEQ ID NO 35
<211> LENGTH: 21
<212> TYPE: DNA
<213> ORGANISM: Homo sapiens
```

```
<400> SEQUENCE: 35
ctgatagaac tctataatgc a                                          21

<210> SEQ ID NO 36
<211> LENGTH: 21
<212> TYPE: DNA
<213> ORGANISM: Homo sapiens

<400> SEQUENCE: 36
cagggtggta aagctaaatg a                                          21

<210> SEQ ID NO 37
<211> LENGTH: 21
<212> TYPE: DNA
<213> ORGANISM: Homo sapiens

<400> SEQUENCE: 37
cacgacggtt ctgccctttta t                                         21

<210> SEQ ID NO 38
<211> LENGTH: 21
<212> TYPE: DNA
<213> ORGANISM: Homo sapiens

<400> SEQUENCE: 38
aaagcctaaa ttggaatgag a                                          21

<210> SEQ ID NO 39
<211> LENGTH: 21
<212> TYPE: DNA
<213> ORGANISM: Homo sapiens

<400> SEQUENCE: 39
atgcaaatgc tgactaataa a                                          21

<210> SEQ ID NO 40
<211> LENGTH: 21
<212> TYPE: DNA
<213> ORGANISM: Homo sapiens

<400> SEQUENCE: 40
gagaaatatg ttaaagtcaa a                                          21

<210> SEQ ID NO 41
<211> LENGTH: 21
<212> TYPE: DNA
<213> ORGANISM: Homo sapiens

<400> SEQUENCE: 41
atggaccatc ctgattatcc a                                          21

<210> SEQ ID NO 42
<211> LENGTH: 21
<212> TYPE: DNA
<213> ORGANISM: Homo sapiens

<400> SEQUENCE: 42
gagggtgttg cacgacatct a                                          21

<210> SEQ ID NO 43
<211> LENGTH: 21
<212> TYPE: DNA
```

<213> ORGANISM: Homo sapiens

<400> SEQUENCE: 43
ctgggaaccc aacgacataa a                                              21

<210> SEQ ID NO 44
<211> LENGTH: 21
<212> TYPE: DNA
<213> ORGANISM: Homo sapiens

<400> SEQUENCE: 44
caggtgagac gccactacca a                                              21

<210> SEQ ID NO 45
<211> LENGTH: 21
<212> TYPE: DNA
<213> ORGANISM: Homo sapiens

<400> SEQUENCE: 45
aaggtgaaga gaagacatta a                                              21

<210> SEQ ID NO 46
<211> LENGTH: 21
<212> TYPE: DNA
<213> ORGANISM: Homo sapiens

<400> SEQUENCE: 46
ctgcactgtc ttactgattt a                                              21

<210> SEQ ID NO 47
<211> LENGTH: 21
<212> TYPE: DNA
<213> ORGANISM: Homo sapiens

<400> SEQUENCE: 47
tcagcactac ttaatagttt a                                              21

<210> SEQ ID NO 48
<211> LENGTH: 21
<212> TYPE: DNA
<213> ORGANISM: Homo sapiens

<400> SEQUENCE: 48
ttgcattcat ttaaactaat a                                              21

<210> SEQ ID NO 49
<211> LENGTH: 21
<212> TYPE: DNA
<213> ORGANISM: Homo sapiens

<400> SEQUENCE: 49
aaggtctact tgtactatca a                                              21

<210> SEQ ID NO 50
<211> LENGTH: 21
<212> TYPE: DNA
<213> ORGANISM: Homo sapiens

<400> SEQUENCE: 50
aaggatgatt ggaggaccta t                                              21

<210> SEQ ID NO 51
<211> LENGTH: 21

<212> TYPE: DNA
<213> ORGANISM: Homo sapiens

<400> SEQUENCE: 51
tccgattctc tatgtcttta a        21

<210> SEQ ID NO 52
<211> LENGTH: 21
<212> TYPE: DNA
<213> ORGANISM: Homo sapiens

<400> SEQUENCE: 52
cgggagaaga tccaagtact a        21

<210> SEQ ID NO 53
<211> LENGTH: 21
<212> TYPE: DNA
<213> ORGANISM: Homo sapiens

<400> SEQUENCE: 53
cagcagctac ctgagtgtca a        21

<210> SEQ ID NO 54
<211> LENGTH: 21
<212> TYPE: DNA
<213> ORGANISM: Homo sapiens

<400> SEQUENCE: 54
ccggaccacc ttcaccagct a        21

<210> SEQ ID NO 55
<211> LENGTH: 21
<212> TYPE: DNA
<213> ORGANISM: Homo sapiens

<400> SEQUENCE: 55
caggttccct gctacgctaa a        21

<210> SEQ ID NO 56
<211> LENGTH: 21
<212> TYPE: DNA
<213> ORGANISM: Homo sapiens

<400> SEQUENCE: 56
cccgtcctgg ctcggcaaca a        21

<210> SEQ ID NO 57
<211> LENGTH: 21
<212> TYPE: DNA
<213> ORGANISM: Homo sapiens

<400> SEQUENCE: 57
tgccatcgtg tggaagatca a        21

<210> SEQ ID NO 58
<211> LENGTH: 21
<212> TYPE: DNA
<213> ORGANISM: Homo sapiens

<400> SEQUENCE: 58
acgtgtgact tcgtccagtt a        21

<210> SEQ ID NO 59

```
<211> LENGTH: 21
<212> TYPE: DNA
<213> ORGANISM: Homo sapiens

<400> SEQUENCE: 59
tggaggctta ttcatctata a                                              21

<210> SEQ ID NO 60
<211> LENGTH: 21
<212> TYPE: DNA
<213> ORGANISM: Homo sapiens

<400> SEQUENCE: 60
ttggaggctt attcatctat a                                              21

<210> SEQ ID NO 61
<211> LENGTH: 21
<212> TYPE: DNA
<213> ORGANISM: Homo sapiens

<400> SEQUENCE: 61
cagaatatct gcccaaatgt a                                              21

<210> SEQ ID NO 62
<211> LENGTH: 21
<212> TYPE: DNA
<213> ORGANISM: Homo sapiens

<400> SEQUENCE: 62
cactggtatc agccaatatg a                                              21

<210> SEQ ID NO 63
<211> LENGTH: 21
<212> TYPE: DNA
<213> ORGANISM: Homo sapiens

<400> SEQUENCE: 63
aaccattaac ccagtagagt t                                              21

<210> SEQ ID NO 64
<211> LENGTH: 21
<212> TYPE: DNA
<213> ORGANISM: Homo sapiens

<400> SEQUENCE: 64
ccagagctga atttaactac a                                              21

<210> SEQ ID NO 65
<211> LENGTH: 21
<212> TYPE: DNA
<213> ORGANISM: Homo sapiens

<400> SEQUENCE: 65
aactttcaga tcagtgaagt g                                              21

<210> SEQ ID NO 66
<211> LENGTH: 21
<212> TYPE: DNA
<213> ORGANISM: Homo sapiens

<400> SEQUENCE: 66
cacagagagc acagatgtca a                                              21
```

```
<210> SEQ ID NO 67
<211> LENGTH: 21
<212> TYPE: DNA
<213> ORGANISM: Homo sapiens

<400> SEQUENCE: 67
ccgggccgcc ctgcacctct a                                              21

<210> SEQ ID NO 68
<211> LENGTH: 21
<212> TYPE: DNA
<213> ORGANISM: Homo sapiens

<400> SEQUENCE: 68
atcagtgaag tggagcccaa a                                              21

<210> SEQ ID NO 69
<211> LENGTH: 21
<212> TYPE: DNA
<213> ORGANISM: Homo sapiens

<400> SEQUENCE: 69
accctgcgga tcccagccta a                                              21

<210> SEQ ID NO 70
<211> LENGTH: 21
<212> TYPE: DNA
<213> ORGANISM: Homo sapiens

<400> SEQUENCE: 70
ccggaaaggt gcctagaaga a                                              21

<210> SEQ ID NO 71
<211> LENGTH: 21
<212> TYPE: DNA
<213> ORGANISM: Homo sapiens

<400> SEQUENCE: 71
caggccctgt agggacagca t                                              21

<210> SEQ ID NO 72
<211> LENGTH: 21
<212> TYPE: DNA
<213> ORGANISM: Homo sapiens

<400> SEQUENCE: 72
ctgcaaagca cctaacacat a                                              21

<210> SEQ ID NO 73
<211> LENGTH: 21
<212> TYPE: DNA
<213> ORGANISM: Homo sapiens

<400> SEQUENCE: 73
caacaagaaa tcatcagtca a                                              21

<210> SEQ ID NO 74
<211> LENGTH: 21
<212> TYPE: DNA
<213> ORGANISM: Homo sapiens

<400> SEQUENCE: 74
ttgggtcaga tgcttgatga a                                              21
```

<210> SEQ ID NO 75
<211> LENGTH: 21
<212> TYPE: DNA
<213> ORGANISM: Homo sapiens

<400> SEQUENCE: 75
cacgatcagc aatgtcttat t                                              21

<210> SEQ ID NO 76
<211> LENGTH: 21
<212> TYPE: DNA
<213> ORGANISM: Homo sapiens

<400> SEQUENCE: 76
cagaaggtat ctaccaaaga t                                              21

<210> SEQ ID NO 77
<211> LENGTH: 21
<212> TYPE: DNA
<213> ORGANISM: Homo sapiens

<400> SEQUENCE: 77
ctcgcctttg tttgccagta a                                              21

<210> SEQ ID NO 78
<211> LENGTH: 21
<212> TYPE: DNA
<213> ORGANISM: Homo sapiens

<400> SEQUENCE: 78
tcccaacacg ctaaatttca a                                              21

<210> SEQ ID NO 79
<211> LENGTH: 21
<212> TYPE: DNA
<213> ORGANISM: Homo sapiens

<400> SEQUENCE: 79
acgagtttcc ctctaatcct a                                              21

<210> SEQ ID NO 80
<211> LENGTH: 21
<212> TYPE: DNA
<213> ORGANISM: Homo sapiens

<400> SEQUENCE: 80
atgatccggc cttacatgaa a                                              21

<210> SEQ ID NO 81
<211> LENGTH: 21
<212> TYPE: DNA
<213> ORGANISM: Homo sapiens

<400> SEQUENCE: 81
ccgattaatt ggagattact a                                              21

<210> SEQ ID NO 82
<211> LENGTH: 21
<212> TYPE: DNA
<213> ORGANISM: Homo sapiens

<400> SEQUENCE: 82
aacaatcaga ttagacacta t                                              21

<210> SEQ ID NO 83
<211> LENGTH: 21
<212> TYPE: DNA
<213> ORGANISM: Homo sapiens

<400> SEQUENCE: 83
acccatagca atggagattg a            21

<210> SEQ ID NO 84
<211> LENGTH: 21
<212> TYPE: DNA
<213> ORGANISM: Homo sapiens

<400> SEQUENCE: 84
caaggagatc ccgctcgaca a            21

<210> SEQ ID NO 85
<211> LENGTH: 21
<212> TYPE: DNA
<213> ORGANISM: Homo sapiens

<400> SEQUENCE: 85
ctggtgatgt tgtgctaaca a            21

<210> SEQ ID NO 86
<211> LENGTH: 21
<212> TYPE: DNA
<213> ORGANISM: Homo sapiens

<400> SEQUENCE: 86
tccgaagatg tcccatacac a            21

<210> SEQ ID NO 87
<211> LENGTH: 21
<212> TYPE: DNA
<213> ORGANISM: Homo sapiens

<400> SEQUENCE: 87
cagcaatggc tccgtcgcct a            21

<210> SEQ ID NO 88
<211> LENGTH: 21
<212> TYPE: DNA
<213> ORGANISM: Homo sapiens

<400> SEQUENCE: 88
aaacttctct gtggcgtaca a            21

<210> SEQ ID NO 89
<211> LENGTH: 21
<212> TYPE: DNA
<213> ORGANISM: Homo sapiens

<400> SEQUENCE: 89
gggaacgagt ttagtatatt a            21

<210> SEQ ID NO 90
<211> LENGTH: 21
<212> TYPE: DNA
<213> ORGANISM: Homo sapiens

<400> SEQUENCE: 90
atgtgcttat ataatcgctt a                                    21

<210> SEQ ID NO 91
<211> LENGTH: 21
<212> TYPE: DNA
<213> ORGANISM: Homo sapiens

<400> SEQUENCE: 91
aacatggatc ctggatatga t                                    21

<210> SEQ ID NO 92
<211> LENGTH: 21
<212> TYPE: DNA
<213> ORGANISM: Homo sapiens

<400> SEQUENCE: 92
tccctataac cttgcatata a                                    21

<210> SEQ ID NO 93
<211> LENGTH: 21
<212> TYPE: DNA
<213> ORGANISM: Homo sapiens

<400> SEQUENCE: 93
tgcgcggagc tgtgtccaat a                                    21

<210> SEQ ID NO 94
<211> LENGTH: 21
<212> TYPE: DNA
<213> ORGANISM: Homo sapiens

<400> SEQUENCE: 94
gcggatgatt tagaattgtc a                                    21

<210> SEQ ID NO 95
<211> LENGTH: 21
<212> TYPE: DNA
<213> ORGANISM: Homo sapiens

<400> SEQUENCE: 95
cacaaagtag accctctccg a                                    21

<210> SEQ ID NO 96
<211> LENGTH: 21
<212> TYPE: DNA
<213> ORGANISM: Homo sapiens

<400> SEQUENCE: 96
cccaccagcc acagaatatt a                                    21

<210> SEQ ID NO 97
<211> LENGTH: 21
<212> TYPE: DNA
<213> ORGANISM: Homo sapiens

<400> SEQUENCE: 97
cactttcatg ttcctcccta a                                    21

<210> SEQ ID NO 98
<211> LENGTH: 21
<212> TYPE: DNA
<213> ORGANISM: Homo sapiens

<400> SEQUENCE: 98

```
ccgcgccttc atcatcacca t                                              21

<210> SEQ ID NO 99
<211> LENGTH: 21
<212> TYPE: DNA
<213> ORGANISM: Homo sapiens

<400> SEQUENCE: 99
aaggctctca attgcactct t                                              21

<210> SEQ ID NO 100
<211> LENGTH: 21
<212> TYPE: DNA
<213> ORGANISM: Homo sapiens

<400> SEQUENCE: 100
caactacatc cctatcttct a                                              21

<210> SEQ ID NO 101
<211> LENGTH: 21
<212> TYPE: DNA
<213> ORGANISM: Homo sapiens

<400> SEQUENCE: 101
atggaggttg atggtaaggt a                                              21

<210> SEQ ID NO 102
<211> LENGTH: 21
<212> TYPE: DNA
<213> ORGANISM: Homo sapiens

<400> SEQUENCE: 102
gagcttgaat ttgaaggtgt a                                              21

<210> SEQ ID NO 103
<211> LENGTH: 21
<212> TYPE: DNA
<213> ORGANISM: Homo sapiens

<400> SEQUENCE: 103
acccaaattg tgatagcata a                                              21

<210> SEQ ID NO 104
<211> LENGTH: 21
<212> TYPE: DNA
<213> ORGANISM: Homo sapiens

<400> SEQUENCE: 104
taaggtagag tcaattatga a                                              21

<210> SEQ ID NO 105
<211> LENGTH: 21
<212> TYPE: DNA
<213> ORGANISM: Homo sapiens

<400> SEQUENCE: 105
caggctggtt tggtaaagaa a                                              21

<210> SEQ ID NO 106
<211> LENGTH: 21
<212> TYPE: DNA
<213> ORGANISM: Homo sapiens
```

```
<400> SEQUENCE: 106
accatgttac cctgtaatta a                                              21

<210> SEQ ID NO 107
<211> LENGTH: 21
<212> TYPE: DNA
<213> ORGANISM: Homo sapiens

<400> SEQUENCE: 107
gaggatatgc ttggtcgggt a                                              21

<210> SEQ ID NO 108
<211> LENGTH: 21
<212> TYPE: DNA
<213> ORGANISM: Homo sapiens

<400> SEQUENCE: 108
cagggtaatc tttgtggcac a                                              21

<210> SEQ ID NO 109
<211> LENGTH: 21
<212> TYPE: DNA
<213> ORGANISM: Homo sapiens

<400> SEQUENCE: 109
cggatttgct tgttccagta a                                              21

<210> SEQ ID NO 110
<211> LENGTH: 21
<212> TYPE: DNA
<213> ORGANISM: Homo sapiens

<400> SEQUENCE: 110
caggttaagc ttgtctggtc a                                              21

<210> SEQ ID NO 111
<211> LENGTH: 21
<212> TYPE: DNA
<213> ORGANISM: Homo sapiens

<400> SEQUENCE: 111
ccggatttgc ttgttccagt a                                              21

<210> SEQ ID NO 112
<211> LENGTH: 21
<212> TYPE: DNA
<213> ORGANISM: Homo sapiens

<400> SEQUENCE: 112
acactcgcag ttaatatcat a                                              21

<210> SEQ ID NO 113
<211> LENGTH: 21
<212> TYPE: DNA
<213> ORGANISM: Homo sapiens

<400> SEQUENCE: 113
aagtgggatc gagacatgta a                                              21

<210> SEQ ID NO 114
<211> LENGTH: 21
<212> TYPE: DNA
<213> ORGANISM: Homo sapiens
```

```
<400> SEQUENCE: 114
ctgggtttca tccatccgac a                                              21

<210> SEQ ID NO 115
<211> LENGTH: 21
<212> TYPE: DNA
<213> ORGANISM: Homo sapiens

<400> SEQUENCE: 115
aacatcttgg tcagatttga a                                              21

<210> SEQ ID NO 116
<211> LENGTH: 21
<212> TYPE: DNA
<213> ORGANISM: Homo sapiens

<400> SEQUENCE: 116
aagatagtta agcgtgcata a                                              21

<210> SEQ ID NO 117
<211> LENGTH: 21
<212> TYPE: DNA
<213> ORGANISM: Homo sapiens

<400> SEQUENCE: 117
cagcacaata agatcctata t                                              21

<210> SEQ ID NO 118
<211> LENGTH: 21
<212> TYPE: DNA
<213> ORGANISM: Homo sapiens

<400> SEQUENCE: 118
ctgggtcaac ctgccggaag a                                              21

<210> SEQ ID NO 119
<211> LENGTH: 21
<212> TYPE: DNA
<213> ORGANISM: Homo sapiens

<400> SEQUENCE: 119
atgcgtgttc acacccacaa a                                              21

<210> SEQ ID NO 120
<211> LENGTH: 21
<212> TYPE: DNA
<213> ORGANISM: Homo sapiens

<400> SEQUENCE: 120
acggtccgtg gaccaggtca a                                              21

<210> SEQ ID NO 121
<211> LENGTH: 21
<212> TYPE: DNA
<213> ORGANISM: Homo sapiens

<400> SEQUENCE: 121
tgggatcatg acgacgatgt a                                              21

<210> SEQ ID NO 122
<211> LENGTH: 21
<212> TYPE: DNA
```

```
<213> ORGANISM: Homo sapiens

<400> SEQUENCE: 122
gtcgaccttg ctggacatta a                                              21

<210> SEQ ID NO 123
<211> LENGTH: 21
<212> TYPE: DNA
<213> ORGANISM: Homo sapiens

<400> SEQUENCE: 123
ctcgcctgac tccatccaga a                                              21

<210> SEQ ID NO 124
<211> LENGTH: 21
<212> TYPE: DNA
<213> ORGANISM: Homo sapiens

<400> SEQUENCE: 124
cccgctcatg aagtacctgg a                                              21

<210> SEQ ID NO 125
<211> LENGTH: 21
<212> TYPE: DNA
<213> ORGANISM: Homo sapiens

<400> SEQUENCE: 125
cagcaagacc aaactcgaca a                                              21

<210> SEQ ID NO 126
<211> LENGTH: 21
<212> TYPE: DNA
<213> ORGANISM: Homo sapiens

<400> SEQUENCE: 126
tcgccttatt tctatcaccc a                                              21

<210> SEQ ID NO 127
<211> LENGTH: 21
<212> TYPE: DNA
<213> ORGANISM: Homo sapiens

<400> SEQUENCE: 127
cagagtgcaa ccagtaagtg a                                              21

<210> SEQ ID NO 128
<211> LENGTH: 21
<212> TYPE: DNA
<213> ORGANISM: Homo sapiens

<400> SEQUENCE: 128
tccgaccacc agctcaatca a                                              21

<210> SEQ ID NO 129
<211> LENGTH: 21
<212> TYPE: DNA
<213> ORGANISM: Homo sapiens

<400> SEQUENCE: 129
tagcatttga tgtctaaata a                                              21

<210> SEQ ID NO 130
<211> LENGTH: 21
```

```
<212> TYPE: DNA
<213> ORGANISM: Homo sapiens

<400> SEQUENCE: 130
aaacgagatc aggttagcaa a                                              21

<210> SEQ ID NO 131
<211> LENGTH: 21
<212> TYPE: DNA
<213> ORGANISM: Homo sapiens

<400> SEQUENCE: 131
ctgggtggag ctacccatga a                                              21

<210> SEQ ID NO 132
<211> LENGTH: 21
<212> TYPE: DNA
<213> ORGANISM: Homo sapiens

<400> SEQUENCE: 132
aagaaaagtg cggactgggt a                                              21

<210> SEQ ID NO 133
<211> LENGTH: 21
<212> TYPE: DNA
<213> ORGANISM: Homo sapiens

<400> SEQUENCE: 133
cccacctgta aagtagattc a                                              21

<210> SEQ ID NO 134
<211> LENGTH: 21
<212> TYPE: DNA
<213> ORGANISM: Homo sapiens

<400> SEQUENCE: 134
taccttctgt ctcttagtct a                                              21

<210> SEQ ID NO 135
<211> LENGTH: 21
<212> TYPE: DNA
<213> ORGANISM: Homo sapiens

<400> SEQUENCE: 135
aagctgatca atggtggtga a                                              21

<210> SEQ ID NO 136
<211> LENGTH: 21
<212> TYPE: DNA
<213> ORGANISM: Homo sapiens

<400> SEQUENCE: 136
ctgaaggcct ctgatctgat a                                              21

<210> SEQ ID NO 137
<211> LENGTH: 21
<212> TYPE: DNA
<213> ORGANISM: Homo sapiens

<400> SEQUENCE: 137
cacagtgagt atgtaacttg a                                              21

<210> SEQ ID NO 138
```

```
<211> LENGTH: 21
<212> TYPE: DNA
<213> ORGANISM: Homo sapiens

<400> SEQUENCE: 138
ccgccgtctg gtggtcctca a                                         21

<210> SEQ ID NO 139
<211> LENGTH: 21
<212> TYPE: DNA
<213> ORGANISM: Homo sapiens

<400> SEQUENCE: 139
cagagctaaa tggctcctta a                                         21

<210> SEQ ID NO 140
<211> LENGTH: 21
<212> TYPE: DNA
<213> ORGANISM: Homo sapiens

<400> SEQUENCE: 140
ctggaagaca tgcctggatt a                                         21

<210> SEQ ID NO 141
<211> LENGTH: 21
<212> TYPE: DNA
<213> ORGANISM: Homo sapiens

<400> SEQUENCE: 141
ccaagtgtga gtgatgagca a                                         21

<210> SEQ ID NO 142
<211> LENGTH: 21
<212> TYPE: DNA
<213> ORGANISM: Homo sapiens

<400> SEQUENCE: 142
cacggtggag ttccaccagc a                                         21

<210> SEQ ID NO 143
<211> LENGTH: 21
<212> TYPE: DNA
<213> ORGANISM: Homo sapiens

<400> SEQUENCE: 143
ccgcagcggc acgcccatga a                                         21

<210> SEQ ID NO 144
<211> LENGTH: 21
<212> TYPE: DNA
<213> ORGANISM: Homo sapiens

<400> SEQUENCE: 144
caccatgagc ttcgtggcat a                                         21

<210> SEQ ID NO 145
<211> LENGTH: 21
<212> TYPE: DNA
<213> ORGANISM: Homo sapiens

<400> SEQUENCE: 145
tcgagcctgt tgagactgtt a                                         21
```

```
<210> SEQ ID NO 146
<211> LENGTH: 21
<212> TYPE: DNA
<213> ORGANISM: Homo sapiens

<400> SEQUENCE: 146
tgccgtgatg tttgtggata a                                              21

<210> SEQ ID NO 147
<211> LENGTH: 21
<212> TYPE: DNA
<213> ORGANISM: Homo sapiens

<400> SEQUENCE: 147
caccgtcagg acatgtgcaa a                                              21

<210> SEQ ID NO 148
<211> LENGTH: 21
<212> TYPE: DNA
<213> ORGANISM: Homo sapiens

<400> SEQUENCE: 148
ctcggtcact gtgtccaaca a                                              21

<210> SEQ ID NO 149
<211> LENGTH: 21
<212> TYPE: DNA
<213> ORGANISM: Homo sapiens

<400> SEQUENCE: 149
ctgagaattg ttgtaaagta a                                              21

<210> SEQ ID NO 150
<211> LENGTH: 21
<212> TYPE: DNA
<213> ORGANISM: Homo sapiens

<400> SEQUENCE: 150
aaggtgtgga ataaccctta a                                              21

<210> SEQ ID NO 151
<211> LENGTH: 21
<212> TYPE: DNA
<213> ORGANISM: Homo sapiens

<400> SEQUENCE: 151
ttcaaatatg ctcaaattta a                                              21

<210> SEQ ID NO 152
<211> LENGTH: 21
<212> TYPE: DNA
<213> ORGANISM: Homo sapiens

<400> SEQUENCE: 152
aaggagctca ttgccaagtt a                                              21

<210> SEQ ID NO 153
<211> LENGTH: 21
<212> TYPE: DNA
<213> ORGANISM: Homo sapiens

<400> SEQUENCE: 153
agccctcgat agaaatctga a                                              21
```

```
<210> SEQ ID NO 154
<211> LENGTH: 21
<212> TYPE: DNA
<213> ORGANISM: Homo sapiens

<400> SEQUENCE: 154
accctgtcgc atggcattca a                                             21

<210> SEQ ID NO 155
<211> LENGTH: 21
<212> TYPE: DNA
<213> ORGANISM: Homo sapiens

<400> SEQUENCE: 155
cacgtccatc cagaataact a                                             21

<210> SEQ ID NO 156
<211> LENGTH: 21
<212> TYPE: DNA
<213> ORGANISM: Homo sapiens

<400> SEQUENCE: 156
ctcgtgggtg accttccgca a                                             21

<210> SEQ ID NO 157
<211> LENGTH: 21
<212> TYPE: DNA
<213> ORGANISM: Homo sapiens

<400> SEQUENCE: 157
aagcgcttca atcaaacact t                                             21

<210> SEQ ID NO 158
<211> LENGTH: 21
<212> TYPE: DNA
<213> ORGANISM: Homo sapiens

<400> SEQUENCE: 158
tgggtgtgag caagttagat a                                             21

<210> SEQ ID NO 159
<211> LENGTH: 21
<212> TYPE: DNA
<213> ORGANISM: Homo sapiens

<400> SEQUENCE: 159
gcccgtccta tgattaaaga a                                             21

<210> SEQ ID NO 160
<211> LENGTH: 21
<212> TYPE: DNA
<213> ORGANISM: Homo sapiens

<400> SEQUENCE: 160
taccacctac ttagtaaaga a                                             21

<210> SEQ ID NO 161
<211> LENGTH: 21
<212> TYPE: DNA
<213> ORGANISM: Homo sapiens

<400> SEQUENCE: 161
ccgcgtcttc tccatgatca t                                             21
```

<210> SEQ ID NO 162
<211> LENGTH: 21
<212> TYPE: DNA
<213> ORGANISM: Homo sapiens

<400> SEQUENCE: 162
cagcgacaac accgacactg a                                              21

<210> SEQ ID NO 163
<211> LENGTH: 21
<212> TYPE: DNA
<213> ORGANISM: Homo sapiens

<400> SEQUENCE: 163
ctggtcatcc gcaaacggaa a                                              21

<210> SEQ ID NO 164
<211> LENGTH: 21
<212> TYPE: DNA
<213> ORGANISM: Homo sapiens

<400> SEQUENCE: 164
acgtaaggac tccaagatgt a                                              21

<210> SEQ ID NO 165
<211> LENGTH: 21
<212> TYPE: DNA
<213> ORGANISM: Homo sapiens

<400> SEQUENCE: 165
cagtctgatc tcaataagga a                                              21

<210> SEQ ID NO 166
<211> LENGTH: 21
<212> TYPE: DNA
<213> ORGANISM: Homo sapiens

<400> SEQUENCE: 166
cagctgatgt gcggaagtca a                                              21

<210> SEQ ID NO 167
<211> LENGTH: 21
<212> TYPE: DNA
<213> ORGANISM: Homo sapiens

<400> SEQUENCE: 167
cacatacgta gatctaacga a                                              21

<210> SEQ ID NO 168
<211> LENGTH: 21
<212> TYPE: DNA
<213> ORGANISM: Homo sapiens

<400> SEQUENCE: 168
aagactgatc acagagctaa a                                              21

<210> SEQ ID NO 169
<211> LENGTH: 21
<212> TYPE: DNA
<213> ORGANISM: Homo sapiens

<400> SEQUENCE: 169
aaggctgtgt attacaagta t                                              21

<210> SEQ ID NO 170
<211> LENGTH: 21
<212> TYPE: DNA
<213> ORGANISM: Homo sapiens

<400> SEQUENCE: 170
agggctaagc atgcatgtta a                                              21

<210> SEQ ID NO 171
<211> LENGTH: 21
<212> TYPE: DNA
<213> ORGANISM: Homo sapiens

<400> SEQUENCE: 171
aagctggtgg atctctacct a                                              21

<210> SEQ ID NO 172
<211> LENGTH: 21
<212> TYPE: DNA
<213> ORGANISM: Homo sapiens

<400> SEQUENCE: 172
cagaagcatg ctgctgaatt a                                              21

<210> SEQ ID NO 173
<211> LENGTH: 21
<212> TYPE: DNA
<213> ORGANISM: Homo sapiens

<400> SEQUENCE: 173
cacccttatg ccacataatt a                                              21

<210> SEQ ID NO 174
<211> LENGTH: 21
<212> TYPE: DNA
<213> ORGANISM: Homo sapiens

<400> SEQUENCE: 174
ctgcaagtgc ttgaccctgt a                                              21

<210> SEQ ID NO 175
<211> LENGTH: 21
<212> TYPE: DNA
<213> ORGANISM: Homo sapiens

<400> SEQUENCE: 175
ctggcgagtc tgtaaactac a                                              21

<210> SEQ ID NO 176
<211> LENGTH: 21
<212> TYPE: DNA
<213> ORGANISM: Homo sapiens

<400> SEQUENCE: 176
tagcagtaat tacaacatgt a                                              21

<210> SEQ ID NO 177
<211> LENGTH: 21
<212> TYPE: DNA
<213> ORGANISM: Homo sapiens

<400> SEQUENCE: 177

| | |
|---|---|
| aagcattgaa gtccaatgca t | 21 |

<210> SEQ ID NO 178
<211> LENGTH: 21
<212> TYPE: DNA
<213> ORGANISM: Homo sapiens

<400> SEQUENCE: 178

| | |
|---|---|
| cagtgtactc ttagcaatcc a | 21 |

<210> SEQ ID NO 179
<211> LENGTH: 21
<212> TYPE: DNA
<213> ORGANISM: Homo sapiens

<400> SEQUENCE: 179

| | |
|---|---|
| ccggcaggat gtactactca t | 21 |

<210> SEQ ID NO 180
<211> LENGTH: 21
<212> TYPE: DNA
<213> ORGANISM: Homo sapiens

<400> SEQUENCE: 180

| | |
|---|---|
| ctggcggttc aacaactcca a | 21 |

<210> SEQ ID NO 181
<211> LENGTH: 21
<212> TYPE: DNA
<213> ORGANISM: Homo sapiens

<400> SEQUENCE: 181

| | |
|---|---|
| cagcactact gcggccacaa a | 21 |

<210> SEQ ID NO 182
<211> LENGTH: 21
<212> TYPE: DNA
<213> ORGANISM: Homo sapiens

<400> SEQUENCE: 182

| | |
|---|---|
| aaggaaacgt tataccttgt a | 21 |

<210> SEQ ID NO 183
<211> LENGTH: 21
<212> TYPE: DNA
<213> ORGANISM: Homo sapiens

<400> SEQUENCE: 183

| | |
|---|---|
| gcggtggaag gaggaatgaa a | 21 |

<210> SEQ ID NO 184
<211> LENGTH: 21
<212> TYPE: DNA
<213> ORGANISM: Homo sapiens

<400> SEQUENCE: 184

| | |
|---|---|
| atggtctgag tttgtcttag a | 21 |

<210> SEQ ID NO 185
<211> LENGTH: 21
<212> TYPE: DNA
<213> ORGANISM: Homo sapiens -continued

```
<400> SEQUENCE: 185
atgtgtgaag ttcttgctct a                                               21

<210> SEQ ID NO 186
<211> LENGTH: 21
<212> TYPE: DNA
<213> ORGANISM: Homo sapiens

<400> SEQUENCE: 186
tagagataag gtgatgtcag a                                               21

<210> SEQ ID NO 187
<211> LENGTH: 21
<212> TYPE: DNA
<213> ORGANISM: Homo sapiens

<400> SEQUENCE: 187
cacctcagtg ctcaagaaca a                                               21

<210> SEQ ID NO 188
<211> LENGTH: 21
<212> TYPE: DNA
<213> ORGANISM: Homo sapiens

<400> SEQUENCE: 188
ctgactccgt catttaataa a                                               21

<210> SEQ ID NO 189
<211> LENGTH: 21
<212> TYPE: DNA
<213> ORGANISM: Homo sapiens

<400> SEQUENCE: 189
cgctgtgatc atgatcttcg a                                               21

<210> SEQ ID NO 190
<211> LENGTH: 21
<212> TYPE: DNA
<213> ORGANISM: Homo sapiens

<400> SEQUENCE: 190
ctgcaccaag tgcatcaagt a                                               21

<210> SEQ ID NO 191
<211> LENGTH: 21
<212> TYPE: DNA
<213> ORGANISM: Homo sapiens

<400> SEQUENCE: 191
tacgagaaac tcaatcaact a                                               21

<210> SEQ ID NO 192
<211> LENGTH: 21
<212> TYPE: DNA
<213> ORGANISM: Homo sapiens

<400> SEQUENCE: 192
ctgcaatagc aagaaagcct a                                               21

<210> SEQ ID NO 193
<211> LENGTH: 21
<212> TYPE: DNA
<213> ORGANISM: Homo sapiens
```

```
<400> SEQUENCE: 193
acagcaggag gtaatatgct a                                              21

<210> SEQ ID NO 194
<211> LENGTH: 21
<212> TYPE: DNA
<213> ORGANISM: Homo sapiens

<400> SEQUENCE: 194
aaggacgatg aaacagttga t                                              21

<210> SEQ ID NO 195
<211> LENGTH: 21
<212> TYPE: DNA
<213> ORGANISM: Homo sapiens

<400> SEQUENCE: 195
tgcctatggg acagtgtaca a                                              21

<210> SEQ ID NO 196
<211> LENGTH: 21
<212> TYPE: DNA
<213> ORGANISM: Homo sapiens

<400> SEQUENCE: 196
aaggtaaccc tggtgtttga g                                              21

<210> SEQ ID NO 197
<211> LENGTH: 21
<212> TYPE: DNA
<213> ORGANISM: Homo sapiens

<400> SEQUENCE: 197
aagcctctct tctgtggaaa c                                              21

<210> SEQ ID NO 198
<211> LENGTH: 21
<212> TYPE: DNA
<213> ORGANISM: Homo sapiens

<400> SEQUENCE: 198
aaggatctga tgcgccagtt t                                              21

<210> SEQ ID NO 199
<211> LENGTH: 21
<212> TYPE: DNA
<213> ORGANISM: Homo sapiens

<400> SEQUENCE: 199
accgacgatt cttctactca a                                              21

<210> SEQ ID NO 200
<211> LENGTH: 21
<212> TYPE: DNA
<213> ORGANISM: Homo sapiens

<400> SEQUENCE: 200
ctgtaagtaa cttcacatta a                                              21

<210> SEQ ID NO 201
<211> LENGTH: 21
<212> TYPE: DNA
```

```
<213> ORGANISM: Homo sapiens

<400> SEQUENCE: 201
caacaacaca ataacactaa a                                              21

<210> SEQ ID NO 202
<211> LENGTH: 21
<212> TYPE: DNA
<213> ORGANISM: Homo sapiens

<400> SEQUENCE: 202
ccaattattg ttacacatta a                                              21

<210> SEQ ID NO 203
<211> LENGTH: 21
<212> TYPE: DNA
<213> ORGANISM: Homo sapiens

<400> SEQUENCE: 203
agccctgacg ctggcctata a                                              21

<210> SEQ ID NO 204
<211> LENGTH: 21
<212> TYPE: DNA
<213> ORGANISM: Homo sapiens

<400> SEQUENCE: 204
cccgttatga tctggatcta t                                              21

<210> SEQ ID NO 205
<211> LENGTH: 21
<212> TYPE: DNA
<213> ORGANISM: Homo sapiens

<400> SEQUENCE: 205
tgggttcgtg gaaggcgtca a                                              21

<210> SEQ ID NO 206
<211> LENGTH: 21
<212> TYPE: DNA
<213> ORGANISM: Homo sapiens

<400> SEQUENCE: 206
catcgtggtc accttcaact a                                              21

<210> SEQ ID NO 207
<211> LENGTH: 21
<212> TYPE: DNA
<213> ORGANISM: Homo sapiens

<400> SEQUENCE: 207
cagggagtaa gttactgcta a                                              21

<210> SEQ ID NO 208
<211> LENGTH: 21
<212> TYPE: DNA
<213> ORGANISM: Homo sapiens

<400> SEQUENCE: 208
ccacgcgttg cccttcacta a                                              21

<210> SEQ ID NO 209
<211> LENGTH: 21
```

```
<212> TYPE: DNA
<213> ORGANISM: Homo sapiens

<400> SEQUENCE: 209
cacgggtaaa gtgatccgtc a                                              21

<210> SEQ ID NO 210
<211> LENGTH: 21
<212> TYPE: DNA
<213> ORGANISM: Homo sapiens

<400> SEQUENCE: 210
cagcaagcag gacgtatgca a                                              21

<210> SEQ ID NO 211
<211> LENGTH: 21
<212> TYPE: DNA
<213> ORGANISM: Homo sapiens

<400> SEQUENCE: 211
ctggagcaga cggtgaccaa a                                              21

<210> SEQ ID NO 212
<211> LENGTH: 21
<212> TYPE: DNA
<213> ORGANISM: Homo sapiens

<400> SEQUENCE: 212
tggcagcatg cccgagctga a                                              21

<210> SEQ ID NO 213
<211> LENGTH: 21
<212> TYPE: DNA
<213> ORGANISM: Homo sapiens

<400> SEQUENCE: 213
ccgcgacctc aaggcttact a                                              21

<210> SEQ ID NO 214
<211> LENGTH: 21
<212> TYPE: DNA
<213> ORGANISM: Homo sapiens

<400> SEQUENCE: 214
ccagaggatt gcccaggtat t                                              21

<210> SEQ ID NO 215
<211> LENGTH: 21
<212> TYPE: DNA
<213> ORGANISM: Homo sapiens

<400> SEQUENCE: 215
tagcagtaca atgattagta a                                              21

<210> SEQ ID NO 216
<211> LENGTH: 21
<212> TYPE: DNA
<213> ORGANISM: Homo sapiens

<400> SEQUENCE: 216
cagggaagtt agtcaaatga a                                              21

<210> SEQ ID NO 217
```

```
<211> LENGTH: 21
<212> TYPE: DNA
<213> ORGANISM: Homo sapiens

<400> SEQUENCE: 217
cacgaacatg cagttattga a                                          21

<210> SEQ ID NO 218
<211> LENGTH: 21
<212> TYPE: DNA
<213> ORGANISM: Homo sapiens

<400> SEQUENCE: 218
ctggatatgt actaacgaat a                                          21

<210> SEQ ID NO 219
<211> LENGTH: 21
<212> TYPE: DNA
<213> ORGANISM: Homo sapiens

<400> SEQUENCE: 219
cacgatagta aggagcattt a                                          21

<210> SEQ ID NO 220
<211> LENGTH: 21
<212> TYPE: DNA
<213> ORGANISM: Homo sapiens

<400> SEQUENCE: 220
caggacgatg agacactcaa a                                          21

<210> SEQ ID NO 221
<211> LENGTH: 21
<212> TYPE: DNA
<213> ORGANISM: Homo sapiens

<400> SEQUENCE: 221
aacgtgatga acgcacctta a                                          21

<210> SEQ ID NO 222
<211> LENGTH: 21
<212> TYPE: DNA
<213> ORGANISM: Homo sapiens

<400> SEQUENCE: 222
gagaaagatt atcatagtcg a                                          21

<210> SEQ ID NO 223
<211> LENGTH: 21
<212> TYPE: DNA
<213> ORGANISM: Homo sapiens

<400> SEQUENCE: 223
ctgggttatc tgcatctcaa a                                          21

<210> SEQ ID NO 224
<211> LENGTH: 21
<212> TYPE: DNA
<213> ORGANISM: Homo sapiens

<400> SEQUENCE: 224
ctcactgaac tcattgatcg a                                          21
```

```
<210> SEQ ID NO 225
<211> LENGTH: 21
<212> TYPE: DNA
<213> ORGANISM: Homo sapiens

<400> SEQUENCE: 225
tggcgcgtga ttgacattac a                                             21

<210> SEQ ID NO 226
<211> LENGTH: 21
<212> TYPE: DNA
<213> ORGANISM: Homo sapiens

<400> SEQUENCE: 226
cacgctggag gatatcatag a                                             21

<210> SEQ ID NO 227
<211> LENGTH: 21
<212> TYPE: DNA
<213> ORGANISM: Homo sapiens

<400> SEQUENCE: 227
cacacgggtg aagggcaaca a                                             21

<210> SEQ ID NO 228
<211> LENGTH: 21
<212> TYPE: DNA
<213> ORGANISM: Homo sapiens

<400> SEQUENCE: 228
agagatgtta accaaattcg a                                             21

<210> SEQ ID NO 229
<211> LENGTH: 21
<212> TYPE: DNA
<213> ORGANISM: Homo sapiens

<400> SEQUENCE: 229
tccgatgatc agaccatccg a                                             21

<210> SEQ ID NO 230
<211> LENGTH: 21
<212> TYPE: DNA
<213> ORGANISM: Homo sapiens

<400> SEQUENCE: 230
aactccagat gggagacttt t                                             21

<210> SEQ ID NO 231
<211> LENGTH: 21
<212> TYPE: DNA
<213> ORGANISM: Homo sapiens

<400> SEQUENCE: 231
cacgttaatt aacgtgccaa t                                             21

<210> SEQ ID NO 232
<211> LENGTH: 21
<212> TYPE: DNA
<213> ORGANISM: Homo sapiens

<400> SEQUENCE: 232
aagatttacc gaggagcatt a                                             21
```

```
<210> SEQ ID NO 233
<211> LENGTH: 21
<212> TYPE: DNA
<213> ORGANISM: Homo sapiens

<400> SEQUENCE: 233
acgattcttc agagtatgca a                                              21

<210> SEQ ID NO 234
<211> LENGTH: 21
<212> TYPE: DNA
<213> ORGANISM: Homo sapiens

<400> SEQUENCE: 234
caggtttcaa gggtagtgaa a                                              21

<210> SEQ ID NO 235
<211> LENGTH: 21
<212> TYPE: DNA
<213> ORGANISM: Homo sapiens

<400> SEQUENCE: 235
cagtacgtat ttggcattca a                                              21

<210> SEQ ID NO 236
<211> LENGTH: 21
<212> TYPE: DNA
<213> ORGANISM: Homo sapiens

<400> SEQUENCE: 236
aggcgtgaat tgcattgatt a                                              21

<210> SEQ ID NO 237
<211> LENGTH: 21
<212> TYPE: DNA
<213> ORGANISM: Homo sapiens

<400> SEQUENCE: 237
ccgagccacc ttctacctaa a                                              21

<210> SEQ ID NO 238
<211> LENGTH: 21
<212> TYPE: DNA
<213> ORGANISM: Homo sapiens

<400> SEQUENCE: 238
caccgactcc actatgttga a                                              21

<210> SEQ ID NO 239
<211> LENGTH: 21
<212> TYPE: DNA
<213> ORGANISM: Homo sapiens

<400> SEQUENCE: 239
aggcccgtgt atttaatgaa a                                              21

<210> SEQ ID NO 240
<211> LENGTH: 21
<212> TYPE: DNA
<213> ORGANISM: Homo sapiens

<400> SEQUENCE: 240
tccgtcggat gtgctacttg a                                              21
```

<210> SEQ ID NO 241
<211> LENGTH: 21
<212> TYPE: DNA
<213> ORGANISM: Homo sapiens

<400> SEQUENCE: 241
cccgacaacc ttgccaccca a                                      21

<210> SEQ ID NO 242
<211> LENGTH: 21
<212> TYPE: DNA
<213> ORGANISM: Homo sapiens

<400> SEQUENCE: 242
ctgcataatg atcccatttc a                                      21

<210> SEQ ID NO 243
<211> LENGTH: 21
<212> TYPE: DNA
<213> ORGANISM: Homo sapiens

<400> SEQUENCE: 243
agggcggaac ctgcggatca a                                      21

<210> SEQ ID NO 244
<211> LENGTH: 21
<212> TYPE: DNA
<213> ORGANISM: Homo sapiens

<400> SEQUENCE: 244
ctggtgtgca tgatgaacga a                                      21

<210> SEQ ID NO 245
<211> LENGTH: 21
<212> TYPE: DNA
<213> ORGANISM: Homo sapiens

<400> SEQUENCE: 245
ccgggacaag ttcgtcatct t                                      21

<210> SEQ ID NO 246
<211> LENGTH: 21
<212> TYPE: DNA
<213> ORGANISM: Homo sapiens

<400> SEQUENCE: 246
cccggaggac ctcaccgtga a                                      21

<210> SEQ ID NO 247
<211> LENGTH: 21
<212> TYPE: DNA
<213> ORGANISM: Homo sapiens

<400> SEQUENCE: 247
cagcccgcgg caatcaataa a                                      21

<210> SEQ ID NO 248
<211> LENGTH: 21
<212> TYPE: DNA
<213> ORGANISM: Homo sapiens

<400> SEQUENCE: 248
accgcacctc acactccttt a                                              21

<210> SEQ ID NO 249
<211> LENGTH: 21
<212> TYPE: DNA
<213> ORGANISM: Homo sapiens

<400> SEQUENCE: 249
gaggtgcgaa actgtcttca a                                              21

<210> SEQ ID NO 250
<211> LENGTH: 21
<212> TYPE: DNA
<213> ORGANISM: Homo sapiens

<400> SEQUENCE: 250
cagggtggag gtgggaatga t                                              21

<210> SEQ ID NO 251
<211> LENGTH: 21
<212> TYPE: DNA
<213> ORGANISM: Homo sapiens

<400> SEQUENCE: 251
ttcaggaact agggaataga a                                              21

<210> SEQ ID NO 252
<211> LENGTH: 21
<212> TYPE: DNA
<213> ORGANISM: Homo sapiens

<400> SEQUENCE: 252
aaggtggaag taagaaagct a                                              21

<210> SEQ ID NO 253
<211> LENGTH: 21
<212> TYPE: DNA
<213> ORGANISM: Homo sapiens

<400> SEQUENCE: 253
cccgacggag cagaagagag a                                              21

<210> SEQ ID NO 254
<211> LENGTH: 21
<212> TYPE: DNA
<213> ORGANISM: Homo sapiens

<400> SEQUENCE: 254
cggcccgaaa tgctcaaaga a                                              21

<210> SEQ ID NO 255
<211> LENGTH: 21
<212> TYPE: DNA
<213> ORGANISM: Homo sapiens

<400> SEQUENCE: 255
ttgctccata gtgttaacct a                                              21

<210> SEQ ID NO 256
<211> LENGTH: 21
<212> TYPE: DNA
<213> ORGANISM: Homo sapiens

<400> SEQUENCE: 256
atgctggtag agggaaagga a    21

<210> SEQ ID NO 257
<211> LENGTH: 21
<212> TYPE: DNA
<213> ORGANISM: Homo sapiens

<400> SEQUENCE: 257
tcgtttcatt gtagtggtta a    21

<210> SEQ ID NO 258
<211> LENGTH: 21
<212> TYPE: DNA
<213> ORGANISM: Homo sapiens

<400> SEQUENCE: 258
caggtcatgt gcaagagcct a    21

<210> SEQ ID NO 259
<211> LENGTH: 21
<212> TYPE: DNA
<213> ORGANISM: Homo sapiens

<400> SEQUENCE: 259
ctgctattca gtcataatca a    21

<210> SEQ ID NO 260
<211> LENGTH: 21
<212> TYPE: DNA
<213> ORGANISM: Homo sapiens

<400> SEQUENCE: 260
caccagcatg ttccagttat a    21

<210> SEQ ID NO 261
<211> LENGTH: 21
<212> TYPE: DNA
<213> ORGANISM: Homo sapiens

<400> SEQUENCE: 261
cccatcatgg gaataaatta a    21

<210> SEQ ID NO 262
<211> LENGTH: 21
<212> TYPE: DNA
<213> ORGANISM: Homo sapiens

<400> SEQUENCE: 262
cagcatggac ttcgtggcct a    21

<210> SEQ ID NO 263
<211> LENGTH: 21
<212> TYPE: DNA
<213> ORGANISM: Homo sapiens

<400> SEQUENCE: 263
taccatgtcc cagatagcca a    21

<210> SEQ ID NO 264
<211> LENGTH: 21
<212> TYPE: DNA
<213> ORGANISM: Homo sapiens

```
<400> SEQUENCE: 264
gcgggaaggt ctctacttca a                                              21

<210> SEQ ID NO 265
<211> LENGTH: 21
<212> TYPE: DNA
<213> ORGANISM: Homo sapiens

<400> SEQUENCE: 265
caggctgagg gtagcaccta a                                              21

<210> SEQ ID NO 266
<211> LENGTH: 21
<212> TYPE: DNA
<213> ORGANISM: Homo sapiens

<400> SEQUENCE: 266
ccggagtgac tctatcacca a                                              21

<210> SEQ ID NO 267
<211> LENGTH: 21
<212> TYPE: DNA
<213> ORGANISM: Homo sapiens

<400> SEQUENCE: 267
tgagttgaat gtcatacaga a                                              21

<210> SEQ ID NO 268
<211> LENGTH: 21
<212> TYPE: DNA
<213> ORGANISM: Homo sapiens

<400> SEQUENCE: 268
cagacacggc catatgcata a                                              21

<210> SEQ ID NO 269
<211> LENGTH: 21
<212> TYPE: DNA
<213> ORGANISM: Homo sapiens

<400> SEQUENCE: 269
caagggtata ccattcctaa a                                              21

<210> SEQ ID NO 270
<211> LENGTH: 21
<212> TYPE: DNA
<213> ORGANISM: Homo sapiens

<400> SEQUENCE: 270
ccggaggatt tctaccctaa t                                              21

<210> SEQ ID NO 271
<211> LENGTH: 21
<212> TYPE: DNA
<213> ORGANISM: Homo sapiens

<400> SEQUENCE: 271
cagcgctttg attacactaa t                                              21

<210> SEQ ID NO 272
<211> LENGTH: 21
<212> TYPE: DNA
<213> ORGANISM: Homo sapiens
```

```
<400> SEQUENCE: 272
ctgggactga taccacaact a                                              21

<210> SEQ ID NO 273
<211> LENGTH: 21
<212> TYPE: DNA
<213> ORGANISM: Homo sapiens

<400> SEQUENCE: 273
tagccatata cagacagtat a                                              21

<210> SEQ ID NO 274
<211> LENGTH: 21
<212> TYPE: DNA
<213> ORGANISM: Homo sapiens

<400> SEQUENCE: 274
atgactgttc ctatactagt a                                              21

<210> SEQ ID NO 275
<211> LENGTH: 21
<212> TYPE: DNA
<213> ORGANISM: Homo sapiens

<400> SEQUENCE: 275
cagggtttga ttgtccctaa t                                              21

<210> SEQ ID NO 276
<211> LENGTH: 21
<212> TYPE: DNA
<213> ORGANISM: Homo sapiens

<400> SEQUENCE: 276
ctggttaagc tccgagaaga a                                              21

<210> SEQ ID NO 277
<211> LENGTH: 21
<212> TYPE: DNA
<213> ORGANISM: Homo sapiens

<400> SEQUENCE: 277
ccgcactatc tacaccatcg a                                              21

<210> SEQ ID NO 278
<211> LENGTH: 21
<212> TYPE: DNA
<213> ORGANISM: Homo sapiens

<400> SEQUENCE: 278
ctgagcttga ccgttgcata a                                              21

<210> SEQ ID NO 279
<211> LENGTH: 21
<212> TYPE: DNA
<213> ORGANISM: Homo sapiens

<400> SEQUENCE: 279
accatttcgt aaagtcgatt a                                              21

<210> SEQ ID NO 280
<211> LENGTH: 21
<212> TYPE: DNA
```

```
<213> ORGANISM: Homo sapiens

<400> SEQUENCE: 280
ctcggtgtac cgcgggacaa a                                              21

<210> SEQ ID NO 281
<211> LENGTH: 21
<212> TYPE: DNA
<213> ORGANISM: Homo sapiens

<400> SEQUENCE: 281
ccggatctag attccgtaga t                                              21

<210> SEQ ID NO 282
<211> LENGTH: 21
<212> TYPE: DNA
<213> ORGANISM: Homo sapiens

<400> SEQUENCE: 282
ctcctagtgc ttagtggtca a                                              21

<210> SEQ ID NO 283
<211> LENGTH: 21
<212> TYPE: DNA
<213> ORGANISM: Homo sapiens

<400> SEQUENCE: 283
caggtggagt ataatgacat a                                              21

<210> SEQ ID NO 284
<211> LENGTH: 21
<212> TYPE: DNA
<213> ORGANISM: Homo sapiens

<400> SEQUENCE: 284
tgggagttcg attatcaaca a                                              21

<210> SEQ ID NO 285
<211> LENGTH: 21
<212> TYPE: DNA
<213> ORGANISM: Homo sapiens

<400> SEQUENCE: 285
ctgtagcaac atggcagaat a                                              21

<210> SEQ ID NO 286
<211> LENGTH: 21
<212> TYPE: DNA
<213> ORGANISM: Homo sapiens

<400> SEQUENCE: 286
cagctgcatg gccaacacga a                                              21

<210> SEQ ID NO 287
<211> LENGTH: 21
<212> TYPE: DNA
<213> ORGANISM: Homo sapiens

<400> SEQUENCE: 287
acccttcagt tccatggcca a                                              21

<210> SEQ ID NO 288
<211> LENGTH: 21
```

```
<212> TYPE: DNA
<213> ORGANISM: Homo sapiens

<400> SEQUENCE: 288
ccggatcaca ttacatggct t                                            21

<210> SEQ ID NO 289
<211> LENGTH: 21
<212> TYPE: DNA
<213> ORGANISM: Homo sapiens

<400> SEQUENCE: 289
ctctctgtaa tttgtgcttt a                                            21

<210> SEQ ID NO 290
<211> LENGTH: 21
<212> TYPE: DNA
<213> ORGANISM: Homo sapiens

<400> SEQUENCE: 290
tagatttggc tgatccaatt a                                            21

<210> SEQ ID NO 291
<211> LENGTH: 21
<212> TYPE: DNA
<213> ORGANISM: Homo sapiens

<400> SEQUENCE: 291
ctggaagaac ttcaaggaac a                                            21

<210> SEQ ID NO 292
<211> LENGTH: 21
<212> TYPE: DNA
<213> ORGANISM: Homo sapiens

<400> SEQUENCE: 292
caggaagggc gtcctggcta a                                            21

<210> SEQ ID NO 293
<211> LENGTH: 21
<212> TYPE: DNA
<213> ORGANISM: Homo sapiens

<400> SEQUENCE: 293
tacgctcgat ttgaggccaa a                                            21

<210> SEQ ID NO 294
<211> LENGTH: 21
<212> TYPE: DNA
<213> ORGANISM: Homo sapiens

<400> SEQUENCE: 294
cagagccatg ttcgactacg a                                            21

<210> SEQ ID NO 295
<211> LENGTH: 21
<212> TYPE: DNA
<213> ORGANISM: Homo sapiens

<400> SEQUENCE: 295
acagacctta agataccagt a                                            21

<210> SEQ ID NO 296
```

```
<211> LENGTH: 21
<212> TYPE: DNA
<213> ORGANISM: Homo sapiens

<400> SEQUENCE: 296
cccaaggaca ccatcattga t                                              21

<210> SEQ ID NO 297
<211> LENGTH: 21
<212> TYPE: DNA
<213> ORGANISM: Homo sapiens

<400> SEQUENCE: 297
caggttcaat aagactgtgc a                                              21

<210> SEQ ID NO 298
<211> LENGTH: 21
<212> TYPE: DNA
<213> ORGANISM: Homo sapiens

<400> SEQUENCE: 298
ccggctgttc ctgagactgc a                                              21

<210> SEQ ID NO 299
<211> LENGTH: 21
<212> TYPE: DNA
<213> ORGANISM: Homo sapiens

<400> SEQUENCE: 299
ctgcatgatt taagtgcttt a                                              21

<210> SEQ ID NO 300
<211> LENGTH: 21
<212> TYPE: DNA
<213> ORGANISM: Homo sapiens

<400> SEQUENCE: 300
cacctactac agcagcttct a                                              21

<210> SEQ ID NO 301
<211> LENGTH: 21
<212> TYPE: DNA
<213> ORGANISM: Homo sapiens

<400> SEQUENCE: 301
ccagtacagg atgcattctt a                                              21

<210> SEQ ID NO 302
<211> LENGTH: 21
<212> TYPE: DNA
<213> ORGANISM: Homo sapiens

<400> SEQUENCE: 302
aagagagaac aatggcagta a                                              21

<210> SEQ ID NO 303
<211> LENGTH: 21
<212> TYPE: DNA
<213> ORGANISM: Homo sapiens

<400> SEQUENCE: 303
tcagatacag ttctccctta a                                              21
```

```
<210> SEQ ID NO 304
<211> LENGTH: 21
<212> TYPE: DNA
<213> ORGANISM: Homo sapiens

<400> SEQUENCE: 304
tgggcggatg ctggtctcta a                                              21

<210> SEQ ID NO 305
<211> LENGTH: 21
<212> TYPE: DNA
<213> ORGANISM: Homo sapiens

<400> SEQUENCE: 305
aagggtatca cagatgactg a                                              21

<210> SEQ ID NO 306
<211> LENGTH: 21
<212> TYPE: DNA
<213> ORGANISM: Homo sapiens

<400> SEQUENCE: 306
tggcgagact tctgacatct a                                              21

<210> SEQ ID NO 307
<211> LENGTH: 21
<212> TYPE: DNA
<213> ORGANISM: Homo sapiens

<400> SEQUENCE: 307
aagctttggt gtttcactta a                                              21

<210> SEQ ID NO 308
<211> LENGTH: 21
<212> TYPE: DNA
<213> ORGANISM: Homo sapiens

<400> SEQUENCE: 308
cagaaagtct atcctatggc a                                              21

<210> SEQ ID NO 309
<211> LENGTH: 21
<212> TYPE: DNA
<213> ORGANISM: Homo sapiens

<400> SEQUENCE: 309
ctacctgatg atcttccaca a                                              21

<210> SEQ ID NO 310
<211> LENGTH: 21
<212> TYPE: DNA
<213> ORGANISM: Homo sapiens

<400> SEQUENCE: 310
tacatccaga aaggccatga a                                              21

<210> SEQ ID NO 311
<211> LENGTH: 21
<212> TYPE: DNA
<213> ORGANISM: Homo sapiens

<400> SEQUENCE: 311
cagatggtta tggtgatcaa a                                              21
```

```
<210> SEQ ID NO 312
<211> LENGTH: 21
<212> TYPE: DNA
<213> ORGANISM: Homo sapiens

<400> SEQUENCE: 312
ctcactgaat ctgaccacca a                                              21

<210> SEQ ID NO 313
<211> LENGTH: 21
<212> TYPE: DNA
<213> ORGANISM: Homo sapiens

<400> SEQUENCE: 313
cagatctccc ttaagagcaa a                                              21

<210> SEQ ID NO 314
<211> LENGTH: 21
<212> TYPE: DNA
<213> ORGANISM: Homo sapiens

<400> SEQUENCE: 314
aactcctcgc agatcgtcat c                                              21

<210> SEQ ID NO 315
<211> LENGTH: 21
<212> TYPE: DNA
<213> ORGANISM: Homo sapiens

<400> SEQUENCE: 315
aagtgaatct ttggaaacaa a                                              21

<210> SEQ ID NO 316
<211> LENGTH: 21
<212> TYPE: DNA
<213> ORGANISM: Homo sapiens

<400> SEQUENCE: 316
cacctgtaag atttaccagt a                                              21

<210> SEQ ID NO 317
<211> LENGTH: 21
<212> TYPE: DNA
<213> ORGANISM: Homo sapiens

<400> SEQUENCE: 317
caagtctgta atgaagtgtt a                                              21

<210> SEQ ID NO 318
<211> LENGTH: 21
<212> TYPE: DNA
<213> ORGANISM: Homo sapiens

<400> SEQUENCE: 318
aaggaatatc atttaaagct a                                              21

<210> SEQ ID NO 319
<211> LENGTH: 21
<212> TYPE: DNA
<213> ORGANISM: Homo sapiens

<400> SEQUENCE: 319
gaggatctag ataatattca a                                              21
```

```
<210> SEQ ID NO 320
<211> LENGTH: 21
<212> TYPE: DNA
<213> ORGANISM: Homo sapiens

<400> SEQUENCE: 320
caggatcgta ctgacagatt a                                              21

<210> SEQ ID NO 321
<211> LENGTH: 21
<212> TYPE: DNA
<213> ORGANISM: Homo sapiens

<400> SEQUENCE: 321
atggctaaac aggttgaaca a                                              21

<210> SEQ ID NO 322
<211> LENGTH: 21
<212> TYPE: DNA
<213> ORGANISM: Homo sapiens

<400> SEQUENCE: 322
cagcgtcgcc ttgcaacact a                                              21

<210> SEQ ID NO 323
<211> LENGTH: 21
<212> TYPE: DNA
<213> ORGANISM: Homo sapiens

<400> SEQUENCE: 323
ccgccgacgc atgatcagca a                                              21

<210> SEQ ID NO 324
<211> LENGTH: 21
<212> TYPE: DNA
<213> ORGANISM: Homo sapiens

<400> SEQUENCE: 324
aacgaatgga tgaagaattt a                                              21

<210> SEQ ID NO 325
<211> LENGTH: 21
<212> TYPE: DNA
<213> ORGANISM: Homo sapiens

<400> SEQUENCE: 325
ctgacctaga ggactatctt a                                              21

<210> SEQ ID NO 326
<211> LENGTH: 21
<212> TYPE: DNA
<213> ORGANISM: Homo sapiens

<400> SEQUENCE: 326
cccgagcagt ctgcggatga a                                              21

<210> SEQ ID NO 327
<211> LENGTH: 21
<212> TYPE: DNA
<213> ORGANISM: Homo sapiens

<400> SEQUENCE: 327
```

```
aagaggacct gaactgccag g                                              21

<210> SEQ ID NO 328
<211> LENGTH: 21
<212> TYPE: DNA
<213> ORGANISM: Homo sapiens

<400> SEQUENCE: 328
ctcccgcatc tacctggcta a                                              21

<210> SEQ ID NO 329
<211> LENGTH: 21
<212> TYPE: DNA
<213> ORGANISM: Homo sapiens

<400> SEQUENCE: 329
caaggaggtc atcaacggaa a                                              21

<210> SEQ ID NO 330
<211> LENGTH: 21
<212> TYPE: DNA
<213> ORGANISM: Homo sapiens

<400> SEQUENCE: 330
ccggaagggt gtggccatta a                                              21

<210> SEQ ID NO 331
<211> LENGTH: 21
<212> TYPE: DNA
<213> ORGANISM: Homo sapiens

<400> SEQUENCE: 331
cccataaact ctatacttct a                                              21

<210> SEQ ID NO 332
<211> LENGTH: 21
<212> TYPE: DNA
<213> ORGANISM: Homo sapiens

<400> SEQUENCE: 332
ccgcatcttg gtgaaacgtg a                                              21

<210> SEQ ID NO 333
<211> LENGTH: 21
<212> TYPE: DNA
<213> ORGANISM: Homo sapiens

<400> SEQUENCE: 333
atgattcgtc gcagaagcct a                                              21

<210> SEQ ID NO 334
<211> LENGTH: 21
<212> TYPE: DNA
<213> ORGANISM: Homo sapiens

<400> SEQUENCE: 334
caggcaatta attaggagta a                                              21

<210> SEQ ID NO 335
<211> LENGTH: 21
<212> TYPE: DNA
<213> ORGANISM: Homo sapiens

<400> SEQUENCE: 335
```

-continued

```
ctgcgacggc ttcttcacta a                                              21

<210> SEQ ID NO 336
<211> LENGTH: 21
<212> TYPE: DNA
<213> ORGANISM: Homo sapiens

<400> SEQUENCE: 336
cacggacgtc acagttgctt t                                              21

<210> SEQ ID NO 337
<211> LENGTH: 21
<212> TYPE: DNA
<213> ORGANISM: Homo sapiens

<400> SEQUENCE: 337
cggccgggaa ggagcatcaa a                                              21

<210> SEQ ID NO 338
<211> LENGTH: 21
<212> TYPE: DNA
<213> ORGANISM: Homo sapiens

<400> SEQUENCE: 338
ccgcccagat tccaacatct a                                              21

<210> SEQ ID NO 339
<211> LENGTH: 21
<212> TYPE: DNA
<213> ORGANISM: Homo sapiens

<400> SEQUENCE: 339
cagaagatct atccctatga a                                              21

<210> SEQ ID NO 340
<211> LENGTH: 21
<212> TYPE: DNA
<213> ORGANISM: Homo sapiens

<400> SEQUENCE: 340
gtggatataa tgatatctat a                                              21

<210> SEQ ID NO 341
<211> LENGTH: 21
<212> TYPE: DNA
<213> ORGANISM: Homo sapiens

<400> SEQUENCE: 341
ctggctgttg tggagacaga a                                              21

<210> SEQ ID NO 342
<211> LENGTH: 21
<212> TYPE: DNA
<213> ORGANISM: Homo sapiens

<400> SEQUENCE: 342
ctggagcttt gggatactca t                                              21

<210> SEQ ID NO 343
<211> LENGTH: 21
<212> TYPE: DNA
<213> ORGANISM: Homo sapiens
```

```
<400> SEQUENCE: 343
cgccaatctc tagatcaaca a                                              21

<210> SEQ ID NO 344
<211> LENGTH: 21
<212> TYPE: DNA
<213> ORGANISM: Homo sapiens

<400> SEQUENCE: 344
ctcctggatt acatctactt a                                              21

<210> SEQ ID NO 345
<211> LENGTH: 21
<212> TYPE: DNA
<213> ORGANISM: Homo sapiens

<400> SEQUENCE: 345
cgggaagtcg atcctgctta t                                              21

<210> SEQ ID NO 346
<211> LENGTH: 21
<212> TYPE: DNA
<213> ORGANISM: Homo sapiens

<400> SEQUENCE: 346
cacctgcact ctttacacat a                                              21

<210> SEQ ID NO 347
<211> LENGTH: 21
<212> TYPE: DNA
<213> ORGANISM: Homo sapiens

<400> SEQUENCE: 347
agggatgatc ccgtcatcga a                                              21

<210> SEQ ID NO 348
<211> LENGTH: 21
<212> TYPE: DNA
<213> ORGANISM: Homo sapiens

<400> SEQUENCE: 348
ctggttcggc gggaagttca a                                              21

<210> SEQ ID NO 349
<211> LENGTH: 21
<212> TYPE: DNA
<213> ORGANISM: Homo sapiens

<400> SEQUENCE: 349
accaatgtac gtcacagaaa t                                              21

<210> SEQ ID NO 350
<211> LENGTH: 21
<212> TYPE: DNA
<213> ORGANISM: Homo sapiens

<400> SEQUENCE: 350
ccgccgttca gtcgccaata t                                              21

<210> SEQ ID NO 351
<211> LENGTH: 21
<212> TYPE: DNA
<213> ORGANISM: Homo sapiens
```

<400> SEQUENCE: 351
ggccgcatgc ttggaggtaa a                                              21

<210> SEQ ID NO 352
<211> LENGTH: 21
<212> TYPE: DNA
<213> ORGANISM: Homo sapiens

<400> SEQUENCE: 352
aagtgagagg tcagactcct a                                              21

<210> SEQ ID NO 353
<211> LENGTH: 21
<212> TYPE: DNA
<213> ORGANISM: Homo sapiens

<400> SEQUENCE: 353
caggatcaat gacatatcac a                                              21

<210> SEQ ID NO 354
<211> LENGTH: 21
<212> TYPE: DNA
<213> ORGANISM: Homo sapiens

<400> SEQUENCE: 354
aaggcgaatt atactctctt a                                              21

<210> SEQ ID NO 355
<211> LENGTH: 21
<212> TYPE: DNA
<213> ORGANISM: Homo sapiens

<400> SEQUENCE: 355
cccgttgaat tccgaggcca t                                              21

<210> SEQ ID NO 356
<211> LENGTH: 21
<212> TYPE: DNA
<213> ORGANISM: Homo sapiens

<400> SEQUENCE: 356
gagaacgaag aatgagtaca a                                              21

<210> SEQ ID NO 357
<211> LENGTH: 21
<212> TYPE: DNA
<213> ORGANISM: Homo sapiens

<400> SEQUENCE: 357
aaacatgtaa tatataattt a                                              21

<210> SEQ ID NO 358
<211> LENGTH: 21
<212> TYPE: DNA
<213> ORGANISM: Homo sapiens

<400> SEQUENCE: 358
atcggataga aattaagcct a                                              21

<210> SEQ ID NO 359
<211> LENGTH: 21
<212> TYPE: DNA

<213> ORGANISM: Homo sapiens

<400> SEQUENCE: 359
tagtgtaata tcaggcctaa a          21

<210> SEQ ID NO 360
<211> LENGTH: 21
<212> TYPE: DNA
<213> ORGANISM: Homo sapiens

<400> SEQUENCE: 360
aaaccactaa ttgttccgtt a          21

<210> SEQ ID NO 361
<211> LENGTH: 21
<212> TYPE: DNA
<213> ORGANISM: Homo sapiens

<400> SEQUENCE: 361
ctgtggtgca tagaacctca a          21

<210> SEQ ID NO 362
<211> LENGTH: 21
<212> TYPE: DNA
<213> ORGANISM: Homo sapiens

<400> SEQUENCE: 362
cagggatgga agaatacacc a          21

<210> SEQ ID NO 363
<211> LENGTH: 21
<212> TYPE: DNA
<213> ORGANISM: Homo sapiens

<400> SEQUENCE: 363
ctgatggtta ttgctgctgc a          21

<210> SEQ ID NO 364
<211> LENGTH: 21
<212> TYPE: DNA
<213> ORGANISM: Homo sapiens

<400> SEQUENCE: 364
tccgatcctg tattccttct a          21

<210> SEQ ID NO 365
<211> LENGTH: 21
<212> TYPE: DNA
<213> ORGANISM: Homo sapiens

<400> SEQUENCE: 365
ctggctgcgc ttcaagtact a          21

<210> SEQ ID NO 366
<211> LENGTH: 21
<212> TYPE: DNA
<213> ORGANISM: Homo sapiens

<400> SEQUENCE: 366
ctgccgaatt gtacacgagt a          21

<210> SEQ ID NO 367
<211> LENGTH: 21

```
<212> TYPE: DNA
<213> ORGANISM: Homo sapiens

<400> SEQUENCE: 367
aagttctgca ttaaactcct a                                    21

<210> SEQ ID NO 368
<211> LENGTH: 21
<212> TYPE: DNA
<213> ORGANISM: Homo sapiens

<400> SEQUENCE: 368
cccgtttcca gcgaaagttc a                                    21

<210> SEQ ID NO 369
<211> LENGTH: 21
<212> TYPE: DNA
<213> ORGANISM: Homo sapiens

<400> SEQUENCE: 369
ttgtgtcatc acaacattaa a                                    21

<210> SEQ ID NO 370
<211> LENGTH: 21
<212> TYPE: DNA
<213> ORGANISM: Homo sapiens

<400> SEQUENCE: 370
cgggcggtac ctggccatga a                                    21

<210> SEQ ID NO 371
<211> LENGTH: 21
<212> TYPE: DNA
<213> ORGANISM: Homo sapiens

<400> SEQUENCE: 371
ccgcgtctgg gttctcagct a                                    21

<210> SEQ ID NO 372
<211> LENGTH: 21
<212> TYPE: DNA
<213> ORGANISM: Homo sapiens

<400> SEQUENCE: 372
cagcgccgag agactgtggt a                                    21

<210> SEQ ID NO 373
<211> LENGTH: 21
<212> TYPE: DNA
<213> ORGANISM: Homo sapiens

<400> SEQUENCE: 373
caggatcagc ataaccgcca a                                    21

<210> SEQ ID NO 374
<211> LENGTH: 21
<212> TYPE: DNA
<213> ORGANISM: Homo sapiens

<400> SEQUENCE: 374
ccgtagcaca gtagaaatga a                                    21

<210> SEQ ID NO 375
```

-continued

```
<211> LENGTH: 21
<212> TYPE: DNA
<213> ORGANISM: Homo sapiens

<400> SEQUENCE: 375
acctaggacg ttagccctta a                                              21

<210> SEQ ID NO 376
<211> LENGTH: 21
<212> TYPE: DNA
<213> ORGANISM: Homo sapiens

<400> SEQUENCE: 376
ctcatagtga tttgccacaa a                                              21

<210> SEQ ID NO 377
<211> LENGTH: 21
<212> TYPE: DNA
<213> ORGANISM: Homo sapiens

<400> SEQUENCE: 377
acgcacgtga tgtacatgca a                                              21

<210> SEQ ID NO 378
<211> LENGTH: 21
<212> TYPE: DNA
<213> ORGANISM: Homo sapiens

<400> SEQUENCE: 378
ctggacctat gctgcaggca a                                              21

<210> SEQ ID NO 379
<211> LENGTH: 21
<212> TYPE: DNA
<213> ORGANISM: Homo sapiens

<400> SEQUENCE: 379
cagcctctat gcccaccgct a                                              21

<210> SEQ ID NO 380
<211> LENGTH: 21
<212> TYPE: DNA
<213> ORGANISM: Homo sapiens

<400> SEQUENCE: 380
caggacgagt gtggtctccc a                                              21

<210> SEQ ID NO 381
<211> LENGTH: 21
<212> TYPE: DNA
<213> ORGANISM: Homo sapiens

<400> SEQUENCE: 381
cagcctgatg atgcagtaga a                                              21

<210> SEQ ID NO 382
<211> LENGTH: 21
<212> TYPE: DNA
<213> ORGANISM: Homo sapiens

<400> SEQUENCE: 382
aagggaaaca agagcataaa t                                              21
```

```
<210> SEQ ID NO 383
<211> LENGTH: 21
<212> TYPE: DNA
<213> ORGANISM: Homo sapiens

<400> SEQUENCE: 383
ttggaactgg gtgttgaaat a                                              21

<210> SEQ ID NO 384
<211> LENGTH: 21
<212> TYPE: DNA
<213> ORGANISM: Homo sapiens

<400> SEQUENCE: 384
cagagtggat tcatcctgta t                                              21

<210> SEQ ID NO 385
<211> LENGTH: 21
<212> TYPE: DNA
<213> ORGANISM: Homo sapiens

<400> SEQUENCE: 385
cacgtccata gaacaggcaa a                                              21

<210> SEQ ID NO 386
<211> LENGTH: 21
<212> TYPE: DNA
<213> ORGANISM: Homo sapiens

<400> SEQUENCE: 386
acccacatat gcagcagtca a                                              21

<210> SEQ ID NO 387
<211> LENGTH: 21
<212> TYPE: DNA
<213> ORGANISM: Homo sapiens

<400> SEQUENCE: 387
ctccgtagcc tcgctgacca a                                              21

<210> SEQ ID NO 388
<211> LENGTH: 21
<212> TYPE: DNA
<213> ORGANISM: Homo sapiens

<400> SEQUENCE: 388
tccgctcgcc gtagcgcttt a                                              21

<210> SEQ ID NO 389
<211> LENGTH: 21
<212> TYPE: DNA
<213> ORGANISM: Homo sapiens

<400> SEQUENCE: 389
tgggatccag tcaacacatt a                                              21

<210> SEQ ID NO 390
<211> LENGTH: 21
<212> TYPE: DNA
<213> ORGANISM: Homo sapiens

<400> SEQUENCE: 390
tagcagagca atcaccacca a                                              21
```

```
<210> SEQ ID NO 391
<211> LENGTH: 21
<212> TYPE: DNA
<213> ORGANISM: Homo sapiens

<400> SEQUENCE: 391
ccaagtcgag ctggtcttct a                                              21

<210> SEQ ID NO 392
<211> LENGTH: 21
<212> TYPE: DNA
<213> ORGANISM: Homo sapiens

<400> SEQUENCE: 392
agggattgag gaggactact a                                              21

<210> SEQ ID NO 393
<211> LENGTH: 21
<212> TYPE: DNA
<213> ORGANISM: Homo sapiens

<400> SEQUENCE: 393
ccggatcata tttacatgga t                                              21

<210> SEQ ID NO 394
<211> LENGTH: 21
<212> TYPE: DNA
<213> ORGANISM: Homo sapiens

<400> SEQUENCE: 394
catcgacttg acgatagata a                                              21

<210> SEQ ID NO 395
<211> LENGTH: 21
<212> TYPE: DNA
<213> ORGANISM: Homo sapiens

<400> SEQUENCE: 395
caccctcgct tcagtacctt a                                              21

<210> SEQ ID NO 396
<211> LENGTH: 21
<212> TYPE: DNA
<213> ORGANISM: Homo sapiens

<400> SEQUENCE: 396
atcaggctct ttgcacaata a                                              21

<210> SEQ ID NO 397
<211> LENGTH: 21
<212> TYPE: DNA
<213> ORGANISM: Homo sapiens

<400> SEQUENCE: 397
agggaagaac atctactata a                                              21

<210> SEQ ID NO 398
<211> LENGTH: 21
<212> TYPE: DNA
<213> ORGANISM: Homo sapiens

<400> SEQUENCE: 398
aacatcagtg ctgatagtga a                                              21
```

```
<210> SEQ ID NO 399
<211> LENGTH: 21
<212> TYPE: DNA
<213> ORGANISM: Homo sapiens

<400> SEQUENCE: 399
cagacggaag ggtaaacaat a                                              21

<210> SEQ ID NO 400
<211> LENGTH: 21
<212> TYPE: DNA
<213> ORGANISM: Homo sapiens

<400> SEQUENCE: 400
cagccgcacc gccgagtaca a                                              21

<210> SEQ ID NO 401
<211> LENGTH: 21
<212> TYPE: DNA
<213> ORGANISM: Homo sapiens

<400> SEQUENCE: 401
cccgccatcc tccaataaag t                                              21

<210> SEQ ID NO 402
<211> LENGTH: 21
<212> TYPE: DNA
<213> ORGANISM: Homo sapiens

<400> SEQUENCE: 402
ctgaaggagc catctcatcc a                                              21

<210> SEQ ID NO 403
<211> LENGTH: 21
<212> TYPE: DNA
<213> ORGANISM: Homo sapiens

<400> SEQUENCE: 403
tggctggtac cctggaggaa a                                              21

<210> SEQ ID NO 404
<211> LENGTH: 21
<212> TYPE: DNA
<213> ORGANISM: Homo sapiens

<400> SEQUENCE: 404
cagactgccc atggcctccc a                                              21

<210> SEQ ID NO 405
<211> LENGTH: 21
<212> TYPE: DNA
<213> ORGANISM: Homo sapiens

<400> SEQUENCE: 405
cagggttctg agaacatttc a                                              21

<210> SEQ ID NO 406
<211> LENGTH: 21
<212> TYPE: DNA
<213> ORGANISM: Homo sapiens

<400> SEQUENCE: 406
```
ctggtgttaa atggagctat t                                                      21

<210> SEQ ID NO 407
<211> LENGTH: 21
<212> TYPE: DNA
<213> ORGANISM: Homo sapiens

<400> SEQUENCE: 407
cagcattcag tttgtcaatg a                                                      21

<210> SEQ ID NO 408
<211> LENGTH: 21
<212> TYPE: DNA
<213> ORGANISM: Homo sapiens

<400> SEQUENCE: 408
cagtatgaac ctgtcctaaa t                                                      21

<210> SEQ ID NO 409
<211> LENGTH: 21
<212> TYPE: DNA
<213> ORGANISM: Homo sapiens

<400> SEQUENCE: 409
aacgatgtgg acgtacagga a                                                      21

<210> SEQ ID NO 410
<211> LENGTH: 21
<212> TYPE: DNA
<213> ORGANISM: Homo sapiens

<400> SEQUENCE: 410
cacgattaca aatgggatca a                                                      21

<210> SEQ ID NO 411
<211> LENGTH: 21
<212> TYPE: DNA
<213> ORGANISM: Homo sapiens

<400> SEQUENCE: 411
aagcaatgga tcggagaaca a                                                      21

<210> SEQ ID NO 412
<211> LENGTH: 21
<212> TYPE: DNA
<213> ORGANISM: Homo sapiens

<400> SEQUENCE: 412
caccggatca caaatacgga a                                                      21

<210> SEQ ID NO 413
<211> LENGTH: 21
<212> TYPE: DNA
<213> ORGANISM: Homo sapiens

<400> SEQUENCE: 413
ctggacgaga tcagcagggt a                                                      21

<210> SEQ ID NO 414
<211> LENGTH: 21
<212> TYPE: DNA
<213> ORGANISM: Homo sapiens

<400> SEQUENCE: 414
cccagctttc actatcggca a									21

<210> SEQ ID NO 415
<211> LENGTH: 21
<212> TYPE: DNA
<213> ORGANISM: Homo sapiens

<400> SEQUENCE: 415
cacccacatg gtcaagttca a									21

<210> SEQ ID NO 416
<211> LENGTH: 21
<212> TYPE: DNA
<213> ORGANISM: Homo sapiens

<400> SEQUENCE: 416
gtcgatgtgc ttgccgatct a									21

<210> SEQ ID NO 417
<211> LENGTH: 21
<212> TYPE: DNA
<213> ORGANISM: Homo sapiens

<400> SEQUENCE: 417
atcagttcta cggatcatca a									21

<210> SEQ ID NO 418
<211> LENGTH: 21
<212> TYPE: DNA
<213> ORGANISM: Homo sapiens

<400> SEQUENCE: 418
ccagctgaac cagcaatgat a									21

<210> SEQ ID NO 419
<211> LENGTH: 21
<212> TYPE: DNA
<213> ORGANISM: Homo sapiens

<400> SEQUENCE: 419
cagaggatag cagcaacttc a									21

<210> SEQ ID NO 420
<211> LENGTH: 21
<212> TYPE: DNA
<213> ORGANISM: Homo sapiens

<400> SEQUENCE: 420
cggagggacc gtgctgacca a									21

<210> SEQ ID NO 421
<211> LENGTH: 21
<212> TYPE: DNA
<213> ORGANISM: Homo sapiens

<400> SEQUENCE: 421
aagctttaac tgagactccg a									21

<210> SEQ ID NO 422
<211> LENGTH: 21
<212> TYPE: DNA
<213> ORGANISM: Homo sapiens

```
<400> SEQUENCE: 422
aagaaagacg agctttacct a                                        21

<210> SEQ ID NO 423
<211> LENGTH: 21
<212> TYPE: DNA
<213> ORGANISM: Homo sapiens

<400> SEQUENCE: 423
accacagtcg tagccactct a                                        21

<210> SEQ ID NO 424
<211> LENGTH: 21
<212> TYPE: DNA
<213> ORGANISM: Homo sapiens

<400> SEQUENCE: 424
caaaggtgtt caaatctcga a                                        21

<210> SEQ ID NO 425
<211> LENGTH: 21
<212> TYPE: DNA
<213> ORGANISM: Homo sapiens

<400> SEQUENCE: 425
ctgggcgtat gattgactta a                                        21

<210> SEQ ID NO 426
<211> LENGTH: 21
<212> TYPE: DNA
<213> ORGANISM: Homo sapiens

<400> SEQUENCE: 426
caggaagtcc tgggtgctaa a                                        21

<210> SEQ ID NO 427
<211> LENGTH: 21
<212> TYPE: DNA
<213> ORGANISM: Homo sapiens

<400> SEQUENCE: 427
caggtattgt tacttgaata a                                        21

<210> SEQ ID NO 428
<211> LENGTH: 21
<212> TYPE: DNA
<213> ORGANISM: Homo sapiens

<400> SEQUENCE: 428
aaggcgggag tgaccgctta a                                        21

<210> SEQ ID NO 429
<211> LENGTH: 21
<212> TYPE: DNA
<213> ORGANISM: Homo sapiens

<400> SEQUENCE: 429
cacgggagtc ataacactaa a                                        21

<210> SEQ ID NO 430
<211> LENGTH: 21
<212> TYPE: DNA
<213> ORGANISM: Homo sapiens
```

<400> SEQUENCE: 430
caacttaggt atacaatata a                                              21

<210> SEQ ID NO 431
<211> LENGTH: 21
<212> TYPE: DNA
<213> ORGANISM: Homo sapiens

<400> SEQUENCE: 431
tagccttgaa atctccttca a                                              21

<210> SEQ ID NO 432
<211> LENGTH: 21
<212> TYPE: DNA
<213> ORGANISM: Homo sapiens

<400> SEQUENCE: 432
tcgaggttta atgcattcaa a                                              21

<210> SEQ ID NO 433
<211> LENGTH: 21
<212> TYPE: DNA
<213> ORGANISM: Homo sapiens

<400> SEQUENCE: 433
ctccttcgtc aatgacatct t                                              21

<210> SEQ ID NO 434
<211> LENGTH: 21
<212> TYPE: DNA
<213> ORGANISM: Homo sapiens

<400> SEQUENCE: 434
caaggccatg ggcatcatga a                                              21

<210> SEQ ID NO 435
<211> LENGTH: 21
<212> TYPE: DNA
<213> ORGANISM: Homo sapiens

<400> SEQUENCE: 435
caccaagtac accagttcca a                                              21

<210> SEQ ID NO 436
<211> LENGTH: 21
<212> TYPE: DNA
<213> ORGANISM: Homo sapiens

<400> SEQUENCE: 436
ccgcctggcg cattacaaca a                                              21

<210> SEQ ID NO 437
<211> LENGTH: 21
<212> TYPE: DNA
<213> ORGANISM: Homo sapiens

<400> SEQUENCE: 437
ctggcagtga ctaatcagta a                                              21

<210> SEQ ID NO 438
<211> LENGTH: 21
<212> TYPE: DNA

```
<213> ORGANISM: Homo sapiens

<400> SEQUENCE: 438
caagagcttc ttagagtagt a                                              21

<210> SEQ ID NO 439
<211> LENGTH: 21
<212> TYPE: DNA
<213> ORGANISM: Homo sapiens

<400> SEQUENCE: 439
cagccggttt attgtgcttc a                                              21

<210> SEQ ID NO 440
<211> LENGTH: 21
<212> TYPE: DNA
<213> ORGANISM: Homo sapiens

<400> SEQUENCE: 440
caagactatg atacaactcc a                                              21

<210> SEQ ID NO 441
<211> LENGTH: 21
<212> TYPE: DNA
<213> ORGANISM: Homo sapiens

<400> SEQUENCE: 441
ccgactatcc ctgcacataa a                                              21

<210> SEQ ID NO 442
<211> LENGTH: 21
<212> TYPE: DNA
<213> ORGANISM: Homo sapiens

<400> SEQUENCE: 442
cagagccgtt tcgccaagga a                                              21

<210> SEQ ID NO 443
<211> LENGTH: 21
<212> TYPE: DNA
<213> ORGANISM: Homo sapiens

<400> SEQUENCE: 443
ccgggtcatt ggcaagctga t                                              21

<210> SEQ ID NO 444
<211> LENGTH: 21
<212> TYPE: DNA
<213> ORGANISM: Homo sapiens

<400> SEQUENCE: 444
aagggcgaga atggaccctg a                                              21

<210> SEQ ID NO 445
<211> LENGTH: 21
<212> TYPE: DNA
<213> ORGANISM: Homo sapiens

<400> SEQUENCE: 445
aaggcttcga gaagattagc a                                              21

<210> SEQ ID NO 446
<211> LENGTH: 21
```

```
<212> TYPE: DNA
<213> ORGANISM: Homo sapiens

<400> SEQUENCE: 446
caccaccaga tgagaagtta a                                              21

<210> SEQ ID NO 447
<211> LENGTH: 21
<212> TYPE: DNA
<213> ORGANISM: Homo sapiens

<400> SEQUENCE: 447
cagggtttgg tgacaataga a                                              21

<210> SEQ ID NO 448
<211> LENGTH: 21
<212> TYPE: DNA
<213> ORGANISM: Homo sapiens

<400> SEQUENCE: 448
cgggcttatg ccaaagatgt a                                              21

<210> SEQ ID NO 449
<211> LENGTH: 21
<212> TYPE: DNA
<213> ORGANISM: Homo sapiens

<400> SEQUENCE: 449
cgggaagcag gagtcaatga a                                              21

<210> SEQ ID NO 450
<211> LENGTH: 21
<212> TYPE: DNA
<213> ORGANISM: Homo sapiens

<400> SEQUENCE: 450
tcccatgaca cggtcctcca a                                              21

<210> SEQ ID NO 451
<211> LENGTH: 21
<212> TYPE: DNA
<213> ORGANISM: Homo sapiens

<400> SEQUENCE: 451
cacggtggtc actggaactc a                                              21

<210> SEQ ID NO 452
<211> LENGTH: 21
<212> TYPE: DNA
<213> ORGANISM: Homo sapiens

<400> SEQUENCE: 452
aacatctttc acaaacactc a                                              21

<210> SEQ ID NO 453
<211> LENGTH: 21
<212> TYPE: DNA
<213> ORGANISM: Homo sapiens

<400> SEQUENCE: 453
cagtgggtgc aggcacaata a                                              21

<210> SEQ ID NO 454
```

```
<211> LENGTH: 21
<212> TYPE: DNA
<213> ORGANISM: Homo sapiens

<400> SEQUENCE: 454
agccaggaag acatgaacaa a                                              21

<210> SEQ ID NO 455
<211> LENGTH: 21
<212> TYPE: DNA
<213> ORGANISM: Homo sapiens

<400> SEQUENCE: 455
ccaagtcttg ctgcaaattt a                                              21

<210> SEQ ID NO 456
<211> LENGTH: 21
<212> TYPE: DNA
<213> ORGANISM: Homo sapiens

<400> SEQUENCE: 456
aacctgatta atttcatcaa t                                              21

<210> SEQ ID NO 457
<211> LENGTH: 21
<212> TYPE: DNA
<213> ORGANISM: Homo sapiens

<400> SEQUENCE: 457
cagcggtctg gttatcgtct a                                              21

<210> SEQ ID NO 458
<211> LENGTH: 21
<212> TYPE: DNA
<213> ORGANISM: Homo sapiens

<400> SEQUENCE: 458
cggcacctac gtagtctgct a                                              21

<210> SEQ ID NO 459
<211> LENGTH: 21
<212> TYPE: DNA
<213> ORGANISM: Homo sapiens

<400> SEQUENCE: 459
cagctggatt caccctcgaa a                                              21

<210> SEQ ID NO 460
<211> LENGTH: 21
<212> TYPE: DNA
<213> ORGANISM: Homo sapiens

<400> SEQUENCE: 460
tcccgactgg ttcgaatgtg a                                              21

<210> SEQ ID NO 461
<211> LENGTH: 21
<212> TYPE: DNA
<213> ORGANISM: Homo sapiens

<400> SEQUENCE: 461
aaggcaaagc acgaaatgtt a                                              21
```

```
<210> SEQ ID NO 462
<211> LENGTH: 21
<212> TYPE: DNA
<213> ORGANISM: Homo sapiens

<400> SEQUENCE: 462
cacgcctact taagacaatt a                                              21

<210> SEQ ID NO 463
<211> LENGTH: 21
<212> TYPE: DNA
<213> ORGANISM: Homo sapiens

<400> SEQUENCE: 463
tcgagttgaa tgaacataga a                                              21

<210> SEQ ID NO 464
<211> LENGTH: 21
<212> TYPE: DNA
<213> ORGANISM: Homo sapiens

<400> SEQUENCE: 464
ctgaggtgat ttatgcctta a                                              21

<210> SEQ ID NO 465
<211> LENGTH: 21
<212> TYPE: DNA
<213> ORGANISM: Homo sapiens

<400> SEQUENCE: 465
cagggctaat gaaccatcta a                                              21

<210> SEQ ID NO 466
<211> LENGTH: 21
<212> TYPE: DNA
<213> ORGANISM: Homo sapiens

<400> SEQUENCE: 466
aagcattgaa tggaagacat t                                              21

<210> SEQ ID NO 467
<211> LENGTH: 21
<212> TYPE: DNA
<213> ORGANISM: Homo sapiens

<400> SEQUENCE: 467
tcgagggtgc tggagaagaa a                                              21

<210> SEQ ID NO 468
<211> LENGTH: 21
<212> TYPE: DNA
<213> ORGANISM: Homo sapiens

<400> SEQUENCE: 468
cagctctgat cgcctacgca a                                              21

<210> SEQ ID NO 469
<211> LENGTH: 21
<212> TYPE: DNA
<213> ORGANISM: Homo sapiens

<400> SEQUENCE: 469
caccttatct taaagcactt a                                              21
```

```
<210> SEQ ID NO 470
<211> LENGTH: 21
<212> TYPE: DNA
<213> ORGANISM: Homo sapiens

<400> SEQUENCE: 470
cggtcctgac ttcaactata a                                              21

<210> SEQ ID NO 471
<211> LENGTH: 21
<212> TYPE: DNA
<213> ORGANISM: Homo sapiens

<400> SEQUENCE: 471
acggtgaaca tcatagttgt a                                              21

<210> SEQ ID NO 472
<211> LENGTH: 21
<212> TYPE: DNA
<213> ORGANISM: Homo sapiens

<400> SEQUENCE: 472
ccctatcaga acggccttct a                                              21

<210> SEQ ID NO 473
<211> LENGTH: 21
<212> TYPE: DNA
<213> ORGANISM: Homo sapiens

<400> SEQUENCE: 473
ccggaaataa aggctgttgt a                                              21

<210> SEQ ID NO 474
<211> LENGTH: 21
<212> TYPE: DNA
<213> ORGANISM: Homo sapiens

<400> SEQUENCE: 474
aagatgctgg cgggcaacga a                                              21

<210> SEQ ID NO 475
<211> LENGTH: 21
<212> TYPE: DNA
<213> ORGANISM: Homo sapiens

<400> SEQUENCE: 475
ctcatctttg ccagtacagg a                                              21

<210> SEQ ID NO 476
<211> LENGTH: 21
<212> TYPE: DNA
<213> ORGANISM: Homo sapiens

<400> SEQUENCE: 476
ctgcgggatt tgttcagttc a                                              21

<210> SEQ ID NO 477
<211> LENGTH: 21
<212> TYPE: DNA
<213> ORGANISM: Homo sapiens

<400> SEQUENCE: 477
acccagtagc tagaatgtta a                                              21
```

<210> SEQ ID NO 478
<211> LENGTH: 21
<212> TYPE: DNA
<213> ORGANISM: Homo sapiens

<400> SEQUENCE: 478
cccggtgatc cctgtggtct a                                              21

<210> SEQ ID NO 479
<211> LENGTH: 21
<212> TYPE: DNA
<213> ORGANISM: Homo sapiens

<400> SEQUENCE: 479
tggagtggat atggaactca t                                              21

<210> SEQ ID NO 480
<211> LENGTH: 21
<212> TYPE: DNA
<213> ORGANISM: Homo sapiens

<400> SEQUENCE: 480
cccagagacg ttggatctca a                                              21

<210> SEQ ID NO 481
<211> LENGTH: 21
<212> TYPE: DNA
<213> ORGANISM: Homo sapiens

<400> SEQUENCE: 481
cagggtagaa acgttgagaa t                                              21

<210> SEQ ID NO 482
<211> LENGTH: 21
<212> TYPE: DNA
<213> ORGANISM: Homo sapiens

<400> SEQUENCE: 482
ctgacgattg cttagcatta a                                              21

<210> SEQ ID NO 483
<211> LENGTH: 21
<212> TYPE: DNA
<213> ORGANISM: Homo sapiens

<400> SEQUENCE: 483
cgcgtccaaa ggctaaatga a                                              21

<210> SEQ ID NO 484
<211> LENGTH: 21
<212> TYPE: DNA
<213> ORGANISM: Homo sapiens

<400> SEQUENCE: 484
aagaacgtga cagatgagca g                                              21

<210> SEQ ID NO 485
<211> LENGTH: 21
<212> TYPE: DNA
<213> ORGANISM: Homo sapiens

<400> SEQUENCE: 485
aagaagtgtc cgagaactaa a        21

<210> SEQ ID NO 486
<211> LENGTH: 21
<212> TYPE: DNA
<213> ORGANISM: Homo sapiens

<400> SEQUENCE: 486
ttcgttaaca ttgaccaaga a        21

<210> SEQ ID NO 487
<211> LENGTH: 21
<212> TYPE: DNA
<213> ORGANISM: Homo sapiens

<400> SEQUENCE: 487
cgcgcgcgag tcgacaagta a        21

<210> SEQ ID NO 488
<211> LENGTH: 21
<212> TYPE: DNA
<213> ORGANISM: Homo sapiens

<400> SEQUENCE: 488
ctgctgtaat ttataaggca a        21

<210> SEQ ID NO 489
<211> LENGTH: 21
<212> TYPE: DNA
<213> ORGANISM: Homo sapiens

<400> SEQUENCE: 489
cagggaggag aggctgcata a        21

<210> SEQ ID NO 490
<211> LENGTH: 21
<212> TYPE: DNA
<213> ORGANISM: Homo sapiens

<400> SEQUENCE: 490
ctgaacatcg tcaaccagaa a        21

<210> SEQ ID NO 491
<211> LENGTH: 21
<212> TYPE: DNA
<213> ORGANISM: Homo sapiens

<400> SEQUENCE: 491
cagcctggat ttccacccgt a        21

<210> SEQ ID NO 492
<211> LENGTH: 21
<212> TYPE: DNA
<213> ORGANISM: Homo sapiens

<400> SEQUENCE: 492
agggaacatc ctcaagagca a        21

<210> SEQ ID NO 493
<211> LENGTH: 21
<212> TYPE: DNA
<213> ORGANISM: Homo sapiens

<400> SEQUENCE: 493

```
ccgagcgagg tttaagccga a                                          21

<210> SEQ ID NO 494
<211> LENGTH: 21
<212> TYPE: DNA
<213> ORGANISM: Homo sapiens

<400> SEQUENCE: 494
aaccctaggg aacatcctca a                                          21

<210> SEQ ID NO 495
<211> LENGTH: 21
<212> TYPE: DNA
<213> ORGANISM: Homo sapiens

<400> SEQUENCE: 495
aacctgtttg acaccgccga a                                          21

<210> SEQ ID NO 496
<211> LENGTH: 21
<212> TYPE: DNA
<213> ORGANISM: Homo sapiens

<400> SEQUENCE: 496
ttgggtgaga ctgtttacaa a                                          21

<210> SEQ ID NO 497
<211> LENGTH: 21
<212> TYPE: DNA
<213> ORGANISM: Homo sapiens

<400> SEQUENCE: 497
tgcgaaggat ctggtagaga a                                          21

<210> SEQ ID NO 498
<211> LENGTH: 21
<212> TYPE: DNA
<213> ORGANISM: Homo sapiens

<400> SEQUENCE: 498
cagctcctac ctggccaatg a                                          21

<210> SEQ ID NO 499
<211> LENGTH: 21
<212> TYPE: DNA
<213> ORGANISM: Homo sapiens

<400> SEQUENCE: 499
ctcgcacttc cacaagacct a                                          21

<210> SEQ ID NO 500
<211> LENGTH: 21
<212> TYPE: DNA
<213> ORGANISM: Homo sapiens

<400> SEQUENCE: 500
ctcggccaag cacatcttca a                                          21

<210> SEQ ID NO 501
<211> LENGTH: 21
<212> TYPE: DNA
<213> ORGANISM: Homo sapiens
```

<400> SEQUENCE: 501
aagggccata ttcaaggtgc a                                    21

<210> SEQ ID NO 502
<211> LENGTH: 21
<212> TYPE: DNA
<213> ORGANISM: Homo sapiens

<400> SEQUENCE: 502
cagcccgacc ttcaagaaga a                                    21

<210> SEQ ID NO 503
<211> LENGTH: 21
<212> TYPE: DNA
<213> ORGANISM: Homo sapiens

<400> SEQUENCE: 503
cgccttcgac attcgcttca a                                    21

<210> SEQ ID NO 504
<211> LENGTH: 21
<212> TYPE: DNA
<213> ORGANISM: Homo sapiens

<400> SEQUENCE: 504
ctggcagttt attgctctta a                                    21

<210> SEQ ID NO 505
<211> LENGTH: 21
<212> TYPE: DNA
<213> ORGANISM: Homo sapiens

<400> SEQUENCE: 505
tcggtgttgc ctaatcaagt a                                    21

<210> SEQ ID NO 506
<211> LENGTH: 21
<212> TYPE: DNA
<213> ORGANISM: Homo sapiens

<400> SEQUENCE: 506
caggtaggat ttctacacct a                                    21

<210> SEQ ID NO 507
<211> LENGTH: 21
<212> TYPE: DNA
<213> ORGANISM: Homo sapiens

<400> SEQUENCE: 507
atggattagt tctcaaatct a                                    21

<210> SEQ ID NO 508
<211> LENGTH: 21
<212> TYPE: DNA
<213> ORGANISM: Homo sapiens

<400> SEQUENCE: 508
accgtatatt tatgaagcat a                                    21

<210> SEQ ID NO 509
<211> LENGTH: 21
<212> TYPE: DNA
<213> ORGANISM: Homo sapiens

```
<400> SEQUENCE: 509
gagcataatt atctcaggta a                                              21

<210> SEQ ID NO 510
<211> LENGTH: 21
<212> TYPE: DNA
<213> ORGANISM: Homo sapiens

<400> SEQUENCE: 510
aagagcctaa caatactcaa a                                              21

<210> SEQ ID NO 511
<211> LENGTH: 21
<212> TYPE: DNA
<213> ORGANISM: Homo sapiens

<400> SEQUENCE: 511
tacggtcaag tatgctaaca a                                              21

<210> SEQ ID NO 512
<211> LENGTH: 21
<212> TYPE: DNA
<213> ORGANISM: Homo sapiens

<400> SEQUENCE: 512
cagcctagat ttccgaaata a                                              21

<210> SEQ ID NO 513
<211> LENGTH: 21
<212> TYPE: DNA
<213> ORGANISM: Homo sapiens

<400> SEQUENCE: 513
tcgcgtagag aaactgcaat a                                              21

<210> SEQ ID NO 514
<211> LENGTH: 21
<212> TYPE: DNA
<213> ORGANISM: Homo sapiens

<400> SEQUENCE: 514
caccatatcc ctatgcataa a                                              21

<210> SEQ ID NO 515
<211> LENGTH: 21
<212> TYPE: DNA
<213> ORGANISM: Homo sapiens

<400> SEQUENCE: 515
gagacgcagg tcagaatgga a                                              21

<210> SEQ ID NO 516
<211> LENGTH: 21
<212> TYPE: DNA
<213> ORGANISM: Homo sapiens

<400> SEQUENCE: 516
acggaggaga tagaacgttt a                                              21

<210> SEQ ID NO 517
<211> LENGTH: 21
<212> TYPE: DNA
```

```
<213> ORGANISM: Homo sapiens

<400> SEQUENCE: 517
gccgataaga tagaagatca a                                              21

<210> SEQ ID NO 518
<211> LENGTH: 21
<212> TYPE: DNA
<213> ORGANISM: Homo sapiens

<400> SEQUENCE: 518
ctcgggaagc tggaaatata a                                              21

<210> SEQ ID NO 519
<211> LENGTH: 21
<212> TYPE: DNA
<213> ORGANISM: Homo sapiens

<400> SEQUENCE: 519
aactggatcg taagaaggca g                                              21

<210> SEQ ID NO 520
<211> LENGTH: 21
<212> TYPE: DNA
<213> ORGANISM: Homo sapiens

<400> SEQUENCE: 520
cacgcacaac ccaagcgcaa a                                              21

<210> SEQ ID NO 521
<211> LENGTH: 21
<212> TYPE: DNA
<213> ORGANISM: Homo sapiens

<400> SEQUENCE: 521
aacgacataa cttacgacaa a                                              21

<210> SEQ ID NO 522
<211> LENGTH: 21
<212> TYPE: DNA
<213> ORGANISM: Homo sapiens

<400> SEQUENCE: 522
taggaatagt atggatatac a                                              21

<210> SEQ ID NO 523
<211> LENGTH: 21
<212> TYPE: DNA
<213> ORGANISM: Homo sapiens

<400> SEQUENCE: 523
ccatagcgtg ttcaacatta a                                              21

<210> SEQ ID NO 524
<211> LENGTH: 21
<212> TYPE: DNA
<213> ORGANISM: Homo sapiens

<400> SEQUENCE: 524
caagaacgct tggatattga a                                              21

<210> SEQ ID NO 525
<211> LENGTH: 21
```

```
<212> TYPE: DNA
<213> ORGANISM: Homo sapiens

<400> SEQUENCE: 525
gccgatcaat aaatcagaga a                                              21

<210> SEQ ID NO 526
<211> LENGTH: 21
<212> TYPE: DNA
<213> ORGANISM: Homo sapiens

<400> SEQUENCE: 526
aagacctgat gtgggagttt a                                              21

<210> SEQ ID NO 527
<211> LENGTH: 21
<212> TYPE: DNA
<213> ORGANISM: Homo sapiens

<400> SEQUENCE: 527
ctggttcaga aagacaggca a                                              21

<210> SEQ ID NO 528
<211> LENGTH: 21
<212> TYPE: DNA
<213> ORGANISM: Homo sapiens

<400> SEQUENCE: 528
caagaactct ttgacatcta a                                              21

<210> SEQ ID NO 529
<211> LENGTH: 21
<212> TYPE: DNA
<213> ORGANISM: Homo sapiens

<400> SEQUENCE: 529
aagggcggag atcgaagact a                                              21

<210> SEQ ID NO 530
<211> LENGTH: 21
<212> TYPE: DNA
<213> ORGANISM: Homo sapiens

<400> SEQUENCE: 530
ctggaatcgt ccagggatta a                                              21

<210> SEQ ID NO 531
<211> LENGTH: 21
<212> TYPE: DNA
<213> ORGANISM: Homo sapiens

<400> SEQUENCE: 531
ctggtacaac ccagagtaga a                                              21

<210> SEQ ID NO 532
<211> LENGTH: 21
<212> TYPE: DNA
<213> ORGANISM: Homo sapiens

<400> SEQUENCE: 532
caggcatatg gatgagttca a                                              21

<210> SEQ ID NO 533
```

```
<211> LENGTH: 21
<212> TYPE: DNA
<213> ORGANISM: Homo sapiens

<400> SEQUENCE: 533
cccaattggt ttctacaacg a                                              21

<210> SEQ ID NO 534
<211> LENGTH: 21
<212> TYPE: DNA
<213> ORGANISM: Homo sapiens

<400> SEQUENCE: 534
ccggacggtg ctgtggtgca a                                              21

<210> SEQ ID NO 535
<211> LENGTH: 21
<212> TYPE: DNA
<213> ORGANISM: Homo sapiens

<400> SEQUENCE: 535
tactttgagt atcgaaggtt a                                              21

<210> SEQ ID NO 536
<211> LENGTH: 21
<212> TYPE: DNA
<213> ORGANISM: Homo sapiens

<400> SEQUENCE: 536
cacctaatcc acagaaagta a                                              21

<210> SEQ ID NO 537
<211> LENGTH: 21
<212> TYPE: DNA
<213> ORGANISM: Homo sapiens

<400> SEQUENCE: 537
caagcgccag attgaatact a                                              21

<210> SEQ ID NO 538
<211> LENGTH: 21
<212> TYPE: DNA
<213> ORGANISM: Homo sapiens

<400> SEQUENCE: 538
tccatgactc ttgacatcct a                                              21

<210> SEQ ID NO 539
<211> LENGTH: 21
<212> TYPE: DNA
<213> ORGANISM: Homo sapiens

<400> SEQUENCE: 539
cagaggaggt cagcaaccta a                                              21

<210> SEQ ID NO 540
<211> LENGTH: 21
<212> TYPE: DNA
<213> ORGANISM: Homo sapiens

<400> SEQUENCE: 540
cagctctttc caagacttca a                                              21
```

```
<210> SEQ ID NO 541
<211> LENGTH: 21
<212> TYPE: DNA
<213> ORGANISM: Homo sapiens

<400> SEQUENCE: 541
ctggcctgtg tgtaagtcaa a                                              21

<210> SEQ ID NO 542
<211> LENGTH: 21
<212> TYPE: DNA
<213> ORGANISM: Homo sapiens

<400> SEQUENCE: 542
cccacagatg tctgttgcca a                                              21

<210> SEQ ID NO 543
<211> LENGTH: 21
<212> TYPE: DNA
<213> ORGANISM: Homo sapiens

<400> SEQUENCE: 543
ctccatcaga tcctttggga a                                              21

<210> SEQ ID NO 544
<211> LENGTH: 21
<212> TYPE: DNA
<213> ORGANISM: Homo sapiens

<400> SEQUENCE: 544
aaggacttcc ctgatgtgct a                                              21

<210> SEQ ID NO 545
<211> LENGTH: 21
<212> TYPE: DNA
<213> ORGANISM: Homo sapiens

<400> SEQUENCE: 545
ccgctggcgg ctcaacttca a                                              21

<210> SEQ ID NO 546
<211> LENGTH: 21
<212> TYPE: DNA
<213> ORGANISM: Homo sapiens

<400> SEQUENCE: 546
ctaggcaaga accgcatcaa a                                              21

<210> SEQ ID NO 547
<211> LENGTH: 21
<212> TYPE: DNA
<213> ORGANISM: Homo sapiens

<400> SEQUENCE: 547
ctggccctac ttggacacca t                                              21

<210> SEQ ID NO 548
<211> LENGTH: 21
<212> TYPE: DNA
<213> ORGANISM: Homo sapiens

<400> SEQUENCE: 548
caggtattcc acatacctta a                                              21
```

```
<210> SEQ ID NO 549
<211> LENGTH: 21
<212> TYPE: DNA
<213> ORGANISM: Homo sapiens

<400> SEQUENCE: 549
cagcacttgc taaacatcta a                                              21

<210> SEQ ID NO 550
<211> LENGTH: 21
<212> TYPE: DNA
<213> ORGANISM: Homo sapiens

<400> SEQUENCE: 550
caggacttaa attacacatc a                                              21

<210> SEQ ID NO 551
<211> LENGTH: 21
<212> TYPE: DNA
<213> ORGANISM: Homo sapiens

<400> SEQUENCE: 551
tcgggcctta gtacccattt a                                              21

<210> SEQ ID NO 552
<211> LENGTH: 21
<212> TYPE: DNA
<213> ORGANISM: Homo sapiens

<400> SEQUENCE: 552
ttgatcaaag ttccctgata t                                              21

<210> SEQ ID NO 553
<211> LENGTH: 21
<212> TYPE: DNA
<213> ORGANISM: Homo sapiens

<400> SEQUENCE: 553
atgggacaaa taagttacat t                                              21

<210> SEQ ID NO 554
<211> LENGTH: 21
<212> TYPE: DNA
<213> ORGANISM: Homo sapiens

<400> SEQUENCE: 554
ctcagtggat tcagagttga t                                              21

<210> SEQ ID NO 555
<211> LENGTH: 21
<212> TYPE: DNA
<213> ORGANISM: Homo sapiens

<400> SEQUENCE: 555
tgcagcctga aagaaccaat a                                              21

<210> SEQ ID NO 556
<211> LENGTH: 21
<212> TYPE: DNA
<213> ORGANISM: Homo sapiens

<400> SEQUENCE: 556
cagggaatta ttcacatggc a                                              21
```

<210> SEQ ID NO 557
<211> LENGTH: 21
<212> TYPE: DNA
<213> ORGANISM: Homo sapiens

<400> SEQUENCE: 557
atgactttga tttctgcata a					21

<210> SEQ ID NO 558
<211> LENGTH: 21
<212> TYPE: DNA
<213> ORGANISM: Homo sapiens

<400> SEQUENCE: 558
cccgaggatg tggagccgca a					21

<210> SEQ ID NO 559
<211> LENGTH: 21
<212> TYPE: DNA
<213> ORGANISM: Homo sapiens

<400> SEQUENCE: 559
aagcctcatc tgggcccaca a					21

<210> SEQ ID NO 560
<211> LENGTH: 21
<212> TYPE: DNA
<213> ORGANISM: Homo sapiens

<400> SEQUENCE: 560
atcatgatgg ttagccattt a					21

<210> SEQ ID NO 561
<211> LENGTH: 21
<212> TYPE: DNA
<213> ORGANISM: Homo sapiens

<400> SEQUENCE: 561
cagctgaaac tttcttgatc a					21

<210> SEQ ID NO 562
<211> LENGTH: 21
<212> TYPE: DNA
<213> ORGANISM: Homo sapiens

<400> SEQUENCE: 562
aaagagcatt atctaagtaa t					21

<210> SEQ ID NO 563
<211> LENGTH: 21
<212> TYPE: DNA
<213> ORGANISM: Homo sapiens

<400> SEQUENCE: 563 aacaacettt agatatgcaa a					21

<210> SEQ ID NO 564
<211> LENGTH: 21
<212> TYPE: DNA
<213> ORGANISM: Homo sapiens

<400> SEQUENCE: 564
ctgctcgggc caagtggtta a                                       21

<210> SEQ ID NO 565
<211> LENGTH: 21
<212> TYPE: DNA
<213> ORGANISM: Homo sapiens

<400> SEQUENCE: 565
aagctagatt gtctaccatc a                                       21

<210> SEQ ID NO 566
<211> LENGTH: 21
<212> TYPE: DNA
<213> ORGANISM: Homo sapiens

<400> SEQUENCE: 566
cccattcggt tctacattat t                                       21

<210> SEQ ID NO 567
<211> LENGTH: 21
<212> TYPE: DNA
<213> ORGANISM: Homo sapiens

<400> SEQUENCE: 567
ccggagtctt agcatgccgt a                                       21

<210> SEQ ID NO 568
<211> LENGTH: 21
<212> TYPE: DNA
<213> ORGANISM: Homo sapiens

<400> SEQUENCE: 568
cgccaaggag ctggtcgatt a                                       21

<210> SEQ ID NO 569
<211> LENGTH: 21
<212> TYPE: DNA
<213> ORGANISM: Homo sapiens

<400> SEQUENCE: 569
tcgacccacc tggaaactga a                                       21

<210> SEQ ID NO 570
<211> LENGTH: 21
<212> TYPE: DNA
<213> ORGANISM: Homo sapiens

<400> SEQUENCE: 570
gcgccttgat tatcaagata a                                       21

<210> SEQ ID NO 571
<211> LENGTH: 21
<212> TYPE: DNA
<213> ORGANISM: Homo sapiens

<400> SEQUENCE: 571
tcggccggcc ctcaaacgct a                                       21

<210> SEQ ID NO 572
<211> LENGTH: 21
<212> TYPE: DNA
<213> ORGANISM: Homo sapiens

<400> SEQUENCE: 572
acggatatcc tgcatgtcca a    21

<210> SEQ ID NO 573
<211> LENGTH: 21
<212> TYPE: DNA
<213> ORGANISM: Homo sapiens

<400> SEQUENCE: 573
ccgggccacc gtgaactcac a    21

<210> SEQ ID NO 574
<211> LENGTH: 21
<212> TYPE: DNA
<213> ORGANISM: Homo sapiens

<400> SEQUENCE: 574
accattggag acagaaactt t    21

<210> SEQ ID NO 575
<211> LENGTH: 21
<212> TYPE: DNA
<213> ORGANISM: Homo sapiens

<400> SEQUENCE: 575
tcgactgttt ctacactgtc a    21

<210> SEQ ID NO 576
<211> LENGTH: 21
<212> TYPE: DNA
<213> ORGANISM: Homo sapiens

<400> SEQUENCE: 576
caccttgaat gccgacaaga a    21

<210> SEQ ID NO 577
<211> LENGTH: 21
<212> TYPE: DNA
<213> ORGANISM: Homo sapiens

<400> SEQUENCE: 577
caccactgtg agtgtagcca a    21

<210> SEQ ID NO 578
<211> LENGTH: 21
<212> TYPE: DNA
<213> ORGANISM: Homo sapiens

<400> SEQUENCE: 578
aaggtcagct cgtatcttca a    21

<210> SEQ ID NO 579
<211> LENGTH: 21
<212> TYPE: DNA
<213> ORGANISM: Homo sapiens

<400> SEQUENCE: 579
tatggacaaa tacatcgtta a    21

<210> SEQ ID NO 580
<211> LENGTH: 21
<212> TYPE: DNA
<213> ORGANISM: Homo sapiens

```
<400> SEQUENCE: 580
aagggtattg gtggcacttc a                                      21

<210> SEQ ID NO 581
<211> LENGTH: 21
<212> TYPE: DNA
<213> ORGANISM: Homo sapiens

<400> SEQUENCE: 581
tcccactagc tgattactat a                                      21

<210> SEQ ID NO 582
<211> LENGTH: 21
<212> TYPE: DNA
<213> ORGANISM: Homo sapiens

<400> SEQUENCE: 582
cacccaaatt tgtgcagcta a                                      21

<210> SEQ ID NO 583
<211> LENGTH: 21
<212> TYPE: DNA
<213> ORGANISM: Homo sapiens

<400> SEQUENCE: 583
aagcctgttc cagtggatca a                                      21

<210> SEQ ID NO 584
<211> LENGTH: 21
<212> TYPE: DNA
<213> ORGANISM: Homo sapiens

<400> SEQUENCE: 584
tagtgtcttg gtgtagtgta a                                      21

<210> SEQ ID NO 585
<211> LENGTH: 21
<212> TYPE: DNA
<213> ORGANISM: Homo sapiens

<400> SEQUENCE: 585
agcaagattg ccatcacgaa a                                      21

<210> SEQ ID NO 586
<211> LENGTH: 21
<212> TYPE: DNA
<213> ORGANISM: Homo sapiens

<400> SEQUENCE: 586
aagggcctgg atgcaaggtt a                                      21

<210> SEQ ID NO 587
<211> LENGTH: 21
<212> TYPE: DNA
<213> ORGANISM: Homo sapiens

<400> SEQUENCE: 587
atcacgtgtg attgacatgt a                                      21

<210> SEQ ID NO 588
<211> LENGTH: 21
<212> TYPE: DNA
<213> ORGANISM: Homo sapiens
```

```
<400> SEQUENCE: 588
ttccatcagg accactatta a                                              21

<210> SEQ ID NO 589
<211> LENGTH: 21
<212> TYPE: DNA
<213> ORGANISM: Homo sapiens

<400> SEQUENCE: 589
cacgtttacc cgcaagccga a                                              21

<210> SEQ ID NO 590
<211> LENGTH: 21
<212> TYPE: DNA
<213> ORGANISM: Homo sapiens

<400> SEQUENCE: 590
cccactcaga gcgaggctaa a                                              21

<210> SEQ ID NO 591
<211> LENGTH: 21
<212> TYPE: DNA
<213> ORGANISM: Homo sapiens

<400> SEQUENCE: 591
accctggcgc ttgtgatgta a                                              21

<210> SEQ ID NO 592
<211> LENGTH: 21
<212> TYPE: DNA
<213> ORGANISM: Homo sapiens

<400> SEQUENCE: 592
gatcccggag ttggaaaaca a                                              21

<210> SEQ ID NO 593
<211> LENGTH: 21
<212> TYPE: DNA
<213> ORGANISM: Homo sapiens

<400> SEQUENCE: 593
ctcggtgcag ccgtatttct a                                              21

<210> SEQ ID NO 594
<211> LENGTH: 21
<212> TYPE: DNA
<213> ORGANISM: Homo sapiens

<400> SEQUENCE: 594
atccacgaaa ctttgcccat a                                              21

<210> SEQ ID NO 595
<211> LENGTH: 21
<212> TYPE: DNA
<213> ORGANISM: Homo sapiens

<400> SEQUENCE: 595
cccaaggtag ttatccttaa a                                              21

<210> SEQ ID NO 596
<211> LENGTH: 21
<212> TYPE: DNA
```

```
<213> ORGANISM: Homo sapiens

<400> SEQUENCE: 596
cagaataatg aatggcataa a                                              21

<210> SEQ ID NO 597
<211> LENGTH: 21
<212> TYPE: DNA
<213> ORGANISM: Homo sapiens

<400> SEQUENCE: 597
atcgatatgg atcgaggatt t                                              21

<210> SEQ ID NO 598
<211> LENGTH: 21
<212> TYPE: DNA
<213> ORGANISM: Homo sapiens

<400> SEQUENCE: 598
ctcgtagggc attgcagcga a                                              21

<210> SEQ ID NO 599
<211> LENGTH: 21
<212> TYPE: DNA
<213> ORGANISM: Homo sapiens

<400> SEQUENCE: 599
tcctttaatg ttgtaattga a                                              21

<210> SEQ ID NO 600
<211> LENGTH: 21
<212> TYPE: DNA
<213> ORGANISM: Homo sapiens

<400> SEQUENCE: 600
tacagggaat ttgtacgttt a                                              21

<210> SEQ ID NO 601
<211> LENGTH: 21
<212> TYPE: DNA
<213> ORGANISM: Homo sapiens

<400> SEQUENCE: 601
ctgcacgtcg agcaatccaa a                                              21

<210> SEQ ID NO 602
<211> LENGTH: 21
<212> TYPE: DNA
<213> ORGANISM: Homo sapiens

<400> SEQUENCE: 602
cacgtgggcg cgctcctgaa a                                              21

<210> SEQ ID NO 603
<211> LENGTH: 21
<212> TYPE: DNA
<213> ORGANISM: Homo sapiens

<400> SEQUENCE: 603
ctccgacggc atgatggact a                                              21

<210> SEQ ID NO 604
<211> LENGTH: 21
```

```
<212> TYPE: DNA
<213> ORGANISM: Homo sapiens

<400> SEQUENCE: 604
atggactagt tggttatatg a                                              21

<210> SEQ ID NO 605
<211> LENGTH: 21
<212> TYPE: DNA
<213> ORGANISM: Homo sapiens

<400> SEQUENCE: 605
aaagatgatt atgtccacga a                                              21

<210> SEQ ID NO 606
<211> LENGTH: 21
<212> TYPE: DNA
<213> ORGANISM: Homo sapiens

<400> SEQUENCE: 606
tcgatcctta gctgaagaat a                                              21

<210> SEQ ID NO 607
<211> LENGTH: 21
<212> TYPE: DNA
<213> ORGANISM: Homo sapiens

<400> SEQUENCE: 607
gtgggtaatc atgttgccaa a                                              21

<210> SEQ ID NO 608
<211> LENGTH: 21
<212> TYPE: DNA
<213> ORGANISM: Homo sapiens

<400> SEQUENCE: 608
acactgatta tccaacatat a                                              21

<210> SEQ ID NO 609
<211> LENGTH: 21
<212> TYPE: DNA
<213> ORGANISM: Homo sapiens

<400> SEQUENCE: 609
atccatataa ttagagaatt t                                              21

<210> SEQ ID NO 610
<211> LENGTH: 21
<212> TYPE: DNA
<213> ORGANISM: Homo sapiens

<400> SEQUENCE: 610
cccgctgtgc ataatcggtt t                                              21

<210> SEQ ID NO 611
<211> LENGTH: 21
<212> TYPE: DNA
<213> ORGANISM: Homo sapiens

<400> SEQUENCE: 611
ctgagccgtt tgacaacact a                                              21

<210> SEQ ID NO 612
```

```
<211> LENGTH: 21
<212> TYPE: DNA
<213> ORGANISM: Homo sapiens

<400> SEQUENCE: 612
aaggagctca gtaaactaga a                                              21

<210> SEQ ID NO 613
<211> LENGTH: 21
<212> TYPE: DNA
<213> ORGANISM: Homo sapiens

<400> SEQUENCE: 613
caggtacttc gtgatccgca t                                              21

<210> SEQ ID NO 614
<211> LENGTH: 21
<212> TYPE: DNA
<213> ORGANISM: Homo sapiens

<400> SEQUENCE: 614
caacatcgca aacatgaaga a                                              21

<210> SEQ ID NO 615
<211> LENGTH: 21
<212> TYPE: DNA
<213> ORGANISM: Homo sapiens

<400> SEQUENCE: 615
ctgcagcttg agctacaatc a                                              21

<210> SEQ ID NO 616
<211> LENGTH: 21
<212> TYPE: DNA
<213> ORGANISM: Homo sapiens

<400> SEQUENCE: 616
acggacagtt gggcaccaat a                                              21

<210> SEQ ID NO 617
<211> LENGTH: 21
<212> TYPE: DNA
<213> ORGANISM: Homo sapiens

<400> SEQUENCE: 617
ccagaagctg gtgatcatca a                                              21

<210> SEQ ID NO 618
<211> LENGTH: 21
<212> TYPE: DNA
<213> ORGANISM: Homo sapiens

<400> SEQUENCE: 618
tagagttaga aggcagacct a                                              21

<210> SEQ ID NO 619
<211> LENGTH: 21
<212> TYPE: DNA
<213> ORGANISM: Homo sapiens

<400> SEQUENCE: 619
caggtgtcat gtggtgatga t                                              21
```

```
<210> SEQ ID NO 620
<211> LENGTH: 21
<212> TYPE: DNA
<213> ORGANISM: Homo sapiens

<400> SEQUENCE: 620
tgccttcgga tcagattatt a                                              21

<210> SEQ ID NO 621
<211> LENGTH: 21
<212> TYPE: DNA
<213> ORGANISM: Homo sapiens

<400> SEQUENCE: 621
cagagctctg tcaaggagta a                                              21

<210> SEQ ID NO 622
<211> LENGTH: 21
<212> TYPE: DNA
<213> ORGANISM: Homo sapiens

<400> SEQUENCE: 622
tacacttggg tgaacatgca a                                              21

<210> SEQ ID NO 623
<211> LENGTH: 21
<212> TYPE: DNA
<213> ORGANISM: Homo sapiens

<400> SEQUENCE: 623
aggcagactt tctacatgca a                                              21

<210> SEQ ID NO 624
<211> LENGTH: 21
<212> TYPE: DNA
<213> ORGANISM: Homo sapiens

<400> SEQUENCE: 624
gtgggtcaat tccttagtat a                                              21

<210> SEQ ID NO 625
<211> LENGTH: 21
<212> TYPE: DNA
<213> ORGANISM: Homo sapiens

<400> SEQUENCE: 625
atccaacttc ccgttcatca a                                              21

<210> SEQ ID NO 626
<211> LENGTH: 21
<212> TYPE: DNA
<213> ORGANISM: Homo sapiens

<400> SEQUENCE: 626
ttggccctct taagagaaga a                                              21

<210> SEQ ID NO 627
<211> LENGTH: 21
<212> TYPE: DNA
<213> ORGANISM: Homo sapiens

<400> SEQUENCE: 627
gagcaaggtg aaatacatca a                                              21
```

<210> SEQ ID NO 628
<211> LENGTH: 21
<212> TYPE: DNA
<213> ORGANISM: Homo sapiens

<400> SEQUENCE: 628
caggctgagg tggaccaaga a                                              21

<210> SEQ ID NO 629
<211> LENGTH: 21
<212> TYPE: DNA
<213> ORGANISM: Homo sapiens

<400> SEQUENCE: 629
accgtctgtg aagtggcttt a                                              21

<210> SEQ ID NO 630
<211> LENGTH: 21
<212> TYPE: DNA
<213> ORGANISM: Homo sapiens

<400> SEQUENCE: 630
gtggaccaag aaggcaacca a                                              21

<210> SEQ ID NO 631
<211> LENGTH: 21
<212> TYPE: DNA
<213> ORGANISM: Homo sapiens

<400> SEQUENCE: 631
cagcacttcc tggaatatta a                                              21

<210> SEQ ID NO 632
<211> LENGTH: 21
<212> TYPE: DNA
<213> ORGANISM: Homo sapiens

<400> SEQUENCE: 632
caagatgtgc atgataagat a                                              21

<210> SEQ ID NO 633
<211> LENGTH: 21
<212> TYPE: DNA
<213> ORGANISM: Homo sapiens

<400> SEQUENCE: 633
gagagtcaac tggctctaat a                                              21

<210> SEQ ID NO 634
<211> LENGTH: 21
<212> TYPE: DNA
<213> ORGANISM: Homo sapiens

<400> SEQUENCE: 634
agggtgcatt agagctgcta a                                              21

<210> SEQ ID NO 635
<211> LENGTH: 21
<212> TYPE: DNA
<213> ORGANISM: Homo sapiens

<400> SEQUENCE: 635
ctggagttag cactaacata a                                              21

```
<210> SEQ ID NO 636
<211> LENGTH: 21
<212> TYPE: DNA
<213> ORGANISM: Homo sapiens

<400> SEQUENCE: 636
cagtgtatta ctgctatgaa a                                              21

<210> SEQ ID NO 637
<211> LENGTH: 21
<212> TYPE: DNA
<213> ORGANISM: Homo sapiens

<400> SEQUENCE: 637
aaccctattg ccaaacctat t                                              21

<210> SEQ ID NO 638
<211> LENGTH: 21
<212> TYPE: DNA
<213> ORGANISM: Homo sapiens

<400> SEQUENCE: 638
ctcactaagg ttggttacta t                                              21

<210> SEQ ID NO 639
<211> LENGTH: 21
<212> TYPE: DNA
<213> ORGANISM: Homo sapiens

<400> SEQUENCE: 639
cagaacaagt agaacagcta a                                              21

<210> SEQ ID NO 640
<211> LENGTH: 21
<212> TYPE: DNA
<213> ORGANISM: Homo sapiens

<400> SEQUENCE: 640
aacgcgttaa tttccctcaa a                                              21

<210> SEQ ID NO 641
<211> LENGTH: 21
<212> TYPE: DNA
<213> ORGANISM: Homo sapiens

<400> SEQUENCE: 641
ccgaaggata tctatcatca t                                              21

<210> SEQ ID NO 642
<211> LENGTH: 21
<212> TYPE: DNA
<213> ORGANISM: Homo sapiens

<400> SEQUENCE: 642
cgcgaacgat ttcccaagtt a                                              21

<210> SEQ ID NO 643
<211> LENGTH: 21
<212> TYPE: DNA
<213> ORGANISM: Homo sapiens

<400> SEQUENCE: 643
```
ccggccggcc tttaacctca a        21

<210> SEQ ID NO 644
<211> LENGTH: 21
<212> TYPE: DNA
<213> ORGANISM: Homo sapiens

<400> SEQUENCE: 644
ccgcagggtg atatacaagt a        21

<210> SEQ ID NO 645
<211> LENGTH: 21
<212> TYPE: DNA
<213> ORGANISM: Homo sapiens

<400> SEQUENCE: 645
tcggtttatc cggaagaaca a        21

<210> SEQ ID NO 646
<211> LENGTH: 21
<212> TYPE: DNA
<213> ORGANISM: Homo sapiens

<400> SEQUENCE: 646
ctgcgggttc acaaccgaaa t        21

<210> SEQ ID NO 647
<211> LENGTH: 21
<212> TYPE: DNA
<213> ORGANISM: Homo sapiens

<400> SEQUENCE: 647
caagagtgct tgcatctaca a        21

<210> SEQ ID NO 648
<211> LENGTH: 21
<212> TYPE: DNA
<213> ORGANISM: Homo sapiens

<400> SEQUENCE: 648
cgccatgtac atggtcaaca a        21

<210> SEQ ID NO 649
<211> LENGTH: 21
<212> TYPE: DNA
<213> ORGANISM: Homo sapiens

<400> SEQUENCE: 649
gcgctacatt gtcatctgta a        21

<210> SEQ ID NO 650
<211> LENGTH: 21
<212> TYPE: DNA
<213> ORGANISM: Homo sapiens

<400> SEQUENCE: 650
ttggcctgtt tgcaacagct a        21

<210> SEQ ID NO 651
<211> LENGTH: 21
<212> TYPE: DNA
<213> ORGANISM: Homo sapiens

<400> SEQUENCE: 651
ctggatgaac acggtggtga a                                              21

<210> SEQ ID NO 652
<211> LENGTH: 21
<212> TYPE: DNA
<213> ORGANISM: Homo sapiens

<400> SEQUENCE: 652
caggctgatg aggtacaatg a                                              21

<210> SEQ ID NO 653
<211> LENGTH: 21
<212> TYPE: DNA
<213> ORGANISM: Homo sapiens

<400> SEQUENCE: 653
gtggatgatc gtggactaca a                                              21

<210> SEQ ID NO 654
<211> LENGTH: 21
<212> TYPE: DNA
<213> ORGANISM: Homo sapiens

<400> SEQUENCE: 654
ctggaagttc gcgcctgtca a                                              21

<210> SEQ ID NO 655
<211> LENGTH: 21
<212> TYPE: DNA
<213> ORGANISM: Homo sapiens

<400> SEQUENCE: 655
ctgagtatag tttgactgta a                                              21

<210> SEQ ID NO 656
<211> LENGTH: 21
<212> TYPE: DNA
<213> ORGANISM: Homo sapiens

<400> SEQUENCE: 656
cccgaagcaa ctggtaagca a                                              21

<210> SEQ ID NO 657
<211> LENGTH: 21
<212> TYPE: DNA
<213> ORGANISM: Homo sapiens

<400> SEQUENCE: 657
ctgcgccata gtagcaggta a                                              21

<210> SEQ ID NO 658
<211> LENGTH: 21
<212> TYPE: DNA
<213> ORGANISM: Homo sapiens

<400> SEQUENCE: 658
ccggagaata tttctctcac a                                              21

<210> SEQ ID NO 659
<211> LENGTH: 21
<212> TYPE: DNA
<213> ORGANISM: Homo sapiens

```
<400> SEQUENCE: 659
ttgaacattt atataatcta a                                              21

<210> SEQ ID NO 660
<211> LENGTH: 21
<212> TYPE: DNA
<213> ORGANISM: Homo sapiens

<400> SEQUENCE: 660
tcgcctctag ctggaaacaa a                                              21

<210> SEQ ID NO 661
<211> LENGTH: 21
<212> TYPE: DNA
<213> ORGANISM: Homo sapiens

<400> SEQUENCE: 661
aggaccgctt attccacttt a                                              21

<210> SEQ ID NO 662
<211> LENGTH: 21
<212> TYPE: DNA
<213> ORGANISM: Homo sapiens

<400> SEQUENCE: 662
ccgcatcgtc tccaaacaac a                                              21

<210> SEQ ID NO 663
<211> LENGTH: 21
<212> TYPE: DNA
<213> ORGANISM: Homo sapiens

<400> SEQUENCE: 663
atcgcagatc aaagtggaca a                                              21

<210> SEQ ID NO 664
<211> LENGTH: 21
<212> TYPE: DNA
<213> ORGANISM: Homo sapiens

<400> SEQUENCE: 664
taggatcctt tctagaagga a                                              21

<210> SEQ ID NO 665
<211> LENGTH: 21
<212> TYPE: DNA
<213> ORGANISM: Homo sapiens

<400> SEQUENCE: 665
caggatctat aaactcttca a                                              21

<210> SEQ ID NO 666
<211> LENGTH: 21
<212> TYPE: DNA
<213> ORGANISM: Homo sapiens

<400> SEQUENCE: 666
tcgctggaca aggacgatca a                                              21

<210> SEQ ID NO 667
<211> LENGTH: 21
<212> TYPE: DNA
<213> ORGANISM: Homo sapiens
```

```
<400> SEQUENCE: 667
caccttcagg acgaacaata t                                               21

<210> SEQ ID NO 668
<211> LENGTH: 21
<212> TYPE: DNA
<213> ORGANISM: Homo sapiens

<400> SEQUENCE: 668
cagggatgtg gtcagattcg a                                               21

<210> SEQ ID NO 669
<211> LENGTH: 21
<212> TYPE: DNA
<213> ORGANISM: Homo sapiens

<400> SEQUENCE: 669
tcgccgcacc ctggagcact a                                               21

<210> SEQ ID NO 670
<211> LENGTH: 21
<212> TYPE: DNA
<213> ORGANISM: Homo sapiens

<400> SEQUENCE: 670
gaccgccaga ttctccctta a                                               21

<210> SEQ ID NO 671
<211> LENGTH: 21
<212> TYPE: DNA
<213> ORGANISM: Homo sapiens

<400> SEQUENCE: 671
cagtatttat tgttcccaca a                                               21

<210> SEQ ID NO 672
<211> LENGTH: 21
<212> TYPE: DNA
<213> ORGANISM: Homo sapiens

<400> SEQUENCE: 672
caggccgagt gtactacttc a                                               21

<210> SEQ ID NO 673
<211> LENGTH: 21
<212> TYPE: DNA
<213> ORGANISM: Homo sapiens

<400> SEQUENCE: 673
cggctacatc cagaagatca a                                               21

<210> SEQ ID NO 674
<211> LENGTH: 21
<212> TYPE: DNA
<213> ORGANISM: Homo sapiens

<400> SEQUENCE: 674
caccggcata ttggaagtgt a                                               21

<210> SEQ ID NO 675
<211> LENGTH: 21
<212> TYPE: DNA
```

```
<213> ORGANISM: Homo sapiens

<400> SEQUENCE: 675
cacgagatag ctgtactttc a                                              21

<210> SEQ ID NO 676
<211> LENGTH: 21
<212> TYPE: DNA
<213> ORGANISM: Homo sapiens

<400> SEQUENCE: 676
ctgatgagta ttgaagtact a                                              21

<210> SEQ ID NO 677
<211> LENGTH: 21
<212> TYPE: DNA
<213> ORGANISM: Homo sapiens

<400> SEQUENCE: 677
caagattact gagatacgga a                                              21

<210> SEQ ID NO 678
<211> LENGTH: 21
<212> TYPE: DNA
<213> ORGANISM: Homo sapiens

<400> SEQUENCE: 678
ccgcaaggag ctgaagctga a                                              21

<210> SEQ ID NO 679
<211> LENGTH: 21
<212> TYPE: DNA
<213> ORGANISM: Homo sapiens

<400> SEQUENCE: 679
ccggagcagc ctcaaagcag a                                              21

<210> SEQ ID NO 680
<211> LENGTH: 21
<212> TYPE: DNA
<213> ORGANISM: Homo sapiens

<400> SEQUENCE: 680
cacgggtgac atatcggtgg a                                              21

<210> SEQ ID NO 681
<211> LENGTH: 21
<212> TYPE: DNA
<213> ORGANISM: Homo sapiens

<400> SEQUENCE: 681
ctcggacagc tcacctcaga a                                              21

<210> SEQ ID NO 682
<211> LENGTH: 21
<212> TYPE: DNA
<213> ORGANISM: Homo sapiens

<400> SEQUENCE: 682
ctgcctgccc tcgatgtata a                                              21

<210> SEQ ID NO 683
<211> LENGTH: 21
```

<212> TYPE: DNA
<213> ORGANISM: Homo sapiens

<400> SEQUENCE: 683
cagggctctg atattccatg a                                              21

<210> SEQ ID NO 684
<211> LENGTH: 21
<212> TYPE: DNA
<213> ORGANISM: Homo sapiens

<400> SEQUENCE: 684
tcgctcaagg cttaactcca a                                              21

<210> SEQ ID NO 685
<211> LENGTH: 21
<212> TYPE: DNA
<213> ORGANISM: Homo sapiens

<400> SEQUENCE: 685
aaggcttaac tccaacacgc a                                              21

<210> SEQ ID NO 686
<211> LENGTH: 21
<212> TYPE: DNA
<213> ORGANISM: Homo sapiens

<400> SEQUENCE: 686
ccggcctttc gaagatttca t                                              21

<210> SEQ ID NO 687
<211> LENGTH: 21
<212> TYPE: DNA
<213> ORGANISM: Homo sapiens

<400> SEQUENCE: 687
cagcctgctg acagacacta a                                              21

<210> SEQ ID NO 688
<211> LENGTH: 21
<212> TYPE: DNA
<213> ORGANISM: Homo sapiens

<400> SEQUENCE: 688
tgggcggacg gttctgaaca a                                              21

<210> SEQ ID NO 689
<211> LENGTH: 21
<212> TYPE: DNA
<213> ORGANISM: Homo sapiens

<400> SEQUENCE: 689
cagcaaggtg ctcatcgcag a                                              21

<210> SEQ ID NO 690
<211> LENGTH: 21
<212> TYPE: DNA
<213> ORGANISM: Homo sapiens

<400> SEQUENCE: 690
cagaaagact gtgcactaca a                                              21

<210> SEQ ID NO 691

```
<211> LENGTH: 21
<212> TYPE: DNA
<213> ORGANISM: Homo sapiens

<400> SEQUENCE: 691
ctgcatcaag caggttcact a                                              21

<210> SEQ ID NO 692
<211> LENGTH: 21
<212> TYPE: DNA
<213> ORGANISM: Homo sapiens

<400> SEQUENCE: 692
cccgcagagc cgcgtcgcca a                                              21

<210> SEQ ID NO 693
<211> LENGTH: 21
<212> TYPE: DNA
<213> ORGANISM: Homo sapiens

<400> SEQUENCE: 693
cagcgcgaga agatcctaaa t                                              21

<210> SEQ ID NO 694
<211> LENGTH: 21
<212> TYPE: DNA
<213> ORGANISM: Homo sapiens

<400> SEQUENCE: 694
caaggattta cccattagaa a                                              21

<210> SEQ ID NO 695
<211> LENGTH: 21
<212> TYPE: DNA
<213> ORGANISM: Homo sapiens

<400> SEQUENCE: 695
taggatggga cttaatgata a                                              21

<210> SEQ ID NO 696
<211> LENGTH: 21
<212> TYPE: DNA
<213> ORGANISM: Homo sapiens

<400> SEQUENCE: 696
aaggataaac ccattgctgt a                                              21

<210> SEQ ID NO 697
<211> LENGTH: 21
<212> TYPE: DNA
<213> ORGANISM: Homo sapiens

<400> SEQUENCE: 697
tggaattaga acaaagccga a                                              21

<210> SEQ ID NO 698
<211> LENGTH: 21
<212> TYPE: DNA
<213> ORGANISM: Homo sapiens

<400> SEQUENCE: 698
atggatctaa tcttagatgt a                                              21
```

```
<210> SEQ ID NO 699
<211> LENGTH: 21
<212> TYPE: DNA
<213> ORGANISM: Homo sapiens

<400> SEQUENCE: 699
caggtcatgg gcattgttca a                                              21

<210> SEQ ID NO 700
<211> LENGTH: 21
<212> TYPE: DNA
<213> ORGANISM: Homo sapiens

<400> SEQUENCE: 700
aacattcaaa tttaccctgt a                                              21

<210> SEQ ID NO 701
<211> LENGTH: 21
<212> TYPE: DNA
<213> ORGANISM: Homo sapiens

<400> SEQUENCE: 701
ttgagtatgt aatgtatgga a                                              21

<210> SEQ ID NO 702
<211> LENGTH: 21
<212> TYPE: DNA
<213> ORGANISM: Homo sapiens

<400> SEQUENCE: 702
aaggtctttc agaaccacta a                                              21

<210> SEQ ID NO 703
<211> LENGTH: 21
<212> TYPE: DNA
<213> ORGANISM: Homo sapiens

<400> SEQUENCE: 703
ctggaaggaa ccatccagta a                                              21

<210> SEQ ID NO 704
<211> LENGTH: 21
<212> TYPE: DNA
<213> ORGANISM: Homo sapiens

<400> SEQUENCE: 704
ctgggaggtt gccactgcaa a                                              21

<210> SEQ ID NO 705
<211> LENGTH: 21
<212> TYPE: DNA
<213> ORGANISM: Homo sapiens

<400> SEQUENCE: 705
cggcaacaag tgggaggctt a                                              21

<210> SEQ ID NO 706
<211> LENGTH: 21
<212> TYPE: DNA
<213> ORGANISM: Homo sapiens

<400> SEQUENCE: 706
tcggcgaacg attcgactca a                                              21
```

```
<210> SEQ ID NO 707
<211> LENGTH: 21
<212> TYPE: DNA
<213> ORGANISM: Homo sapiens

<400> SEQUENCE: 707
cagtggagca ttgaacatcg a                                              21

<210> SEQ ID NO 708
<211> LENGTH: 21
<212> TYPE: DNA
<213> ORGANISM: Homo sapiens

<400> SEQUENCE: 708
caagagaatc tacgaggcct a                                              21

<210> SEQ ID NO 709
<211> LENGTH: 21
<212> TYPE: DNA
<213> ORGANISM: Homo sapiens

<400> SEQUENCE: 709
aagctttggc tttacggaat a                                              21

<210> SEQ ID NO 710
<211> LENGTH: 21
<212> TYPE: DNA
<213> ORGANISM: Homo sapiens

<400> SEQUENCE: 710
ccgcctgaca gtgaagtatg a                                              21

<210> SEQ ID NO 711
<211> LENGTH: 21
<212> TYPE: DNA
<213> ORGANISM: Homo sapiens

<400> SEQUENCE: 711
caggagctct tccaggatca a                                              21

<210> SEQ ID NO 712
<211> LENGTH: 21
<212> TYPE: DNA
<213> ORGANISM: Homo sapiens

<400> SEQUENCE: 712
agggacattt gcatactcct a                                              21

<210> SEQ ID NO 713
<211> LENGTH: 21
<212> TYPE: DNA
<213> ORGANISM: Homo sapiens

<400> SEQUENCE: 713
cacccggact cctccaagat a                                              21

<210> SEQ ID NO 714
<211> LENGTH: 21
<212> TYPE: DNA
<213> ORGANISM: Homo sapiens

<400> SEQUENCE: 714
cagccaggag gcggagtgga a                                              21
```

```
<210> SEQ ID NO 715
<211> LENGTH: 21
<212> TYPE: DNA
<213> ORGANISM: Homo sapiens

<400> SEQUENCE: 715
ctgagtgtta atgatgcctt t                                              21

<210> SEQ ID NO 716
<211> LENGTH: 21
<212> TYPE: DNA
<213> ORGANISM: Homo sapiens

<400> SEQUENCE: 716
atggtggtac aggatggcat a                                              21

<210> SEQ ID NO 717
<211> LENGTH: 21
<212> TYPE: DNA
<213> ORGANISM: Homo sapiens

<400> SEQUENCE: 717
tgggaaggag acagacttat t                                              21

<210> SEQ ID NO 718
<211> LENGTH: 21
<212> TYPE: DNA
<213> ORGANISM: Homo sapiens

<400> SEQUENCE: 718
acgggcatgt atcgatacaa a                                              21

<210> SEQ ID NO 719
<211> LENGTH: 21
<212> TYPE: DNA
<213> ORGANISM: Homo sapiens

<400> SEQUENCE: 719
atggcttgtc atcctgaata a                                              21

<210> SEQ ID NO 720
<211> LENGTH: 21
<212> TYPE: DNA
<213> ORGANISM: Homo sapiens

<400> SEQUENCE: 720
caacgtcgtc atcaactata a                                              21

<210> SEQ ID NO 721
<211> LENGTH: 21
<212> TYPE: DNA
<213> ORGANISM: Homo sapiens

<400> SEQUENCE: 721
ctcatcgtgg accacaacat a                                              21

<210> SEQ ID NO 722
<211> LENGTH: 21
<212> TYPE: DNA
<213> ORGANISM: Homo sapiens

<400> SEQUENCE: 722
```
aacatgcttc ctgctatgta a                                              21

<210> SEQ ID NO 723
<211> LENGTH: 21
<212> TYPE: DNA
<213> ORGANISM: Homo sapiens

<400> SEQUENCE: 723
cccaaggtct atgctaaatt a                                              21

<210> SEQ ID NO 724
<211> LENGTH: 21
<212> TYPE: DNA
<213> ORGANISM: Homo sapiens

<400> SEQUENCE: 724
caccatctgc ttgactatgt a                                              21

<210> SEQ ID NO 725
<211> LENGTH: 21
<212> TYPE: DNA
<213> ORGANISM: Homo sapiens

<400> SEQUENCE: 725
ccgggcgcca atctcagcca a                                              21

<210> SEQ ID NO 726
<211> LENGTH: 21
<212> TYPE: DNA
<213> ORGANISM: Homo sapiens

<400> SEQUENCE: 726
cccaccagac tcatttgtaa a                                              21

<210> SEQ ID NO 727
<211> LENGTH: 21
<212> TYPE: DNA
<213> ORGANISM: Homo sapiens

<400> SEQUENCE: 727
accagtgccc ttcaccaatt a                                              21

<210> SEQ ID NO 728
<211> LENGTH: 21
<212> TYPE: DNA
<213> ORGANISM: Homo sapiens

<400> SEQUENCE: 728
aataataata ataatgaatg a                                              21

<210> SEQ ID NO 729
<211> LENGTH: 21
<212> TYPE: DNA
<213> ORGANISM: Homo sapiens

<400> SEQUENCE: 729
cacctctgag acgtccctgt a                                              21

<210> SEQ ID NO 730
<211> LENGTH: 21
<212> TYPE: DNA
<213> ORGANISM: Homo sapiens

<400> SEQUENCE: 730
caggctactt cgaaccagga a								21

<210> SEQ ID NO 731
<211> LENGTH: 21
<212> TYPE: DNA
<213> ORGANISM: Homo sapiens

<400> SEQUENCE: 731
ccgagtgttc ttcgagaact t								21

<210> SEQ ID NO 732
<211> LENGTH: 21
<212> TYPE: DNA
<213> ORGANISM: Homo sapiens

<400> SEQUENCE: 732
ggcggagttg gtggaaatta t								21

<210> SEQ ID NO 733
<211> LENGTH: 21
<212> TYPE: DNA
<213> ORGANISM: Homo sapiens

<400> SEQUENCE: 733
cccgcgggcc aaggtggcca a								21

<210> SEQ ID NO 734
<211> LENGTH: 21
<212> TYPE: DNA
<213> ORGANISM: Homo sapiens

<400> SEQUENCE: 734
ctcgcccaaa gaagactaca a								21

<210> SEQ ID NO 735
<211> LENGTH: 21
<212> TYPE: DNA
<213> ORGANISM: Homo sapiens

<400> SEQUENCE: 735
ctcccaggac aggctcctta a								21

<210> SEQ ID NO 736
<211> LENGTH: 21
<212> TYPE: DNA
<213> ORGANISM: Homo sapiens

<400> SEQUENCE: 736
cgcgcaaacg tccataactg a								21

<210> SEQ ID NO 737
<211> LENGTH: 21
<212> TYPE: DNA
<213> ORGANISM: Homo sapiens

<400> SEQUENCE: 737
cagagccaaa tcaaaggcta t								21

<210> SEQ ID NO 738
<211> LENGTH: 21
<212> TYPE: DNA
<213> ORGANISM: Homo sapiens

```
<400> SEQUENCE: 738
ctgcctgtgt ctcgtcttgt a                                              21

<210> SEQ ID NO 739
<211> LENGTH: 21
<212> TYPE: DNA
<213> ORGANISM: Homo sapiens

<400> SEQUENCE: 739
cagggcagga ttcatcaaat t                                              21

<210> SEQ ID NO 740
<211> LENGTH: 21
<212> TYPE: DNA
<213> ORGANISM: Homo sapiens

<400> SEQUENCE: 740
cacagttggt ctgaaatcaa a                                              21

<210> SEQ ID NO 741
<211> LENGTH: 21
<212> TYPE: DNA
<213> ORGANISM: Homo sapiens

<400> SEQUENCE: 741
tgggtgtgtt ccgaaagttt a                                              21

<210> SEQ ID NO 742
<211> LENGTH: 21
<212> TYPE: DNA
<213> ORGANISM: Homo sapiens

<400> SEQUENCE: 742
ctccggaggg ctgtaccttt a                                              21

<210> SEQ ID NO 743
<211> LENGTH: 21
<212> TYPE: DNA
<213> ORGANISM: Homo sapiens

<400> SEQUENCE: 743
cagggttcca gacgcataca a                                              21

<210> SEQ ID NO 744
<211> LENGTH: 21
<212> TYPE: DNA
<213> ORGANISM: Homo sapiens

<400> SEQUENCE: 744
tagcgaacac tttgactcca a                                              21

<210> SEQ ID NO 745
<211> LENGTH: 21
<212> TYPE: DNA
<213> ORGANISM: Homo sapiens

<400> SEQUENCE: 745
cactgtttaa ttggaattgt a                                              21

<210> SEQ ID NO 746
<211> LENGTH: 21
<212> TYPE: DNA
<213> ORGANISM: Homo sapiens
```

```
<400> SEQUENCE: 746
aagtgagttc aagaatcttt a                                              21

<210> SEQ ID NO 747
<211> LENGTH: 21
<212> TYPE: DNA
<213> ORGANISM: Homo sapiens

<400> SEQUENCE: 747
ttgagatagt tcactgttta a                                              21

<210> SEQ ID NO 748
<211> LENGTH: 21
<212> TYPE: DNA
<213> ORGANISM: Homo sapiens

<400> SEQUENCE: 748
aagtattcag aagacactta a                                              21

<210> SEQ ID NO 749
<211> LENGTH: 21
<212> TYPE: DNA
<213> ORGANISM: Homo sapiens

<400> SEQUENCE: 749
ctggtgaagt ctgaactgga a                                              21

<210> SEQ ID NO 750
<211> LENGTH: 21
<212> TYPE: DNA
<213> ORGANISM: Homo sapiens

<400> SEQUENCE: 750
caggaaggtg aacaagtgct a                                              21

<210> SEQ ID NO 751
<211> LENGTH: 21
<212> TYPE: DNA
<213> ORGANISM: Homo sapiens

<400> SEQUENCE: 751
cacgatgacc tcacccagta t                                              21

<210> SEQ ID NO 752
<211> LENGTH: 21
<212> TYPE: DNA
<213> ORGANISM: Homo sapiens

<400> SEQUENCE: 752
ccctatgacc atgcccgcat a                                              21

<210> SEQ ID NO 753
<211> LENGTH: 21
<212> TYPE: DNA
<213> ORGANISM: Homo sapiens

<400> SEQUENCE: 753
aatgcaggaa ctggcaaatc t                                              21

<210> SEQ ID NO 754
<211> LENGTH: 21
<212> TYPE: DNA
```

```
<213> ORGANISM: Homo sapiens

<400> SEQUENCE: 754
cacacttgaa atactagatc a                                              21

<210> SEQ ID NO 755
<211> LENGTH: 21
<212> TYPE: DNA
<213> ORGANISM: Homo sapiens

<400> SEQUENCE: 755
aagatgactc aaatcataca a                                              21

<210> SEQ ID NO 756
<211> LENGTH: 21
<212> TYPE: DNA
<213> ORGANISM: Homo sapiens

<400> SEQUENCE: 756
caggtccgtg acgagaagtt a                                              21

<210> SEQ ID NO 757
<211> LENGTH: 21
<212> TYPE: DNA
<213> ORGANISM: Homo sapiens

<400> SEQUENCE: 757
atccatgttc ttagagcctc a                                              21

<210> SEQ ID NO 758
<211> LENGTH: 21
<212> TYPE: DNA
<213> ORGANISM: Homo sapiens

<400> SEQUENCE: 758
atggccagag tgggtcgtca a                                              21

<210> SEQ ID NO 759
<211> LENGTH: 21
<212> TYPE: DNA
<213> ORGANISM: Homo sapiens

<400> SEQUENCE: 759
aacaattaac tgagcaaatt a                                              21

<210> SEQ ID NO 760
<211> LENGTH: 21
<212> TYPE: DNA
<213> ORGANISM: Homo sapiens

<400> SEQUENCE: 760
cagggatcac atcactctta a                                              21

<210> SEQ ID NO 761
<211> LENGTH: 21
<212> TYPE: DNA
<213> ORGANISM: Homo sapiens

<400> SEQUENCE: 761
caccacagac accagatatt a                                              21

<210> SEQ ID NO 762
<211> LENGTH: 21
```

```
<212> TYPE: DNA
<213> ORGANISM: Homo sapiens

<400> SEQUENCE: 762
ctggtagata gaagagctaa a                                              21

<210> SEQ ID NO 763
<211> LENGTH: 21
<212> TYPE: DNA
<213> ORGANISM: Homo sapiens

<400> SEQUENCE: 763
caggtggatg tagagatcaa a                                              21

<210> SEQ ID NO 764
<211> LENGTH: 21
<212> TYPE: DNA
<213> ORGANISM: Homo sapiens

<400> SEQUENCE: 764
aggatgagtc atggaattta a                                              21

<210> SEQ ID NO 765
<211> LENGTH: 21
<212> TYPE: DNA
<213> ORGANISM: Homo sapiens

<400> SEQUENCE: 765
caggctgaag ctcctaaact t                                              21

<210> SEQ ID NO 766
<211> LENGTH: 21
<212> TYPE: DNA
<213> ORGANISM: Homo sapiens

<400> SEQUENCE: 766
ccgcgaggag ctggccggca a                                              21

<210> SEQ ID NO 767
<211> LENGTH: 21
<212> TYPE: DNA
<213> ORGANISM: Homo sapiens

<400> SEQUENCE: 767
accggcgaag cgaaactgtc a                                              21

<210> SEQ ID NO 768
<211> LENGTH: 21
<212> TYPE: DNA
<213> ORGANISM: Homo sapiens

<400> SEQUENCE: 768
cacgactttc accacgtacc a                                              21

<210> SEQ ID NO 769
<211> LENGTH: 21
<212> TYPE: DNA
<213> ORGANISM: Homo sapiens

<400> SEQUENCE: 769
ccgcccaatt atcgcgacca a                                              21

<210> SEQ ID NO 770
```

```
<211> LENGTH: 21
<212> TYPE: DNA
<213> ORGANISM: Homo sapiens

<400> SEQUENCE: 770
ccgcttccca tccttccttt a                                              21

<210> SEQ ID NO 771
<211> LENGTH: 21
<212> TYPE: DNA
<213> ORGANISM: Homo sapiens

<400> SEQUENCE: 771
ctccagtacc tggaatccca a                                              21

<210> SEQ ID NO 772
<211> LENGTH: 21
<212> TYPE: DNA
<213> ORGANISM: Homo sapiens

<400> SEQUENCE: 772
gagcatgtgg aaggaccgga a                                              21

<210> SEQ ID NO 773
<211> LENGTH: 21
<212> TYPE: DNA
<213> ORGANISM: Homo sapiens

<400> SEQUENCE: 773
caggaggtcg ccggctccct a                                              21

<210> SEQ ID NO 774
<211> LENGTH: 21
<212> TYPE: DNA
<213> ORGANISM: Homo sapiens

<400> SEQUENCE: 774
ctccatggaa gaagccatca a                                              21

<210> SEQ ID NO 775
<211> LENGTH: 21
<212> TYPE: DNA
<213> ORGANISM: Homo sapiens

<400> SEQUENCE: 775
tccctaatat ttagggcaat a                                              21

<210> SEQ ID NO 776
<211> LENGTH: 21
<212> TYPE: DNA
<213> ORGANISM: Homo sapiens

<400> SEQUENCE: 776
ccggctatac aaggatcaga a                                              21

<210> SEQ ID NO 777
<211> LENGTH: 21
<212> TYPE: DNA
<213> ORGANISM: Homo sapiens

<400> SEQUENCE: 777
atcggtttct tcagtgcctt a                                              21
```

```
<210> SEQ ID NO 778
<211> LENGTH: 21
<212> TYPE: DNA
<213> ORGANISM: Homo sapiens

<400> SEQUENCE: 778
tcgcaacttt gtcaactaca a                                          21

<210> SEQ ID NO 779
<211> LENGTH: 21
<212> TYPE: DNA
<213> ORGANISM: Homo sapiens

<400> SEQUENCE: 779
ctccatgaca tctctaccga a                                          21

<210> SEQ ID NO 780
<211> LENGTH: 21
<212> TYPE: DNA
<213> ORGANISM: Homo sapiens

<400> SEQUENCE: 780
aacccggaac ttgcagaaat a                                          21

<210> SEQ ID NO 781
<211> LENGTH: 21
<212> TYPE: DNA
<213> ORGANISM: Homo sapiens

<400> SEQUENCE: 781
agacgtcatc tttactacta a                                          21

<210> SEQ ID NO 782
<211> LENGTH: 21
<212> TYPE: DNA
<213> ORGANISM: Homo sapiens

<400> SEQUENCE: 782
atggcaatgt ctctcatcca a                                          21

<210> SEQ ID NO 783
<211> LENGTH: 21
<212> TYPE: DNA
<213> ORGANISM: Homo sapiens

<400> SEQUENCE: 783
cgccttcgtg aacatcacct a                                          21

<210> SEQ ID NO 784
<211> LENGTH: 21
<212> TYPE: DNA
<213> ORGANISM: Homo sapiens

<400> SEQUENCE: 784
ccgtgttctc acagttatta a                                          21

<210> SEQ ID NO 785
<211> LENGTH: 21
<212> TYPE: DNA
<213> ORGANISM: Homo sapiens

<400> SEQUENCE: 785
tgcagcaatg gccaagatca a                                          21
```

```
<210> SEQ ID NO 786
<211> LENGTH: 21
<212> TYPE: DNA
<213> ORGANISM: Homo sapiens

<400> SEQUENCE: 786
caggaaattc tacaagggca a                                              21

<210> SEQ ID NO 787
<211> LENGTH: 21
<212> TYPE: DNA
<213> ORGANISM: Homo sapiens

<400> SEQUENCE: 787
cgaggagaac ctgaagacca a                                              21

<210> SEQ ID NO 788
<211> LENGTH: 21
<212> TYPE: DNA
<213> ORGANISM: Homo sapiens

<400> SEQUENCE: 788
caaggttatc agtgagctga a                                              21

<210> SEQ ID NO 789
<211> LENGTH: 21
<212> TYPE: DNA
<213> ORGANISM: Homo sapiens

<400> SEQUENCE: 789
aaggaggagt ctgaagagtc a                                              21

<210> SEQ ID NO 790
<211> LENGTH: 21
<212> TYPE: DNA
<213> ORGANISM: Homo sapiens

<400> SEQUENCE: 790
cagcgccaag gacatcaaga a                                              21

<210> SEQ ID NO 791
<211> LENGTH: 21
<212> TYPE: DNA
<213> ORGANISM: Homo sapiens

<400> SEQUENCE: 791
cagcgtgggt atcgaggcgg a                                              21

<210> SEQ ID NO 792
<211> LENGTH: 21
<212> TYPE: DNA
<213> ORGANISM: Homo sapiens

<400> SEQUENCE: 792
accgcgcatg ctccttcctt t                                              21

<210> SEQ ID NO 793
<211> LENGTH: 21
<212> TYPE: DNA
<213> ORGANISM: Homo sapiens

<400> SEQUENCE: 793
aaccggattg ccatttatga a                                              21
```

```
<210> SEQ ID NO 794
<211> LENGTH: 21
<212> TYPE: DNA
<213> ORGANISM: Homo sapiens

<400> SEQUENCE: 794
gacatttcta ctggtacctt a                                              21

<210> SEQ ID NO 795
<211> LENGTH: 21
<212> TYPE: DNA
<213> ORGANISM: Homo sapiens

<400> SEQUENCE: 795
accaatgagg gtatccagta t                                              21

<210> SEQ ID NO 796
<211> LENGTH: 21
<212> TYPE: DNA
<213> ORGANISM: Homo sapiens

<400> SEQUENCE: 796
ccatatcttt gcatccttca a                                              21

<210> SEQ ID NO 797
<211> LENGTH: 21
<212> TYPE: DNA
<213> ORGANISM: Homo sapiens

<400> SEQUENCE: 797
tcgggcggat tgaggatgtc a                                              21

<210> SEQ ID NO 798
<211> LENGTH: 21
<212> TYPE: DNA
<213> ORGANISM: Homo sapiens

<400> SEQUENCE: 798
atcaccgccc tacacatcaa a                                              21

<210> SEQ ID NO 799
<211> LENGTH: 21
<212> TYPE: DNA
<213> ORGANISM: Homo sapiens

<400> SEQUENCE: 799
tgggatgaag gtaaaggcag a                                              21

<210> SEQ ID NO 800
<211> LENGTH: 21
<212> TYPE: DNA
<213> ORGANISM: Homo sapiens

<400> SEQUENCE: 800
atgattgagc cgcgcacgct a                                              21

<210> SEQ ID NO 801
<211> LENGTH: 21
<212> TYPE: DNA
<213> ORGANISM: Homo sapiens

<400> SEQUENCE: 801
```
acgcggcaat ggtctcatca a    21

<210> SEQ ID NO 802
<211> LENGTH: 21
<212> TYPE: DNA
<213> ORGANISM: Homo sapiens

<400> SEQUENCE: 802
tcggacgcaa gaagacagcg a    21

<210> SEQ ID NO 803
<211> LENGTH: 21
<212> TYPE: DNA
<213> ORGANISM: Homo sapiens

<400> SEQUENCE: 803
cccgcgctcg ctaccagaaa t    21

<210> SEQ ID NO 804
<211> LENGTH: 21
<212> TYPE: DNA
<213> ORGANISM: Homo sapiens

<400> SEQUENCE: 804
ctgacttact gtttcaacaa a    21

<210> SEQ ID NO 805
<211> LENGTH: 21
<212> TYPE: DNA
<213> ORGANISM: Homo sapiens

<400> SEQUENCE: 805
ctggctgtcc tgaaatatta t    21

<210> SEQ ID NO 806
<211> LENGTH: 21
<212> TYPE: DNA
<213> ORGANISM: Homo sapiens

<400> SEQUENCE: 806
tcgaggttga accctcggat a    21

<210> SEQ ID NO 807
<211> LENGTH: 21
<212> TYPE: DNA
<213> ORGANISM: Homo sapiens

<400> SEQUENCE: 807
ctcgaactcc tatgccatta a    21

<210> SEQ ID NO 808
<211> LENGTH: 21
<212> TYPE: DNA
<213> ORGANISM: Homo sapiens

<400> SEQUENCE: 808
cgcgtggtct acgccgagtg a    21

<210> SEQ ID NO 809
<211> LENGTH: 21
<212> TYPE: DNA
<213> ORGANISM: Homo sapiens

<400> SEQUENCE: 809
ttcccagctg ctgcccaata a    21

<210> SEQ ID NO 810
<211> LENGTH: 21
<212> TYPE: DNA
<213> ORGANISM: Homo sapiens

<400> SEQUENCE: 810
caggctgtgt tctcaggatg a    21

<210> SEQ ID NO 811
<211> LENGTH: 21
<212> TYPE: DNA
<213> ORGANISM: Homo sapiens

<400> SEQUENCE: 811
caggtccaca atattcatac t    21

<210> SEQ ID NO 812
<211> LENGTH: 21
<212> TYPE: DNA
<213> ORGANISM: Homo sapiens

<400> SEQUENCE: 812
ttggatcatc tgcaccaatt a    21

<210> SEQ ID NO 813
<211> LENGTH: 21
<212> TYPE: DNA
<213> ORGANISM: Homo sapiens

<400> SEQUENCE: 813
ggcgaggtaa atggtcttaa a    21

<210> SEQ ID NO 814
<211> LENGTH: 21
<212> TYPE: DNA
<213> ORGANISM: Homo sapiens

<400> SEQUENCE: 814
ttcatcgtga tcttaaacct a    21

<210> SEQ ID NO 815
<211> LENGTH: 21
<212> TYPE: DNA
<213> ORGANISM: Homo sapiens

<400> SEQUENCE: 815
ctccctttca tgttaatcaa a    21

<210> SEQ ID NO 816
<211> LENGTH: 21
<212> TYPE: DNA
<213> ORGANISM: Homo sapiens

<400> SEQUENCE: 816
caggtcgttc ttatctagag a    21

<210> SEQ ID NO 817
<211> LENGTH: 21
<212> TYPE: DNA
<213> ORGANISM: Homo sapiens

<400> SEQUENCE: 817
caggatacaa ggcagatcca a                                              21

<210> SEQ ID NO 818
<211> LENGTH: 21
<212> TYPE: DNA
<213> ORGANISM: Homo sapiens

<400> SEQUENCE: 818
ccgcacctta tcaattgcaa a                                              21

<210> SEQ ID NO 819
<211> LENGTH: 21
<212> TYPE: DNA
<213> ORGANISM: Homo sapiens

<400> SEQUENCE: 819
acggactgta gtaatggata a                                              21

<210> SEQ ID NO 820
<211> LENGTH: 21
<212> TYPE: DNA
<213> ORGANISM: Homo sapiens

<400> SEQUENCE: 820
ctgccatatt gtagctcaat a                                              21

<210> SEQ ID NO 821
<211> LENGTH: 21
<212> TYPE: DNA
<213> ORGANISM: Homo sapiens

<400> SEQUENCE: 821
ccgaagatga ctcggataca a                                              21

<210> SEQ ID NO 822
<211> LENGTH: 21
<212> TYPE: DNA
<213> ORGANISM: Homo sapiens

<400> SEQUENCE: 822
agggtgcgtg aacgcagtga a                                              21

<210> SEQ ID NO 823
<211> LENGTH: 21
<212> TYPE: DNA
<213> ORGANISM: Homo sapiens

<400> SEQUENCE: 823
ctgggctcca ttggcgtcaa a                                              21

<210> SEQ ID NO 824
<211> LENGTH: 21
<212> TYPE: DNA
<213> ORGANISM: Homo sapiens

<400> SEQUENCE: 824
ctggacgtat ttatggctcc a                                              21

<210> SEQ ID NO 825
<211> LENGTH: 21
<212> TYPE: DNA
<213> ORGANISM: Homo sapiens

```
<400> SEQUENCE: 825
cacggtgggc cggcttgaca a                                              21

<210> SEQ ID NO 826
<211> LENGTH: 21
<212> TYPE: DNA
<213> ORGANISM: Homo sapiens

<400> SEQUENCE: 826
cacggctact gtgttggaca t                                              21

<210> SEQ ID NO 827
<211> LENGTH: 21
<212> TYPE: DNA
<213> ORGANISM: Homo sapiens

<400> SEQUENCE: 827
acccgtgttc atctcatccg a                                              21

<210> SEQ ID NO 828
<211> LENGTH: 21
<212> TYPE: DNA
<213> ORGANISM: Homo sapiens

<400> SEQUENCE: 828
caggatgctg ttgctgtagg a                                              21

<210> SEQ ID NO 829
<211> LENGTH: 21
<212> TYPE: DNA
<213> ORGANISM: Homo sapiens

<400> SEQUENCE: 829
cagcctgcgc tggttggtga a                                              21

<210> SEQ ID NO 830
<211> LENGTH: 21
<212> TYPE: DNA
<213> ORGANISM: Homo sapiens

<400> SEQUENCE: 830
cccgtcaaat ctgtgcctta t                                              21

<210> SEQ ID NO 831
<211> LENGTH: 21
<212> TYPE: DNA
<213> ORGANISM: Homo sapiens

<400> SEQUENCE: 831
ccgatccatg aagctaatgt a                                              21

<210> SEQ ID NO 832
<211> LENGTH: 21
<212> TYPE: DNA
<213> ORGANISM: Homo sapiens

<400> SEQUENCE: 832
tagggagagg ctcgtcaaca a                                              21

<210> SEQ ID NO 833
<211> LENGTH: 21
<212> TYPE: DNA
```

<213> ORGANISM: Homo sapiens

<400> SEQUENCE: 833
caccgtgtcc ttcctcgagt a                                    21

<210> SEQ ID NO 834
<211> LENGTH: 21
<212> TYPE: DNA
<213> ORGANISM: Homo sapiens

<400> SEQUENCE: 834
cagcgagatc ctgaagggcg a                                    21

<210> SEQ ID NO 835
<211> LENGTH: 21
<212> TYPE: DNA
<213> ORGANISM: Homo sapiens

<400> SEQUENCE: 835
cagggcctcc tggacaggaa a                                    21

<210> SEQ ID NO 836
<211> LENGTH: 21
<212> TYPE: DNA
<213> ORGANISM: Homo sapiens

<400> SEQUENCE: 836
tccgactgct ttggacctaa a                                    21

<210> SEQ ID NO 837
<211> LENGTH: 21
<212> TYPE: DNA
<213> ORGANISM: Homo sapiens

<400> SEQUENCE: 837
caggtgcttt gcaagatatc a                                    21

<210> SEQ ID NO 838
<211> LENGTH: 21
<212> TYPE: DNA
<213> ORGANISM: Homo sapiens

<400> SEQUENCE: 838
ccgcaaattg tggctactaa t                                    21

<210> SEQ ID NO 839
<211> LENGTH: 21
<212> TYPE: DNA
<213> ORGANISM: Homo sapiens

<400> SEQUENCE: 839
cagcaatttg tccgtcaact a                                    21

<210> SEQ ID NO 840
<211> LENGTH: 21
<212> TYPE: DNA
<213> ORGANISM: Homo sapiens

<400> SEQUENCE: 840
atggagatac agaccactca a                                    21

<210> SEQ ID NO 841
<211> LENGTH: 21

```
<212> TYPE: DNA
<213> ORGANISM: Homo sapiens

<400> SEQUENCE: 841
tccatggaac ctactaccaa a                                              21

<210> SEQ ID NO 842
<211> LENGTH: 21
<212> TYPE: DNA
<213> ORGANISM: Homo sapiens

<400> SEQUENCE: 842
ccggagacag gccaccgaat a                                              21

<210> SEQ ID NO 843
<211> LENGTH: 21
<212> TYPE: DNA
<213> ORGANISM: Homo sapiens

<400> SEQUENCE: 843
cagcagacag atcaacagct a                                              21

<210> SEQ ID NO 844
<211> LENGTH: 21
<212> TYPE: DNA
<213> ORGANISM: Homo sapiens

<400> SEQUENCE: 844
caacagctat gtcaagaata a                                              21

<210> SEQ ID NO 845
<211> LENGTH: 21
<212> TYPE: DNA
<213> ORGANISM: Homo sapiens

<400> SEQUENCE: 845
caccagctta gaaatgacta t                                              21

<210> SEQ ID NO 846
<211> LENGTH: 21
<212> TYPE: DNA
<213> ORGANISM: Homo sapiens

<400> SEQUENCE: 846
agggttatga acccagtgta a                                              21

<210> SEQ ID NO 847
<211> LENGTH: 21
<212> TYPE: DNA
<213> ORGANISM: Homo sapiens

<400> SEQUENCE: 847
cagaagggta gttatcctga t                                              21

<210> SEQ ID NO 848
<211> LENGTH: 21
<212> TYPE: DNA
<213> ORGANISM: Homo sapiens

<400> SEQUENCE: 848
aacctatgac aaactcaaca a                                              21

<210> SEQ ID NO 849
```

```
<211> LENGTH: 21
<212> TYPE: DNA
<213> ORGANISM: Homo sapiens

<400> SEQUENCE: 849
ctggaaagtg aaataaccta t                                              21

<210> SEQ ID NO 850
<211> LENGTH: 21
<212> TYPE: DNA
<213> ORGANISM: Homo sapiens

<400> SEQUENCE: 850
tgcgagcttc cgggaagaat a                                              21

<210> SEQ ID NO 851
<211> LENGTH: 21
<212> TYPE: DNA
<213> ORGANISM: Homo sapiens

<400> SEQUENCE: 851
ctgggaggta ttggagggaa a                                              21

<210> SEQ ID NO 852
<211> LENGTH: 21
<212> TYPE: DNA
<213> ORGANISM: Homo sapiens

<400> SEQUENCE: 852
aacgccgtgt ttgttaagaa t                                              21

<210> SEQ ID NO 853
<211> LENGTH: 21
<212> TYPE: DNA
<213> ORGANISM: Homo sapiens

<400> SEQUENCE: 853
cggcgtaaat ggagttggta a                                              21

<210> SEQ ID NO 854
<211> LENGTH: 21
<212> TYPE: DNA
<213> ORGANISM: Homo sapiens

<400> SEQUENCE: 854
aactcctgtc ttgctagaca a                                              21

<210> SEQ ID NO 855
<211> LENGTH: 21
<212> TYPE: DNA
<213> ORGANISM: Homo sapiens

<400> SEQUENCE: 855
tccatgcttg gagaaggaca a                                              21

<210> SEQ ID NO 856
<211> LENGTH: 21
<212> TYPE: DNA
<213> ORGANISM: Homo sapiens

<400> SEQUENCE: 856
caggatccac tatcaggcct a                                              21
```

```
<210> SEQ ID NO 857
<211> LENGTH: 21
<212> TYPE: DNA
<213> ORGANISM: Homo sapiens

<400> SEQUENCE: 857
ccggctgctt ctgcacttcc a                                              21

<210> SEQ ID NO 858
<211> LENGTH: 21
<212> TYPE: DNA
<213> ORGANISM: Homo sapiens

<400> SEQUENCE: 858
ctcgctggat gaggacaatg a                                              21

<210> SEQ ID NO 859
<211> LENGTH: 21
<212> TYPE: DNA
<213> ORGANISM: Homo sapiens

<400> SEQUENCE: 859
caggataaga cggaatggaa a                                              21

<210> SEQ ID NO 860
<211> LENGTH: 21
<212> TYPE: DNA
<213> ORGANISM: Homo sapiens

<400> SEQUENCE: 860
cgcaaggatt atgatcccaa a                                              21

<210> SEQ ID NO 861
<211> LENGTH: 21
<212> TYPE: DNA
<213> ORGANISM: Homo sapiens

<400> SEQUENCE: 861
cagcatgtag gtagcgtcct a                                              21

<210> SEQ ID NO 862
<211> LENGTH: 21
<212> TYPE: DNA
<213> ORGANISM: Homo sapiens

<400> SEQUENCE: 862
ctcattcagg agcgctatga a                                              21

<210> SEQ ID NO 863
<211> LENGTH: 21
<212> TYPE: DNA
<213> ORGANISM: Homo sapiens

<400> SEQUENCE: 863
acgatgacta ttcatcatct a                                              21

<210> SEQ ID NO 864
<211> LENGTH: 21
<212> TYPE: DNA
<213> ORGANISM: Homo sapiens

<400> SEQUENCE: 864
gaccgggaag atgaatacaa a                                              21
```

```
<210> SEQ ID NO 865
<211> LENGTH: 21
<212> TYPE: DNA
<213> ORGANISM: Homo sapiens

<400> SEQUENCE: 865
aagcataggc ggaccatgat a                                              21

<210> SEQ ID NO 866
<211> LENGTH: 21
<212> TYPE: DNA
<213> ORGANISM: Homo sapiens

<400> SEQUENCE: 866
tacgagtttg cttggtcaga a                                              21

<210> SEQ ID NO 867
<211> LENGTH: 21
<212> TYPE: DNA
<213> ORGANISM: Homo sapiens

<400> SEQUENCE: 867
aacattcgac ttccacctga a                                              21

<210> SEQ ID NO 868
<211> LENGTH: 21
<212> TYPE: DNA
<213> ORGANISM: Homo sapiens

<400> SEQUENCE: 868
aacagcttat gtggtctatg a                                              21

<210> SEQ ID NO 869
<211> LENGTH: 21
<212> TYPE: DNA
<213> ORGANISM: Homo sapiens

<400> SEQUENCE: 869
aagaatgcat gtgatcacct a                                              21

<210> SEQ ID NO 870
<211> LENGTH: 21
<212> TYPE: DNA
<213> ORGANISM: Homo sapiens

<400> SEQUENCE: 870
aaatatggac ctattcgtca a                                              21

<210> SEQ ID NO 871
<211> LENGTH: 21
<212> TYPE: DNA
<213> ORGANISM: Homo sapiens

<400> SEQUENCE: 871
cacgatgagg aagttcctgg a                                              21

<210> SEQ ID NO 872
<211> LENGTH: 21
<212> TYPE: DNA
<213> ORGANISM: Homo sapiens

<400> SEQUENCE: 872
ccgacctttg atgagaactc a                                              21
```

```
<210> SEQ ID NO 873
<211> LENGTH: 21
<212> TYPE: DNA
<213> ORGANISM: Homo sapiens

<400> SEQUENCE: 873
gccctgagtt ctggtgccaa a                                        21

<210> SEQ ID NO 874
<211> LENGTH: 21
<212> TYPE: DNA
<213> ORGANISM: Homo sapiens

<400> SEQUENCE: 874
caggatctct ccgagcagca a                                        21

<210> SEQ ID NO 875
<211> LENGTH: 21
<212> TYPE: DNA
<213> ORGANISM: Homo sapiens

<400> SEQUENCE: 875
ccggcttgag ctcaccacct a                                        21

<210> SEQ ID NO 876
<211> LENGTH: 21
<212> TYPE: DNA
<213> ORGANISM: Homo sapiens

<400> SEQUENCE: 876
agggatatcc atgcttatgt a                                        21

<210> SEQ ID NO 877
<211> LENGTH: 21
<212> TYPE: DNA
<213> ORGANISM: Homo sapiens

<400> SEQUENCE: 877
cagcgtcttc cattccagaa a                                        21

<210> SEQ ID NO 878
<211> LENGTH: 21
<212> TYPE: DNA
<213> ORGANISM: Homo sapiens

<400> SEQUENCE: 878
tccatctgtc tgtttctatt a                                        21

<210> SEQ ID NO 879
<211> LENGTH: 21
<212> TYPE: DNA
<213> ORGANISM: Homo sapiens

<400> SEQUENCE: 879
caagaacatg atggaaattg a                                        21

<210> SEQ ID NO 880
<211> LENGTH: 21
<212> TYPE: DNA
<213> ORGANISM: Homo sapiens

<400> SEQUENCE: 880
```
tcccgtgttt ccggtatgca t                                              21

<210> SEQ ID NO 881
<211> LENGTH: 21
<212> TYPE: DNA
<213> ORGANISM: Homo sapiens

<400> SEQUENCE: 881
cacgtcgaat gccactttga a                                              21

<210> SEQ ID NO 882
<211> LENGTH: 21
<212> TYPE: DNA
<213> ORGANISM: Homo sapiens

<400> SEQUENCE: 882
cgccggcatg atctacaaat a                                              21

<210> SEQ ID NO 883
<211> LENGTH: 21
<212> TYPE: DNA
<213> ORGANISM: Homo sapiens

<400> SEQUENCE: 883
caccttgatt ggctatgtct a                                              21

<210> SEQ ID NO 884
<211> LENGTH: 21
<212> TYPE: DNA
<213> ORGANISM: Homo sapiens

<400> SEQUENCE: 884
caccgatggc tggatctatg a                                              21

<210> SEQ ID NO 885
<211> LENGTH: 21
<212> TYPE: DNA
<213> ORGANISM: Homo sapiens

<400> SEQUENCE: 885
caggaccagt ccattgtccg a                                              21

<210> SEQ ID NO 886
<211> LENGTH: 21
<212> TYPE: DNA
<213> ORGANISM: Homo sapiens

<400> SEQUENCE: 886
tgccactagc tttgcatact a                                              21

<210> SEQ ID NO 887
<211> LENGTH: 21
<212> TYPE: DNA
<213> ORGANISM: Homo sapiens

<400> SEQUENCE: 887
ctccctgtga tcagttacca a                                              21

<210> SEQ ID NO 888
<211> LENGTH: 21
<212> TYPE: DNA
<213> ORGANISM: Homo sapiens

<400> SEQUENCE: 888
ctcgtatgaa ttcttctgta a                                              21

<210> SEQ ID NO 889
<211> LENGTH: 21
<212> TYPE: DNA
<213> ORGANISM: Homo sapiens

<400> SEQUENCE: 889
cagggtgagc ccaaggtcta t                                              21

<210> SEQ ID NO 890
<211> LENGTH: 21
<212> TYPE: DNA
<213> ORGANISM: Homo sapiens

<400> SEQUENCE: 890
tccgctggac ctcttcaaga a                                              21

<210> SEQ ID NO 891
<211> LENGTH: 21
<212> TYPE: DNA
<213> ORGANISM: Homo sapiens

<400> SEQUENCE: 891
agccgtcatt attaacagga a                                              21

<210> SEQ ID NO 892
<211> LENGTH: 21
<212> TYPE: DNA
<213> ORGANISM: Homo sapiens

<400> SEQUENCE: 892
gacggctatc ttaaagttta t                                              21

<210> SEQ ID NO 893
<211> LENGTH: 21
<212> TYPE: DNA
<213> ORGANISM: Homo sapiens

<400> SEQUENCE: 893
tgggaccagt acaattctca a                                              21

<210> SEQ ID NO 894
<211> LENGTH: 21
<212> TYPE: DNA
<213> ORGANISM: Homo sapiens

<400> SEQUENCE: 894
atgatcgcgg atggattatt a                                              21

<210> SEQ ID NO 895
<211> LENGTH: 21
<212> TYPE: DNA
<213> ORGANISM: Homo sapiens

<400> SEQUENCE: 895
gagggttggt ttattatcaa a                                              21

<210> SEQ ID NO 896
<211> LENGTH: 21
<212> TYPE: DNA
<213> ORGANISM: Homo sapiens

```
<400> SEQUENCE: 896
acggatctgg atatacacta t                                              21

<210> SEQ ID NO 897
<211> LENGTH: 21
<212> TYPE: DNA
<213> ORGANISM: Homo sapiens

<400> SEQUENCE: 897
acgcttatga ctcctaatgt a                                              21

<210> SEQ ID NO 898
<211> LENGTH: 21
<212> TYPE: DNA
<213> ORGANISM: Homo sapiens

<400> SEQUENCE: 898
cagcacccaa tagactattt a                                              21

<210> SEQ ID NO 899
<211> LENGTH: 21
<212> TYPE: DNA
<213> ORGANISM: Homo sapiens

<400> SEQUENCE: 899
ttgcacgaag ctcgcattga a                                              21

<210> SEQ ID NO 900
<211> LENGTH: 21
<212> TYPE: DNA
<213> ORGANISM: Homo sapiens

<400> SEQUENCE: 900
taggagccgt taagtatata t                                              21

<210> SEQ ID NO 901
<211> LENGTH: 21
<212> TYPE: DNA
<213> ORGANISM: Homo sapiens

<400> SEQUENCE: 901
aacagtaaag tgcttcatat t                                              21

<210> SEQ ID NO 902
<211> LENGTH: 21
<212> TYPE: DNA
<213> ORGANISM: Homo sapiens

<400> SEQUENCE: 902
tacgatgtta cgcaaccact a                                              21

<210> SEQ ID NO 903
<211> LENGTH: 21
<212> TYPE: DNA
<213> ORGANISM: Homo sapiens

<400> SEQUENCE: 903
aagattgagc ggcgacagca a                                              21

<210> SEQ ID NO 904
<211> LENGTH: 21
<212> TYPE: DNA
<213> ORGANISM: Homo sapiens
```

```
<400> SEQUENCE: 904
ctccggagaa tgggtatttg a                                              21

<210> SEQ ID NO 905
<211> LENGTH: 21
<212> TYPE: DNA
<213> ORGANISM: Homo sapiens

<400> SEQUENCE: 905
ccggagagag tttgaggtgt a                                              21

<210> SEQ ID NO 906
<211> LENGTH: 21
<212> TYPE: DNA
<213> ORGANISM: Homo sapiens

<400> SEQUENCE: 906
ctcctccaac tcgtgctgaa a                                              21

<210> SEQ ID NO 907
<211> LENGTH: 21
<212> TYPE: DNA
<213> ORGANISM: Homo sapiens

<400> SEQUENCE: 907
aagggctatc tggtatctgt a                                              21

<210> SEQ ID NO 908
<211> LENGTH: 21
<212> TYPE: DNA
<213> ORGANISM: Homo sapiens

<400> SEQUENCE: 908
ttggcggcca tttctcttga a                                              21

<210> SEQ ID NO 909
<211> LENGTH: 21
<212> TYPE: DNA
<213> ORGANISM: Homo sapiens

<400> SEQUENCE: 909
gccgtggtta cgatgagttt a                                              21

<210> SEQ ID NO 910
<211> LENGTH: 21
<212> TYPE: DNA
<213> ORGANISM: Homo sapiens

<400> SEQUENCE: 910
aaagattact cactgaacta a                                              21

<210> SEQ ID NO 911
<211> LENGTH: 21
<212> TYPE: DNA
<213> ORGANISM: Homo sapiens

<400> SEQUENCE: 911
aaggtctagg tcactagtgg a                                              21

<210> SEQ ID NO 912
<211> LENGTH: 21
<212> TYPE: DNA
```

```
<213> ORGANISM: Homo sapiens

<400> SEQUENCE: 912
caggccgaaa cttcccaaca a                                              21

<210> SEQ ID NO 913
<211> LENGTH: 21
<212> TYPE: DNA
<213> ORGANISM: Homo sapiens

<400> SEQUENCE: 913
tagactaaac caagtattgt a                                              21

<210> SEQ ID NO 914
<211> LENGTH: 21
<212> TYPE: DNA
<213> ORGANISM: Homo sapiens

<400> SEQUENCE: 914
accgcggact taaagcaata a                                              21

<210> SEQ ID NO 915
<211> LENGTH: 21
<212> TYPE: DNA
<213> ORGANISM: Homo sapiens

<400> SEQUENCE: 915
cagccgcttt ccagtgatgt a                                              21

<210> SEQ ID NO 916
<211> LENGTH: 21
<212> TYPE: DNA
<213> ORGANISM: Homo sapiens

<400> SEQUENCE: 916
acagatctca atgatgcaat a                                              21

<210> SEQ ID NO 917
<211> LENGTH: 21
<212> TYPE: DNA
<213> ORGANISM: Homo sapiens

<400> SEQUENCE: 917
tccagtggct atcaaggtga a                                              21

<210> SEQ ID NO 918
<211> LENGTH: 21
<212> TYPE: DNA
<213> ORGANISM: Homo sapiens

<400> SEQUENCE: 918
atggaatgta atcacgagta t                                              21

<210> SEQ ID NO 919
<211> LENGTH: 21
<212> TYPE: DNA
<213> ORGANISM: Homo sapiens

<400> SEQUENCE: 919
atgatgttga tttatcttta a                                              21

<210> SEQ ID NO 920
<211> LENGTH: 21
```

```
<212> TYPE: DNA
<213> ORGANISM: Homo sapiens

<400> SEQUENCE: 920
aaagatattc atcttgattt a                                              21

<210> SEQ ID NO 921
<211> LENGTH: 21
<212> TYPE: DNA
<213> ORGANISM: Homo sapiens

<400> SEQUENCE: 921
cagcgctgga atcctataat a                                              21

<210> SEQ ID NO 922
<211> LENGTH: 21
<212> TYPE: DNA
<213> ORGANISM: Homo sapiens

<400> SEQUENCE: 922
taggtctttc gtggtcagta a                                              21

<210> SEQ ID NO 923
<211> LENGTH: 21
<212> TYPE: DNA
<213> ORGANISM: Homo sapiens

<400> SEQUENCE: 923
cgccacctaa acagaaatct a                                              21

<210> SEQ ID NO 924
<211> LENGTH: 21
<212> TYPE: DNA
<213> ORGANISM: Homo sapiens

<400> SEQUENCE: 924
cccgccgtcg ttcaaggtct a                                              21

<210> SEQ ID NO 925
<211> LENGTH: 21
<212> TYPE: DNA
<213> ORGANISM: Homo sapiens

<400> SEQUENCE: 925
ctcgatcatc tccggagcta a                                              21

<210> SEQ ID NO 926
<211> LENGTH: 21
<212> TYPE: DNA
<213> ORGANISM: Homo sapiens

<400> SEQUENCE: 926
cagggatgtc ttcaaatcag a                                              21

<210> SEQ ID NO 927
<211> LENGTH: 21
<212> TYPE: DNA
<213> ORGANISM: Homo sapiens

<400> SEQUENCE: 927
cacgaaatac tcctacaagt a                                              21

<210> SEQ ID NO 928
```

-continued

```
<211> LENGTH: 21
<212> TYPE: DNA
<213> ORGANISM: Homo sapiens

<400> SEQUENCE: 928
cacgccaact gtagccaggt a                                                   21

<210> SEQ ID NO 929
<211> LENGTH: 21
<212> TYPE: DNA
<213> ORGANISM: Homo sapiens

<400> SEQUENCE: 929
cacctcgtgc gcggccatca a                                                   21

<210> SEQ ID NO 930
<211> LENGTH: 21
<212> TYPE: DNA
<213> ORGANISM: Homo sapiens

<400> SEQUENCE: 930
taggaacaat ggtcacttgt a                                                   21

<210> SEQ ID NO 931
<211> LENGTH: 21
<212> TYPE: DNA
<213> ORGANISM: Homo sapiens

<400> SEQUENCE: 931
agggatgtcc tcaaccagct a                                                   21

<210> SEQ ID NO 932
<211> LENGTH: 21
<212> TYPE: DNA
<213> ORGANISM: Homo sapiens

<400> SEQUENCE: 932
atgacagatt ctggaggata a                                                   21

<210> SEQ ID NO 933
<211> LENGTH: 21
<212> TYPE: DNA
<213> ORGANISM: Homo sapiens

<400> SEQUENCE: 933
tcgaaagtgg ccagaaatga a                                                   21

<210> SEQ ID NO 934
<211> LENGTH: 21
<212> TYPE: DNA
<213> ORGANISM: Homo sapiens

<400> SEQUENCE: 934
cacatcgacc acgagattga a                                                   21

<210> SEQ ID NO 935
<211> LENGTH: 21
<212> TYPE: DNA
<213> ORGANISM: Homo sapiens

<400> SEQUENCE: 935
tcagtgtatg ctaggcaaca a                                                   21
```

```
<210> SEQ ID NO 936
<211> LENGTH: 21
<212> TYPE: DNA
<213> ORGANISM: Homo sapiens

<400> SEQUENCE: 936
ctgccgcatc atgaagattg a                                              21

<210> SEQ ID NO 937
<211> LENGTH: 21
<212> TYPE: DNA
<213> ORGANISM: Homo sapiens

<400> SEQUENCE: 937
cagggtgatg tgattatccg a                                              21

<210> SEQ ID NO 938
<211> LENGTH: 21
<212> TYPE: DNA
<213> ORGANISM: Homo sapiens

<400> SEQUENCE: 938
ctgcaaggaa ctgcccggca a                                              21

<210> SEQ ID NO 939
<211> LENGTH: 21
<212> TYPE: DNA
<213> ORGANISM: Homo sapiens

<400> SEQUENCE: 939
ccgtatctgg agaatgaaca a                                              21

<210> SEQ ID NO 940
<211> LENGTH: 21
<212> TYPE: DNA
<213> ORGANISM: Homo sapiens

<400> SEQUENCE: 940
ctgcgtcacg tggaacacca a                                              21

<210> SEQ ID NO 941
<211> LENGTH: 21
<212> TYPE: DNA
<213> ORGANISM: Homo sapiens

<400> SEQUENCE: 941
ccacgttgtc gtggcctcca a                                              21

<210> SEQ ID NO 942
<211> LENGTH: 21
<212> TYPE: DNA
<213> ORGANISM: Homo sapiens

<400> SEQUENCE: 942
ctgggacatc gtgcggcact a                                              21

<210> SEQ ID NO 943
<211> LENGTH: 21
<212> TYPE: DNA
<213> ORGANISM: Homo sapiens

<400> SEQUENCE: 943
cccggatcac tcaagcaata a                                              21
```

<210> SEQ ID NO 944
<211> LENGTH: 21
<212> TYPE: DNA
<213> ORGANISM: Homo sapiens

<400> SEQUENCE: 944
gagcggaacc tgaatcccaa a                                              21

<210> SEQ ID NO 945
<211> LENGTH: 21
<212> TYPE: DNA
<213> ORGANISM: Homo sapiens

<400> SEQUENCE: 945
tcgcaggcga ttcaacatta a                                              21

<210> SEQ ID NO 946
<211> LENGTH: 21
<212> TYPE: DNA
<213> ORGANISM: Homo sapiens

<400> SEQUENCE: 946
tccgggattg ttgctgacat a                                              21

<210> SEQ ID NO 947
<211> LENGTH: 21
<212> TYPE: DNA
<213> ORGANISM: Homo sapiens

<400> SEQUENCE: 947
cagctccgaa ttcaggaact a                                              21

<210> SEQ ID NO 948
<211> LENGTH: 21
<212> TYPE: DNA
<213> ORGANISM: Homo sapiens

<400> SEQUENCE: 948
aaggagattg atgatgtcat t                                              21

<210> SEQ ID NO 949
<211> LENGTH: 21
<212> TYPE: DNA
<213> ORGANISM: Homo sapiens

<400> SEQUENCE: 949
aatggagtag attgtacatt a                                              21

<210> SEQ ID NO 950
<211> LENGTH: 21
<212> TYPE: DNA
<213> ORGANISM: Homo sapiens

<400> SEQUENCE: 950
atggagtaga ttgtacatta a                                              21

<210> SEQ ID NO 951
<211> LENGTH: 21
<212> TYPE: DNA
<213> ORGANISM: Homo sapiens

<400> SEQUENCE: 951
aagggataat acatgatcaa a                                              21

<210> SEQ ID NO 952
<211> LENGTH: 21
<212> TYPE: DNA
<213> ORGANISM: Homo sapiens

<400> SEQUENCE: 952
ttggtgcata tgttacccaa a                                              21

<210> SEQ ID NO 953
<211> LENGTH: 21
<212> TYPE: DNA
<213> ORGANISM: Homo sapiens

<400> SEQUENCE: 953
caggagggag agagagacac a                                              21

<210> SEQ ID NO 954
<211> LENGTH: 21
<212> TYPE: DNA
<213> ORGANISM: Homo sapiens

<400> SEQUENCE: 954
cagcagaagt gggtgcagga a                                              21

<210> SEQ ID NO 955
<211> LENGTH: 21
<212> TYPE: DNA
<213> ORGANISM: Homo sapiens

<400> SEQUENCE: 955
ctgcatgtgt gtccagcctg a                                              21

<210> SEQ ID NO 956
<211> LENGTH: 21
<212> TYPE: DNA
<213> ORGANISM: Homo sapiens

<400> SEQUENCE: 956
tgggtcggga ttctcaggtc a                                              21

<210> SEQ ID NO 957
<211> LENGTH: 21
<212> TYPE: DNA
<213> ORGANISM: Homo sapiens

<400> SEQUENCE: 957
caagctgcac atccagatga a                                              21

<210> SEQ ID NO 958
<211> LENGTH: 21
<212> TYPE: DNA
<213> ORGANISM: Homo sapiens

<400> SEQUENCE: 958
acgcaagtcg tggatgagta a                                              21

<210> SEQ ID NO 959
<211> LENGTH: 21
<212> TYPE: DNA
<213> ORGANISM: Homo sapiens

<400> SEQUENCE: 959
cggcagtcag atcctgcata a                                              21

<210> SEQ ID NO 960
<211> LENGTH: 21
<212> TYPE: DNA
<213> ORGANISM: Homo sapiens

<400> SEQUENCE: 960
tacctgcttc ttccagagaa a                                              21

<210> SEQ ID NO 961
<211> LENGTH: 21
<212> TYPE: DNA
<213> ORGANISM: Homo sapiens

<400> SEQUENCE: 961
ccgcaacaaa ttcgcccatc a                                              21

<210> SEQ ID NO 962
<211> LENGTH: 21
<212> TYPE: DNA
<213> ORGANISM: Homo sapiens

<400> SEQUENCE: 962
agagtgggta ctgttcggta a                                              21

<210> SEQ ID NO 963
<211> LENGTH: 21
<212> TYPE: DNA
<213> ORGANISM: Homo sapiens

<400> SEQUENCE: 963
cagcgtatct ccatgcaaga a                                              21

<210> SEQ ID NO 964
<211> LENGTH: 21
<212> TYPE: DNA
<213> ORGANISM: Homo sapiens

<400> SEQUENCE: 964
ctgcggaagc ctgtcaggtt a                                              21

<210> SEQ ID NO 965
<211> LENGTH: 21
<212> TYPE: DNA
<213> ORGANISM: Homo sapiens

<400> SEQUENCE: 965
caccgagaag ctcaaggcta a                                              21

<210> SEQ ID NO 966
<211> LENGTH: 21
<212> TYPE: DNA
<213> ORGANISM: Homo sapiens

<400> SEQUENCE: 966
cacgtgcaga aactcagcca a                                              21

<210> SEQ ID NO 967
<211> LENGTH: 21
<212> TYPE: DNA
<213> ORGANISM: Homo sapiens

<400> SEQUENCE: 967
ctcagattac tacttgacga a                                              21

<210> SEQ ID NO 968
<211> LENGTH: 21
<212> TYPE: DNA
<213> ORGANISM: Homo sapiens

<400> SEQUENCE: 968
ggccaagaaa ttcattgata a                                              21

<210> SEQ ID NO 969
<211> LENGTH: 21
<212> TYPE: DNA
<213> ORGANISM: Homo sapiens

<400> SEQUENCE: 969
cagcagcacg cttgacaatg a                                              21

<210> SEQ ID NO 970
<211> LENGTH: 21
<212> TYPE: DNA
<213> ORGANISM: Homo sapiens

<400> SEQUENCE: 970
cagagcatac ctggaaatga a                                              21

<210> SEQ ID NO 971
<211> LENGTH: 21
<212> TYPE: DNA
<213> ORGANISM: Homo sapiens

<400> SEQUENCE: 971
cacgcagagt ttgtgcagca a                                              21

<210> SEQ ID NO 972
<211> LENGTH: 21
<212> TYPE: DNA
<213> ORGANISM: Homo sapiens

<400> SEQUENCE: 972
ctggatatta cctctccaga a                                              21

<210> SEQ ID NO 973
<211> LENGTH: 21
<212> TYPE: DNA
<213> ORGANISM: Homo sapiens

<400> SEQUENCE: 973
gagcccttga ggataatat a                                               21

<210> SEQ ID NO 974
<211> LENGTH: 21
<212> TYPE: DNA
<213> ORGANISM: Homo sapiens

<400> SEQUENCE: 974
ttgcgtcagg tcctaagaca a                                              21

<210> SEQ ID NO 975
<211> LENGTH: 21
<212> TYPE: DNA
<213> ORGANISM: Homo sapiens

```
<400> SEQUENCE: 975
aaggatctag atgataccett t                                              21

<210> SEQ ID NO 976
<211> LENGTH: 21
<212> TYPE: DNA
<213> ORGANISM: Homo sapiens

<400> SEQUENCE: 976
agctccgtaa tttgactgaa a                                               21

<210> SEQ ID NO 977
<211> LENGTH: 21
<212> TYPE: DNA
<213> ORGANISM: Homo sapiens

<400> SEQUENCE: 977
ccggttggaa cctgcaataa a                                               21

<210> SEQ ID NO 978
<211> LENGTH: 21
<212> TYPE: DNA
<213> ORGANISM: Homo sapiens

<400> SEQUENCE: 978
caagggtacc gtggccatca a                                               21

<210> SEQ ID NO 979
<211> LENGTH: 21
<212> TYPE: DNA
<213> ORGANISM: Homo sapiens

<400> SEQUENCE: 979
cgcagtcact tcacaaggca a                                               21

<210> SEQ ID NO 980
<211> LENGTH: 21
<212> TYPE: DNA
<213> ORGANISM: Homo sapiens

<400> SEQUENCE: 980
gaaggtggcc acatccaaga a                                               21

<210> SEQ ID NO 981
<211> LENGTH: 21
<212> TYPE: DNA
<213> ORGANISM: Homo sapiens

<400> SEQUENCE: 981
ctgcctcacc ctcaataaat a                                               21

<210> SEQ ID NO 982
<211> LENGTH: 21
<212> TYPE: DNA
<213> ORGANISM: Homo sapiens

<400> SEQUENCE: 982
tgagccctaa tttatctta a                                                21

<210> SEQ ID NO 983
<211> LENGTH: 21
<212> TYPE: DNA
<213> ORGANISM: Homo sapiens
```

```
<400> SEQUENCE: 983
ctctggaaac cgcaccttta a                                              21

<210> SEQ ID NO 984
<211> LENGTH: 21
<212> TYPE: DNA
<213> ORGANISM: Homo sapiens

<400> SEQUENCE: 984
ctcgaggctt ctgacctttg a                                              21

<210> SEQ ID NO 985
<211> LENGTH: 21
<212> TYPE: DNA
<213> ORGANISM: Homo sapiens

<400> SEQUENCE: 985
aaggtttact ctggttataa a                                              21

<210> SEQ ID NO 986
<211> LENGTH: 21
<212> TYPE: DNA
<213> ORGANISM: Homo sapiens

<400> SEQUENCE: 986
cagcatcgcc gagaaggtta a                                              21

<210> SEQ ID NO 987
<211> LENGTH: 21
<212> TYPE: DNA
<213> ORGANISM: Homo sapiens

<400> SEQUENCE: 987
atgccgcgag ctgggcttta a                                              21

<210> SEQ ID NO 988
<211> LENGTH: 21
<212> TYPE: DNA
<213> ORGANISM: Homo sapiens

<400> SEQUENCE: 988
caaggactac tccaccaagt a                                              21

<210> SEQ ID NO 989
<211> LENGTH: 21
<212> TYPE: DNA
<213> ORGANISM: Homo sapiens

<400> SEQUENCE: 989
ccggcagctg atgttctctc a                                              21

<210> SEQ ID NO 990
<211> LENGTH: 21
<212> TYPE: DNA
<213> ORGANISM: Homo sapiens

<400> SEQUENCE: 990
tacatctgga ttgtagccat a                                              21

<210> SEQ ID NO 991
<211> LENGTH: 21
<212> TYPE: DNA
```

<213> ORGANISM: Homo sapiens

<400> SEQUENCE: 991
aagatagtac tgaatggagt a                                              21

<210> SEQ ID NO 992
<211> LENGTH: 21
<212> TYPE: DNA
<213> ORGANISM: Homo sapiens

<400> SEQUENCE: 992
ctggccctga gcatgcataa a                                              21

<210> SEQ ID NO 993
<211> LENGTH: 21
<212> TYPE: DNA
<213> ORGANISM: Homo sapiens

<400> SEQUENCE: 993
tcccaatttg acaatcgtat t                                              21

<210> SEQ ID NO 994
<211> LENGTH: 21
<212> TYPE: DNA
<213> ORGANISM: Homo sapiens

<400> SEQUENCE: 994
agcagttgtg actgacatgt a                                              21

<210> SEQ ID NO 995
<211> LENGTH: 21
<212> TYPE: DNA
<213> ORGANISM: Homo sapiens

<400> SEQUENCE: 995
aacacacatc atgtcagcct a                                              21

<210> SEQ ID NO 996
<211> LENGTH: 21
<212> TYPE: DNA
<213> ORGANISM: Homo sapiens

<400> SEQUENCE: 996
cagcaattca gcaataactt a                                              21

<210> SEQ ID NO 997
<211> LENGTH: 21
<212> TYPE: DNA
<213> ORGANISM: Homo sapiens

<400> SEQUENCE: 997
ctgaagtgct acttaccgaa a                                              21

<210> SEQ ID NO 998
<211> LENGTH: 21
<212> TYPE: DNA
<213> ORGANISM: Homo sapiens

<400> SEQUENCE: 998
caggattaca tggccgaagg a                                              21

<210> SEQ ID NO 999
<211> LENGTH: 21

-continued

```
<212> TYPE: DNA
<213> ORGANISM: Homo sapiens

<400> SEQUENCE: 999
accgccatcc tctgcctcaa a                                              21

<210> SEQ ID NO 1000
<211> LENGTH: 21
<212> TYPE: DNA
<213> ORGANISM: Homo sapiens

<400> SEQUENCE: 1000
gccgcgctac acctacttca a                                              21

<210> SEQ ID NO 1001
<211> LENGTH: 21
<212> TYPE: DNA
<213> ORGANISM: Homo sapiens

<400> SEQUENCE: 1001
cccgactgtg ctgctcgcga a                                              21

<210> SEQ ID NO 1002
<211> LENGTH: 21
<212> TYPE: DNA
<213> ORGANISM: Homo sapiens

<400> SEQUENCE: 1002
caggaactac gtggagatca t                                              21

<210> SEQ ID NO 1003
<211> LENGTH: 21
<212> TYPE: DNA
<213> ORGANISM: Homo sapiens

<400> SEQUENCE: 1003
ccggctgaag ctggagcgga a                                              21

<210> SEQ ID NO 1004
<211> LENGTH: 21
<212> TYPE: DNA
<213> ORGANISM: Homo sapiens

<400> SEQUENCE: 1004
ccgtgtggac ttccacaaca a                                              21

<210> SEQ ID NO 1005
<211> LENGTH: 21
<212> TYPE: DNA
<213> ORGANISM: Homo sapiens

<400> SEQUENCE: 1005
caagtatgag acggcactca a                                              21

<210> SEQ ID NO 1006
<211> LENGTH: 21
<212> TYPE: DNA
<213> ORGANISM: Homo sapiens

<400> SEQUENCE: 1006
cagcagcaag ttcgtcaagg a                                              21

<210> SEQ ID NO 1007
```

```
<211> LENGTH: 21
<212> TYPE: DNA
<213> ORGANISM: Homo sapiens

<400> SEQUENCE: 1007
cacgtacaac acgcaggtca a                                              21

<210> SEQ ID NO 1008
<211> LENGTH: 21
<212> TYPE: DNA
<213> ORGANISM: Homo sapiens

<400> SEQUENCE: 1008
ccgcgtgtac aagtcactga a                                              21

<210> SEQ ID NO 1009
<211> LENGTH: 21
<212> TYPE: DNA
<213> ORGANISM: Homo sapiens

<400> SEQUENCE: 1009
ccggaccttg tcttcgagga a                                              21

<210> SEQ ID NO 1010
<211> LENGTH: 21
<212> TYPE: DNA
<213> ORGANISM: Homo sapiens

<400> SEQUENCE: 1010
aaggagaacc tcgttgacaa a                                              21

<210> SEQ ID NO 1011
<211> LENGTH: 21
<212> TYPE: DNA
<213> ORGANISM: Homo sapiens

<400> SEQUENCE: 1011
cccgacttct ttggccagtg a                                              21

<210> SEQ ID NO 1012
<211> LENGTH: 21
<212> TYPE: DNA
<213> ORGANISM: Homo sapiens

<400> SEQUENCE: 1012
atgagattgc gtggctattt a                                              21

<210> SEQ ID NO 1013
<211> LENGTH: 21
<212> TYPE: DNA
<213> ORGANISM: Homo sapiens

<400> SEQUENCE: 1013
cccgactgga accaaaggtc a                                              21

<210> SEQ ID NO 1014
<211> LENGTH: 21
<212> TYPE: DNA
<213> ORGANISM: Homo sapiens

<400> SEQUENCE: 1014
cccattgtaa agcgacttca a                                              21
```

```
<210> SEQ ID NO 1015
<211> LENGTH: 21
<212> TYPE: DNA
<213> ORGANISM: Homo sapiens

<400> SEQUENCE: 1015
tacatgttac tccctaatca a                                              21

<210> SEQ ID NO 1016
<211> LENGTH: 21
<212> TYPE: DNA
<213> ORGANISM: Homo sapiens

<400> SEQUENCE: 1016
ttctcagaat atgaatacga a                                              21

<210> SEQ ID NO 1017
<211> LENGTH: 21
<212> TYPE: DNA
<213> ORGANISM: Homo sapiens

<400> SEQUENCE: 1017
atggttagtc gaatggctaa a                                              21

<210> SEQ ID NO 1018
<211> LENGTH: 21
<212> TYPE: DNA
<213> ORGANISM: Homo sapiens

<400> SEQUENCE: 1018
tttgtactat atactgttaa a                                              21

<210> SEQ ID NO 1019
<211> LENGTH: 21
<212> TYPE: DNA
<213> ORGANISM: Homo sapiens

<400> SEQUENCE: 1019
aagctctatc gggaaacaaa t                                              21

<210> SEQ ID NO 1020
<211> LENGTH: 21
<212> TYPE: DNA
<213> ORGANISM: Homo sapiens

<400> SEQUENCE: 1020
accgagggcg atgaagaagc a                                              21

<210> SEQ ID NO 1021
<211> LENGTH: 21
<212> TYPE: DNA
<213> ORGANISM: Homo sapiens

<400> SEQUENCE: 1021
gaggatcatg ctgttcacca a                                              21

<210> SEQ ID NO 1022
<211> LENGTH: 21
<212> TYPE: DNA
<213> ORGANISM: Homo sapiens

<400> SEQUENCE: 1022
aacaccatgc atgccatgca a                                              21
```

<210> SEQ ID NO 1023
<211> LENGTH: 21
<212> TYPE: DNA
<213> ORGANISM: Homo sapiens

<400> SEQUENCE: 1023
ccggcccgag ctgattgact a                                              21

<210> SEQ ID NO 1024
<211> LENGTH: 21
<212> TYPE: DNA
<213> ORGANISM: Homo sapiens

<400> SEQUENCE: 1024
aaggatgatc cactcacaaa t                                              21

<210> SEQ ID NO 1025
<211> LENGTH: 21
<212> TYPE: DNA
<213> ORGANISM: Homo sapiens

<400> SEQUENCE: 1025
aacgattaca tgcagccaga a                                              21

<210> SEQ ID NO 1026
<211> LENGTH: 21
<212> TYPE: DNA
<213> ORGANISM: Homo sapiens

<400> SEQUENCE: 1026
gggaacgagt ttagtatatt a                                              21

<210> SEQ ID NO 1027
<211> LENGTH: 21
<212> TYPE: DNA
<213> ORGANISM: Homo sapiens

<400> SEQUENCE: 1027
atgtgcttat ataatcgctt a                                              21

<210> SEQ ID NO 1028
<211> LENGTH: 21
<212> TYPE: DNA
<213> ORGANISM: Homo sapiens

<400> SEQUENCE: 1028
aacatggatc ctggatatga t                                              21

<210> SEQ ID NO 1029
<211> LENGTH: 21
<212> TYPE: DNA
<213> ORGANISM: Homo sapiens

<400> SEQUENCE: 1029
tccctataac cttgcatata a                                              21

<210> SEQ ID NO 1030
<211> LENGTH: 21
<212> TYPE: DNA
<213> ORGANISM: Homo sapiens

<400> SEQUENCE: 1030
caggctggtt tggtaaagaa a                                              21

```
<210> SEQ ID NO 1031
<211> LENGTH: 21
<212> TYPE: DNA
<213> ORGANISM: Homo sapiens

<400> SEQUENCE: 1031
accatgttac cctgtaatta a                                              21

<210> SEQ ID NO 1032
<211> LENGTH: 21
<212> TYPE: DNA
<213> ORGANISM: Homo sapiens

<400> SEQUENCE: 1032
gaggatatgc ttggtcgggt a                                              21

<210> SEQ ID NO 1033
<211> LENGTH: 21
<212> TYPE: DNA
<213> ORGANISM: Homo sapiens

<400> SEQUENCE: 1033
cagggtaatc tttgtggcac a                                              21

<210> SEQ ID NO 1034
<211> LENGTH: 21
<212> TYPE: DNA
<213> ORGANISM: Homo sapiens

<400> SEQUENCE: 1034
tagcatttga tgtctaaata a                                              21

<210> SEQ ID NO 1035
<211> LENGTH: 21
<212> TYPE: DNA
<213> ORGANISM: Homo sapiens

<400> SEQUENCE: 1035
aaacgagatc aggttagcaa a                                              21

<210> SEQ ID NO 1036
<211> LENGTH: 21
<212> TYPE: DNA
<213> ORGANISM: Homo sapiens

<400> SEQUENCE: 1036
ctgggtggag ctacccatga a                                              21

<210> SEQ ID NO 1037
<211> LENGTH: 21
<212> TYPE: DNA
<213> ORGANISM: Homo sapiens

<400> SEQUENCE: 1037
aagaaaagtg cggactgggt a                                              21

<210> SEQ ID NO 1038
<211> LENGTH: 21
<212> TYPE: DNA
<213> ORGANISM: Homo sapiens

<400> SEQUENCE: 1038
```
cccacctgta aagtagattc a					21

<210> SEQ ID NO 1039
<211> LENGTH: 21
<212> TYPE: DNA
<213> ORGANISM: Homo sapiens

<400> SEQUENCE: 1039
taccttctgt ctcttagtct a					21

<210> SEQ ID NO 1040
<211> LENGTH: 21
<212> TYPE: DNA
<213> ORGANISM: Homo sapiens

<400> SEQUENCE: 1040
aagctgatca atggtggtga a					21

<210> SEQ ID NO 1041
<211> LENGTH: 21
<212> TYPE: DNA
<213> ORGANISM: Homo sapiens

<400> SEQUENCE: 1041
ctgaaggcct ctgatctgat a					21

<210> SEQ ID NO 1042
<211> LENGTH: 21
<212> TYPE: DNA
<213> ORGANISM: Homo sapiens

<400> SEQUENCE: 1042
cccgacggag cagaagagag a					21

<210> SEQ ID NO 1043
<211> LENGTH: 21
<212> TYPE: DNA
<213> ORGANISM: Homo sapiens

<400> SEQUENCE: 1043
cggcccgaaa tgctcaaaga a					21

<210> SEQ ID NO 1044
<211> LENGTH: 21
<212> TYPE: DNA
<213> ORGANISM: Homo sapiens

<400> SEQUENCE: 1044
ttgctccata gtgttaacct a					21

<210> SEQ ID NO 1045
<211> LENGTH: 21
<212> TYPE: DNA
<213> ORGANISM: Homo sapiens

<400> SEQUENCE: 1045
atgctggtag agggaaagga a					21

<210> SEQ ID NO 1046
<211> LENGTH: 21
<212> TYPE: DNA
<213> ORGANISM: Homo sapiens

<400> SEQUENCE: 1046
cccatcatgg gaataaatta a                                              21

<210> SEQ ID NO 1047
<211> LENGTH: 21
<212> TYPE: DNA
<213> ORGANISM: Homo sapiens

<400> SEQUENCE: 1047
cagcatggac ttcgtggcct a                                              21

<210> SEQ ID NO 1048
<211> LENGTH: 21
<212> TYPE: DNA
<213> ORGANISM: Homo sapiens

<400> SEQUENCE: 1048
taccatgtcc cagatagcca a                                              21

<210> SEQ ID NO 1049
<211> LENGTH: 21
<212> TYPE: DNA
<213> ORGANISM: Homo sapiens

<400> SEQUENCE: 1049
gcgggaaggt ctctacttca a                                              21

<210> SEQ ID NO 1050
<211> LENGTH: 21
<212> TYPE: DNA
<213> ORGANISM: Homo sapiens

<400> SEQUENCE: 1050
cacgtccata gaacaggcaa a                                              21

<210> SEQ ID NO 1051
<211> LENGTH: 21
<212> TYPE: DNA
<213> ORGANISM: Homo sapiens

<400> SEQUENCE: 1051
acccacatat gcagcagtca a                                              21

<210> SEQ ID NO 1052
<211> LENGTH: 21
<212> TYPE: DNA
<213> ORGANISM: Homo sapiens

<400> SEQUENCE: 1052
ctccgtagcc tcgctgacca a                                              21

<210> SEQ ID NO 1053
<211> LENGTH: 21
<212> TYPE: DNA
<213> ORGANISM: Homo sapiens

<400> SEQUENCE: 1053
tccgctcgcc gtagcgcttt a                                              21

<210> SEQ ID NO 1054
<211> LENGTH: 21
<212> TYPE: DNA
<213> ORGANISM: Homo sapiens

```
<400> SEQUENCE: 1054
ccggatcata tttacatgga t                                              21

<210> SEQ ID NO 1055
<211> LENGTH: 21
<212> TYPE: DNA
<213> ORGANISM: Homo sapiens

<400> SEQUENCE: 1055
catcgacttg acgatagata a                                              21

<210> SEQ ID NO 1056
<211> LENGTH: 21
<212> TYPE: DNA
<213> ORGANISM: Homo sapiens

<400> SEQUENCE: 1056
caccctcgct tcagtacctt a                                              21

<210> SEQ ID NO 1057
<211> LENGTH: 21
<212> TYPE: DNA
<213> ORGANISM: Homo sapiens

<400> SEQUENCE: 1057
atcaggctct ttgcacaata a                                              21

<210> SEQ ID NO 1058
<211> LENGTH: 21
<212> TYPE: DNA
<213> ORGANISM: Homo sapiens

<400> SEQUENCE: 1058
cccgccatcc tccaataaag t                                              21

<210> SEQ ID NO 1059
<211> LENGTH: 21
<212> TYPE: DNA
<213> ORGANISM: Homo sapiens

<400> SEQUENCE: 1059
ctgaaggagc catctcatcc a                                              21

<210> SEQ ID NO 1060
<211> LENGTH: 21
<212> TYPE: DNA
<213> ORGANISM: Homo sapiens

<400> SEQUENCE: 1060
tggctggtac cctggaggaa a                                              21

<210> SEQ ID NO 1061
<211> LENGTH: 21
<212> TYPE: DNA
<213> ORGANISM: Homo sapiens

<400> SEQUENCE: 1061
cagactgccc atggcctccc a                                              21

<210> SEQ ID NO 1062
<211> LENGTH: 21
<212> TYPE: DNA
<213> ORGANISM: Homo sapiens
```

```
<400> SEQUENCE: 1062
ctggacgaga tcagcagggt a                                              21

<210> SEQ ID NO 1063
<211> LENGTH: 21
<212> TYPE: DNA
<213> ORGANISM: Homo sapiens

<400> SEQUENCE: 1063
cccagctttc actatcggca a                                              21

<210> SEQ ID NO 1064
<211> LENGTH: 21
<212> TYPE: DNA
<213> ORGANISM: Homo sapiens

<400> SEQUENCE: 1064
cacccacatg gtcaagttca a                                              21

<210> SEQ ID NO 1065
<211> LENGTH: 21
<212> TYPE: DNA
<213> ORGANISM: Homo sapiens

<400> SEQUENCE: 1065
gtcgatgtgc ttgccgatct a                                              21

<210> SEQ ID NO 1066
<211> LENGTH: 21
<212> TYPE: DNA
<213> ORGANISM: Homo sapiens

<400> SEQUENCE: 1066
atcagttcta cggatcatca a                                              21

<210> SEQ ID NO 1067
<211> LENGTH: 21
<212> TYPE: DNA
<213> ORGANISM: Homo sapiens

<400> SEQUENCE: 1067
ccagctgaac cagcaatgat a                                              21

<210> SEQ ID NO 1068
<211> LENGTH: 21
<212> TYPE: DNA
<213> ORGANISM: Homo sapiens

<400> SEQUENCE: 1068
cagaggatag cagcaacttc a                                              21

<210> SEQ ID NO 1069
<211> LENGTH: 21
<212> TYPE: DNA
<213> ORGANISM: Homo sapiens

<400> SEQUENCE: 1069
cggagggacc gtgctgacca a                                              21

<210> SEQ ID NO 1070
<211> LENGTH: 21
<212> TYPE: DNA
```

```
<213> ORGANISM: Homo sapiens

<400> SEQUENCE: 1070
ctgggcgtat gattgactta a                                              21

<210> SEQ ID NO 1071
<211> LENGTH: 21
<212> TYPE: DNA
<213> ORGANISM: Homo sapiens

<400> SEQUENCE: 1071
caggaagtcc tgggtgctaa a                                              21

<210> SEQ ID NO 1072
<211> LENGTH: 21
<212> TYPE: DNA
<213> ORGANISM: Homo sapiens

<400> SEQUENCE: 1072
caggtattgt tacttgaata a                                              21

<210> SEQ ID NO 1073
<211> LENGTH: 21
<212> TYPE: DNA
<213> ORGANISM: Homo sapiens

<400> SEQUENCE: 1073
aaggcgggag tgaccgctta a                                              21

<210> SEQ ID NO 1074
<211> LENGTH: 21
<212> TYPE: DNA
<213> ORGANISM: Homo sapiens

<400> SEQUENCE: 1074
aaggcttcga gaagattagc a                                              21

<210> SEQ ID NO 1075
<211> LENGTH: 21
<212> TYPE: DNA
<213> ORGANISM: Homo sapiens

<400> SEQUENCE: 1075
caccaccaga tgagaagtta a                                              21

<210> SEQ ID NO 1076
<211> LENGTH: 21
<212> TYPE: DNA
<213> ORGANISM: Homo sapiens

<400> SEQUENCE: 1076
cagggtttgg tgacaataga a                                              21

<210> SEQ ID NO 1077
<211> LENGTH: 21
<212> TYPE: DNA
<213> ORGANISM: Homo sapiens

<400> SEQUENCE: 1077
cgggcttatg ccaaagatgt a                                              21

<210> SEQ ID NO 1078
<211> LENGTH: 21
```

```
<212> TYPE: DNA
<213> ORGANISM: Homo sapiens

<400> SEQUENCE: 1078
cgggaagcag gagtcaatga a                                           21

<210> SEQ ID NO 1079
<211> LENGTH: 21
<212> TYPE: DNA
<213> ORGANISM: Homo sapiens

<400> SEQUENCE: 1079
tcccatgaca cggtcctcca a                                           21

<210> SEQ ID NO 1080
<211> LENGTH: 21
<212> TYPE: DNA
<213> ORGANISM: Homo sapiens

<400> SEQUENCE: 1080
cacggtggtc actggaactc a                                           21

<210> SEQ ID NO 1081
<211> LENGTH: 21
<212> TYPE: DNA
<213> ORGANISM: Homo sapiens

<400> SEQUENCE: 1081
aacatctttc acaaacactc a                                           21

<210> SEQ ID NO 1082
<211> LENGTH: 21
<212> TYPE: DNA
<213> ORGANISM: Homo sapiens

<400> SEQUENCE: 1082
ttgggtgaga ctgtttacaa a                                           21

<210> SEQ ID NO 1083
<211> LENGTH: 21
<212> TYPE: DNA
<213> ORGANISM: Homo sapiens

<400> SEQUENCE: 1083
tgcgaaggat ctggtagaga a                                           21

<210> SEQ ID NO 1084
<211> LENGTH: 21
<212> TYPE: DNA
<213> ORGANISM: Homo sapiens

<400> SEQUENCE: 1084
cagctcctac ctggccaatg a                                           21

<210> SEQ ID NO 1085
<211> LENGTH: 21
<212> TYPE: DNA
<213> ORGANISM: Homo sapiens

<400> SEQUENCE: 1085
ctcgcacttc cacaagacct a                                           21

<210> SEQ ID NO 1086
```

```
<211> LENGTH: 21
<212> TYPE: DNA
<213> ORGANISM: Homo sapiens

<400> SEQUENCE: 1086
caagaactct tgacatcta a                                              21

<210> SEQ ID NO 1087
<211> LENGTH: 21
<212> TYPE: DNA
<213> ORGANISM: Homo sapiens

<400> SEQUENCE: 1087
aagggcggag atcgaagact a                                             21

<210> SEQ ID NO 1088
<211> LENGTH: 21
<212> TYPE: DNA
<213> ORGANISM: Homo sapiens

<400> SEQUENCE: 1088
ctggaatcgt ccagggatta a                                             21

<210> SEQ ID NO 1089
<211> LENGTH: 21
<212> TYPE: DNA
<213> ORGANISM: Homo sapiens

<400> SEQUENCE: 1089
ctggtacaac ccagagtaga a                                             21

<210> SEQ ID NO 1090
<211> LENGTH: 21
<212> TYPE: DNA
<213> ORGANISM: Homo sapiens

<400> SEQUENCE: 1090
caggcatatg gatgagttca a                                             21

<210> SEQ ID NO 1091
<211> LENGTH: 21
<212> TYPE: DNA
<213> ORGANISM: Homo sapiens

<400> SEQUENCE: 1091
cccaattggt ttctacaacg a                                             21

<210> SEQ ID NO 1092
<211> LENGTH: 21
<212> TYPE: DNA
<213> ORGANISM: Homo sapiens

<400> SEQUENCE: 1092
ccggacggtg ctgtggtgca a                                             21

<210> SEQ ID NO 1093
<211> LENGTH: 21
<212> TYPE: DNA
<213> ORGANISM: Homo sapiens

<400> SEQUENCE: 1093
tactttgagt atcgaaggtt a                                             21
```

```
<210> SEQ ID NO 1094
<211> LENGTH: 21
<212> TYPE: DNA
<213> ORGANISM: Homo sapiens

<400> SEQUENCE: 1094
atcatgatgg ttagccattt a                                            21

<210> SEQ ID NO 1095
<211> LENGTH: 21
<212> TYPE: DNA
<213> ORGANISM: Homo sapiens

<400> SEQUENCE: 1095
cagctgaaac tttcttgatc a                                            21

<210> SEQ ID NO 1096
<211> LENGTH: 21
<212> TYPE: DNA
<213> ORGANISM: Homo sapiens

<400> SEQUENCE: 1096
aaagagcatt atctaagtaa t                                            21

<210> SEQ ID NO 1097
<211> LENGTH: 21
<212> TYPE: DNA
<213> ORGANISM: Homo sapiens

<400> SEQUENCE: 1097
aacaaccttt agatatgcaa a                                            21

<210> SEQ ID NO 1098
<211> LENGTH: 21
<212> TYPE: DNA
<213> ORGANISM: Homo sapiens

<400> SEQUENCE: 1098
tagtgtcttg gtgtagtgta a                                            21

<210> SEQ ID NO 1099
<211> LENGTH: 21
<212> TYPE: DNA
<213> ORGANISM: Homo sapiens

<400> SEQUENCE: 1099
agcaagattg ccatcacgaa a                                            21

<210> SEQ ID NO 1100
<211> LENGTH: 21
<212> TYPE: DNA
<213> ORGANISM: Homo sapiens

<400> SEQUENCE: 1100
aagggcctgg atgcaaggtt a                                            21

<210> SEQ ID NO 1101
<211> LENGTH: 21
<212> TYPE: DNA
<213> ORGANISM: Homo sapiens

<400> SEQUENCE: 1101
atcacgtgtg attgacatgt a                                            21
```

<210> SEQ ID NO 1102
<211> LENGTH: 21
<212> TYPE: DNA
<213> ORGANISM: Homo sapiens

<400> SEQUENCE: 1102
ttccatcagg accactatta a                                              21

<210> SEQ ID NO 1103
<211> LENGTH: 21
<212> TYPE: DNA
<213> ORGANISM: Homo sapiens

<400> SEQUENCE: 1103
cacgtttacc cgcaagccga a                                              21

<210> SEQ ID NO 1104
<211> LENGTH: 21
<212> TYPE: DNA
<213> ORGANISM: Homo sapiens

<400> SEQUENCE: 1104
cccactcaga gcgaggctaa a                                              21

<210> SEQ ID NO 1105
<211> LENGTH: 21
<212> TYPE: DNA
<213> ORGANISM: Homo sapiens

<400> SEQUENCE: 1105
accctggcgc ttgtgatgta a                                              21

<210> SEQ ID NO 1106
<211> LENGTH: 21
<212> TYPE: DNA
<213> ORGANISM: Homo sapiens

<400> SEQUENCE: 1106
cagaataatg aatggcataa a                                              21

<210> SEQ ID NO 1107
<211> LENGTH: 21
<212> TYPE: DNA
<213> ORGANISM: Homo sapiens

<400> SEQUENCE: 1107
atcgatatgg atcgaggatt t                                              21

<210> SEQ ID NO 1108
<211> LENGTH: 21
<212> TYPE: DNA
<213> ORGANISM: Homo sapiens

<400> SEQUENCE: 1108
ctcgtagggc attgcagcga a                                              21

<210> SEQ ID NO 1109
<211> LENGTH: 21
<212> TYPE: DNA
<213> ORGANISM: Homo sapiens

<400> SEQUENCE: 1109
tcctttaatg ttgtaattga a                                              21

<210> SEQ ID NO 1110
<211> LENGTH: 21
<212> TYPE: DNA
<213> ORGANISM: Homo sapiens

<400> SEQUENCE: 1110
acactgatta tccaacatat a    21

<210> SEQ ID NO 1111
<211> LENGTH: 21
<212> TYPE: DNA
<213> ORGANISM: Homo sapiens

<400> SEQUENCE: 1111
atccatataa ttagagaatt t    21

<210> SEQ ID NO 1112
<211> LENGTH: 21
<212> TYPE: DNA
<213> ORGANISM: Homo sapiens

<400> SEQUENCE: 1112
cccgctgtgc ataatcggtt t    21

<210> SEQ ID NO 1113
<211> LENGTH: 21
<212> TYPE: DNA
<213> ORGANISM: Homo sapiens

<400> SEQUENCE: 1113
ctgagccgtt tgacaacact a    21

<210> SEQ ID NO 1114
<211> LENGTH: 21
<212> TYPE: DNA
<213> ORGANISM: Homo sapiens

<400> SEQUENCE: 1114
aaggagctca gtaaactaga a    21

<210> SEQ ID NO 1115
<211> LENGTH: 21
<212> TYPE: DNA
<213> ORGANISM: Homo sapiens

<400> SEQUENCE: 1115
caggtacttc gtgatccgca t    21

<210> SEQ ID NO 1116
<211> LENGTH: 21
<212> TYPE: DNA
<213> ORGANISM: Homo sapiens

<400> SEQUENCE: 1116
caacatcgca aacatgaaga a    21

<210> SEQ ID NO 1117
<211> LENGTH: 21
<212> TYPE: DNA
<213> ORGANISM: Homo sapiens

<400> SEQUENCE: 1117
ctgcagcttg agctacaatc a                           21

<210> SEQ ID NO 1118
<211> LENGTH: 21
<212> TYPE: DNA
<213> ORGANISM: Homo sapiens

<400> SEQUENCE: 1118
ccggccggcc tttaacctca a                           21

<210> SEQ ID NO 1119
<211> LENGTH: 21
<212> TYPE: DNA
<213> ORGANISM: Homo sapiens

<400> SEQUENCE: 1119
ccgcagggtg atatacaagt a                           21

<210> SEQ ID NO 1120
<211> LENGTH: 21
<212> TYPE: DNA
<213> ORGANISM: Homo sapiens

<400> SEQUENCE: 1120
tcggtttatc cggaagaaca a                           21

<210> SEQ ID NO 1121
<211> LENGTH: 21
<212> TYPE: DNA
<213> ORGANISM: Homo sapiens

<400> SEQUENCE: 1121
ctgcgggttc acaaccgaaa t                           21

<210> SEQ ID NO 1122
<211> LENGTH: 21
<212> TYPE: DNA
<213> ORGANISM: Homo sapiens

<400> SEQUENCE: 1122
tcgctggaca aggacgatca a                           21

<210> SEQ ID NO 1123
<211> LENGTH: 21
<212> TYPE: DNA
<213> ORGANISM: Homo sapiens

<400> SEQUENCE: 1123
caccttcagg acgaacaata t                           21

<210> SEQ ID NO 1124
<211> LENGTH: 21
<212> TYPE: DNA
<213> ORGANISM: Homo sapiens

<400> SEQUENCE: 1124
cagggatgtg gtcagattcg a                           21

<210> SEQ ID NO 1125
<211> LENGTH: 21
<212> TYPE: DNA
<213> ORGANISM: Homo sapiens

<400> SEQUENCE: 1125

```
tcgccgcacc ctggagcact a                                          21

<210> SEQ ID NO 1126
<211> LENGTH: 21
<212> TYPE: DNA
<213> ORGANISM: Homo sapiens

<400> SEQUENCE: 1126
tcggcgaacg attcgactca a                                          21

<210> SEQ ID NO 1127
<211> LENGTH: 21
<212> TYPE: DNA
<213> ORGANISM: Homo sapiens

<400> SEQUENCE: 1127
cagtggagca ttgaacatcg a                                          21

<210> SEQ ID NO 1128
<211> LENGTH: 21
<212> TYPE: DNA
<213> ORGANISM: Homo sapiens

<400> SEQUENCE: 1128
caagagaatc tacgaggcct a                                          21

<210> SEQ ID NO 1129
<211> LENGTH: 21
<212> TYPE: DNA
<213> ORGANISM: Homo sapiens

<400> SEQUENCE: 1129
aagctttggc tttacggaat a                                          21

<210> SEQ ID NO 1130
<211> LENGTH: 21
<212> TYPE: DNA
<213> ORGANISM: Homo sapiens

<400> SEQUENCE: 1130
aatgcaggaa ctggcaaatc t                                          21

<210> SEQ ID NO 1131
<211> LENGTH: 21
<212> TYPE: DNA
<213> ORGANISM: Homo sapiens

<400> SEQUENCE: 1131
cacacttgaa atactagatc a                                          21

<210> SEQ ID NO 1132
<211> LENGTH: 21
<212> TYPE: DNA
<213> ORGANISM: Homo sapiens

<400> SEQUENCE: 1132
aagatgactc aaatcataca a                                          21

<210> SEQ ID NO 1133
<211> LENGTH: 21
<212> TYPE: DNA
<213> ORGANISM: Homo sapiens
```

<400> SEQUENCE: 1133
caggtccgtg acgagaagtt a					21

<210> SEQ ID NO 1134
<211> LENGTH: 21
<212> TYPE: DNA
<213> ORGANISM: Homo sapiens

<400> SEQUENCE: 1134
ctgggctcca ttggcgtcaa a					21

<210> SEQ ID NO 1135
<211> LENGTH: 21
<212> TYPE: DNA
<213> ORGANISM: Homo sapiens

<400> SEQUENCE: 1135
ctggacgtat ttatggctcc a					21

<210> SEQ ID NO 1136
<211> LENGTH: 21
<212> TYPE: DNA
<213> ORGANISM: Homo sapiens

<400> SEQUENCE: 1136
cacggtgggc cggcttgaca a					21

<210> SEQ ID NO 1137
<211> LENGTH: 21
<212> TYPE: DNA
<213> ORGANISM: Homo sapiens

<400> SEQUENCE: 1137
cacggctact gtgttggaca t					21

<210> SEQ ID NO 1138
<211> LENGTH: 21
<212> TYPE: DNA
<213> ORGANISM: Homo sapiens

<400> SEQUENCE: 1138
ccgatccatg aagctaatgt a					21

<210> SEQ ID NO 1139
<211> LENGTH: 21
<212> TYPE: DNA
<213> ORGANISM: Homo sapiens

<400> SEQUENCE: 1139
tagggagagg ctcgtcaaca a					21

<210> SEQ ID NO 1140
<211> LENGTH: 21
<212> TYPE: DNA
<213> ORGANISM: Homo sapiens

<400> SEQUENCE: 1140
caccgtgtcc ttcctcgagt a					21

<210> SEQ ID NO 1141
<211> LENGTH: 21
<212> TYPE: DNA
<213> ORGANISM: Homo sapiens

```
<400> SEQUENCE: 1141
cagcgagatc ctgaagggcg a                                              21

<210> SEQ ID NO 1142
<211> LENGTH: 21
<212> TYPE: DNA
<213> ORGANISM: Homo sapiens

<400> SEQUENCE: 1142
cagcagacag atcaacagct a                                              21

<210> SEQ ID NO 1143
<211> LENGTH: 21
<212> TYPE: DNA
<213> ORGANISM: Homo sapiens

<400> SEQUENCE: 1143
caacagctat gtcaagaata a                                              21

<210> SEQ ID NO 1144
<211> LENGTH: 21
<212> TYPE: DNA
<213> ORGANISM: Homo sapiens

<400> SEQUENCE: 1144
caccagctta gaaatgacta t                                              21

<210> SEQ ID NO 1145
<211> LENGTH: 21
<212> TYPE: DNA
<213> ORGANISM: Homo sapiens

<400> SEQUENCE: 1145
agggttatga acccagtgta a                                              21

<210> SEQ ID NO 1146
<211> LENGTH: 21
<212> TYPE: DNA
<213> ORGANISM: Homo sapiens

<400> SEQUENCE: 1146
cagaagggta gttatcctga t                                              21

<210> SEQ ID NO 1147
<211> LENGTH: 21
<212> TYPE: DNA
<213> ORGANISM: Homo sapiens

<400> SEQUENCE: 1147
aacctatgac aaactcaaca a                                              21

<210> SEQ ID NO 1148
<211> LENGTH: 21
<212> TYPE: DNA
<213> ORGANISM: Homo sapiens

<400> SEQUENCE: 1148
ctggaaagtg aaataaccta t                                              21

<210> SEQ ID NO 1149
<211> LENGTH: 21
<212> TYPE: DNA
```

```
<213> ORGANISM: Homo sapiens

<400> SEQUENCE: 1149
tgcgagcttc cgggaagaat a                                              21

<210> SEQ ID NO 1150
<211> LENGTH: 21
<212> TYPE: DNA
<213> ORGANISM: Homo sapiens

<400> SEQUENCE: 1150
ctgggaggta ttggagggaa a                                              21

<210> SEQ ID NO 1151
<211> LENGTH: 21
<212> TYPE: DNA
<213> ORGANISM: Homo sapiens

<400> SEQUENCE: 1151
aacgccgtgt ttgttaagaa t                                              21

<210> SEQ ID NO 1152
<211> LENGTH: 21
<212> TYPE: DNA
<213> ORGANISM: Homo sapiens

<400> SEQUENCE: 1152
cggcgtaaat ggagttggta a                                              21

<210> SEQ ID NO 1153
<211> LENGTH: 21
<212> TYPE: DNA
<213> ORGANISM: Homo sapiens

<400> SEQUENCE: 1153
aactcctgtc ttgctagaca a                                              21

<210> SEQ ID NO 1154
<211> LENGTH: 21
<212> TYPE: DNA
<213> ORGANISM: Homo sapiens

<400> SEQUENCE: 1154
tccatgcttg gagaaggaca a                                              21

<210> SEQ ID NO 1155
<211> LENGTH: 21
<212> TYPE: DNA
<213> ORGANISM: Homo sapiens

<400> SEQUENCE: 1155
caggatccac tatcaggcct a                                              21

<210> SEQ ID NO 1156
<211> LENGTH: 21
<212> TYPE: DNA
<213> ORGANISM: Homo sapiens

<400> SEQUENCE: 1156
ccggctgctt ctgcacttcc a                                              21

<210> SEQ ID NO 1157
<211> LENGTH: 21
```

```
<212> TYPE: DNA
<213> ORGANISM: Homo sapiens

<400> SEQUENCE: 1157
ctcgctggat gaggacaatg a                                              21

<210> SEQ ID NO 1158
<211> LENGTH: 21
<212> TYPE: DNA
<213> ORGANISM: Homo sapiens

<400> SEQUENCE: 1158
ccgtatctgg agaatgaaca a                                              21

<210> SEQ ID NO 1159
<211> LENGTH: 21
<212> TYPE: DNA
<213> ORGANISM: Homo sapiens

<400> SEQUENCE: 1159
ctgcgtcacg tggaacacca a                                              21

<210> SEQ ID NO 1160
<211> LENGTH: 21
<212> TYPE: DNA
<213> ORGANISM: Homo sapiens

<400> SEQUENCE: 1160
ccacgttgtc gtggcctcca a                                              21

<210> SEQ ID NO 1161
<211> LENGTH: 21
<212> TYPE: DNA
<213> ORGANISM: Homo sapiens

<400> SEQUENCE: 1161
ctgggacatc gtgcggcact a                                              21

<210> SEQ ID NO 1162
<211> LENGTH: 21
<212> TYPE: DNA
<213> ORGANISM: Homo sapiens

<400> SEQUENCE: 1162
ccgcaacaaa ttcgcccatc a                                              21

<210> SEQ ID NO 1163
<211> LENGTH: 21
<212> TYPE: DNA
<213> ORGANISM: Homo sapiens

<400> SEQUENCE: 1163
agagtgggta ctgttcggta a                                              21

<210> SEQ ID NO 1164
<211> LENGTH: 21
<212> TYPE: DNA
<213> ORGANISM: Homo sapiens

<400> SEQUENCE: 1164
cagcgtatct ccatgcaaga a                                              21

<210> SEQ ID NO 1165
```

```
<211> LENGTH: 21
<212> TYPE: DNA
<213> ORGANISM: Homo sapiens

<400> SEQUENCE: 1165
ctgcggaagc ctgtcaggtt a                                              21

<210> SEQ ID NO 1166
<211> LENGTH: 21
<212> TYPE: DNA
<213> ORGANISM: Homo sapiens

<400> SEQUENCE: 1166
gagcccttga ggaataatat a                                              21

<210> SEQ ID NO 1167
<211> LENGTH: 21
<212> TYPE: DNA
<213> ORGANISM: Homo sapiens

<400> SEQUENCE: 1167
ttgcgtcagg tcctaagaca a                                              21

<210> SEQ ID NO 1168
<211> LENGTH: 21
<212> TYPE: DNA
<213> ORGANISM: Homo sapiens

<400> SEQUENCE: 1168
aaggatctag atgataccdt t                                              21

<210> SEQ ID NO 1169
<211> LENGTH: 21
<212> TYPE: DNA
<213> ORGANISM: Homo sapiens

<400> SEQUENCE: 1169
agctccgtaa tttgactgaa a                                              21

<210> SEQ ID NO 1170
<211> LENGTH: 21
<212> TYPE: DNA
<213> ORGANISM: Homo sapiens

<400> SEQUENCE: 1170
ctgcctcacc ctcaataaat a                                              21

<210> SEQ ID NO 1171
<211> LENGTH: 21
<212> TYPE: DNA
<213> ORGANISM: Homo sapiens

<400> SEQUENCE: 1171
tgagccctaa tttatcttta a                                              21

<210> SEQ ID NO 1172
<211> LENGTH: 21
<212> TYPE: DNA
<213> ORGANISM: Homo sapiens

<400> SEQUENCE: 1172
ctctggaaac cgcaccttta a                                              21
```

```
<210> SEQ ID NO 1173
<211> LENGTH: 21
<212> TYPE: DNA
<213> ORGANISM: Homo sapiens

<400> SEQUENCE: 1173
ctcgaggctt ctgacctttg a                                        21
```